(12) United States Patent
Maderna et al.

(10) Patent No.: US 10,086,085 B2
(45) Date of Patent: Oct. 2, 2018

(54) BIFUNCTIONAL CYTOTOXIC AGENTS

(71) Applicant: Pfizer Inc., New York, NY (US)

(72) Inventors: Andreas Maderna, Stony Point, NY (US); Matthew David Doroski, Mystic, CT (US); Zecheng Chen, New City, NY (US); Hud Lawrence Risley, Baltic, CT (US); Jeffrey Michael Casavant, Franklin, CT (US); Christopher John O'Donnell, Mystic, CT (US); Alexander M. Porte, Madison, CT (US); Chakrapani Subramanyam, South Glastonbury, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/605,697

(22) Filed: Jan. 26, 2015

(65) Prior Publication Data

US 2015/0209445 A1 Jul. 30, 2015

Related U.S. Application Data

(60) Provisional application No. 62/046,685, filed on Sep. 5, 2014, provisional application No. 61/932,118, filed on Jan. 27, 2014.

(51) Int. Cl.

| | | |
|---|---|---|
| *C07D 487/04* | (2006.01) | |
| *C07D 487/06* | (2006.01) | |
| *C07D 209/30* | (2006.01) | |
| *A61K 31/404* | (2006.01) | |
| *A61K 31/407* | (2006.01) | |
| *A61K 47/48* | (2006.01) | |
| *A61K 31/433* | (2006.01) | |
| *A61K 31/4439* | (2006.01) | |
| *A61K 31/454* | (2006.01) | |
| *A61K 31/675* | (2006.01) | |
| *A61K 31/7056* | (2006.01) | |
| *A61K 38/05* | (2006.01) | |
| *A61K 38/06* | (2006.01) | |
| *C07D 401/14* | (2006.01) | |
| *C07D 405/14* | (2006.01) | |
| *C07D 409/14* | (2006.01) | |
| *C07D 417/14* | (2006.01) | |
| *C07F 9/6561* | (2006.01) | |
| *C07H 17/02* | (2006.01) | |
| *C07K 5/06* | (2006.01) | |
| *C07K 5/08* | (2006.01) | |
| *C07K 9/00* | (2006.01) | |
| *A61K 47/68* | (2017.01) | |

(52) U.S. Cl.
CPC ...... *A61K 47/48384* (2013.01); *A61K 31/404* (2013.01); *A61K 31/407* (2013.01); *A61K 31/433* (2013.01); *A61K 31/4439* (2013.01); *A61K 31/454* (2013.01); *A61K 31/675* (2013.01); *A61K 31/7056* (2013.01); *A61K 38/05* (2013.01); *A61K 38/06* (2013.01); *A61K 47/6803* (2017.08); *A61K 47/6807* (2017.08); *A61K 47/6811* (2017.08); *C07D 401/14* (2013.01); *C07D 405/14* (2013.01); *C07D 409/14* (2013.01); *C07D 417/14* (2013.01); *C07D 487/04* (2013.01); *C07F 9/6561* (2013.01); *C07H 17/02* (2013.01); *C07K 5/06* (2013.01); *C07K 5/08* (2013.01); *C07K 9/003* (2013.01)

(58) Field of Classification Search
CPC .. C07D 487/04; C07D 487/06; C07D 209/30; A61K 31/404; A61K 31/407
USPC ................. 548/427, 433; 514/411
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,225,539 A | 7/1993 | Winter | |
| 5,545,806 A | 8/1996 | Lonberg et al. | |
| 5,569,825 A | 10/1996 | Lonberg et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 2006/0205670 A1 | 9/2006 | Bradshaw et al. | |
| 2009/0118349 A1 | 5/2009 | Szekely et al. | |

FOREIGN PATENT DOCUMENTS

| | | |
|---|---|---|
| DE | 102009051799 A1 | 11/2009 |
| EP | 0012023 A1 | 6/1980 |
| EP | 0171496 A2 | 2/1986 |
| EP | 0173494 A2 | 3/1986 |
| EP | 0184187 A2 | 6/1986 |
| EP | 0359454 A1 * 3/1990 ........... C07D 519/00 |

(Continued)

OTHER PUBLICATIONS

Fukuda, Y., S. Seto, H. Furuta, H. Ebisu, Y. Oomori, and S. Terashima "Novel Seco Cyclopropa[c]pyrrolo[3,2-e]indole Bisalkylators Bearing a 3,3'-Arylenebisacryloyl Group as a Linker" J. Med. Chem. (2001), 44: pp. 1396-1406.*

(Continued)

*Primary Examiner* — Matthew P Coughlin
*Assistant Examiner* — Sagar Patel
(74) *Attorney, Agent, or Firm* — David Rubin

(57) ABSTRACT

Cytotoxic dimers comprising CBI-based and/or CPI-based sub-units, antibody drug conjugates comprising such dimers, and to methods for using the same to treat cancer and other conditions.

13 Claims, No Drawings

(56) References Cited

FOREIGN PATENT DOCUMENTS

| | | |
|---|---|---|
| EP | 0404097 A2 | 12/1990 |
| WO | 8601533 A1 | 3/1986 |
| WO | 8702671 A1 | 5/1987 |
| WO | 9311161 A1 | 6/1993 |
| WO | 9734631 A1 | 9/1997 |
| WO | 2005037992 A2 | 4/2005 |
| WO | 2005112919 A2 | 12/2005 |
| WO | 2007038658 A2 | 4/2007 |
| WO | 2010062171 A2 | 6/2010 |
| WO | 2011054837 A2 | 5/2011 |
| WO | 2012059882 A2 | 5/2012 |
| WO | 2012162482 A1 | 11/2012 |
| WO | 2013041606 A1 | 3/2013 |
| WO | 2013068946 A2 | 5/2013 |
| WO | 2014144878 A2 | 9/2014 |

OTHER PUBLICATIONS

Mitchell et al., "Interstrand DNA Cross-linking with Dimers of the Spirocyclopropyl Alkylating Moiety of CC-1065" J. Am. Chem. Soc. (1989), 111: pp. 6428-6429. (Year: 1989).*
Adamo et al., "Three multicomponent reactions of 3,5-dimethyl-4-nitroisoxazole." Tetrahedron 63:9741-9745(2007).
Beidler et al., "Cloning and High Level Expression of a Chimeric Antibody With Specificity for Human Carcinoembryonic Antigen." The Journal of Immunology 141(11):4053-4060(1988).
Better et al., "*Escherichia coli* Secretion of an Active Chimeric Antibody Fragment." Science 240:1041-1043(1988).
Boger et al., "Bifunctional Alkylating Agents Derived from Duocarmycin SA: Potent Antitumor Activity with Altered Sequence Selectivity." Bioorganic & Medicinal Chemistry Letters 10:495-498(2000).
Brulikova et al., "DNA Interstrand Cross-Linking Agents and their Chemotherapeutic Potential." Current Medicinal Chemistry 19:364-385(2012).
Chothia et al., "Canonical Structures for the Hypervariable Regions of Immunoglobulins." J. Mol. Biol. 196:901-917 (1987).
Ding et al., "DNA interstrand cross-linking, DNA sequence specificity, and induced conformational changes produced by a dimeric analog of (+)-CC-1065." Anti-Cancer Drug Design 6:427-452(1991).
Filosa et al., "Design, synthesis and biological evaluation of novel bicyclo[1.1.1]pentane-based w-acidic amino acids as glutamate receptors ligands." Bioorganic and Medicinal Chemistry 17:242-250(2009).
Ghosh et al., "Chemical and Biological Explorations of the Family of CC-1065 and the Duocarmycin Natural Products." Current Topics in Medicinal Chemistry 9:1494-1524(2009).
Holliger et al., ""Diabodies": Small bivalent and bispecific antibody fragments." Proc. Natl. Acad. Sci. 90:6444-6448 (1993).
Hoogenboom et al., "By-passing Immunisation Human Antibodies from Synthetic Repertoires of Germline VH Gene Segments Rearranged in Vitro." J. Mol. Biol. 227:381-388(1992).
Jespers et al., "Guiding the Selection of Human Antibodies from Phage Display Repertoires to a Single Repertoires of an Antigen." BioTechnology 12:899-903(1994).
Jia et al., "Design, Synthesis and Cytotoxicity Evaluation of 1-Chloromethyl-5-hydroxy-1,2-dihydro-3H-benz[e]indole (seco-CBI) Dimers." Bioorganic & Medicinal Chemistry 8:1607-1617(2000).
Jones et al., "Replacing the complementarity-determining regions in a human antibody with those from a mouse." Nature 321:522-525(1986).
Kabat, E., "Origins of Antibody Complementarity and Specificity-Hypervariable Regions and the Minigene Hypothesis." The Journal of Immunology 125(3):969(1980).
Karaki et al., "Visible-Light-Triggered Release of Nitric Oxide from N-Pyramidal Nitrosamines." Chem. Eur. J. 18:1127-1141(2012).
Kelly, Robert C., et al., "Coupling of Cyclopropapyrroloindole (CPI) Derivatives. The Preparation of CC-1065, and Analogues." J. Am. Chem. Soc. 109:6837-6838 (1987).
Kleemann et al., "Renin Inhibitory Pentols Showing Improved Enteral Bioavailability." J. Med. Chem. 35:559-567 (1992).
Kozbor et al., "The production of monoclonal antibodies from human lymphocytes." Immunology Today 4(3):72-79 (1983).
Laguzza et al., "New Antitumor Monoclonal Antibody-Vinca Conjugates LY203725 and Related Compounds: Design, Preparation, and Representative in Vivo Activity." J. Med. Chem. 32:548-555(1989).
Lajiness et al., "Design, Synthesis, and Evaluation of Duocarmycin O-Amino Phenol Prodrugs Subject to Tunable Reductive Activation." J. Med. Chem. 53:7731-7738(2010).
Langer, Robert, "New Methods of Drug Delivery." Science 249:1527-1533(1990).
Lee et al., "Nucleotide Preferences for DNA Interstrand Cross-Linking Induced by the Cyclopropylpyrroloindole Analogue U-77,779." Biochemistry 32:2592-2600(1993).
Lee et al., "DNA Interstrand Cross-Links Induced by the Cyclopropylpyrroloindole Antitumor Agent Bizelesin Are Reversible upon Exposure to Alkali." Biochemistry 32:9108-9114(1993).
Lee et al., "Mapping of DNA Alkylation Sites Induced by Adozelesin and Bizelesin inHuman Cells by Ligation-Mediated Polymerase Chain Reaction." Biochemistry 33:6024-6030 (1994).
Lee et al., "Replacement of the Bizelesin Ureadiyl Linkage by a Guanidinium Moiety Retards Translocation from Monoalkylation to Cross-Linking Sites on DNA." J. Am. Chem. Soc. 119:3434-3442(1997).
Liu et al., "Production of a Mouse-Human Chimeric Monoclonal Antibody to CD20 With Potent Fc-Dependent Biologic Activity." The Journal of Immunology 139(10):3521-3526(1987).
Liu et al., "Chimeric mouse-human IgG1 antibody that can mediate lysis of cancer cells." Proc. Natl. Acad. Sci. 84:3439-3443(1987).
Lonberg et al., "Human Antibodies from Transgenic Mice." Intern. Rev. Immunol. 13:65-93(1995).
Marks et al., "By-passing Immunization Human Antibodies from V-gene Libraries Displayed on Phage." J. Mol. Biol. 222:581-597(1991).
Mitchell et al., "Interstrand DNA Cross-linking with Dimers of the Spirocyclopropyl Alkylating Moiety of CC-1065." J. Am. Chem. Soc. 111:6428-6429(1989).
Morrison, Sherie L., "Transfectomas Provide Novel Chimeric Antibodies." Science 229:1202-1207(1985).
Nishimura et al., "Recombinant Human-Mouse Chimeric Monoclonal Antibody Specific for Common Acute Lymphocytic Leukemia Antigen." Cancer Research 47:999-1005(1987).
Oi et al., "Chimeric Antibodies." BioTechniques 4(3):214-221(1986).
Olsson et al., "Human-Human Monoclonal Antibody-Producing Hybridomas: Technical Aspects." Methods in Enzymology 92:3-16(1982).
Pitot et al., "A Phase I Study of Bizelesin (NSC 615291) in Patients with Advanced Solid Tumors." Clinical Cancer Research 8:712-717(2002).
Presta, Leonard G., "Antibody Engineering." Current Opinion in Structural Biology 2:593-596(1992).
Rahman et al., "Effect of base sequence on the DNA cross-linking properties of pyrrolobenzodiazepine (PBD) dimers." Nucleic Acids Research 39(13)5800-5812(2011).
Riechmann et al., "Reshaping human antibodies for therapy." Nature 332:323-327(1988).
Schwartz et al., "A phase I study of bizelesin, a highly potent and selective DNA-interactive agent, in patients with advanced solid malignancies." Annals of Oncology 14:775-782(2003).
Shaw et al., "Mouse/Human Chimeric Antibodies to a Tumor-Associated Antigen: Biologic Activity of the Four Human IgG Subclasses." Journal of the National Cancer Institute 80(19)1553-1559(1988).
Smellie et al., "Sequence-Selective Recognition of Duplex DNA through Covalent Interstrand Cross-Linking: Kinetic and Molecular Modeling Studies with Pyrrolobenzodiazepine Dimers." Biochemistry 42:8232-8239(2003).

(56) References Cited

OTHER PUBLICATIONS

Sun et al., "Analysis of the Monoalkylation and Cross-Linking Sequence Specificity of Bizelesin, a Bifunctional Alkylation Agent Related to (+)-CC-1065." J. Am. Chem. Soc. 115:5925-5933(1993).

Sun et al., "Chimeric antibody with human constant regions and mouse variable regions directed against carcinoma-associated antigen 17-1A." Proc. Natl. Acad. Sci. 84:214-218(1987).

Teng et al., "Construction and testing of mouse-human heteromyelomas for human monoclonal antibody production." Proc. Natl. Acad. Sci. 80:7308-7312(1983).

Thompson et al., "Determination of the Structural Role of the Internal Guanine-Cytosine Base Pair in Recognition of a Seven-Base-Pair Sequence Cross-Linked by Bizelesin." Biochemistry 34:11005-11016(1995).

Thompson et al., "Solution Conformation of a Bizelesin A-tract Duplex Adduct: DNA-DNA Cross-linking of an A-tract Straightens Out Bent DNA." J. Mol. Biol. 252:86-101(1995).

Tietze et al., "Glycosidic Prodrugs of Highly Potent Bifunctional Duocarmycin Derivatives for Selective Treatment of Cancer." Angew. Chem. Int. Ed. 49:7336-7339(2010).

Verhoeyen et al., "Reshaping Human Antibodies: Grafting an Antilysozyme Activity." Science 239:1534-1536 (1988).

Walker et al., "Preclinical pharmacology of bizelesin, a potent bifunctional analog of the DNA-binding antibiotic CC-1065." Cancer Chemother Pharmacol 34:317-322(1994).

Wirth et al., "Duocarmycin Analogues Target Aldehyde Dehydrogenase 1 in Lung Cancer Cells." Angew. Chem. Int. Ed. 51:2874-2877(2012).

Wirth et al., "The Two Faces of Potent Antitumor Duocarmycin-Based Drugs: A Structural Dissection Reveals Disparate Motifs for DNA versus Aldehyde Dehydrogenase 1 Affinity." Angew. Chem. Int. Ed. 52:6921-6925(2013).

Wolfe et al. "A Novel, Unusually Efficacious Duocarmycin Carbamate Prodrug That Releases No Residual Byproduct." Journal of Medicinal Chemistry 55:5878-5886(2012).

Wood et al., "The synthesis and in vivo assembly of functional antibodies in yeast." Nature 314:446-449(1985).

Zhao et al., "Synthesis and Biological Evaluation of Antibody Conjugates of Phosphate Prodrugs of Cytotoxic DNA Alkylators for the Targeted Treatment of Cancer." Journal of Medicinal Chemistry 55:766-782(2012).

Zhou et al., "Design and Synthesis of a Novel DNA-DNA Interstrand Adenine-Guanine Cross-Linking Agent." J. Am. Chem. Soc. 123:4865-4866(2001).

Mitchell et al., "Synthesis and DNA Cross-Linking by a Rigid CPI Dimer." J. Am. Chem. Soc. 113, 8994-8995 (1991).

Fukuda Y., et al., "The Novel Cyclopropapyrroloindole(CPI) Bisalkylators Bearing 3,3'-(1,4-Phenylene)Diacryloyl Group As a Linker", Bioorganic & Medicinal Chemistry Letters, 1998, vol. 8, 2003-2004.

Lillo, Antonietta, et al., "A Human Single-Chain Antibody Specific for Integrin alpha 3 beta 1 Capable of Cell Internalization and Delivery of Antitumor Agents", Chemistry & Biology, 2004, vol. 11, 897-906.

International Search Report dated May 6, 2015 for International Application No. PCT/IB2015/050280, filed on Jan. 14, 2015.

PCT Written Opinion for International Application No. PCT/IB2015/050280 filed on Jan. 14, 2015.

Patani et al., "Bioisosterism: A Rational Approach in Drug Design", Chemical Review, 96, 3147-3176 (1996).

Wu et al., "Arming antibodies: prospects and challenges for immunoconjugates", Nature Biotechnology, 23(9), 1137-1146 (2005).

* cited by examiner

BIFUNCTIONAL CYTOTOXIC AGENTS

CROSS-REFERENCE TO RELATED APPLICATIONS

This is a United States Non-Provisional Application which claims the benefit of U.S. Provisional application Ser. No. 61/932,118, filed on Jan. 27, 2014, and U.S. Provisional application Ser. No. 62/046,685, filed on Sep. 5, 2014; the contents of which are hereby incorporated by reference in their entireties.

FIELD OF THE INVENTION

The present invention is directed to novel bifunctional CBI and CPI dimers useful for the treatment for proliferative diseases. The dimers can function as stand-alone drugs, payloads in antibody-drug-conjugates (ADCs), and linker-payload compounds useful in connection with the production or administration of such ADCs. The present invention further relates to compositions including the aforementioned dimers, linker-payloads and ADCs, and methods for using these dimers, linker-payloads and ADCs, to treat pathological conditions including cancer.

BACKGROUND

CPI-based monomers have been the subject of recent publications. For instance, the compounds (+)-CC-1065 and the duocarmycins are natural products isolated from the culture broth of *Streptomyces* species, which have been shown to exert ultrapotent activity against cultured cancer cells and in experimental animals. (+)-Yatakemycin has been isolated from *Streptomyces* sp. and represents the most potent member of this class of natural products. The biological activity of these natural products is believed to be related to a characteristic sequence-selective DNA alkylation of adenine N3 in AT-rich sites by the least substituted carbon of the activated cyclopropane. This minor groove binding is thought to initiate a cascade of cellular events leading to apoptosis as observed for the duocarmycins ("Chemical and Biological Explorations of the Family of CC-1065 and the Duocarmycin Natural Products", Current Topics in Medicinal Chemistry, 2009, 9, 1494-1524). The key structural motif in these and related analogs is the CPI structures which is the reactive group that alkylates DNA:

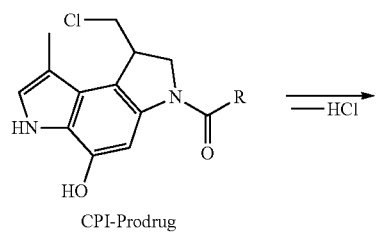

CPI-Prodrug

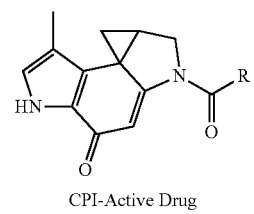

CPI-Active Drug

The CPI prodrug form converts to the active drug species in the biological medium by an intramolecular cyclization reaction. (The term "CPI" is derived from the chemical name: 1,2,8,8a-tetrahydrocyclopropa[c]pyrrolo[3,2-e]indol-4(5H)-one.) The CPI prodrug thus converts to an active drug species by an intramolecular cyclization reaction. The phenol synthetic precursors (prodrug form) possess indistinguishable biological properties (DNA alkylation efficiency and selectivity, in vitro cytotoxic activity, in vivo antitumor activity) in comparison to the cyclopropane derivatives themselves (active form) ("Design, Synthesis, and Evaluation of Duocarmycin O-Amino Phenol Prodrugs Subject to Tunable Reductive Activation", J. Med. Chem. 2010, 53, 7731-7738). In other words, it does not matter whether the CPI warhead is in its active cyclopropanated form or in its prodrug form. Important to note is that in these compounds only one CPI motif is present, hence these compounds act as DNA mono-alkylators. Several other synthetic analogs of the CPI structures have subsequently been developed, i.e. those shown in ("Chemical and Biological Explorations of the Family of CC-1065 and the Duocarmycin Natural Products", Current Topics in Medicinal Chemistry, 2009, 9, 1494-1524). Of note in this reference are the synthetic analogs CBI, Cpzl, CFI, CI and CBQ. Mono-alkylating duocramycin analogs have been extensively studied in pre-clinical and clinical studies ("Chemical and Biological Explorations of the Family of CC-1065 and the Duocarmycin Natural Products, Current Topics in Medicinal Chemistry, 2009, 9, 1494-1524).

A separate but related class of compounds are bifunctional analogs that contain two active DNA alkylation motifs (i.e. a CPI). These compounds are different to the conventional duoacrmyins in that they lack the moiety within duocarmycins, which functions as the DNA recognition motifs. Instead, these bifunctional compounds simply contain two alkylation (i.e. two CPI motifs) fused together. Due to the presence of two reactive alkylation motifs these compounds are active DNA cross linkers, whereas compounds with only one alkylation motif (all duocarmycins) are only DNA mono-alkylators.

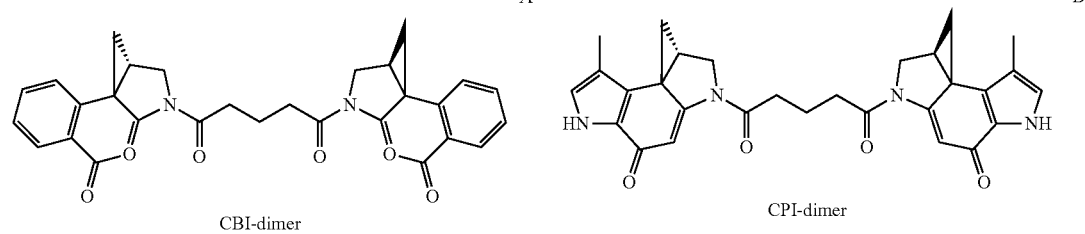

CBI-dimer　　　　　　　CPI-dimer

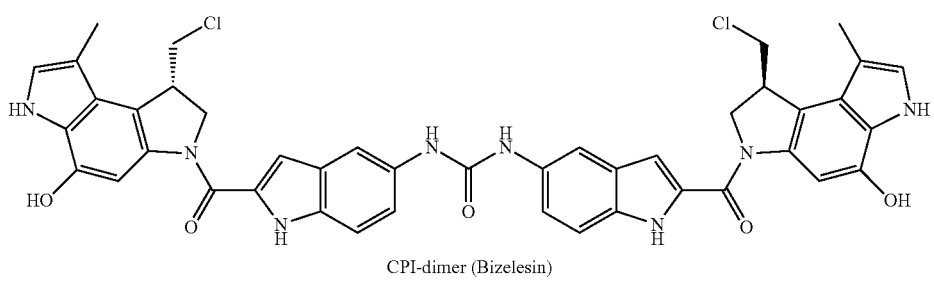

CPI-dimer (Bizelesin)

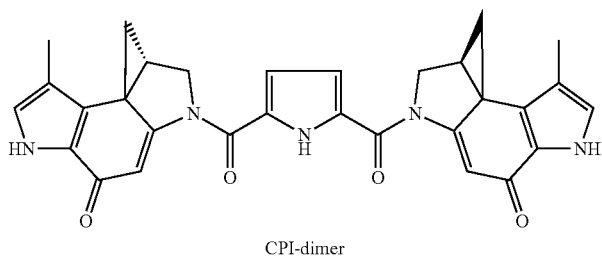

CPI-dimer

The compounds shown above are representative examples from the literature and are reported to be potent cytotoxins: A ("Glycosidic Prodrugs of Highly Potent Bifunctional Duocarmycin Derivatives for Selective Treatment of Cancer", Angew. Chem. Int. Ed. 2010, 49, 7336-7339; "Duocarmycin Analogues Target Aldehyde Dehydrogenase 1 in LungCancer Cells", Angew. Chem. Int. Ed. 2012, 51, 2874-2877; "Bifunctional prodrugs and drugs", WO 2011/054837, DE 10 2009 051 799; "The Two Faces of Potent Antitumor Duocarmycin-Based Drugs: A Structural Dissection Reveals Disparate Motifs for DNA versus Aldehyde Dehydrogenase 1 Affinity", Angew. Chem. Int. Ed. 2013, 52, 1-6. B ("Interstrand DNA Cross-linking with Dimers of the Spirocyclopropyl Alkylating Moiety of CC-1065", J. Am. Chem. SOC. 1989, 11 1, 6428-6429; "CC-1065 analogs having two CPI subunits useful as antitumor agents and ultraviolet light absorbers", Eur. Pat. Appl. (1990), EP 359454, also for compounds C and D; C ("Synthesis and DNA Cross-Linking by a Rigid CPI Dimer", J. Am. Chem. SOC. 1991, 113, 8994-8995; "Nucleotide Preferences for DNA Interstrand Cross-Linking Induced by the Cyclopropylpyrroloindole Analogue U-77,779", Biochemistry 1993, 32, 2592-2600; "Determination of the Structural Role of the Internal Guanine-Cytosine Base Pair in Recognition of a Seven-Base-Pair Sequence Cross-Linked by Bizelesin", Biochemistry 1995, 34, 11005-11016; "Analysis of the Monoalkylation and Cross-Linking Sequence Specificity of Bizelesin, a Bifunctional Alkylation Agent Related to (+)-CC-1065", J. Am. Chem. SOC. 1993, 115, 5925-5933; "Mapping of DNA Alkylation Sites Induced by Adozelesin and Bizelesin in Human Cells by Ligation-Mediated Polymerase Chain Reaction", Biochemistry 1994, 33, 6024-6030; "DNA Interstrand Cross-Links Induced by the Cyclopropylpyrroloindole Antitumor Agent Bizelesin Are Reversible upon Exposure to Alkali", Biochemistry 1993, 32, 9108-9114; "Replacement of the Bizelesin Ureadiyl Linkage by a Guanidinium Moiety Retards Translocation from Monoalkylation to Cross-Linking Sites on DNA", J. Am. Chem. Soc. 1997, 119, 3434-3442; "DNA interstrand cross-linking, DNA sequence specificity, and induced conformational changes produced by a dimeric analog of (+)-CC-1065", Anti-Cancer Drug Design (1991), 6, 427-452; "A phase I study of bizelesin, a highly potent and selective DNAinteractive agent, in patients with advanced solid malignancies", Ann Oncol. 2003 May; 14(5):775-782; "A Phase I study of bizelesin (NSC 615291) in patients with advanced solid tumors", Clin Cancer Res. 2002, 3, 712-717; "Solution conformation of a bizelesin A-tract duplex adduct: DNA-DNA cross-linking of an A-tract straightens out bent DNA", J Mol Biol. 1995, 252, 86-101; "Preclinical pharmacology of bizelesin, a potent bifunctional analog of the DNA-binding antibiotic CC-1065", Cancer Chemother Pharmacol. 1994, 34, 317-322. D ("CC-1065 analogs having two CPI subunits useful as antitumor agents and ultraviolet light absorbers", Eur. Pat. Appl. (1990), EP 359454. The active DNA alkylation motif can in principle exist in either a prodrug form that converts to the active drug in the biological medium, or in its active state which does not require further conversion. The prodrug-to-active drug conversion for the bifunctional cross linkers is exemplified with the CBI dimer shown below:

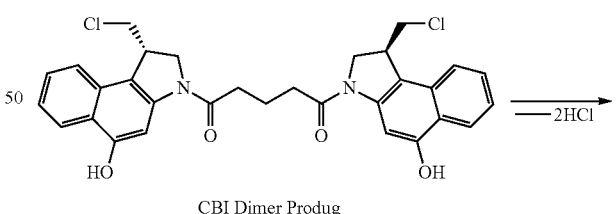

CBI Dimer Produg

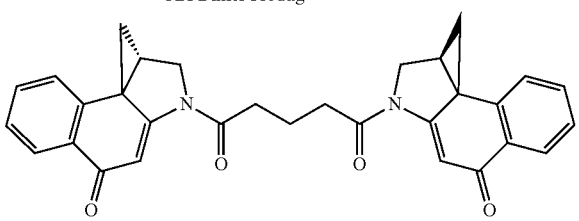

CBI Dimer Active Drug

The same conversion takes place for all bifunctional cross linkers that exist in their prodrug states. Other related bifunctional cross linkers have been reported. ("Chemical and Biological Explorations of the Family of CC-1065 and the Duocarmycin Natural Products", Current Topics in Medicinal Chemistry, 2009, 9, 1494-1524; "DNA interstrand cross-linking agents and their chemotherapeutic potential", Curr Med Chem. 2012, 19, 364-385; "Design and Synthesis of a Novel DNA-DNA Interstrand Adenine-Guanine Cross-Linking Agent", J. Am. Chem. Soc. 2001, 123, 4865-4866; "Effect of base sequence on the DNA cross-linking properties of pyrrolobenzodiazepine (PBD) dimers", Nucleic Acids Res. 2011, 39, 5800-5812; "Sequence-selective recognition of duplex DNA through covalent interstrand cross-linking: kinetic and molecular modeling studies with pyrrolobenzodiazepine dimers", Biochemistry. 2003, 42, 8232-8239; "Bifunctional alkylating agents derived from duocarmycin SA: potent antitumor activity with altered sequence selectivity", Bioorg Med Chem Lett. 2000, 10, 495-498; "Design, Synthesis and Cytotoxicity Evaluation of 1-Chloromethyl-5-hydroxy-1,2-dihydro-3H-benz[e]indole (seco-CBI) Dimers", Bioorganic & Medicinal Chemistry 2000, 8, 1607-1617.

A phosphate pro-drug strategy for monomeric seco-CBI containing cytotoxins has been described by Zhao et al. ("Synthesis and biological evaluation of antibody conjugates of phosphate prodrugs of cytotoxic DNA alkylators for the targeted treatment of cancer", J. Med. Chem. 2012, 55, 766-782) and Zhang et al. ("Immunoconjugates containing phosphate-prodrugged DNA minor groove binding agents, compositions containing them, and methods of making them and their use for treating cancer", WO 2012/162482).

None of the above-mentioned compounds, which have two CBI and/or CPI cores linked together to form a dimeric species (so called CBI dimers, CPI dimers, or CBI/CPI dimers), have been considered for use in an antibody drug conjugates (ADCs) as a payload.

Conjugation of drugs to antibodies, either directly or via linkers, involves a consideration of a variety of factors, including the identity and location of the chemical group for conjugation of the drug, the mechanism of drug release, the structural elements providing drug release, and the structural modification to the released free drug. In addition, if the drug is to be released after antibody internalization, the mechanism of drug release must be consonant with the intracellular trafficking of the conjugate.

While a number of different drug classes have been tried for delivery by antibodies, only a few drug classes have proved efficacious as antibody drug conjugates while maintaining a suitable toxicity profile. One such class is the auristatins, derivatives of the natural product dolastatin 10. Representative auristatins include (N-methylvaline-valine-dolaisoleuine-dolaproine-norephedrine) and (N-methylvaline-valine-dolaisoleuine-dolaproine-phenylalanine). Other related tubulin binding agents include the maytansines (for instance see "Cell-binding agent-maytansinoid conjugates linked via a noncleavable linker, preparation methods, and methods using them for targeting specific cell populations" published as WO 2005/037992). Other cytotoxic drugs that have been employed in linkage with antibodies include DNA-binding drugs such as calicheamicin that causes sequence-specific double-stranded DNA cleavage. Another class of DNA binding cytotoxic drugs employed in ADCs includes dimeric pyrrolobenzodiazepines (for instance see "Preparation of unsymmetrical pyrrolobenzodiazepines dimers for inclusion in targeted conjugates" published as WO2013/041606). Another such class of drug where antibody delivery has been attempted is DNA binding alkylating agents, such as the duocarmycin analog CC-1065 (see "Preparation of CC-1065 analogs and their conjugates for treatment of cancer" published as WO2010/062171) and related compounds (see "Antibody-drug peptide conjugates for use as cytotoxins in cancer treatment" published as WO 2007/038658, and "Immunoconjugates containing phosphate-prodrugged DNA minor groove binding agents, compositions containing them, and methods of making them and their use for treating cancer" published as WO2012/162482). However, these drugs all have limitations relating to disease indications and treatment profile, and thus there remains a need for additional drugs with improved properties deliverable via antibody conjugation. Accordingly, the present invention provides novel ADCs with dimers as payloads.

SUMMARY OF THE INVENTION

The invention describes new structural dimer analogs that contain novel linker elements. These new spacer motifs lead to compounds with different biological properties, for example improved activities in tumor cell proliferation assays and plasma stabilities. This invention also describes new spacer elements for the corresponding CPI dimers and CBI-CPI mixed structures. Moreover, the invention provides Moreover, the present invention is the first to disclose such these compounds in connection with an ADC a modality, and incorporating these compounds within a targeted ADC is a significant advance.

The present invention is directed to cytotoxic dimers comprising CBI-based and/or CPI-based (including seco forms of CBI and/or CPI, as detailed herein) sub-units, to antibody drug conjugates comprising such dimers, and to methods for using the same to treat cancer. Both CBI and CPI structures can be represented by their seco form and can be substituted and derivatized as detailed herein.

Thus, the present invention relates to compounds and pharmaceutical compositions containing them, to their preparation, and to uses for the compounds, primarily but not exclusively anti-cancer agents. According to one aspect, the present invention relates to "payload" compound of Formula I:

$$F^1\text{-}L^1\text{-}T\text{-}L^2\text{-}F^2 \qquad \text{(Formula I)}$$

or a pharmaceutically acceptable salt or solvate thereof, wherein:

$F^1$ and $F^2$ are each independently selected from ring systems A, B, C and D:

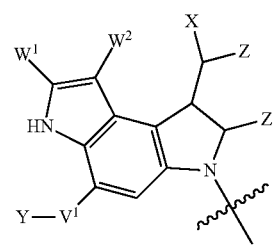

(Ring System A)

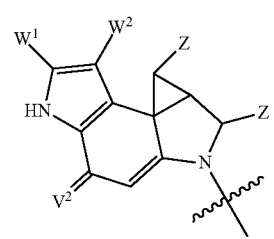

(Ring System B)

-continued (Ring System C)

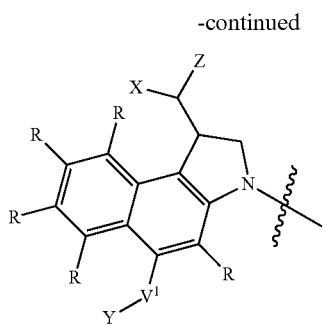

(Ring System D)

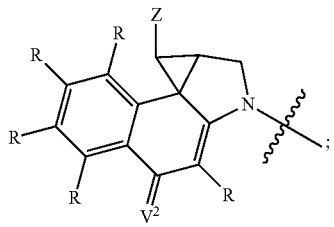

each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —$NH(C_1$-$C_8$ alkyl), —$N(C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —$NH(C_1$-$C_8$ alkyl), —$N(C_1$-$C_8$ alkyl)$_2$, —$C_1$-$C_{10}$ alkyl-N($C_1$-$C_8$ alkyl)$_2$, —$C_1$-$C_3$ alkylthio, —$NO_2$ or —$C_1$-$C_{10}$ heterocyclyl, for each ring system in which R appears;

each $V^1$ is independently a bond, O, N(R) or S, for each ring system in which $V^1$ appears;

each $V^2$ is independently O, N(R) or S, for each ring system in which $V^2$ appears;

$W^1$ and $W^2$ are each independently H, —$C_1$-$C_5$ alkyl, -phenyl, —C(O)OR, —C(O)SR, —C(O)NHN(R)$_2$ or —C(O)N(R)$_2$ for each ring system in which $W^1$ and $W^2$ appear;

each X is independently —OH, —O-acyl, azido, halo, cyanate, thiocyanate, isocyanate, thioisocyanate, or

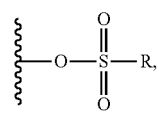

for each ring system in which X appears;

each Y is independently selected from the group consisting of H, —$C_1$-$C_6$ alkyl-$R^A$, —C(O)$R^A$, —C(S)$R^A$, —C(O)OR$^A$, —S(O)$_2$OR$^A$, —C(O)N(R$^A$)$_2$, —C(S)N(R$^A$)$_2$, glycosyl, —$NO_2$ and —PO(OR$^A$)$_2$, for each ring system in which Y appears, wherein each $R^A$ is independently selected from the group consisting of H, —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl and —$C_1$-$C_{20}$ alkylN(R)$_2$, wherein said —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl and —$C_1$-$C_{20}$ alkylN(R)$_2$ are optionally substituted with 1 to 3 substituents independently selected from R;

each Z is independently selected from the group consisting of H, —$C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)OC$_1$-$C_8$ alkyl, —C(O)N(C$_1$-$C_8$ alkyl)$_2$, —C(O)OH, —C(O)NHNH$_2$, and —C(O)-halo, and wherein said $C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)OC$_1$-$C_8$ alkyl, —C(O)N(C$_1$-$C_8$ alkyl)$_2$, —C(O)OH, —C(O)NHNH$_2$ and —C(O)-halo are each optionally substituted with 1 to 3 substituents independently selected from R, for each ring system in which Z appears;

$L^1$ and $L^2$ are each independently selected from a direct bond, carbonyl, or a carbonyl acyl group bonded to $F^1$ or $F^2$ at the acyl moiety, where the carbonyl acyl group is selected from the group consisting of:

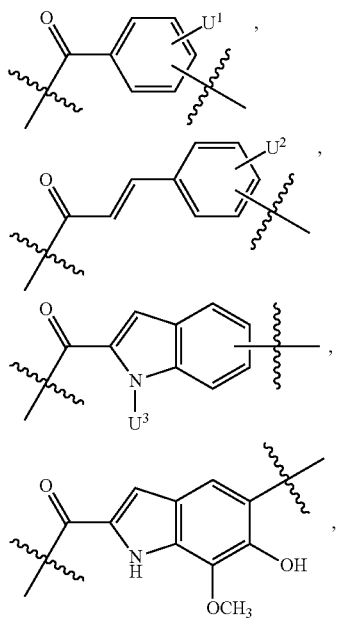

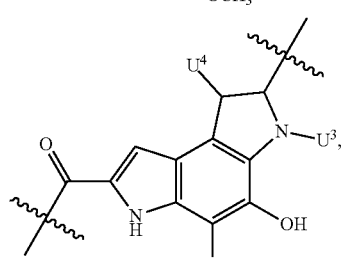

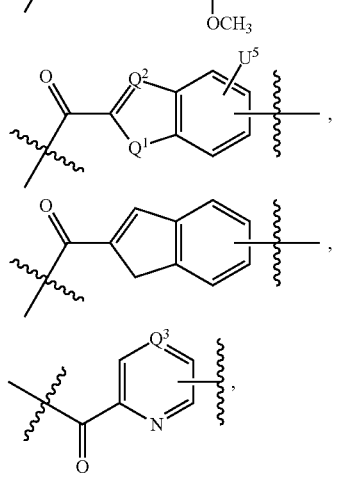

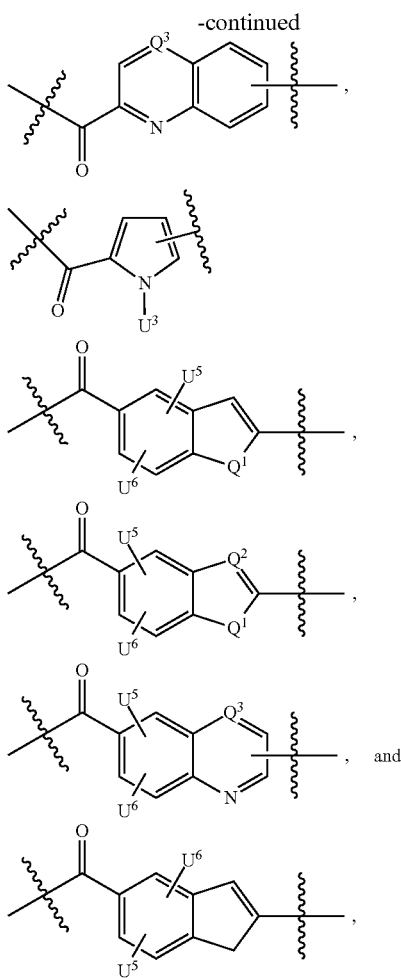

wherein
U¹ is selected from H, —CH₃, —OH, —OCH₃, —NO₂, —NH₂, —NHNHAc, —NHNHC(O)CH₃, —NHC(O)phenyl or -halo,
U² is H, —OH or —OCH₃,
U³ is H, —CH₃ or —C₂H₅,
U⁴ is H or CH₃S—,
U⁵ and U⁶ are each independently selected from H, -halo, —C₁-C₄ alkyl, —C₁-C₃ alkoxy, —C₁-C₆ dialkylamino, —NO₂, —NHC(O)C₁-C₁₀ alkyl, —OH, —NH₂, —NHC(O)NH₂, —NHC(O)CH₃ or —NHC(O)phenyl,
Q¹ is —O—, —S—, or —NH—, and
Q² and Q³ are each independently —CH— or —N—;
T is selected from:
—NHC(O)—,
—C(O)NH—,
—C(O)O—,
—OC(O)—,
—NR$^B$-T¹-NR$^C$— where R$^B$ and R$^C$ are each independently H or —C₁-C₈ alkyl, or together R$^B$ and R$^C$ join T¹ is to form a ring and together are (CH₂)₂₋₃, where T¹ is selected from —C(O)—, —C(O)(CH₂)$_n$C(O)— where n is an integer from 0 to 50, —C(O)PhC(O)— where Ph is 1,3- or 1,4-phenylene,
—C(O)hetC(O)— wherein het is a mono-, bi-, or tricyclic heteroaryl of 5 to 12 members, containing one, two, or three heteroatoms independently selected from O, N, S, P and B, wherein het is optionally substituted with 1 to 8 substituents each independently selected from the group consisting of —C₁-C₈ alkyl, —C₁-C₈ heteroalkyl, —C₆-C₁₄ aryl, aralkyl, —C₁-C₁₀ heterocyclyl, —C₃-C₈ carbocyclycl, —NH₂, —NHR$^D$ and —NO₂, and said optional substituents on het are optionally substituted with R$^E$, where at least one of F¹ and F² is selected from the group consisting of Ring System C and Ring System D when T is —C(O)hetC(O)—,
wherein each R$^D$ is independently selected from the group consisting of H, —C₁-C₈ alkyl, —C(O)—C₁-C₈ alkyl, —C₁-C₈ heteroalkyl, —C₆-C₁₄ aryl, -aralkyl, —C₁-C₁₀ heterocyclyl, —C₃-C₈ carbocyclyl, —C(O)OC₁-C₈ alkyl, —C(O)N(C₁-C₈ alkyl)₂, and —C(O)-halo, optionally substituted with R$^E$,
wherein each R$^E$ is independently selected from the group consisting of H, —C₁-C₈ alkyl, —C₁-C₈ heteroalkyl, —C₆-C₁₄ aryl, -aralkyl, —C₁-C₁₀ heterocyclyl, —C₃-C₈ carbocyclyl, —C(O)OC₁-C₈ alkyl, —C(O)N(C₁-C₈ alkyl)₂, and —C(O)-halo, and wherein each R$^E$ is optionally substituted with 1 to 3 substituents independently selected from R, —C(A¹)X¹-T²-X¹C(B¹)—, where T² is:

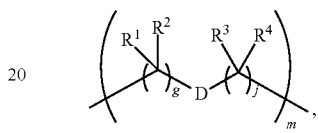

wherein each X¹ is independently a bond, —NR$^E$—, —O— or —S—, wherein A¹ and B¹ are each independently =O or =S, wherein R¹, R², R³, and R⁴ are each independently R$^E$ or R¹ and R² form a ring system, or R³ and R⁴ form a ring system, or both R¹ and R², and R³ and R⁴, each independently form ring systems, or R¹ and R³ form a ring system, or R² and R⁴ form a ring system, or both R¹ and R³, and R² and R⁴, each independently form ring systems,
where said ring systems are independently selected from —C₁-C₁₀ heterocyclyl or —C₃-C₈ carbocyclycl, or R¹, R², R³ and R⁴ are each bonds to different carbons on D, wherein g and j are each independently an integer from 0 to 50 and m is an integer from 1 to 50, and wherein D is a bond or is selected from the group consisting of —S—, —C₁-C₈ alkylene-, —C₆-C₁₄ arylene-, —C₆-C₁₄ heteroarylene-, —C₁-C₈ heteroalkylene-, -aralkylene-, —C₁-C₁₀ heterocyclo and —C₃-C₈ carbocyclo, where said —C₁-C₈ alkylene-, —C₆-C₁₄ arylene-, —C₆-C₁₄ heteroarylene-, —C₁-C₈ heteroalkylene-, -aralkylene, —C₁-C₁₀ heterocyclo and —C₃-C₈ carbocyclo are optionally substituted with —R$^E$, —C(O)R$^E$, —C(O)OR$^E$, —N(R$^E$)₂, —N(R)C(O)R$^E$ or —N(R)C(O)OR$^E$, and D is additionally optionally substituted by 1 to 2 R, with the proviso that if g is 0, J is 0 and T² is —C₁-C₈ alkylene-, then one of F¹ and F² is selected from the group consisting of Ring System A and Ring System B, and the other of F¹ and F² is selected from the group consisting of Ring System C and Ring System D, and
-G¹-T²-G²-, where G¹ and G² are each independently —S(O)X¹— or —S(O)₂X¹—.
In embodiments of the invention variable n is 0 to 50, preferably 0 to 25, preferably 0 to 10, and preferably 1-5. Preferably, variable n may be 0, 1, 2, 3, 4 or 5.
In other embodiments of the invention the variable —Y— is C(O)N(R$^A$)₂ or C(S)N(R$^A$)₂ where one R$^A$ is hydrogen or —C₁-C₂₀ alkyl and the other R$^A$ is —C₁-C₂₀ alkyl-N(R)₂, such that the structure:
Connection to rest of payload

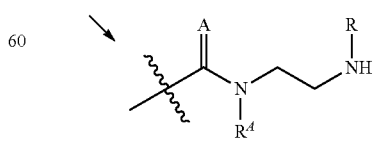

is formed, where A is oxygen or sulphur.
As noted above, embodiments of the present invention includes those where R¹, R², R³ and R⁴ are each bonds to different carbons on D. When D is a 6-membered carbocyclic ring (bold, below), this embodiment may take the form of a cubane:

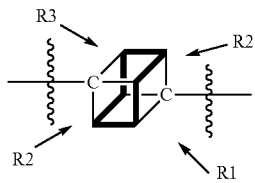

Other forms of cubanes (for instance substituted forms as outlined herein) and non-cubanes are also possible and included within the invention.

According to another aspect of the invention there is provided a "linker-payload" compound of Formula IIA:

L-P    (Formula IIA)

or a pharmaceutically acceptable salt or solvate thereof, wherein:
P is:

$F^1$-$L^1$-T-$L^2$-$F^2$ wherein:
$F^1$ and $F^2$ are each independently selected from ring systems A, B, C and D:

(Ring System A)

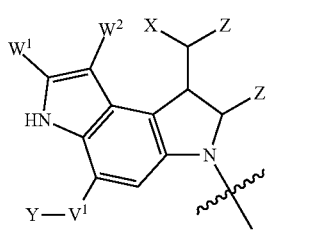

(Ring System B)

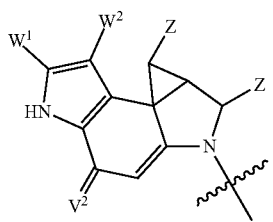

(Ring System C)

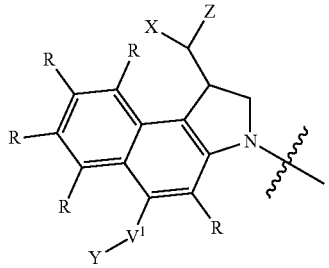

(Ring System D)

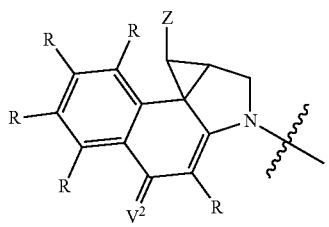

each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —NH($C_1$-$C_8$ alkyl), —N($C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —$NO_2$ or —$C_1$-$C_{10}$ heterocyclyl, for each ring system in which R appears;

each $V^1$ is independently a bond, O, N(R) or S, for each ring system in which $V^1$ appears;

each $V^2$ is independently O, N(R) or S, for each ring system in which $V^2$ appears;

$W^1$ and $W^2$ are each independently H, —$C_1$-$C_5$ alkyl, -phenyl, —C(O)OR, —C(O)SR, —C(O)NHN(R)$_2$ or —C(O)N(R)$_2$ for each ring system in which $W^1$ and $W^2$ appear;

each X is independently selected from —OH, —O-acyl, azido, halo, cyanate, thiocyanate, isocyanate, thioisocyanate, or

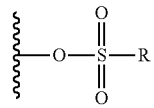

for each ring system in which X appears;

each Y is independently selected from a bond, H, —C(O)$R^A$, —C(S)$R^A$, —C(O)O$R^A$, —S(O)$_2$O$R^A$, —C(O)N($R^A$)$_2$, —C(S)N($R^A$)$_2$, glycosyl, —$NO_2$ and —P(O)(O$R^A$)$_2$ for each ring system in which Y appears, wherein each $R^A$ is independently selected from H, —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl, —$C_1$-$C_{20}$ alkylN(R)$_2$, —$C_1$-$C_{20}$ alkylene, —$C_1$-$C_8$ heteroalkylene, —$C_6$-$C_{14}$ arylene, aralkylene, —$C_1$-$C_{10}$ heterocyclo, —$C_3$-$C_8$ carbocyclo and —$C_1$-$C_{20}$ alkylN(R)—, and $R^F$ where said $R^A$ is optionally substituted with 1 to 3 substituents independently selected from R, and wherein one Y is divalent and is bonded to L, $R^F$ is —N($R^6$)QN($R^5$)C(O)— and is bonded to L at the carbonyl adjacent N($R^5$), wherein $R^5$ and $R^6$ are each independently selected from the group consisting of H, —$C_1$-$C_8$ alkyl, —$C_1$-$C_8$ heteroalkyl, —$C_6$-$C_{14}$ aryl, -aralkyl, —$C_1$-$C_{10}$ heterocyclyl and —$C_3$-$C_8$ carbocyclyl, or $R^5$ or $R^6$ joins with a substituted carbon on Q to form a —$C_1$-$C_{10}$ heterocyclic or —$C_6$-$C_{14}$ heteroaryl ring, or $R^5$ and $R^6$ join together to form a —$C_1$-$C_{10}$ heterocyclic or —$C_6$-$C_{14}$ heteroaryl ring system, and where Q is —$C_1$-$C_8$ alkylene-, —$C_1$-$C_8$ heteroalkylene-, —$C_6$-$C_{14}$ arylene-, -aralkylene-, —$C_1$-$C_{10}$ heterocyclo- or —$C_3$-$C_8$ carbocyclo-, wherein Q, $R^5$ and $R^6$ are each independently optionally substituted with 1 to 3 substituents independently selected from R;

each Z is independently selected from the group consisting of H, —$C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, —C(O)OH, —C(O)NHNH$_2$ and —C(O)-halo, and wherein said $C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, —C(O)OH, —C(O)NHNH$_2$ and —C(O)-halo are each optionally substituted with 1 to 3 substituents independently selected from R, for each ring system in which Z appears;

L¹ and L² are each independently selected from a direct bond, carbonyl, or a carbonyl acyl group bonded to F¹ or F² at the acyl moiety, where the carbonyl acyl group is selected from the group consisting of:

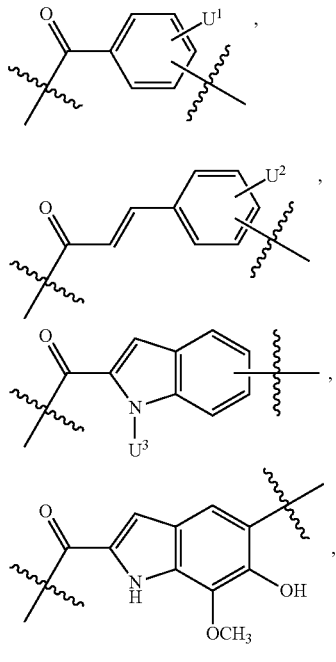

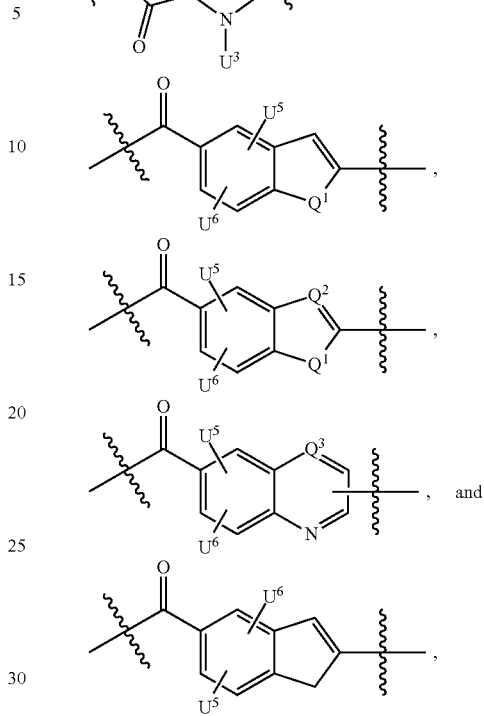

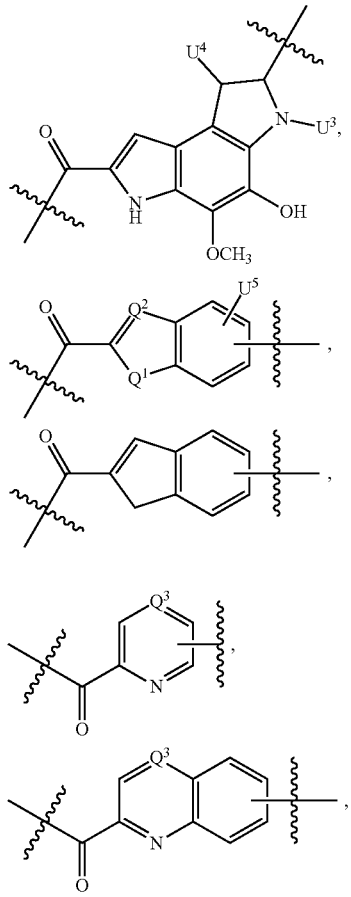

wherein
U¹ is selected from H, —CH₃, —OH, —OCH₃, —NO₂, —NH₂, —NHNHAc, —NHNHC(O)CH₃, —NHC(O)phenyl or -halo,
U² is H, —OH or —OCH₃,
U³ is H, —CH₃ or —C₂H₅,
U⁴ is H or CH₃S—,
U⁵ and U⁶ are each independently selected from H, -halo, —C₁-C₄ alkyl, —C₁-C₃ alkoxy, —C₁-C₆ dialkylamino, —NO₂, —NHC(O)C₁-C₁₀ alkyl, —OH, —NH₂, —NHC(O)NH₂, —NHC(O)CH₃ or —NHC(O)phenyl,
Q¹ is —O—, —S— or —NH—, and
Q² and Q³ are each independently —CH— or —N—;
T is selected from:
—NHC(O)—,
—C(O)NH—,
—C(O)O—,
—OC(O)—,
—NR^B-T¹-NR^C— where R^B and R^C are each independently H or —C₁-C₈ alkyl, or together R^B and R^C join T¹ is to form a ring and together are (CH₂)₂₋₃, where T¹ is selected from —C(O)—, —C(O)(CH₂)ₙC(O)— where n is an integer from 0 to 50, —C(O)PhC(O)— where Ph is 1,3- or 1,4-phenylene,
—C(O)hetC(O)— wherein het is a mono-, bi-, or tricyclic heteroaryl of 5 to 12 members, containing one, two, or three heteroatoms independently selected from O, N, S, P and B, where het is optionally substituted with 1 to 8 substituents each independently selected from the group consisting of —C₁-C₈ alkyl, —C₁-C₈ heteroalkyl, —C₆-C₁₄ aryl, aralkyl, —C₁-C₁₀ heterocyclyl, —C₃-C₈ carbocyclycl, —NH₂, —NHR^D and —NO₂, and said optional substituents on het are optionally substituted with R^E, where at least one of F¹ and F² is selected from the group consisting of Ring System C and Ring System D when T is —C(O)hetC(O)—, wherein each R^D is independently selected from the group consisting of H, —C₁-C₈ alkyl, —C(O)—C₁-C₈ alkyl, —C₁-C₈ heteroalkyl, —C₆-C₁₄ aryl, -aralkyl, —C₁-C₁₀ heterocyclyl, —C₃-C₈ carbocyclyl, —C(O)OC₁-C₈ alkyl, —C(O)N(C₁-C₈ alkyl)₂, and —C(O)-halo, optionally substituted with R^E, wherein each R^E is independently selected from the group consisting of H, —C₁-C₈ alkyl, —C₁-C₈ heteroalkyl, -aryl, -aralkyl, —C₁-C₁₀ heterocyclyl, —C₃-C₈ carbocyclyl, —C(O)OC₁-C₈ alkyl, —C(O)N(C₁-C₈ alkyl)₂, and —C(O)-halo, and wherein each R^E is optionally substituted with 1 to 3 substituents independently selected from R, —C(A¹)X¹-T²-X¹C(B¹)—, where T² is:

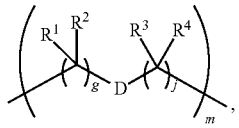

wherein each X¹ is independently a bond, —NR^E—, —O— or —S—, wherein A¹ and B¹ are each independently ═O or ═S, wherein R¹, R², R³, and R⁴ are each independently R^E or R¹ and R² form a ring system, or R³ and R⁴ form a ring system, or both R¹ and R², and R³ and R⁴, each independently form ring systems, or R¹ and R³ form a ring system, or R² and R⁴ form a ring system, or both R¹ and R³, and R² and R⁴, each independently form ring systems, where said ring systems are independently selected from —C₁-C₁₀ heterocyclyl or —C₃-C₈ carbocyclycl, or R¹, R², R³ and R⁴ are each bonds to different carbons on D, wherein g and j are each independently an integer from 0 to 50 and m is an integer from 1 to 50, and wherein D is a bond or is selected from the group consisting of —S—, —C₁-C₈ alkylene-, —C₆-C₁₄ arylene-, —C₆-C₁₄ heteroarylene-, —C₁-C₈ heteroalkylene-, -aralkylene, —C₁-C₁₀ heterocyclo and —C₃-C₈ carbocyclo, where said —C₁-C₈ alkylene-, —C₆-C₁₄ arylene-, —C₆-C₁₄ heteroarylene-, —C₁-C₈ heteroalkylene-, -aralkylene, —C₁-C₁₀ heterocyclo and —C₃-C₈ carbocyclo are optionally substituted with —R^E, —C(O)R^E, —C(O)OR^E, —N(R^E)₂, —N(R)C(O)R^E or —N(R)C(O)OR^E, and D is additionally optionally substituted by 1 to 2 R, and -G¹-T²-G²-, where G¹ and G² are each independently —S(O)X¹— or —S(O)₂X¹—;

L is L^A-L^B-(L^C)₁₋₃, wherein L^A is selected from the group consisting of -halo, —N(R)₂, —CON(R)₂, —S-aryl optionally substituted with —NO₂ or —CON(R)₂, —S-heteroaryl optionally substituted with —NO₂, alkyl-SO₂-heteroaryl, arylSO₂-heteroaryl-,

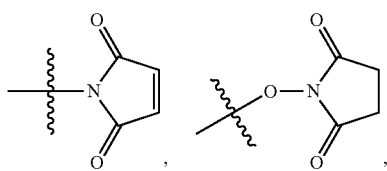

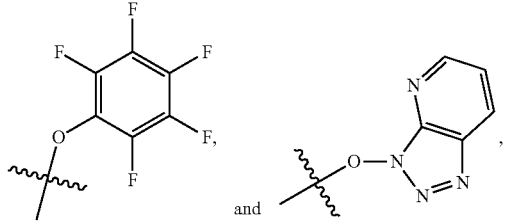
and

L^B is L^B1-L^B2-L^B3 wherein L^B1 is absent or is one or more components selected from the group consisting of —C(O)—, —C(S)—, —C(O)NR—, —C(O)C₁-C₆alkyl-, —C(O)NRC₁-C₆alkyl-, —C₁-C₆alkyl(OCH₂CH₂)₁₋₆—, —C(O)C₁-C₆alkylNRC(O)—, —C(O)C₁-C₆alkyl(OCH₂CH₂)₁₋₆—, —C₁-C₆alkyl(OCH₂CH₂)₁₋₆—C(O)—, —C₁-C₆alkyl-S—S—C₁-C₆alkylNRC(O)CH₂—, —C₁-C₆alkyl(OCH₂CH₂)₁₋₆NRC(O)CH₂—, —C(O)C₁-C₆alkyl-NRC(O)C₁₋₆alkyl-, —N═CR-phenyl-O—C₁-C₆alkyl-, —N═CR-phenyl-O—C₁-C₆alkyl-C(O)—, —C(O)—C₁-C₆alkyl(OCH₂CH₂)₁₋₆NRC(O)—, —C(O)C₁-C₆alkyl-phenyl(NR—C(O)C₁-C₆alkyl)₁₋₄-, —C(O)C₁-C₆alkyl(OCH₂CH₂)₁₋₆—NRC(O)C₁-C₆alkyl-, —C₁-C₆alkyl-, —S—, —C(O)—CH(NR—C(O)C₁-C₆alkyl)-C₁-C₆alkyl- and (—CH₂—CH₂—O—)₁₋₂₀, wherein L^B2 is AA₀₋₁₂, wherein AA is a natural amino acid, a non-natural amino acid or —(CR¹⁵)ₒ—S—S—(CR¹⁵)ₚ where o and p are each independently an integer from 1 to 20, L^B3 is -PABA-, -PABC- or absent;

L^C is absent or independently selected from the group consisting of —C₁-C₆alkylene-, —NRC₃-C₈-heterocyclylNR—, —NRC₃-C₈-carbocyclylNR—, —NRC₁-C₆alkylNR—, —NRC₁-C₆alkylene-, —S—, —NR—, —NRNR—, —O(CR₂)₁₋₄S—S(CR₂)₁₋₄N(R)—, —NRC₁-C₆-alkylenephenyleneNR—, —NRC₁-C₆alkylenephenyleneSO₂NR—, —OC₁-C₆alkylS—SC₁-C₆alkylC(COOR)NR—, —NRC(COOR)C₁-C₆alkylS—SC₁-C₆alkylO—,

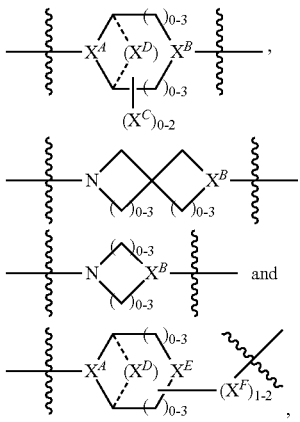

wherein
X^A is CR or N,
X^B is CH, CR(C(R)₂)₁₋₃NR, CR(C(R)₂)₁₋₃O, CR(C(R)₂)₁₋₃C(O)NR, CR—(C(R)₂)₁₋₃C(O)NRNR, CR(C(R)₂)₁₋₃SO₂NR, CR(C(R)₂)₁₋₃NRNR, CR(C(R)₂)₁₋₃NRC(O) or N,
each X^C is R,
each X^F is —(CH₂)₁₋₅—, or is absent;
X^E is O, S, C(R)₂, C(R)(C(R)₂)₁₋₃—NR₂ or NR and each X^F is (C(R)₂)₁₋₃—NR or C(R)₂—(C(R)₂)₁₋₃—O.

In other embodiments of the invention the variable —Y— is C(O)N(R$^A$)$_2$ or C(S)N(R$^A$)$_2$ where one R$^A$ is hydrogen or —C$_1$-C$_{20}$ alkyl and the other R$^A$ is —C$_1$-C$_{20}$ alkyl-N(R)—, such that the structure:

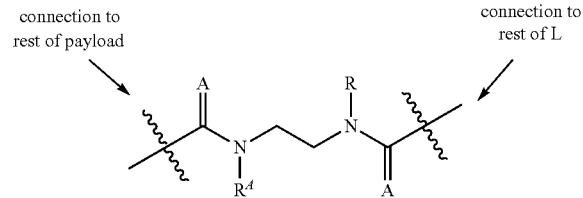

is formed, where each A is independently oxygen or sulphur.

According to still another aspect of the invention there is provided an antibody drug conjugate compound of Formula IIIA:

AB-(L-P)$_{1-20}$        (Formula IIIA)

or a pharmaceutically acceptable salt or solvate thereof, wherein:

AB is an antibody;

P is:

F$^1$-L$^1$-T-L$^2$-F$^2$ wherein:

F$^1$ and F$^2$ are each independently selected from ring systems A, B, C and D:

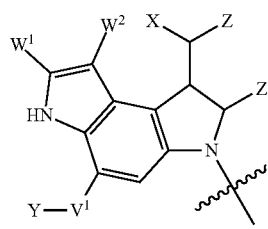 (Ring System A)

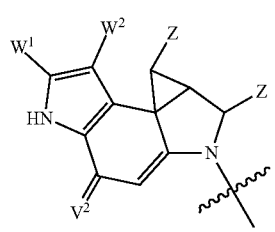 (Ring System B)

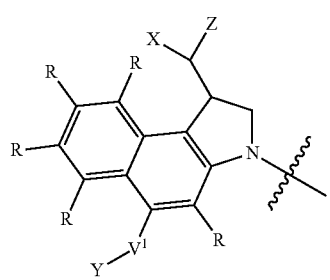 (Ring System C)

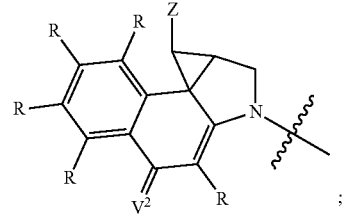 (Ring System D)

each R is independently selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears;

each V$^1$ is independently a bond, O, N(R) or S, for each ring system in which V$^1$ appears;

each V$^2$ is independently O, N(R) or S, for each ring system in which V$^2$ appears;

W$^1$ and W$^2$ are each independently H, —C$_1$-C$_5$ alkyl, -phenyl, —C(O)OR, —C(O)SR, —C(O)NHN(R)$_2$ or —C(O)N(R)$_2$ for each ring system in which W$^1$ and W$^2$ appear;

each X is independently selected from —OH, —O-acyl, azido, halo, cyanate, thiocyanate, isocyanate, thioisocyanate, or

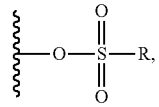

for each ring system in which X appears;

each Y is independently selected from a bond, H, —C(O)R$^A$, —C(S)R$^A$, —C(O)OR$^A$, —S(O)$_2$OR$^A$, —C(O)N(R$^A$)$_2$, —C(S)N(R$^A$)$_2$, glycosyl, —NO$_2$ and —P(O)(OR$^A$)$_2$ for each ring system in which Y appears, wherein each R$^A$ is independently selected from H, —C$_1$-C$_{20}$ alkyl, —C$_1$-C$_8$ heteroalkyl, —C$_6$-C$_{14}$ aryl, aralkyl, —C$_1$-C$_{10}$ heterocyclyl, —C$_3$-C$_8$ carbocyclyl, —C$_1$-C$_{20}$ alkylN(R)$_2$, —C$_1$-C$_{20}$ alkylene, —C$_1$-C$_8$ heteroalkylene, —C$_6$-C$_{14}$ arylene, aralkylene, —C$_1$-C$_{10}$ heterocyclo, —C$_3$-C$_8$ carbocyclo and —C$_1$-C$_{20}$ alkylN(R)—, and R$^F$ where said R$^A$ is optionally substituted with 1 to 3 substituents independently selected from R, and wherein one Y is divalent and is bonded to L, R$^F$ is —N(R$^6$)QN(R$^5$)C(O)— and is bonded to L at the carbonyl adjacent N(R$^5$), wherein R$^5$ and R$^6$ are each independently selected from the group consisting of H, —C$_1$-C$_8$ alkyl, —C$_1$-C$_8$ heteroalkyl, —C$_6$-C$_{14}$ aryl, -aralkyl, —C$_1$-C$_{10}$ heterocyclyl and —C$_3$-C$_8$ carbocyclyl, or R$^5$ or R$^6$ joins with a substituted carbon on Q to form a —C$_1$-C$_{10}$ heterocyclic or —C$_6$-C$_{14}$ heteroaryl ring, or R$^5$ and R$^6$ join together to form a —C$_1$-C$_{10}$ heterocyclic or —C$_6$-C$_{14}$ heteroaryl ring system, and where Q is —C$_1$-C$_8$ alkylene-, —C$_1$-C$_8$ heteroalkylene-, —C$_6$-C$_{14}$ arylene-, -aralkylene-, —C$_1$-C$_{10}$ heterocyclo- or —C$_3$-C$_8$ carbocyclo-, wherein Q, R$^5$ and R$^6$ are each independently optionally substituted with 1 to 3 substituents independently selected from R;

each Z is independently selected from the group consisting of H, —$C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, —C(O)OH, —C(O)NHNH$_2$ and —C(O)-halo, and wherein said $C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, —C(O)OH, —C(O)NHNH$_2$ and —C(O)-halo are each optionally substituted with 1 to 3 substituents independently selected from R, for each ring system in which Z appears;

$L^1$ and $L^2$ are each independently selected from a direct bond, carbonyl, or a carbonyl acyl group bonded to $F^1$ or $F^2$ at the acyl moiety, where the carbonyl acyl group is selected from the group consisting of:

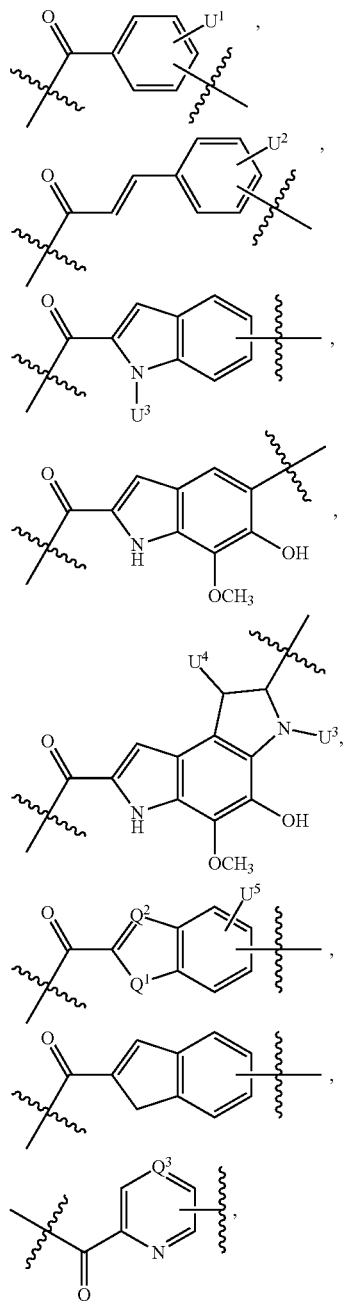

wherein $U^1$ is selected from H, —CH$_3$, —OH, —OCH$_3$, —NO$_2$, —NH$_2$, —NHNHAc, —NHNHC(O)CH$_3$, —NHC(O)phenyl or -halo, $U^2$ is H, —OH or —OCH$_3$, $U^3$ is H, —CH$_3$ or —$C_2$H$_5$, $U^4$ is H or CH$_3$S—, $U^5$ and $U^6$ are each independently selected from H, -halo, —$C_1$-$C_4$ alkyl, —$C_1$-$C_3$ alkoxy, —$C_1$-$C_6$ dialkylamino, —NO$_2$, —NHC(O)$C_1$-$C_{10}$ alkyl, —OH, —NH$_2$, —NHC(O)NH$_2$, —NHC(O)CH$_3$ or —NHC(O)phenyl, $Q^1$ is —O—, —S— or —NH—, $Q^2$ and $Q^3$ are each independently —CH— or —N—;

T is selected from:
—NHC(O)—,
—C(O)NH—,
—C(O)O—,
—OC(O)—,
—NR$^B$-T$^1$-NR$^C$— where R$^B$ and R$^C$ are each independently H or —$C_1$-$C_8$ alkyl, or together R$^B$ and R$^C$ join to form a ring and together are (CH$_2$)$_{2-3}$, where T$^1$ is selected from —C(O)—, —C(O)(CH$_2$)$_n$—C(O)— where n is an integer from 0 to 50, —C(O)PhC(O)— where Ph is 1,3- or 1,4-phenylene,
—C(O)hetC(O)— wherein het is a mono-, bi-, or tricyclic heteroaryl of 5 to 12 members, containing one, two, or three heteroatoms independently selected from O, N, S, P and B, where het is optionally substituted with 1 to 8 substituents each independently selected from the group consisting of —$C_1$-$C_8$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl, —$NH_2$, —$NHR^D$ and —$NO_2$, and said optional substituents on het are optionally substituted with $R^E$, where at least one of $F^1$ and $F^2$ is selected from the group consisting of Ring System C and Ring System D when T is —C(O)hetC(O)—, wherein each $R^D$ is independently selected from the group consisting of H or —$C_1$-$C_8$ alkyl, —C(O)—$C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, and —C(O)-halo, optionally substituted with $R^E$, wherein each $R^E$ is independently selected from the group consisting of H, —$C_1$-$C_8$ alkyl, —$C_1$-$C_8$ heteroalkyl, -aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, and —C(O)-halo, and wherein each $R^E$ is optionally substituted with 1 to 3 substituents independently selected from R, —C($A^1$)$X^1$-$T^2$-$X^1$C($B^1$)—, where $T^2$ is:

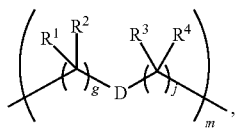

wherein each $X^1$ is independently a bond, —$NR^E$—, —O— or —S—, wherein $A^1$ and $B^1$ are each independently =O or =S, wherein $R^1$, $R^2$, $R^3$, and $R^4$ are each independently $R^E$ or $R^1$ and $R^2$ form a ring system, or $R^3$ and $R^4$ form a ring system, or both $R^1$ and $R^2$, and $R^3$ and $R^4$, each independently form ring systems, or $R^1$ and $R^3$ form a ring system, or $R^2$ and $R^4$ form a ring system, or both $R^1$ and $R^3$, and $R^2$ and $R^4$, each independently form ring systems, where said ring systems are independently selected from —$C_1$-$C_{10}$ heterocyclyl or —$C_3$-$C_8$ carbocyclyl, or $R^1$, $R^2$, $R^3$ and $R^4$ are each bonds to different carbons on D, wherein g and j are each independently an integer from 0 to 50 and m is an integer from 1 to 50, and wherein D is a bond or is selected from the group consisting of —S—, —$C_1$-$C_8$ alkylene-, —$C_6$-$C_{14}$ arylene-, —$C_6$-$C_{14}$ heteroarylene-, —$C_1$-$C_8$ heteroalkylene-, -aralkylene, —$C_1$-$C_{10}$ heterocyclo and —$C_3$-$C_8$ carbocyclo, where said —$C_1$-$C_8$ alkylene-, —$C_6$-$C_{14}$ arylene-, —$C_6$-$C_{14}$ heteroarylene-, —$C_1$-$C_8$ heteroalkylene-, -aralkylene, —$C_1$-$C_{10}$ heterocyclo and —$C_3$-$C_8$ carbocyclo are optionally substituted with —$R^E$, —C(O)$R^E$, —C(O)O$R^E$, —N($R^E$)$_2$, —N(R)C(O)$R^E$ or —N(R)C(O)O$R^E$, and D is additionally optionally substituted by 1 to 2 R, and -$G^1$-$T^2$-$G^2$-, where $G^1$ and $G^2$ are each independently —S(O)$X^1$— or —S(O)$_2$$X^1$—;

L is $L^A$-$L^B$-($L^C$)$_{1-3}$;

$L^A$ is selected from: a bond to AB, —NR-(bond to AB), alkyl-$SO_2$-heteroaryl, aryl$SO_2$-heteroaryl-,

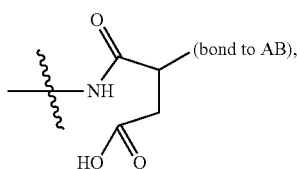

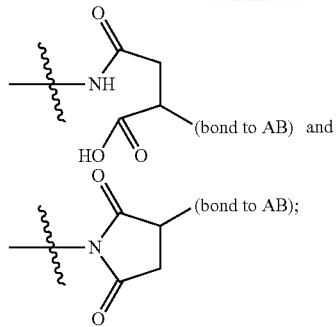

$L^B$ is $L^{B1}$-$L^{B2}$-$L^{B3}$ wherein $L^{B1}$ is absent or is one or more components selected from the group consisting of —C(O)—, —C(S)—, —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-6}$—, —C(O)$C_1$-$C_6$alkylNRC(O)—, —C(O)$C_1$-$C_6$alkyl(OCH$_2$CH$_2$)$_{1-6}$—, —$C_1$-$C_6$alkyl(OCH$_2$CH$_2$)$_{1-6}$—C(O)—, —$C_1$-$C_6$alkyl-S—S—$C_1$-$C_6$alkylNRC(O)CH$_2$—, —$C_1$-$C_6$alkyl(OCH$_2$CH$_2$)$_{1-6}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR-phenyl-O—$C_1$-$C_6$alkyl-C(O)—, —C(O)—$C_1$-$C_6$alkyl(OCH$_2$CH$_2$)$_{1-6}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-6}$NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl- and (—CH$_2$—CH$_2$—O—)$_{1-20}$;

$L^{B2}$ is AA$_{0-12}$, wherein AA is a natural amino acid, a non-natural amino acid or —(CR$^{15}$)$_o$—S—S—(CR$^{15}$)$_p$ where o and p are each independently an integer from 1 to 20, $L^{B3}$ is -PABA-, -PABC- or is absent, $L^C$ is absent or is independently selected from the group consisting of —$C_1$-$C_6$alkylene-, —NR$C_3$-$C_8$-heterocyclylNR—, —NR$C_3$-$C_8$-carbocyclylNR—, —NR$C_1$-$C_6$alkylNR—, —NR$C_1$-$C_6$alkylene-, —S—, —NR—, —NRNR—, —O(CR$_2$)$_{1-4}$S—S(CR$_2$)$_{1-4}$N(R)—, —NR$C_1$-$C_8$-alkylenephenyleneNR—, —NR$C_1$-$C_8$alkylenephenyleneSO$_2$NR—, —O$C_1$-$C_6$alkylS—S$C_1$-$C_6$alkylC(COOR)NR—, —NRC(COOR)$C_1$-$C_6$alkylS—S$C_1$-$C_6$alkylO—,

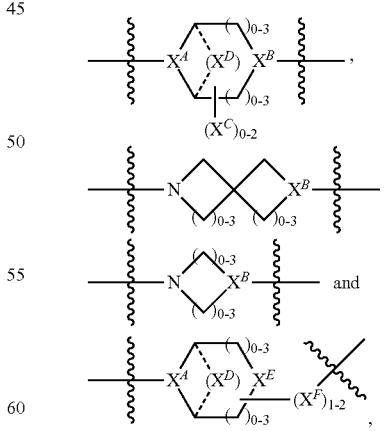

wherein
$X^A$ is CR or N,
$X^B$ is CH, CR(C(R)$_2$)$_{1-3}$NR, CR(C(R)$_2$)$_{1-3}$O, CR(C(R)$_2$)$_{1-3}$C(O)NR, CR—(C(R)$_2$)$_{1-3}$C(O)NRNR, CR(C(R)$_2$)$_{1-3}$SO$_2$NR, CR(C(R)$_2$)$_{1-3}$NRNR, CR(C(R)$_2$)$_{1-3}$NRC(O) or N, each $X^C$ is R;
each $X^C$ is —(CH$_2$)$_{1-5}$—, or is absent;
$X^E$ is O, S, C(R)$_2$, C(R)(C(R)$_2$)$_{1-3}$—NR$_2$ or NR, and
each $X^F$ is (C(R)$_2$)$_{1-3}$—NR or C(R)$_2$—(C(R)$_2$)$_{1-3}$—O.

According to another aspect of the invention there is provided a "linker-payload" compound of Formula IIB:

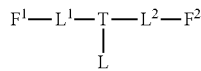
(Formula IIB)

or a pharmaceutically acceptable salt or solvate thereof, wherein:
$F^1$ and $F^2$ are each independently selected from ring systems A, B, C and D:

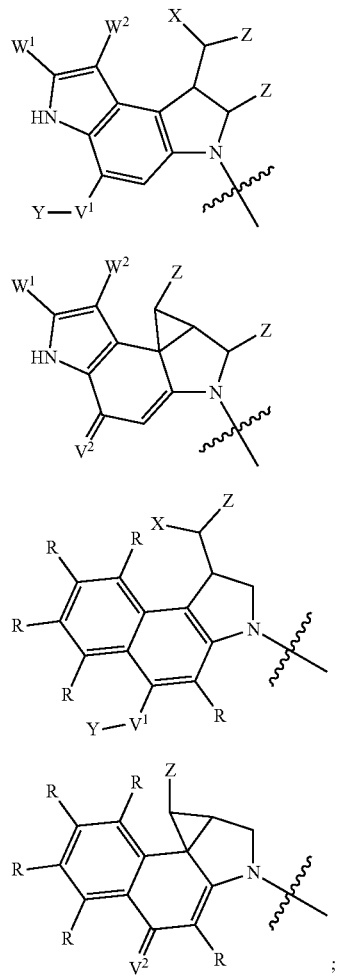

(Ring System A)

(Ring System B)

(Ring System C)

(Ring System D)

each R is independently selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$ or —C$_1$-C$_{10}$ heterocyclyl, for each ring system in which R appears;
each $V^1$ is independently a bond, O, N(R) or S, for each ring system in which $V^1$ appears;
each $V^2$ is independently O, N(R) or S, for each ring system in which $V^2$ appears;
$W^1$ and $W^2$ are each independently H, —C$_1$-C$_5$ alkyl, -phenyl, —C(O)OR, —C(O)SR, —C(O)NHN(R)$_2$ or —C(O)N(R)$_2$ for each ring system in which $W^1$ and $W^2$ appear;
each X is independently —OH, —O-acyl, azido, halo, cyanate, thiocyanate, isocyanate, thioisocyanate, or

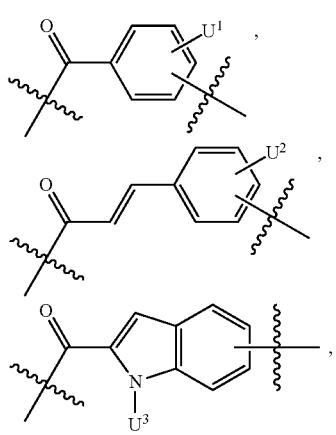

for each ring system in which X appears;
each Y is independently selected from the group consisting of H, —C$_1$-C$_6$ alkyl-R$^A$—C(O)R$^A$, —C(S)R$^A$, —C(O)OR$^A$, —S(O)$_2$OR$^A$, —C(O)N(R$^A$)$_2$, —C(S)N(R$^A$)$_2$, glycosyl, —NO$_2$ and —PO(OR$^A$)$_2$, for each ring system in which Y appears, wherein each R$^A$ is independently selected from the group consisting of H, —C$_1$-C$_{20}$ alkyl, —C$_1$-C$_8$ heteroalkyl, —C$_6$-C$_{14}$ aryl, aralkyl, —C$_1$-C$_{10}$ heterocyclyl, —C$_3$-C$_8$ carbocyclyl and —C$_1$-C$_{20}$ alkylN(R)$_2$, wherein said —C$_1$-C$_{20}$ alkyl, —C$_1$-C$_8$ heteroalkyl, —C$_6$-C$_{14}$ aryl, aralkyl, —C$_1$-C$_{10}$ heterocyclyl, —C$_3$-C$_8$ carbocyclyl and —C$_1$-C$_{20}$ alkylN(R)$_2$ are optionally substituted with 1 to 3 substituents independently selected from R;
each Z is independently selected from the group consisting of H, —C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, —C(O)OH, —C(O)NHNH$_2$ and —C(O)-halo, and wherein said C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, —C(O)OH, —C(O)NHNH$_2$ and —C(O)-halo are each optionally substituted with 1 to 3 substituents independently selected from R, for each ring system in which Z appears;
$L^1$ and $L^2$ are each independently selected from a direct bond, carbonyl, or a carbonyl acyl group bonded to $F^1$ or $F^2$ at the acyl moiety, where the carbonyl acyl group is selected from the group consisting of:

-continued

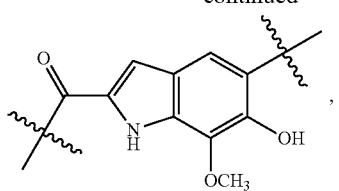,

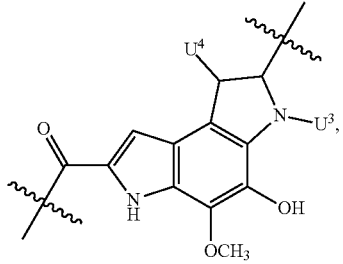

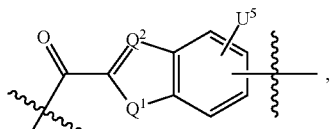,

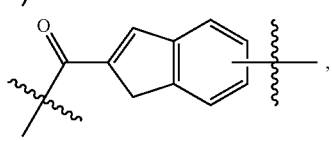,

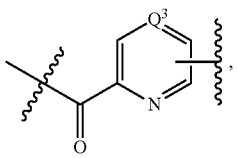,

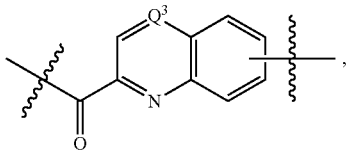,

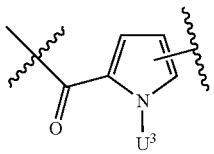,

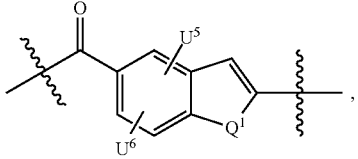,

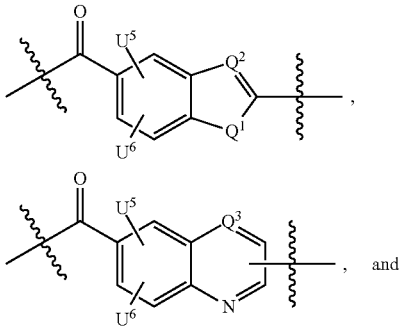, and

-continued

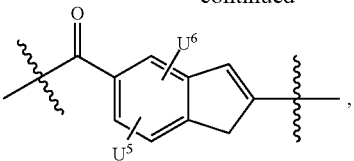, wherein
$U^1$ is selected from H, —CH$_3$, —OH, —OCH$_3$, —NO$_2$, —NH$_2$, —NHNHAc, —NHNHC(O)CH$_3$, —NH—C(O)phenyl or -halo,
$U^2$ is H, —OH or —OCH$_3$,
$U^3$ is H, —CH$_3$ or —C$_2$H$_5$,
$U^4$ is H or CH$_3$S—,
$U^5$ and $U^6$ are each independently selected from H, -halo, —C$_1$-C$_4$ alkyl, —C$_1$-C$_3$ alkoxy, —C$_1$-C$_6$ dialkylamino, —NO$_2$, —NHC(O)C$_1$-C$_{10}$ alkyl, —OH, —NH$_2$, —NHC(O)NH$_2$, —NHC(O)CH$_3$ or —NHC(O)phenyl,
$Q^1$ is —O—, —S— or —NH—, and
$Q^2$ and $Q^3$ are each independently —CH— or —N—;
T is selected from:
—C(A$^1$)X$^1$-T$^2$-X$^1$C(B$^1$)—, where T$^2$ is:

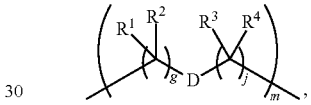

wherein each $X^1$ is independently a bond, —NR$^E$—, —O— or —S—, wherein A$^1$ and B$^1$ are each independently =O or =S, wherein R$^1$, R$^2$, R$^3$, and R$^4$ are each independently R$^E$, or R$^1$ and R$^2$ form a ring system, or R$^3$ and R$^4$ form a ring system, or both R$^1$ and R$^2$, and R$^3$ and R$^4$ each independently form ring systems, or R$^1$ and R$^3$ form a ring system, or R$^2$ and R$^4$ form a ring system, or both R$^1$ and R$^3$, and R$^2$ and R$^4$ each independently form ring systems, where the ring systems are independently selected from —C$_1$-C$_{10}$ heterocyclyl or —C$_3$-C$_8$ carbocyclycl, or R$^1$, R$^2$, R$^3$ and R$^4$ are each bonds to different carbons on D, wherein g and j are each independently an integer from 0 to 50 and m is an integer from 1 to 50, and wherein D is selected from the group consisting of —C$_1$-C$_8$ alkylene-, —C$_6$-C$_{14}$ arylene-, —C$_6$-C$_{14}$ heteroarylene-, —C$_1$-C$_8$ heteroalkylene-, -aralkylene, —C$_1$-C$_{10}$ heterocyclo and —C$_3$-C$_8$ carbocyclo, where said —C$_1$-C$_8$ alkylene-, —C$_6$-C$_{14}$ arylene-, —C$_6$-C$_{14}$ heteroarylene-, —C$_1$-C$_8$ heteroalkylene-, -aralkylene, —C$_1$-C$_{10}$ heterocyclo and —C$_3$-C$_8$ carbocyclo are substituted with one member of the group selected from N(R$^E$)C(O)— where the carbonyl is bonded to L, and —C(O)— where the carbonyl is bonded to L, and additionally optionally substituted by 1 to 2 R;
where each $R^E$ is independently selected from the group consisting of H, —C$_1$-C$_8$ alkyl, —C$_1$-C$_8$ heteroalkyl, -aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, and —C(O)-halo, and wherein each R$^E$ is optionally substituted with 1 to 3 substituents independently selected from R;
L is L$^A$-L$^B$-(L$^C$)$_{1-3}$;
L$^A$ is selected from -halo, —N(R)$_2$, —CON(R)$_2$, —S-aryl optionally substituted with —NO$_2$ or —CONR$_2$, —S-heteroaryl optionally substituted with —NO$_2$, alkyl-SO$_2$-heteroaryl, arylSO$_2$-heteroaryl-,

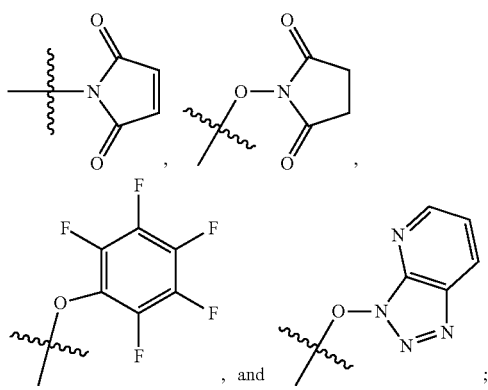

$L^B$ is $L^{B1}$-$L^{B2}$-$L^{B3}$
wherein $L^{B1}$ is absent or is one or more components selected from the group consisting of —C(O)—, —C(S)—, —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-6}$—, —C(O)$C_1$-$C_6$alkylNRC(O)—, —C(O)$C_1$-$C_6$alkyl(OCH$_2$CH$_2$)$_{1-6}$—, —$C_1$-$C_6$alkyl (OCH$_2$CH$_2$)$_{1-6}$—C(O)—, —$C_1$-$C_6$alkyl-S—S—$C_1$-$C_6$alkylNRC(O)CH$_2$—, —$C_1$-$C_6$alkyl(OCH$_2$CH$_2$)$_{1-6}$NRC(O)CH$_2$—, —C(O)$C_1$-$C_6$alkyl-NRC(O)$C_{1-6}$alkyl-, —N=CR-phenyl-O—$C_1$-$C_6$alkyl-, —N=CR-phenyl-O—$C_1$-$C_6$alkyl-C(O)—, —C(O)—$C_1$-$C_6$alkyl(OCH$_2$CH$_2$)$_{1-6}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-6}$—NRC(O)$C_1$-$C_6$alkyl-, —S—, —C(O)—CH(NR—C(O)$C_1$-$C_6$alkyl)-$C_1$-$C_6$alkyl- and (—CH$_2$—CH$_2$—O—)$_{1-20}$;
$L^{B2}$ is AA$_{0-12}$, wherein AA is a natural amino acid, a non-natural amino acid or —(CR$^{15}$)$_o$—S—S—(CR$^{15}$)$_p$ where o and p are each independently an integer from 1 to 20,
$L^{B3}$ is -PABA-, -PABC- or is absent;
$L^C$ is absent or is independently selected from the group consisting of —$C_1$-$C_6$alkylene-, —NR$C_3$-$C_8$-heterocyclylNR—, —NR$C_3$-$C_8$-carbocyclylNR—, —NR$C_1$-$C_6$alkylNR—, —NR$C_1$-$C_6$alkylene-, —S—, —NR—, —NRNR—, —O—(CR$_2$)$_{1-4}$S—S(CR$_2$)$_{1-4}$N(R)—, —NR$C_1$-$C_6$-alkylenephenyleneNR—, —NR$C_1$-$C_6$alkylenephenyleneSO$_2$NR—, —O$C_1$-$C_6$alkylS—S$C_1$-$C_6$alkylC(COOR)NR—, —NRC(COOR)$C_1$-$C_6$alkylS—S$C_1$-$C_6$alkylO—,

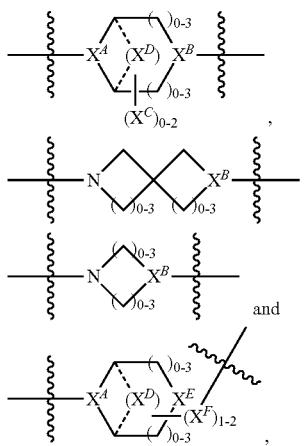

and wherein
$X^A$ is CR or N,
$X^B$ is CH, CR(C(R)$_2$)$_{1-3}$NR, CR(C(R)$_2$)$_{1-3}$O, CR(C(R)$_2$)$_{1-3}$C(O)NR, CR—(C(R)$_2$)$_{1-3}$C(O)NRNR, CR(C(R)$_2$)$_{1-3}$SO$_2$NR, CR(C(R)$_2$)$_{1-3}$NRNR, CR(C(R)$_2$)$_{1-3}$NRC(O) or N;
each $X^C$ is R;
each $X^C$ is —(CH$_2$)$_{1-5}$—, or is absent;
$X^E$ is O, S, C(R)$_2$, C(R)(C(R)$_2$)$_{1-3}$—NR$_2$ or NR, and
each $X^F$ is (C(R)$_2$)$_{1-3}$—NR or C(R)$_2$—(C(R)$_2$)$_{1-3}$—O.

According to yet another aspect of the invention there is provided an antibody drug conjugate compound of Formula IIIB:

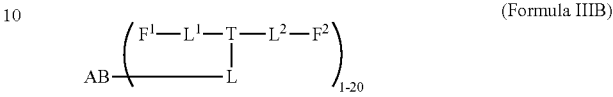

(Formula IIIB)

or a pharmaceutically acceptable salt or solvate thereof, wherein:
AB is an antibody;
$F^1$ and $F^2$ are each independently selected from ring systems A, B, C and D:

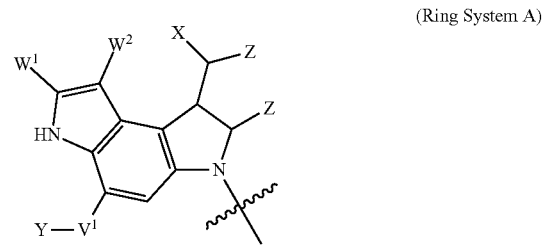

(Ring System A)

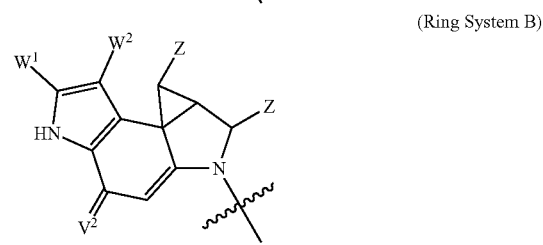

(Ring System B)

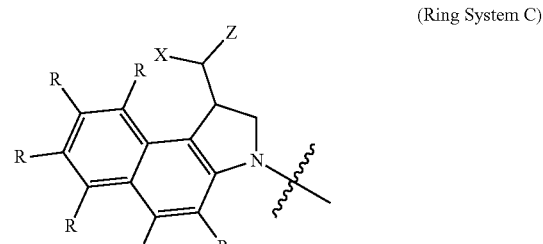

(Ring System C)

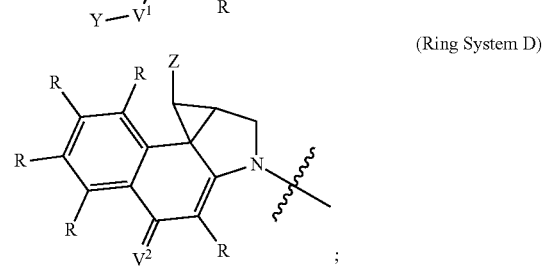

(Ring System D)

each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —NH$_2$, —NH($C_1$-$C_8$ alkyl), —N($C_1$-$C_8$ alkyl)$_2$, —NO$_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —C$_1$-C$_{10}$ alkyl, —C$_1$-C$_{10}$ alkoxy, -halo, —C$_1$-C$_{10}$ alkylthio, -trifluoromethyl, —NH$_2$, —NH(C$_1$-C$_8$ alkyl), —N(C$_1$-C$_8$ alkyl)$_2$, —C$_1$-C$_{10}$ alkyl-N (C$_1$-C$_8$ alkyl)$_2$, —C$_1$-C$_3$ alkylthio, —NO$_2$ or —C$_1$-C$_{10}$ heterocyclyl, for each ring system in which R appears;
each V$^1$ is independently a bond, O, N(R) or S, for each ring system in which V$^1$ appears;
each V$^2$ is independently O, N(R) or S, for each ring system in which V$^2$ appears;
W$^1$ and W$^2$ are each independently H, —C$_1$-C$_5$ alkyl, -phenyl, —C(O)OR, —C(O)SR, —C(O)NHN(R)$_2$ or —C(O)N(R)$_2$ for each ring system in which W$^1$ and W$^2$ appear;
each X is independently —OH, —O-acyl, azido, halo, cyanate, thiocyanate, isocyanate, thioisocyanate, or

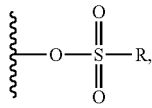

for each ring system in which X appears;
each Y is independently selected from the group consisting of H, —C$_1$-C$_6$ alkyl-R$^A$—C(O)R$^A$, —C(S)R$^A$, —C(O)OR$^A$, —S(O)$_2$OR$^A$, —C(O)N(R$^A$)$_2$, —C(S)N(R$^A$)$_2$, glycosyl, —NO$_2$ and —PO(OR$^A$)$_2$, for each ring system in which Y appears, wherein each R$^A$ is independently selected from the group consisting of H, —C$_1$-C$_{20}$ alkyl, —C$_1$-C$_8$ heteroalkyl, —C$_6$-C$_{14}$ aryl, aralkyl, —C$_1$-C$_{10}$ heterocyclyl, —C$_3$-C$_8$ carbocyclyl and —C$_1$-C$_{20}$ alkylN(R)$_2$, wherein said —C$_1$-C$_{20}$ alkyl, —C$_1$-C$_8$ heteroalkyl, —C$_6$-C$_{14}$ aryl, aralkyl, —C$_1$-C$_{10}$ heterocyclyl, —C$_3$-C$_8$ carbocyclyl and —C$_1$-C$_{20}$ alkylN (R)$_2$ are optionally substituted with 1 to 3 substituents independently selected from R;
each Z is independently selected from the group consisting of H, —C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, —C(O)OH, —C(O)NHNH$_2$ and —C(O)-halo, and wherein said C$_1$-C$_8$ alkyl, —C$_1$-C$_8$ heteroalkyl, —C$_6$-C$_{14}$ aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, —C(O)OH, —C(O)NHNH$_2$ and —C(O)-halo are each optionally substituted with 1 to 3 substituents independently selected from R, for each ring system in which Z appears;
L$^1$ and L$^2$ are each independently selected from a direct bond, carbonyl, or a carbonyl acyl group bonded to F$^1$ or F$^2$ at the acyl moiety, where the carbonyl acyl group is selected from the group consisting of:

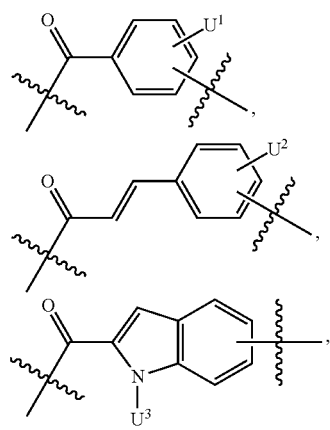

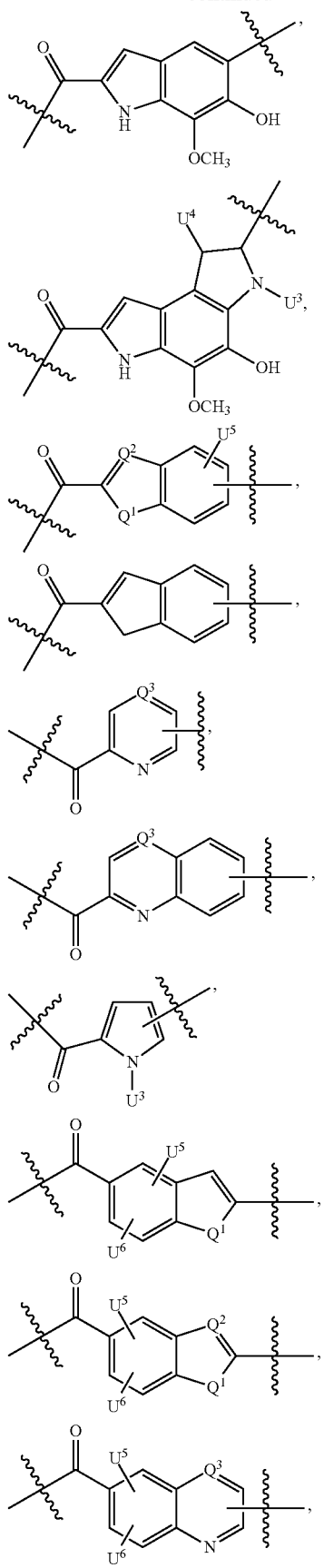

and

-continued

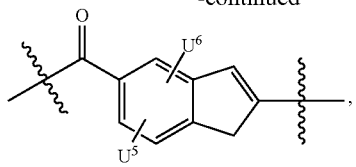

wherein
$U^1$ is selected from H, —CH$_3$, —OH, —OCH$_3$, —NO$_2$, —NH$_2$, —NHNHAc, —NHNHC(O)CH$_3$, —NH—C(O)phenyl or -halo, $U^2$ is H, —OH or —OCH$_3$, $U^3$ is H, —CH$_3$ or —C$_2$H$_5$, $U^4$ is H or CH$_3$S—, $U^5$ and $U^6$ are each independently selected from H, -halo, —C$_1$-C$_4$ alkyl, —C$_1$-C$_3$ alkoxy, —C$_1$-C$_6$ dialkylamino, —NO$_2$, —NHC(O)C$_1$-C$_{10}$ alkyl, —OH, —NH$_2$, —NHC(O)NH$_2$, —NHC(O)CH$_3$ or —NHC(O)phenyl, $Q^1$ is —O—, —S— or —NH—, and $Q^2$ and $Q^3$ are each independently —CH— or —N—;

T is selected from:

—C(A$^1$)X$^1$-T$^2$-X$^1$C(B$^1$)—, where T$^2$ is:

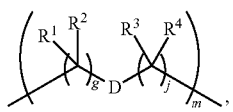

wherein each X$^1$ is independently a bond, —NR$^E$—, —O— or —S—, wherein A$^1$ and B$^1$ are each independently =O or =S, wherein R$^1$, R$^2$, R$^3$, and R$^4$ are each independently R$^E$, or R$^1$ and R$^2$ form a ring system, or R$^3$ and R$^4$ form a ring system, or both R$^1$ and R$^2$, and R$^3$ and R$^4$ each independently form ring systems, or R$^1$ and R$^3$ form a ring system, or R$^2$ and R$^4$ form a ring system, or both R$^1$ and R$^3$, and R$^2$ and R$^4$ each independently form ring systems, where the ring systems are independently selected from —C$_1$-C$_{10}$ heterocyclyl or —C$_3$-C$_8$ carbocyclycl, or R$^1$, R$^2$, R$^3$ and R$^4$ are each bonds to different carbons on D, wherein g and j are each independently an integer from 0 to 50 and m is an integer from 1 to 50, and wherein D is selected from the group consisting of —C$_1$-C$_8$ alkylene-, —C$_6$-C$_{14}$ arylene-, —C$_6$-C$_{14}$ heteroarylene-, —C$_1$-C$_8$ heteroalkylene-, -aralkylene, —C$_1$-C$_{10}$ heterocyclo and —C$_3$-C$_8$ carbocyclo, where said —C$_1$-C$_8$ alkylene-, —C$_6$-C$_{14}$ arylene-, —C$_6$-C$_{14}$ heteroarylene-, —C$_1$-C$_8$ heteroalkylene-, -aralkylene, —C$_1$-C$_{10}$ heterocyclo and —C$_3$-C$_8$ carbocyclo are substituted with one member of the group selected from N(R$^E$)C(O)— where the carbonyl is bonded to L, and —C(O)— where the carbonyl is bonded to L, and additionally optionally substituted by 1 to 2 R;

where each R$^E$ is independently selected from the group consisting of H, —C$_1$-C$_8$ alkyl, —C$_1$-C$_8$ heteroalkyl, -aryl, -aralkyl, —C$_1$-C$_{10}$ heterocyclyl, —C$_3$-C$_8$ carbocyclyl, —C(O)OC$_1$-C$_8$ alkyl, —C(O)N(C$_1$-C$_8$ alkyl)$_2$, and —C(O)-halo, and wherein each R$^E$ is optionally substituted with 1 to 3 substituents independently selected from R;

L is L$^A$-L$^B$-(L$^C$)$_{1-3}$;

L$^A$ is selected from: a bond to AB, —NR-(bond to AB), alkyl-SO$_2$-heteroaryl, arylSO$_2$-heteroaryl-,

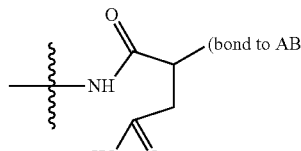

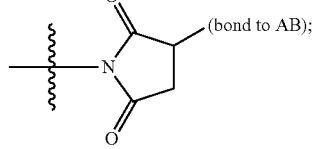

L$^B$ is L$^{B1}$-L$^{B2}$-L$^{B3}$ wherein L$^{B1}$ is absent or is one or more components selected from the group consisting of —C(O)—, —C(S)—, —C(O)NR—, —C(O)C$_1$-C$_8$alkyl-, —C(O)NRC$_1$-C$_8$alkyl-, —C$_1$-C$_8$alkyl(OCH$_2$CH$_2$)$_{1-8}$—, —C(O)C$_1$-C$_6$alkylNRC(O)—, —C(O)C$_1$-C$_6$alkyl(OCH$_2$CH$_2$)$_{1-8}$—, —C$_1$-C$_8$alkyl(OCH$_2$CH$_2$)$_{1-8}$—C(O)—, —C$_1$-C$_8$alkyl-S—S—C$_1$-C$_8$alkylNRC(O)CH$_2$—, —C$_1$-C$_8$alkyl(OCH$_2$CH$_2$)$_{1-6}$NRC(O)CH$_2$—, —C(O)C$_1$-C$_8$alkyl-NRC(O)C$_1$-C$_8$alkyl-, —N=CR-phenyl-O—C$_1$-C$_8$alkyl-, —N=CR-phenyl-O—C$_1$-C$_8$alkyl-C(O)—, —C(O)—C$_1$-C$_8$alkyl(OCH$_2$CH$_2$)$_{1-6}$NRC(O)—, —C(O)C$_1$-C$_8$alkyl-phenyl(NR—C(O)C$_1$-C$_8$alkyl)$_{1-4}$-, —C(O)C$_1$-C$_8$alkyl(OCH$_2$CH$_2$)$_{1-8}$—NRC(O)C$_1$-C$_8$alkyl-, —C$_1$-C$_8$alkyl-, —S—, —C(O)—CH(NR—C(O)C$_1$-C$_8$alkyl)-C$_1$-C$_6$alkyl- and (—CH$_2$—CH$_2$—O—)$_{1-20}$;

L$^{B2}$ is AA$_{0-12}$, wherein AA is a natural amino acid, a non-natural amino acid or —(CR$^{15}$)$_o$—S—S—(CR$^{15}$)$_p$— where o and p are each independently an integer from 1 to 20, L$^{B3}$ is -PABA-, -PABC- or is absent;

L$^C$ is absent or is independently selected from the group consisting of —C$_1$-C$_6$alkylene-, —NRC$_3$-C$_8$-heterocyclylNR—, —NRC$_3$-C$_8$-carbocyclylNR—, —NRC$_1$-C$_6$alkylNR—, —NRC$_1$-C$_6$alkylene-, —S—, —NR—, —NRNR—, —O(CR$_2$)$_{1-4}$S—S(CR$_2$)$_{1-4}$N(R)—, —NRC$_1$-C$_8$-alkylenephenyleneNR—, —NRC$_1$-C$_8$alkylenephenyleneSO$_2$NR—, —OC$_1$-C$_8$alkylS—SC$_1$-C$_8$alkylC(COOR)NR—, —NRC(COOR)C$_1$-C$_8$alkylS—SC$_1$-C$_8$alkylO—,

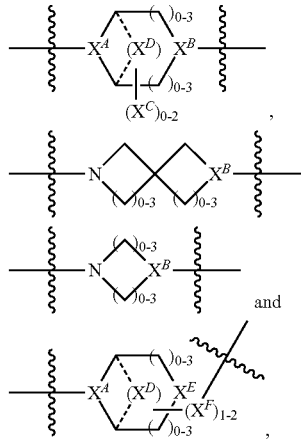

wherein
$X^A$ is CR or N,
$X^B$ is CH, CR(C(R)$_2$)$_{1-3}$NR, CR(C(R)$_2$)$_{1-3}$O, CR(C(R)$_2$)$_{1-3}$C(O)NR, CR—(C(R)$_2$)$_{1-3}$C(O)NRNR, CR(C(R)$_2$)$_{1-3}$SO$_2$NR, CR(C(R)$_2$)$_{1-3}$NRNR, CR(C(R)$_2$)$_{1-3}$NRC(O) or N;

each $X^C$ is R;
each $X^C$ is —$(CH_2)_{1-5}$—, or is absent;
$X^E$ is O, S, $C(R)_2$, $C(R)(C(R)_2)_{1-3}$—$NR_2$ or NR, and
each $X^F$ is $(C(R)_2)_{1-3}$—NR or $C(R)_2$—$(C(R)_2)_{1-3}$—O.

Additional aspects of the invention include compounds such as those mentioned herein where
each R is independently selected from the group consisting of H, —$C_1$-$C_{20}$ alkyl and —$NH_2$;
each $V^1$ is independently O or N(R) for each ring system in which $V^1$ appears;
each $V^2$ is independently O or N(R) for each ring system in which $V^2$ appears;
$W^1$ and $W^2$ are each independently H, —$C_1$-$C_5$ alkyl, —C(O)OR, or —C(O)$NR_2$ for each ring system in which $W^1$ and $W^2$ appear;
each X is independently halo, for each ring system in which X appears;
each Y is independently selected from the group consisting of H, —C(O)$R^A$, —C(O)N($R^A$)$_2$, glycosyl, —$NO_2$ and —PO(O$R^A$)$_2$, for each ring system in which Y appears, wherein each $R^A$ is independently selected from the group consisting of H, —$C_1$-$C_{20}$ alkyl, —$C_1$-$C_8$ heteroalkyl, —$C_3$-$C_8$ carbocyclyl and —$C_1$-$C_{20}$ alkylN(R)$_2$, wherein said —$C_1$-$C_{20}$ alkyl, —$C_1$-$C_8$ heteroalkyl, —$C_3$-$C_8$ carbocyclyl and —$C_1$-$C_{20}$ alkylN(R)$_2$ are optionally substituted with 1 to 3 substituents independently selected from R;
$L^1$ and $L^2$ are each independently selected from a direct bond and carbonyl; and
T is selected from:
—$NR^B$-$T^1$-$NR^C$— where $R^B$ and $R^C$ are each independently H or —$C_1$-$C_8$ alkyl,
—C(O)hetC(O)— wherein het is a monocyclic heteroaryl of 5 to 12 members, containing one or two heteroatoms independently selected from O, N and S, wherein het is optionally substituted with 1 to 8 substituents each independently selected from the group consisting of —$C_1$-$C_8$ alkyl, —$NH_2$, and —$NH_2$, and said optional substituents on het are optionally substituted with —$C_1$-$C_8$ alkyl, where at least one of $F^1$ and $F^2$ is selected from the group consisting of Ring System C and Ring System D when T is —C(O)hetC(O)—, and —C($A^1$)$X^1$-$T^2$-$X^1$C($B^1$)—, where $T^2$ is:

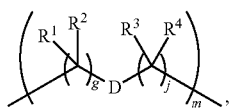

wherein each $X^1$ is a bond, wherein $A^1$ and $B^1$ are each independently =O, wherein $R^1$, $R^2$, $R^3$, and $R^4$ are each independently H or $R^1$ and $R^2$ form a ring system, or $R^3$ and $R^4$ form a ring system, or both $R^1$ and $R^2$, and $R^3$ and $R^4$, each independently form ring systems, or $R^1$ and $R^3$ form a ring system, or $R^2$ and $R^4$ form a ring system, or both $R^1$ and $R^3$, and $R^2$ and $R^4$, each independently form ring systems, where said ring systems are independently selected from —$C_1$-$C_{10}$ heterocyclyl or —$C_3$-$C_8$ carbocyclycl, and wherein D is a bond or is selected from the group consisting of —S—, —$C_1$-$C_8$ alkylene-, —$C_6$-$C_{14}$ arylene-, —$C_6$-$C_{14}$ heteroarylene-, —$C_1$-$C_{10}$ heterocyclo and —$C_3$-$C_8$ carbocyclo, where said —$C_1$-$C_8$ alkylene-, —$C_6$-$C_{14}$ arylene-, —$C_6$-$C_{14}$ heteroarylene-, —$C_1$-$C_{10}$ heterocyclo and —$C_3$-$C_8$ carbocyclo are optionally substituted with —$NH_2$, —N(R)C(O)H or —N(R)C(O)OH.

Additional aspects of the invention include compounds such as those mentioned herein where two or more R optionally join to form a ring or rings.

Additional aspects of the invention include compounds such as those mentioned herein where
each R is independently selected from the group consisting of H, —$C_1$-$C_{20}$ alkyl and —$NH_2$;
each $V^1$ is independently O or N(R) for each ring system in which $V^1$ appears;
each $V^2$ is independently O or N(R) for each ring system in which $V^2$ appears;
$W^1$ and $W^2$ are each independently H, —$C_1$-$C_5$ alkyl, —C(O)OR, or —C(O)$NR_2$ for each ring system in which $W^1$ and $W^2$ appear;
each X is independently halo, for each ring system in which X appears;
each Y is independently selected from a bond, H, —C(O)$R^A$, —C(S)$R^A$, —C(O)O$R^A$, —S(O)$_2$O$R^A$, —C(O)N($R^A$)$_2$, —C(S)N($R^A$)$_2$, glycosyl, —$NO_2$ and —P(O)(O$R^A$)$_2$ for each ring system in which Y appears, wherein each $R^A$ is independently selected from H, —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl, —$C_1$-$C_{20}$ alkylN(R)$_2$, —$C_1$-$C_{20}$ alkylene, —$C_1$-$C_8$ heteroalkylene, —$C_6$-$C_{14}$ arylene, aralkylene, —$C_1$-$C_{10}$ heterocyclo, —$C_3$-$C_8$ carbocyclo and —$C_1$-$C_{20}$ alkylN(R)—, and $R^F$ where said $R^A$ is optionally substituted with 1 to 3 substituents independently selected from R, and wherein one Y is divalent and is bonded to L,
$R^F$ is —N($R^6$)QN($R^5$)C(O)— and is bonded to L at the carbonyl adjacent N($R^5$), wherein $R^5$ and $R^6$ are each independently selected from the group consisting of H, —$C_1$-$C_8$ alkyl, and —$C_1$-$C_8$ heteroalkyl, or $R^5$ or $R^6$ joins with a substituted carbon on Q to form a —$C_1$-$C_{10}$ heterocyclic or —$C_6$-$C_{14}$ heteroaryl ring, or $R^5$ and $R^6$ join together to form a —$C_1$-$C_{10}$ heterocyclic or —$C_6$-$C_{14}$ heteroaryl ring system, and where Q is —$C_1$-$C_8$ alkylene-, —$C_6$-$C_{14}$ arylene-, or —$C_3$-$C_8$ carbocyclo-, wherein Q, $R^5$ and $R^6$ are each independently optionally substituted with 1 to 3 substituents independently selected from R;
$L^1$ $L^1$ and $L^2$ are each independently selected from a direct bond and carbonyl; and
T is selected from:
—$NR^B$-$T^1$-$NR^C$— where $R^B$ and $R^C$ are each independently H or —$C_1$-$C_8$ alkyl,
—C(O)hetC(O)— wherein het is a monocyclic heteroaryl of 5 to 12 members, containing one or two heteroatoms independently selected from O, N and S, wherein het is optionally substituted with 1 to 8 substituents each independently selected from the group consisting of —$C_1$-$C_8$ alkyl, —$NH_2$, and —$NH_2$, and said optional substituents on het are optionally substituted with —$C_1$-$C_8$ alkyl, where at least one of $F^1$ and $F^2$ is selected from the group consisting of Ring System C and Ring System D when T is —C(O)hetC(O)—, and —C($A^1$)$X^1$-$T^2$-$X^1$C($B^1$)—, where $T^2$ is:

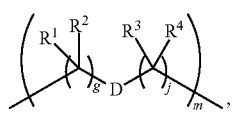

wherein each $X^1$ is a bond, wherein $A^1$ and $B^1$ are each independently =O, wherein $R^1$, $R^2$, $R^3$, and $R^4$ are each independently H or $R^1$ and $R^2$ form a ring system, or $R^3$ and $R^4$ form a ring system, or both $R^1$ and $R^2$, and $R^3$ and $R^4$, each independently form ring systems, or $R^1$ and $R^3$ form a ring system, or $R^2$ and $R^4$ form a ring system, or both $R^1$ and $R^3$, and $R^2$ and $R^4$, each independently form ring systems, where said ring systems are independently selected from —$C_1$-$C_{10}$ heterocyclyl or —$C_3$-$C_8$ carbocyclycl, and wherein D is a bond or is selected from the group consisting of —S—, —$C_1$-$C_8$ alkylene-, —$C_6$-$C_{14}$ arylene-, —$C_6$-$C_{14}$ heteroarylene-, —$C_1$-$C_{10}$ heterocyclo and —$C_3$-$C_8$ carbocyclo, where said —$C_1$-$C_8$ alkylene-, —$C_6$-$C_{14}$ arylene-, —$C_6$-$C_{14}$ heteroarylene-, —$C_1$-$C_{10}$ heterocyclo and —$C_3$-$C_8$ carbocyclo are optionally substituted with —$NH_2$, —N(R)C(O)H or —N(R)C(O)OH.

Additional aspects of the invention include compounds such as those mentioned herein where
each R is independently selected from the group consisting of H, —$C_1$-$C_{20}$ alkyl and —$NH_2$;
each $V^1$ is independently O or N(R) for each ring system in which $V^1$ appears;
each $V^2$ is independently O or N(R) for each ring system in which $V^2$ appears;
$W^1$ and $W^2$ are each independently H, —$C_1$-$C_5$ alkyl, —C(O)OR, or —C(O)$NR_2$ for each ring system in which $W^1$ and $W^2$ appear;
each X is independently halo, for each ring system in which X appears;
each Y is independently selected from the group consisting of H, —C(O)$R^A$, —C(O)N($R^A$)$_2$, glycosyl, —$NO_2$ and —PO(O$R^A$)$_2$, for each ring system in which Y appears, wherein each $R^A$ is independently selected from the group consisting of H, —$C_1$-$C_{20}$ alkyl, —$C_1$-$C_8$ heteroalkyl, —$C_3$-$C_8$ carbocyclyl and —$C_1$-$C_{20}$ alkylN(R)$_2$, wherein said —$C_1$-$C_{20}$ alkyl, —$C_1$-$C_8$ heteroalkyl, —$C_3$-$C_8$ carbocyclyl and —$C_1$-$C_{20}$ alkylN(R)$_2$ are optionally substituted with 1 to 3 substituents independently selected from R;
$L^1$ and $L^2$ are each independently selected from a direct bond and carbonyl; and
T is —C($A^1$)$X^1$-$T^2$-$X^1$C($B^1$)—, where $T^2$ is:

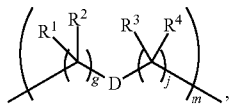

wherein each $X^1$ is a bond, wherein $A^1$ and $B^1$ are each independently =O, wherein $R^1$, $R^2$, $R^3$, and $R^4$ are each independently H or $R^1$ and $R^2$ form a ring system, or $R^3$ and $R^4$ form a ring system, or both $R^1$ and $R^2$, and $R^3$ and $R^4$, each independently form ring systems, or $R^1$ and $R^3$ form a ring system, or $R^2$ and $R^4$ form a ring system, or both $R^1$ and $R^3$, and $R^2$ and $R^4$, each independently form ring systems, where said ring systems are independently selected from —$C_1$-$C_{10}$ heterocyclyl or —$C_3$-$C_8$ carbocyclycl, and wherein D is a bond or is selected from the group consisting of —S—, —$C_1$-$C_8$ alkylene-, —$C_6$-$C_{14}$ arylene-, —$C_6$-$C_{14}$ heteroarylene-, —$C_1$-$C_{10}$ heterocyclo and —$C_3$-$C_8$ carbocyclo, where said —$C_1$-$C_8$ alkylene-, —$C_6$-$C_{14}$ arylene-, —$C_6$-$C_{14}$ heteroarylene-, —$C_1$-$C_{10}$ heterocyclo and —$C_3$-$C_8$ carbocyclo are optionally substituted with —$NH_2$, —N(R)C(O)H or —N(R)C(O)OH.

Additional aspects of the invention include compounds such as those mentioned herein where
$L^A$ is selected from the group consisting of -halo, —N(R)$_2$, —CON(R)$_2$, —S-aryl optionally substituted with —$NO_2$ or —CON(R)$_2$, —S-heteroaryl optionally substituted with —$NO_2$, alkyl-$SO_2$-heteroaryl, aryl$SO_2$-heteroaryl-, and

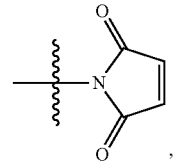 [SMILES: *N1C(=O)C=CC1=O]

$L^B$ is $L^{B1}$-$L^{B2}$-$L^{B3}$ wherein $L^{B1}$ is absent or is one or more components selected from the group consisting of —C(O)—, —C(S)—, —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-6}$—, —C(O)$C_1$-$C_6$alkylNRC(O)—, —C(O)$C_1$-$C_6$alkyl(OCH$_2$CH$_2$)$_{1-6}$—, —$C_1$-$C_6$alkyl(OCH$_2$CH$_2$)$_{1-6}$—C(O)—, —$C_1$-$C_6$alkyl-S—S—$C_1$-$C_6$alkylNRC(O)CH$_2$—, —$C_1$-$C_6$alkyl(OCH$_2$CH$_2$)$_{1-6}$NRC(O)CH$_2$—, —C(O)$C_1$-$C_6$alkyl-NRC(O)$C_{1-6}$alkyl-, —C(O)—$C_1$-$C_6$alkyl(OCH$_2$CH$_2$)$_{1-6}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-6}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl- and (—CH$_2$—CH$_2$—O—)$_{1-20}$, wherein $L^{B2}$ is $AA_{0-12}$, wherein AA is a natural amino acid, a non-natural amino acid or —(CR$^{15}$)$_o$—S—S—(CR$^{15}$)$_p$ where o and p are each independently an integer from 1 to 20, and $L^{B3}$ is -PABA-, -PABC- or is absent; and
$L^C$ is absent.

Additional aspects of the invention include antibody drug conjugates such as those mentioned herein where $L^A$ is selected from: a bond to AB, —NR-(bond to AB), alkyl-$SO_2$-heteroaryl, arylSO$_2$-heteroaryl-,

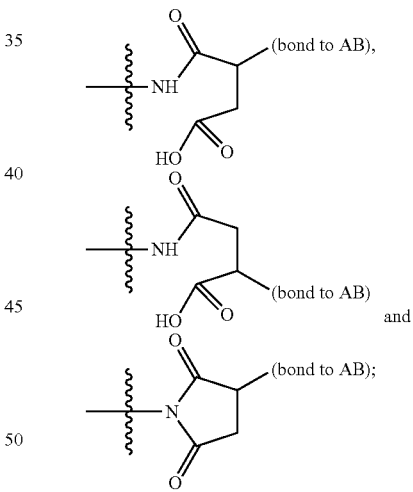

$L^B$ is $L^{B1}$-$L^{B2}$-$L^{B3}$ wherein $L^{B1}$ is absent or is one or more components selected from the group consisting of —C(O)—, —C(S)—, —C(O)NR—, —C(O)$C_1$-$C_6$alkyl-, —C(O)NR$C_1$-$C_6$alkyl-, —$C_1$-$C_6$alkyl(OCH$_2$CH$_2$)$_{1-6}$—, —C(O)$C_1$-$C_6$alkylNRC(O)—, —C(O)$C_1$-$C_6$alkyl(OCH$_2$CH$_2$)$_{1-6}$—, —$C_1$-$C_6$alkyl(OCH$_2$CH$_2$)$_{1-6}$—C(O)—, —$C_1$-$C_6$alkyl-S—S—$C_1$-$C_6$alkylNRC(O)CH$_2$—, —$C_1$-$C_6$alkyl(OCH$_2$CH$_2$)$_{1-6}$NRC(O)CH$_2$—, —C(O)$C_1$-$C_6$alkyl-NRC(O)$C_{1-6}$alkyl-, —C(O)—$C_1$-$C_6$alkyl(OCH$_2$CH$_2$)$_{1-6}$NRC(O)—, —C(O)$C_1$-$C_6$alkyl-phenyl(NR—C(O)$C_1$-$C_6$alkyl)$_{1-4}$-, —C(O)$C_1$-$C_6$alkyl(OCH$_2$CH$_2$)$_{1-6}$—NRC(O)$C_1$-$C_6$alkyl-, —$C_1$-$C_6$alkyl-, —S—, —C(O)—CH(NR—C(O)$C_1$-$C_6$alkyl)-$C_1$-$C_6$alkyl- and (—CH$_2$—CH$_2$—O—)$_{1-20}$, wherein $L^{B2}$ is $AA_{0-12}$, wherein AA is a natural amino acid, a non-natural amino acid or —(CR$^{15}$)$_o$—S—S—(CR$^{15}$)$_p$ where o and p are each independently an integer from 1 to 20, and L$^{B3}$ is -PABA-, -PABC- or absent; and L$^C$ is absent.

Additional aspects of the invention include compounds such as those mentioned herein where R$^E$ is selected from:

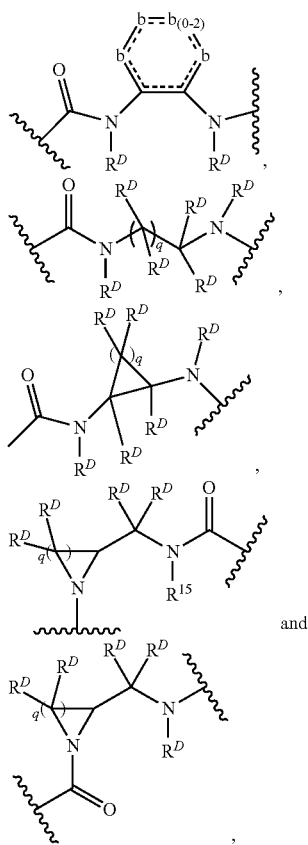

wherein q is 1-10, and each b is independently CR$^D$, N, NR$^D$, O or S.

Additional aspects of the invention include compounds such as those mentioned herein where one or more W is C$_1$-C$_3$ alkyl.

Additional aspects of the invention include compounds such as those mentioned herein where X is chloro.

Additional aspects of the invention include compounds such as those mentioned herein where one Y is H or —C(O)C$_1$-C$_{10}$alkyl.

Additional aspects of the invention include compounds such as those mentioned herein where one or more Z is H.

Additional aspects of the invention include compounds such as those mentioned herein where T is selected from an amide, or amino-tether-amino of the formula —NH—C(O)—NH— or —NH—C(O)-het-C(O)—NH—.

Additional aspects of the invention include compounds such as those mentioned herein where the amide is —C(O)NH— or —NHC(O)—.

Additional aspects of the invention include compounds such as those mentioned herein where het is a heteroaryl selected from pyrrol-2-,5-diyl-, fur-2,5-diyl-, indol-2,5-diyl, benzofuran-2,5-diyl, and 3,6-dihydrobenzo[1,2-b:4,3-b]dipyrrol-2,7-diyl.

Additional aspects of the invention include compounds such as those mentioned herein where L$^1$ and L$^2$ are selected from carbonyl, 2-carbonylindole-5-yl, 2-carbonyl-6-hydroxy-7-methoxyindol-5-yl, 2-carbonyl-1,2,3,6-tetrahydrobenzo[1,2-b:4,3-b]dipyrrol-7-yl, 2-carbonyl-4-hydroxy-5-methoxy-1,2,3,6-tetrahydrobenzo[1,2-b:4,3-b']dipyrrol-7-yl, and 2-carbonyl-4-hydroxy-5-methoxy-1,2,3,6-tetrahydrobenzo[1,2-b:4,3-b']dipyrrol-7-yl.

Additional aspects of the invention are those compounds recited herein where one or more of the following apply: W is methyl; X is a halogen; Y is hydrogen or —COR where R is C$_1$-C$_{10}$alkyl; and Z is hydrogen.

The invention also includes compound as described herein where T is selected from an amide (i.e., —C(O)NH— or —NHC(O)—); or an amino-tether-amino of the formula —NH-T'-NH where T' is carbonyl or —C—(O)-het-C(O)—. Where T is an amino-tether-amino of the formula NH-T'-NH, T' may be carbonyl (i.e., —C—(O)—) or —C(O)-het-C(O)— where het is a heteroaryl selected from pyrrol-2-,5-diyl-; fur-2,5-diyl-; indol-2,5-diyl; benzofuran-2,5-diyl; or 3,6-dihydrobenzo[1,2-b:4,3-b]dipyrrol-2,7-diyl.

Also included in embodiments of the invention are those compounds as described herein where L$^1$ and L$^2$ are selected from 2-carbonylindole-5-yl; 2-carbonyl-6-hydroxy-7-methoxyindol-5-yl; 2-carbonyl-1,2,3,6-tetrahydrobenzo[1,2-b:4,3-b]dipyrrol-7-yl; 2-carbonyl-4-hydroxy-5-methoxy-1,2,3,6-tetrahydrobenzo[1,2-b:4,3-b']dipyrrol-7-yl; and 2-carbonyl-4-hydroxy-5-methoxy-1,2,3,6-tetrahydrobenzo[1,2-b:4,3-b']dipyrrol-7-yl.

Another aspect of the invention includes compounds as described herein where L$^A$ is

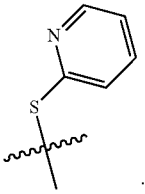 [SMILES: *Sc1ccccn1]

The invention includes, as well, linker-payloads or an antibody-drug-conjugates comprising a radical of the payload compounds described herein.

Importantly, the invention includes pharmaceutical compositions of the compounds, and any pharmaceutically acceptable salts or solvates thereof, described herein, where the pharmaceutical composition includes a pharmaceutically acceptable excipient.

The invention further relates to methods of treating cancer comprising administering to a patient in need thereof a therapeutically effective amount of a one or more of compound described herein, or a pharmaceutical composition or compositions comprising one or more of these compounds.

Some compounds, including payloads, linker-payloads and ADCs depicted herein, are shown in a specific stereoisomeric form. The invention, however, is meant to include all stereoisomeric forms of these compounds. For instance, a compound with two stereoisomeric centers may be depicted as the R, S form of the compound, but the invention conveys all stereoisomeric forms, e.g., R,R; R,S; S,R and S,S.

DETAILED DESCRIPTION

The present invention is directed to cytotoxic bifunctional compounds, to antibody drug conjugates (ADCs) comprising said cytotoxic bifunctional compounds, and to methods for using the same to treat cancer and other pathological conditions. The invention also relates to methods of using such compounds and/or conjugates in vitro, in situ, and in vivo for the detection, diagnosis or treatment of mammalian cells, or associated pathological conditions.

Definitions and Abbreviations

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "antibody" (or "Ab") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. An intact antibody has primarily two regions: a variable region and a constant region. The variable region binds to and interacts with a target antigen. The variable region includes a complementary determining region (CDR) that recognizes and binds to a specific binding site on a particular antigen. The constant region may be recognized by and interact with the immune system (see, e.g., Janeway et al., 2001, Immuno. Biology, 5th Ed., Garland Publishing, New York). An antibody can be of any type or class (e.g., IgG, IgE, IgM, IgD, and IgA) or subclass (e.g., IgG1, IgG2, IgG3, IgG4, IgA1 and IgA2). The antibody can be derived from any suitable species. In some embodiments, the antibody is of human or murine origin. An antibody can be, for example, human, humanized or chimeric.

The terms "specifically binds" and "specific binding" refer to antibody binding to a predetermined antigen. Typically, the antibody binds with an affinity of at least about $1 \times 10^7$ M$^{-1}$, and binds to the predetermined antigen with an affinity that is at least two-fold greater than its affinity for binding to a non-specific antigen (e.g., BSA, casein) other than the predetermined antigen or a closely-related antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "monoclonal antibodies" specifically includes "chimeric" antibodies in which a portion of the heavy and/or light chain is identical to or homologous with the corresponding sequence of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

As used herein, "H(C)—" refers to trastuzumab (trade name HERCEPTIN®) which is a monoclonal antibody that interferes with the HER2/neu receptor, bound through one of its' cystine to compound of the invention. As used herein, "H(K)—" refers to trastuzumab which is a monoclonal antibody that interferes with the HER2/neu receptor, bound through one of its' lysines to compound of the invention.

An "intact antibody" is one which comprises an antigen-binding variable region as well as a light chain constant domain ($C_L$) and heavy chain constant domains, $C_{H1}$, $C_{H2}$, $C_{H3}$ and $C_{H4}$, as appropriate for the antibody class. The constant domains may be native sequence constant domains (e.g., human native sequence constant domains) or amino acid sequence variants thereof.

An intact antibody may have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (ADCC) and antibody-dependent cell-mediated phagocytosis.

An "antibody fragment" comprises a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immuno specifically bind to a target antigen (e.g., a cancer cell antigen, a viral antigen or a microbial antigen).

The term "variable" in the context of an antibody refers to certain portions of the variable domains of the antibody that differ extensively in sequence and are used in the binding and specificity of each particular antibody for its particular antigen. This variability is concentrated in three segments called "hypervariable regions" in the light chain and the heavy chain variable domains. The more highly conserved portions of variable domains are called the framework regions (FRs). The variable domains of native heavy and light chains each comprise four FRs connected by three hypervariable regions.

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (L3) in the heavy chain variable domain; Kabat et al. (Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (142) and 96-101 (H3) in the heavy chain variable domain; Chothia and Lesk, 1987, J. Mol. Biol. 196:901-917). FR residues are those variable domain residues other than the hypervariable region residues as herein defined.

A "single-chain Fv" or "scFv" antibody fragment comprises the V.sub.H and V.sub.L domains of an antibody, wherein these domains are present in a single polypeptide chain. Typically, the Fv polypeptide further comprises a polypeptide linker between the V.sub.H and V.sub.L domains which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

The term "diabody" refers to small antibody fragments with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., 1993, Proc. Natl. Acad. Sci. USA 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., 1986, Nature 321:522-525; Riechmann et al., 1988, Nature 332:323-329; and Presta, 1992, Curr. Op. Struct. Biol. 2:593-596.

As used herein, "isolated" means separated from other components of (a) a natural source, such as a plant or animal cell or cell culture, or (b) a synthetic organic chemical reaction mixture. As used herein, "purified" means that when isolated, the isolate contains at least 95%, and in another aspect at least 98%, of a compound (e.g., a conjugate) by weight of the isolate.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., a breast, ovarian, stomach, endometrial, salivary gland, lung, kidney, colon, thyroid, pancreatic or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit the growth of and/or kill existing cancer cells, it may be cytostatic and/or cytotoxic. For cancer therapy, efficacy can, for example, be measured by assessing the time to disease progression (TTP) and/or determining the response rate (RR).

The term "substantial amount" refers to a majority, i.e. greater than 50% of a population, of a mixture or a sample.

The term "intracellular metabolite" refers to a compound resulting from a metabolic process or reaction inside a cell on an antibody-drug conjugate (ADC). The metabolic process or reaction may be an enzymatic process such as proteolytic cleavage of a peptide linker of the ADC. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an ADC or the like, whereby the covalent attachment, e.g., the linker, between the drug moiety and the antibody is broken, resulting in the free drug, or other metabolite of the conjugate dissociated from the antibody inside the cell. The cleaved moieties of the ADC are thus intracellular metabolites.

The term "bioavailability" refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

The term "cytotoxic activity" refers to a cell-killing, a cytostatic or an anti-proliferative effect of a ADC or an intracellular metabolite of said ADC. Cytotoxic activity may be expressed as the $IC_{50}$ value, which is the concentration (molar or mass) per unit volume at which half the cells survive.

A "disorder" is any condition that would benefit from treatment with a drug or antibody-drug conjugate. This includes chronic and acute disorders or diseases including those pathological conditions which predispose a mammal to the disorder in question. Non-limiting examples of disorders to be treated herein include benign and malignant cancers; leukemia and lymphoid malignancies, neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition or disorder in mammals that is typically characterized by unregulated cell growth. A "tumor" comprises one or more cancerous cells.

Examples of a "patient" include, but are not limited to, a human, rat, mouse, guinea pig, monkey, pig, goat, cow, horse, dog, cat, bird and fowl. In an exemplary embodiment, the patient is a human.

The terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of inhibiting replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: inhibiting the growth, multiplication or replication of the pathogen that causes the infectious disease and ameliorating one or more symptoms of an infectious disease.

The term "package insert" is used to refer to instructions customarily included in commercial packages of therapeutic products, that contain information about the indication(s), usage, dosage, administration, contraindications and/or warnings concerning the use of such therapeutic products.

As used herein, the terms "cell," "cell line," and "cell culture" are used interchangeably and all such designations include progeny. The words "transformants" and "transformed cells" include the primary subject cell and cultures or progeny derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, CBI refers to 1,2,9,9a-tetrahydro-4H-benzo[e]cyclopropa[c]indol-4-one, or a substituted or derivatized form thereof. CBI can also refer to the seco form of CBI, or seco-CBI, which is also know as 1-(chloromethyl)-2,3-dihydro-1H-benzo[e]indol-5-ol, or a substituted or derivatized form (or forms) thereof.

As used herein, CPI refers to 1,2,8,8a-tetrahydrocyclopropa[c]pyrrolo[3,2-e]indol-4(5H)-one or a substituted or derivatized form thereof. CPI can also refer to the seco form of CPI, or seco-CPI, which is also know as 8-(chloromethyl)-1-methyl-3,6,7,8-tetrahydropyrrolo[3,2-e]indol-4-ol, or a substituted or derivatized form (or forms) thereof.

Unless otherwise indicated, the term "alkyl" by itself or as part of another term refers to a straight chain or branched, saturated hydrocarbon having the indicated number of carbon atoms (e.g., "$C_1$-$C_8$" alkyl refer to an alkyl group having from 1 to 8 carbon atoms). Alkyl groups typically comprise from 1 to 20 carbon atoms, preferably from 1 to 8 carbon atoms, and more preferably from 1 to 4 carbon atoms. When the number of carbon atoms is not indicated, the alkyl group has from 1 to 8 carbon atoms. Representative straight chain $C_1$-$C_8$ alkyls include, but are not limited to, methyl, ethyl, n-propyl, n-butyl, n-pentyl, n-hexyl, n-heptyl and n-octyl; while branched $C_1$-$C_8$ alkyls include, but are not limited to, -isopropyl, -sec-butyl, -isobutyl, -tent-butyl, -isopentyl, and -2-methylbutyl; unsaturated $C_2$-$C_8$ alkyls include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexyl, 2-hexyl, 3-hexyl, acetylenyl, propynyl, 1-butynyl, 2-butynyl, 1-pentynyl, 2-pentynyl and 3-methyl-1-butynyl. Reference to "alkyl" herein refers to unsubstituted and substituted moieties as described above.

Unless otherwise indicated, "alkylene," by itself of as part of another term, refers to a saturated, branched or straight chain or cyclic hydrocarbon radical of the stated number of carbon atoms, typically 1-18 carbon atoms, and having two monovalent radical centers derived by the removal of two hydrogen atoms from the same or two different carbon atoms of a parent alkane.) Alkylene groups typically comprise from 1 to 18 carbon atoms, preferably from 1 to 10 carbon atoms, more preferably from 1 to 8 carbon atoms, and most preferably from 1 to 4 carbon atoms. Typical alkylene radicals include, but are not limited to: methylene (—$CH_2$—), 1,2-ethylene —$CH_2CH_2$—), 1,3-propylene (—$CH_2CH_2CH_2$—), 1,4-butylene (—$CH_2CH_2CH_2CH_2$—), and the like. A "$C_1$-$C_{10}$" straight chain alkylene is a straight chain, saturated hydrocarbon group of the formula —$(CH_2)_{1-10}$—. Examples of a $C_1$-$C_{10}$ alkylene include methylene, ethylene, propylene, butylene, pentylene, hexylene, heptylene, ocytylene, nonylene and decalene. Reference to "alkylene" herein refers to unsubstituted and substituted moieties as described above.

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Up to two heteroatoms may be consecutive. Heteroalkyl groups typically comprise from 1 to 15 carbon atoms, preferably from 1 to 12 carbon atoms, more preferably from 1 to 8 carbon atoms, and most preferably from 1 to 4 carbon atoms. Reference to "heteroalkyl" herein refers to unsubstituted and substituted moieties as described above.

Unless otherwise indicated, the term "heteroalkylene" by itself or as part of another substituent means a divalent group derived from heteroalkyl (as discussed above). For heteroalkylene groups, heteroatoms can also occupy either or both of the chain termini. Reference to "heteroalkylene" herein refers to unsubstituted and substituted moieties as described above.

Unless otherwise indicated, "aryl," by itself or an part of another term, means a substituted or unsubstituted monovalent carbocyclic aromatic hydrocarbon radical of 5-20, preferably 5-14 or 6-14, carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like. A substituted carbocyclic aromatic group (e.g., an aryl group) can be substituted with one or more, preferably 1 to 5, of the following groups: $C_1$-$C_8$ alkyl, —O—($C_1$-$C_8$ alkyl), —C(O)$R^9$, —OC(O)$R^9$, —C(O)O$R^9$, —C(O)NH$_2$, —C(O)NHR', —C(O)N($R^1$)$_2$, —NHC(O)R', —S(O)$_2$R', —S(O)R', —OH, halogen, —N$_3$, —NH$_2$, —NH($R^9$), —N($R^9$)$_2$ and —CN; wherein each $R^9$ is independently selected from —H, $C_1$-$C_8$ alkyl and unsubstituted aryl. In some embodiments, a substituted carbocyclic aromatic group can further include one or more of: —NHC(=NH)NH$_2$, —NHCONH$_2$, —S(=O)$_2$$R^9$ and —SR$^9$. "Arylene" is the corresponding divalent moiety.

"Substituted alkyl" (or "substituted alkylene", "substituted heteroalkyl", or "substituted heteroalkylene") means an the relevant alkyl alkyl-containing group or radical as discussed above in which one or more hydrogen atoms are each independently replaced with a substituent. Typical substituents include, but are not limited to, —X, —$R^{10}$, —O—, —OR$^{10}$, —SR$^{10}$, —S—, —NR$^{10}_2$, —NR$^{10}_3$, =NR$^{10}$, —CX$_3$, —CN, —OCN, —SCN, —N=C=O, —NCS, —NO, —NO$_2$, =N$_2$, —N$_3$, —NR$^{10}$C(=O)R$^{10}$R$^{10}$, —C(=O)NR$^{10}_2$, —SO$_3^-$, —SO$_3$H, —S(=O)$_2$R$^{10}$, —OS(=O)$_2$OR$^{10}$, —S(=O)$_2$NR$^{10}$, —S(=O)R$^{10}$, —OP(=O)(OR$^{10}$)$_2$, —P(=O)(OR$^{10}$)$_2$, —PO$_3^{2-}$, PO$_3$H$_2$, —AsO$_2$H$_2$, —C(=O)R$^{10}$, —C(=O)X, —C(=S)R$^{10}$, —CO$_2$R$^{10}$, —CO$_2^-$, —C(=S)OR$^{10}$, —C(=O)SR$^{10}$, —C(=S)SR$^{10}$, —C(=O)NR$^{10}_2$, —C(=S)NR$^{10}_2$, or —C(=NR$^{10}$)NR$^{10}_2$, where each X is independently a halogen: —F, —Cl, —Br, or —I; and each $R^{10}$ is independently —H, $C_1$-$C_{20}$ alkyl, $C_1$-$C_{20}$ heteroalkyl, $C_6$-$C_{20}$ aryl, $C_1$-$C_{10}$ heterocyclyl, a protecting group or a prodrug moiety. Aryl, alkylene and heteroalkylene groups as described above may also be similarly substituted.

Unless otherwise indicated, "aralkyl" by itself or part of another term, means an alkyl group, as defined above, substituted with an aryl group, as defined above.

Unless otherwise indicated, "$C_3$-$C_{10}$ heterocyclyl" by itself or as part of another term, refers to a monovalent substituted or unsubstituted aromatic or non-aromatic monocyclic, bicyclic or tricyclic ring system having from 2 to 10, 2 to 14, or 2-20 carbon atoms, preferably 3 to 8, carbon atoms (also referred to as ring members) and one to four heteroatom ring members independently selected from N, O, P or S, and derived by removal of one hydrogen atom from a ring atom of a parent ring system. One or more N, C or S atoms in the heterocyclyl can be oxidized. The ring that includes the heteroatom can be aromatic or nonaromatic. Aromatic heterocycles are sometimes refered to herein as heteroaryls. Unless otherwise noted, the heterocyclyl is attached to its pendant group at any heteroatom or carbon atom that results in a stable structure. Representative examples of a $C_2$-$C_{10}$ heterocyclyl include, but are not limited to, tetrahyrofuranyl, oxetanyl, pyranyl, pyrrolidinyl, piperidinyl, piperazinyl, benzofuranyl, benzothiophene, benzothiazolyl, indolyl, benzopyrazolyl, pyrrolyl, thiophenyl (thiopene), furanyl, thiazolyl, imidazolyl, pyrazolyl, triazolyl, quinolinyl including moieties such as 1,2,3,4-tetrshyhro-quinolinyl, pyrimidinyl, pyridinyl, pyridonyl, pyrazinyl, pyridazinyl, isothiazolyl, isoxazolyl, tetrazolyl, epoxide, oxetane and BODIPY (substituted or unsubstituted). A $C_2$-$C_{10}$ heterocyclyl can be substituted with up to seven groups including, but not limited to, $C_1$-$C_8$ alkyl, $C_1$-$C_8$ heteroalkyl, —OR$^{11}$, aryl, —C(O)R$^{11}$, —OC(O)R$^{11}$, —C(O)OR$^{11}$, —C(O)NH$_2$, —C(O)NHR$^{11}$, —C(O)N(R$^{11}$)$_2$, —NHC(O)R$^{11}$, —S(=O)$_2$R$^{11}$, —S(O)R$^{11}$, halogen, —N$_3$, —NH$_2$, —NH(R$^{11}$), —N(R$^{11}$)$_2$ and —CN; wherein each $R^{11}$ is independently selected from —H, $C_1$-$C_8$ alkyl, $C_1$-$C_8$ heteroalkyl and aryl. In some embodiments, a substituted heterocyclyl can also include one or more of: —NHC(=NH)NH$_2$, —NHCONH$_2$, —S(=O)$_2$R$^{11}$ and —SR$^{11}$. Heterocyclo or $C_2$-$C_{10}$ heterocyclo is the corresponding divalent moiety. Divalent aromatic heterocycles are sometimes referred to herein as heteroarylene or $C_2$-$C_{10}$ heteroarylene.

As noted above, aromatic heterocycles are sometimes refered to herein as heteroaryls, and preferably contain 5-14, 6-14, or 6-20 carbon atons in addition to heteroatoms. Heteroaryls may be monocyclic, bicyclic, or tricyclic ring systems. Representative heteroaryls include but are not limited to triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, and quinoxalinyl. Heteroaryls are optionally substituted. Typical substituents include, but are not limited to, —X, —$R^h$, —O—, —OR$^h$, —SR$^h$, —S$^-$, —NR$_2$, —NR$_3$, =NR$^h$, —CX$_3$, —CN, —OCN, —SCN, —N=C=O, —NCS, —NO, —NO$_2$, =N$_2$, —N$_3$, —NR$^h$C(=O)R$^h$, —C(=O)NR$^h_2$, —SO$_3^-$, —SO$_3$H, —S(=O)$_2$R$^h$, —OS(=O)$_2$OR$^h$, —S(=O)$_2$NR$^h$, —S(=O)R$^h$, —OP(=O)(OR$^h$)$_2$, —P(=O)(OR$^h$)$_2$, —PO$_3^{2-}$, PO$_3$H$_2$, —AsO$_2$H$_2$, —C(=O)R$^h$, —C(=O)X, —C(=S)R$^h$, —CO$_2$R$^h$, —CO$_2^-$, —C(=S)OR$^h$, —C(=O)SR$^h$, —C(=S)SR$^h$, —C(=O)NR$^h_2$, —C(=S)NR$^h_2$, —C(=NR)NR$^h_2$, $C_1$-$C_{20}$ heteroalkyl, $C_6$-$C_{20}$ aryl, $C_3$-$C_8$ heterocyclyl, a protecting group or a prodrug moiety, where each X is independently a halogen: —F, —Cl, —Br, or —I; and each $R^h$ is independently —H or $C_1$-$C_6$ alkyl. Divalent aromatic heterocycles are sometimes referred to herein as heteroarylenes or $C_1$-$C_{10}$ heteroarylenes.

Unless otherwise indicated, "heteroaralkyl" by itself or part of another term, means an alkyl group, as defined above, substituted with an aromatic heterocyclyl group, as defined above. Heteroaralklo is the corresponding divalent moiety.

Unless otherwise indicated, "$C_3$-$C_8$ carbocyclyl" by itself or as part of another term, is a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative $C_3$-$C_8$ carbocyclyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(1.1.1.) pentane, and bicyclo(2.2.2.)octane. A $C_3$-$C_8$ carbocyclyl group can be unsubstituted or substituted with up to seven groups including, but not limited to, $C_1$-$C_8$ alkyl, $C_1$-$C_8$ heteroalkyl, —OR$^{11}$, aryl, —C(O)R$^{11}$, —OC(O)R$^{11}$, —C(O)OR$^{11}$, —C(O)NH$_2$, —C(O)NHR$^{11}$, —C(O)N(R$^{11}$)$_2$, —NHC(O)R$^{11}$, —S(=O)$_2$R$^{11}$, —S(=O)R$^{11}$, —OH, -halogen, —N₃, —NH₂, —NH(R¹¹), —N(R¹¹)₂ and —CN; where each R¹¹ is independently selected from —H, C₁-C₈ alkyl, C₁-C₈ heteroalkyl and aryl. "C₃-C₈ carbocyclo" is the corresponding divalent moiety.

As used herein, an azido substituent refers to —N=N=N; a cyanate substituent refers to —O—CN; a thiocyanate substituent refers to —S—CN; an isocyanate substituent refers to —N=C=O; and a thioisocyanate substituent refers to —S—N=C=O.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Glycosyl" refers to the structure:

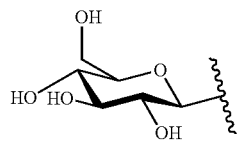

or substituted forms of same, for instance including the references structure substituted to form structures such as:

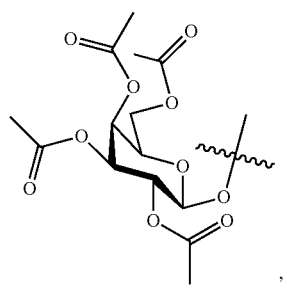

,

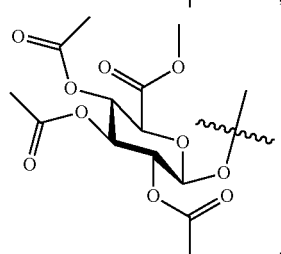

,

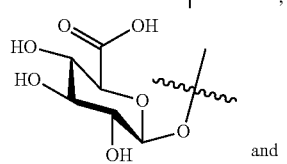

and

-continued

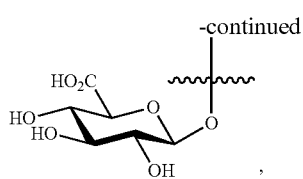

, and many others.

Stereochemical definitions and conventions used herein generally follow S. P. Parker, Ed., McGraw-Hill Dictionary of Chemical Terms, McGraw-Hill Book Company, New York (1984); and Eliel and Wilen, Stereochemistry of Organic Compounds, John Wiley & Sons, Inc., New York (1994). Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

As used herein, "-PABA-" or "PABA" refers to the p-aminobenzoic acid and moieties derived therefrom, for instance the structure:

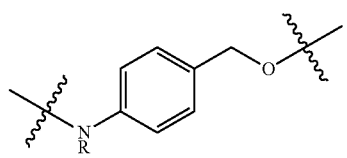

or variants thereof.

As used herein, "-PABC-" or "PABC" refers to p-aminobenzyloxycarbonyl and moieties derived therefrom, for instance the structure:

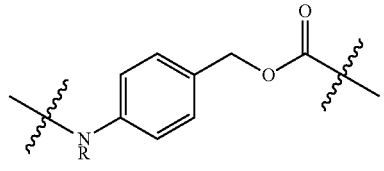

or variants thereof.

An amino acid "derivative" includes an amino acid having substitutions or modifications by covalent attachment of a parent amino acid, such as, e.g., by alkylation, glycosylation, acetylation, phosphorylation, and the like. Further included within the definition of "derivative" is, for example, one or more analogs of an amino acid with substituted linkages, as well as other modifications known in the art.

A "natural amino acid" refers to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context.

"Protecting group" refers to a moiety that when attached to a reactive group in a molecule masks, reduces or prevents that reactivity. Examples of protecting groups can be found in T. W. Greene and P. G. M. Wuts, Protective Groups in Organic Synthesis, 3rd edition, John Wiley & Sons, New York, 1999, and Harrison and Harrison et al., Compendium of Synthetic Organic Methods, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers.

Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The phrase "pharmaceutically acceptable salt," as used herein, refers to pharmaceutically acceptable organic or inorganic salts of a compound. The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, malate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refer to an association of one or more solvent molecules and a compound or conjugate of the invention. Examples of solvents that form pharmaceutically acceptable solvates include, but are not limited to, water, isopropanol, ethanol, methanol, DMSO, ethyl acetate, acetic acid, and ethanolamine.

The terms "loading" or "drug loading" or "payload loading" represent or refer to the average number of payloads ("payload" and "payloads" are used interchangeable herein with "drug" and "drugs") per antibody in an ADC molecule. Drug loading may range from 1 to 20 drugs per antibody. This is sometimes referred to as the DAR, or drug to antibody ratio. Compositions of the ADCs described herein typically have DAR's of from 1-20, and in certain embodiments from 1-8, from 2-8, from 2-6, from 2-5 and from 2-4. Typical DAR values are 2, 4, 6 and 8. The average number of drugs per antibody, or DAR value, may be characterized by conventional means such as UV/visible spectroscopy, mass spectrometry, ELISA assay, and HPLC. The quantitative DAR value may also be determined. In some instances, separation, purification, and characterization of homogeneous ADCs having a particular DAR value may be achieved by means such as reverse phase HPLC or electrophoresis. DAR may be limited by the number of attachment sites on the antibody. For example, where the attachment is a cysteine thiol, an antibody may have only one or several cysteine thiol groups, or may have only one or several sufficiently reactive thiol groups through which a Linker unit may be attached. In some embodiments, the cysteine thiol is a thiol group of a cysteine residue that forms an interchain disulfide bond. In some embodiments, the cysteine thiol is a thiol group of a cysteine residue that does not form an interchain disulfide bond. Typically, fewer than the theoretical maximum of drug moieties are conjugated to an antibody during a conjugation reaction. An antibody may contain, for example, many lysine residues that do not react with a linker or linker intermediate. Only the most reactive lysine groups may react with a reactive linker reagent.

Generally, antibodies do not contain many, if any, free and reactive cysteine thiol groups which may be linked to a drug via a linker. Most cysteine thiol residues in the antibodies exist as disulfide bridges and must be reduced with a reducing agent such as dithiothreitol (DTT). The antibody may be subjected to denaturing conditions to reveal reactive nucleophilic groups such as lysine or cysteine. The loading (drug/antibody ratio) of an ADC may be controlled in several different manners, including: (i) limiting the molar excess of drug-linker relative to the antibody, (ii) limiting the conjugation reaction time or temperature, and (iii) partial or limiting reductive conditions for cysteine thiol modification. Where more than one nucleophilic group reacts with a drug-linker then the resulting product is a mixture of ADCs with a distribution of one or more drugs moieties per antibody. The average number of drugs per antibody may be calculated from the mixture by, for example, dual ELISA antibody assay, specific for antibody and specific for the drug. Individual ADCs may be identified in the mixture by mass spectroscopy, and separated by HPLC, e. g, hydrophobic interaction chromatography.

Below is a list of abbreviations and definitions that may not otherwise be defined or described in this application: DMSO (refers to dimethyl sulfoxide), HRMS (refers to high resolution mass spectrometry), DAD (refers to diode array detection), TFA (refers to 2,2,2-trifluoroacetic acid or trifluoroacetic acid), TFF (refers to tangential flow filtration), EtOH (refers to ethanol), MW (refers to molecular weight), HPLC (refers to high performance liquid chromatography), prep HPLC (refers to preparative high performance liquid chromatography), etc. (refers to and so forth), trityl (refers 1,1',1"-ethane-1,1,1-triyltribenzene), THF (refers to tetrahydrofuran), NHS (refers to 1-Hydroxy-2,5-pyrrolidinedione), Cbz (refers to carboxybenzyl), eq. (refers to equivalent), n-BuLi (refers to n-butyllithium), OAc (refers to acetate), MeOH (refers to methanol), i-Pr (refers to isopropyl or propan-2-yl), NMM (refers to 4-methylmorpholine), and "-" (in a table refers to no data available at this time).

Divalent moieties and substituents used herein are meant to refer to said moieties or substituents bound or linked in either direction or both directions. For instance, the moiety —C(O)NR— (in the definition of $L^{B1}$, and elsewhere) is meant to convey —C(O)NR— as well as —NRC(O)—, the moiety —C(O)$C_1$-$C_6$alkyl- is meant to convey —C(O)$C_1$-$C_6$alkyl- as well as —$C_1$-$C_6$alkylC(O)—, and so on. More generally, a description of a non-symmetrical divalent moiety linked on its "left" and "right" sides is meant to convey both the moiety as presented (left side of the moiety linked on left side as written, right side of the moiety linked on the right side as written) and the reverse of the moiety as presented (left side of the moiety linked on right side as written, right side of the moiety linked on the left side as written).

The terms "bond" and "absent" are both used herein to describe a variable which does not include an atom or atoms. Thus, where a divalent variable that is "absent" is understood to mean that the adjacent moieties are bound to one another. For example, if $L^{B2}$ is absent it is understood that $L^{B1}$ maybe bound to $L^{B3}$; or if $L^{B1}$ and $L^{B2}$ are both absent it is understood that $L^A$ may be bound to $L^{B3}$. Similarly, if a divalent variable is defined as being a "bond" this is understood to mean that there are no atoms present and the adjacent moieties are bound to one another. Thus, for instance, where variable "D" is defined as being a bond it is appreciated that the carbons adjacent D (in the structure defining $T^2$) are bound to one another. An absent monovalent variable is understood to be a hydrogen or an electron pair capable of further covalent bonding.

The Antibody Unit (A, Ab or AB)

As noted above, the term "antibody" (or "A", "Ab" or "AB") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. In addition, while certain aspects of the invention described herein refer to antibody drug conjugates, it is further envisioned that the antibody portion of the conjugate might be replaced with anything that specifically binds or reactively associates or complexes with a receptor, antigen or other receptive moiety associated with a given target-cell population. For example, instead of containing an antibody a conjugates of the invention could contain a targeting molecule that binds to, complexes with, or reacts with a receptor, antigen or other receptive moiety of a cell population sought to be therapeutically or otherwise biologically modified. Example of such molecules include smaller molecular weight proteins, polypeptide or peptides, lectins, glycoproteins, non-peptides, vitamins, nutrient-transport molecules (such as, but not limited to, transferrin), or any other cell binding molecule or substances. In certain aspects, the antibody or other such targeting molecule acts to deliver a drug to the particular target cell population with which the antibody or other targeting molecule interacts.

In another aspect, the present invention relates to an antibody drug conjugate compound of Formulae IIIA or IIIB wherein the antibody AB is selected from: trastuzumab, trastuzumab mutants (for instance the trastuzumab mutants disclosed herein or in international patent application PCT/IB2012/056234), oregovomab, edrecolomab, cetuximab, a humanized monoclonal antibody to the vitronectin receptor ($\alpha_v\beta_3$), alemtuzumab, anti-HLA-DR antibodies including a humanized anti-HLA-DR antibody for the treatment of non-Hodgkin's lymphoma, 131I Lym-1, anti-HLA-Dr10 antibodies including a murine anti-HLA-Dr10 antibody for the treatment of non-Hodgkin's lymphoma, anti-cd33 antibodies, anti-cd22 antibodies including a humanized anti-CD22 mAb for the treatment of Hodgkin's Disease or non-Hodgkin's lymphoma, labetuzumab, bevacizumab, ibritumomab tiuxetan, ofatumumab, panitumumab, rituximab, tositumomab, ipilimumab, and gemtuzumab.

Heteroatoms that may be present on an antibody unit include sulfur (in one embodiment, from a sulfhydryl group of an antibody), oxygen (in one embodiment, from a carbonyl, carboxyl or hydroxyl group of an antibody) and nitrogen (in one embodiment, from a primary or secondary amino group of an antibody). These hetero atoms can be present on the antibody in the antibody's natural state, for example a naturally-occurring antibody, or can be introduced into the antibody via chemical modification.

In one embodiment, an antibody unit has a sulfhydryl group and the antibody unit bonds via the sulfhydryl group's sulfur atom.

In another embodiment, the antibody has lysine residues that can react with activated esters (such esters include, but are not limited to, N-hydroxysuccinimde, pentafluorophenyl, and p-nitrophenyl esters) and thus form an amide bond consisting of the nitrogen atom of the antibody unit and a carbonyl.

In yet another aspect, the antibody unit has one or more lysine residues that can be chemically modified to introduce one or more sulfhydryl groups. The reagents that can be used to modify lysines include, but are not limited to, N-succinimidyl S-acetylthioacetate (SATA) and 2-Iminothiolane hydrochloride (Traut's Reagent).

In another embodiment, the antibody unit can have one or more carbohydrate groups that can be chemically modified to have one or more sulfhydryl groups.

In yet another embodiment, the antibody unit can have one or more carbohydrate groups that can be oxidized to provide an aldehyde group (see, e.g., Laguzza, et al., 1989, J. Med. Chem. 32(3):548-55). The corresponding aldehyde can form a bond with a reactive site such as, for example, hydrazine and hydroxylamine. Other protocols for the modification of proteins for the attachment or association of drugs are described in Coligan et al., Current Protocols in Protein Science, vol. 2, John Wiley & Sons (2002) (incorporated herein by reference).

When the conjugates comprise non-immunoreactive protein, polypeptide, or peptide units instead of an antibody, useful non-immunoreactive protein, polypeptide, or peptide units include, but are not limited to, transferrin, epidermal growth factors ("EGF"), bombesin, gastrin, gastrin-releasing peptide, platelet-derived growth factor, IL-2, IL-6, transforming growth factors ("TOP"), such as TGF-$\alpha$ and TGF-$\delta$, vaccinia growth factor ("VGF"), insulin and insulin-like growth factors I and II, somatostatin, lectins and apoprotein from low density lipoprotein.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric monoclonal antibodies. Human monoclonal antibodies may be made by any of numerous techniques known in the art (e.g., Teng et al., 1983, Proc. Natl. Acad. Sci. USA. 80:7308-7312; Kozbor et al., 1983, Immunology Today 4:72-79; and Olsson et al., 1982, Meth. Enzymol. 92:3-16).

The antibody can also be a bispecific antibody. Methods for making bispecific antibodies are known in the art and are discussed infra.

The antibody can be a functionally active fragment, derivative or analog of an antibody that immunospecifically binds to target cells (e.g., cancer cell antigens, viral antigens, or microbial antigens) or other antibodies that bind to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (for location of the CDR sequences, see, e.g., Kabat et al., 1991, Sequences of Proteins of Immunological Interest, Fifth Edition, National Institute of Health, Bethesda, Md.; Kabat E et al., 1980, J. Immunology 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. No. 4,816,567; and U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239: 1534; and Beidler et al., 1988, J. Immunol. 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (now Amgen, Freemont, Calif.) and Medarex (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903). Human antibodies can also be produced using various techniques known in the art, including phage display libraries (see, e.g., Hoogenboom and Winter, 1991, J. Mol. Biol. 227:381; Marks et al., 1991, J. Mol. Biol. 222:581; Quan and Carter, 2002, The rise of monoclonal antibodies as therapeutics, In Anti-IgE and Allergic Disease, Jardieu and Fick, eds., Marcel Dekker, New York, N.Y., Chapter 20, pp. 427-469).

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, OVAREX which is a murine antibody for the treatment of ovarian cancer; PANOREX (Glaxo Wellcome, NC) which is a murine $IgG_{2a}$ antibody for the treatment of colorectal cancer; Cetuximab ERBITUX (Imclone Systems Inc., NY) which is an anti-EGFR IgG chimeric antibody for the treatment of epidermal growth factor positive cancers, such as head and neck cancer; Vitaxin (Medlmmune, Inc., MD) which is a humanized antibody for the treatment of sarcoma; CAMPATH I/H (Leukosite, MA) which is a humanized $IgG_1$ antibody for the treatment of chronic lymphocytic leukemia (CLL); SMART ID10 (Protein Design Labs, Inc., CA) which is a humanized anti-HLA-DR antibody for the treatment of non-Hodgkin's lymphoma; ONCOLYM (Techniclone, Inc., CA) which is a radiolabeled murine anti-HLA-Dr10 antibody for the treatment of non-Hodgkin's lymphoma; ALLOMUNE (BioTransplant, CA) which is a humanized anti-CD2 mAb for the treatment of Hodgkin's Disease or non-Hodgkin's lymphoma; and CEACIDE (Immunomedics, NJ) which is a humanized anti-CEA antibody for the treatment of colorectal cancer.

In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

The Linker Unit (L)

A linker (sometimes referred to as "[linker]" herein) is a bifunctional compound which can be used to link a drug and an antibody to form an antibody drug conjugate (ADC). Such conjugates are useful, for example, in the formation of immunoconjugates directed against tumor associated antigens. Such conjugates allow the selective delivery of cytotoxic drugs to tumor cells.

In an ADC the linker serves to attach the payload to the antibody.

In one aspect, a second section of the linker unit is introduced which has a second reactive site e.g., an electrophilic group that is reactive to a nucleophilic group present on an antibody unit (e.g., an antibody). Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups. The electrophilic group provides a convenient site for antibody attachment.

In another embodiment, a linker unit has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide. The electrophilic group on an antibody provides a convenient site for attachment to a linker unit.

Amino functional groups are also useful reactive sites for a linker unit because they can react with carboxylic acid, or activated esters of a compound to form an amide linkage. Typically, the peptide-based compounds of the invention can be prepared by forming a peptide bond between two or more amino acids and/or peptide fragments. Such peptide bonds can be prepared, for example, according to the liquid phase synthesis method (see, e.g., Schroder and Lubke, "The Peptides", volume 1, pp 76-136, 1965, Academic Press) that is well known in the field of peptide chemistry.

In the context of the invention, particularly but not limited to linker components such as $L_1$, $L_2$ (including $L_2^A$, $L_2^B$ and $L_2^C$) and $L_3$, the language "selected from one or more of" or "one or more of" indicates that multiple components, which may be the same or different, are or may be arranged sequentially. Thus, for example, $L_3$ may be —$C_{1-6}$alkyl-, —NR— or the other individually listed components, but also —$C_{1-6}$alkyl-NR—, or any other combination of 2 or more listed components.

In another embodiment, a linker unit has a reactive site that can react with antibody nucleophiles, such as cysteines. The reactive site is comprised of a heterocycle that is substituted with a sulfone. The sulfone is then replaced by the antibody nucleophile (i.e. cysteine) and the newly formed bond between the antibody and the heterocycle connects the antibody to the linker. See, WO 2014/144878.

Synthesis of Compounds and Antibody Drug Conjugates Thereof

The compounds and conjugates of the invention can be made using the synthetic procedures outlined below in the Exemplification. As described in more detail below, the compounds and conjugates of the invention can be prepared using a section of a linker unit having a reactive site for binding to the compound. In one aspect, a second section of the linker unit is introduced which has a second reactive site e.g., an electrophilic group that is reactive to a nucleophilic group present on an antibody unit (e.g., an antibody). Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups. The electrophilic group provides a convenient site for antibody attachment.

In another embodiment, a linker unit has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide. The electrophilic group on an antibody provides a convenient site for attachment to a linker unit.

Amino functional groups are also useful reactive sites for a linker unit because they can react with carboxylic acid, or activated esters of a compound to form an amide linkage. Typically, the peptide-based compounds of the invention can be prepared by forming a peptide bond between two or more amino acids and/or peptide fragments. Such peptide bonds can be prepared, for example, according to the liquid phase synthesis method (see, e.g., Schroder and Lubke, "The Peptides", volume 1, pp 76-136, 1965, Academic Press) that is well known in the field of peptide chemistry.

As described in more detail below, the conjugates can be prepared using a section of the linker having a reactive site for binding to a compound of the invention and introducing another section of the linker unit having a reactive site for an antibody. In one aspect, a linker unit has a reactive site which has an electrophilic group that is reactive with a nucleophilic group present on an antibody unit, such as an antibody. The electrophilic group provides a convenient site for antibody attachment. Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups.

In another embodiment, a linker unit has a reactive site which has a nucleophilic group that is reactive with an electrophilic group present on an antibody unit. The electrophilic group on an antibody provides a convenient site for attachment to a linker unit. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide.

Conjugation with Transglutaminase

In certain embodiments, a compound of the invention may be covalently crosslinked to an Fc-containing or Fab-containing polypeptide engineered with an acyl donor glutamine-containing tag (e.g., Gln-containing peptide tags or Q-tags) or an endogenous glutamine made reactive (i.e., the ability to form a covalent bond as an acyl donor in the presence of an amine and a transglutaminase) by polypeptide engineering (e.g., via amino acid deletion, insertion, substitution, mutation, or any combination thereof on the polypeptide), in the presence of transglutaminase, provided that the compound of the invention comprises an amine donor agent (e.g., small molecule comprising or attached to a reactive amine), thereby forming a stable and homogenous population of an engineered Fc-containing polypeptide conjugate with the amine donor agent being site-specifically conjugated to the Fc-containing or Fab-containing polypeptide through the acyl donor glutamine-containing tag or the exposed/accessible/reactive endogenous glutamine. For example, compounds of the invention may be conjugated as described in International Patent Application Serial No. PCT/IB2011/054899, whose entire contents are incorporated herein by reference. In certain embodiments, to facilitate conjugation of the compound of the invention to an Fc-containing or Fab-containing polypeptide engineered with an acyl donor glutamine-containing tag or an endogenous glutamine made reactive by polypeptide engineering in the presence of transglutaminase, Z is $NH_2$.

Conjugation to the Human Light Chain Kappa Domain Constant Region

In certain embodiments, a compound of the invention may be covalently attached to the side chain of $K^{188}$ of the human light chain kappa domain constant region (CLκ) (full light chain numbering according to Kabat). For example, compounds of the invention may be conjugated as described in U.S. patent application Ser. No. 13/180,204, whose entire contents are incorporated herein by reference. In certain embodiments, to facilitate conjugation to K188 CLκ, Z is

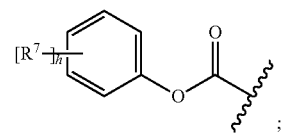

$R^7$ is independently selected for each occurrence from the group consisting of F, Cl, I, Br, $NO_2$, CN and $CF_3$; and h is 1, 2, 3, 4 or 5.

In certain embodiments, the invention provides for a composition comprising a compound of the invention covalently conjugated to an antibody (or antigen binding portion thereof), wherein at least about 50%, or at least about 60%, or at least about 70%, or at least about 80%, or at least about 90% of the compound of the invention in the composition is conjugated to the antibody or antigen binding portion thereof at $K^{188}$ CLκ.

In certain embodiments, the compounds of the invention may be conjugated to the combining site of a catalytic antibody, such as aldolase antibodies, or antigen binding portion thereof. Aldolase antibodies contain combining site portions that, when unencumbered (for example by conjugation), catalyze an aldol addition reaction between an aliphatic ketone donor and an aldehyde acceptor. The contents of US Patent Application Publication No. US 2006/205670 are incorporated herein by reference, in particular pages 78-118 describing linkers, and paragraphs [0153]-[0233] describing antibodies, useful fragments, variants and modifications thereof, h38C2, combining sites and complimentary determining regions (CDRs), and related antibody technology. The term "combining site" includes the CDRs and the adjacent framework residues that are involved in antigen binding.

Compositions and Methods of Administration

In other embodiments, another aspect of the invention relates to pharmaceutical compositions including an effective amount of a compound of the invention and/or antibody drug conjugate thereof and a pharmaceutically acceptable carrier or vehicle. In certain embodiments, the compositions are suitable for veterinary or human administration.

The present pharmaceutical compositions can be in any form that allows for the composition to be administered to a patient. For example, the composition can be in the form of a solid or liquid. Typical routes of administration include, without limitation, parenteral, ocular and intra-tumor. Parenteral administration includes subcutaneous injections, intravenous, intramuscular or intrasternal injection or infusion techniques. In one aspect, the compositions are administered parenterally. In a specific embodiment, the compositions are administered intravenously.

Pharmaceutical compositions can be formulated so as to allow a compound of the invention and/or antibody drug conjugate thereof to be bioavailable upon administration of the composition to a patient. Compositions can take the form of one or more dosage units, where for example, a tablet can be a single dosage unit, and a container of a compound of the invention and/or antibody drug conjugate thereof in liquid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors.

Relevant factors include, without limitation, the type of animal (e.g., human), the particular form of the a compound of the invention and/or antibody drug conjugate thereof, the manner of administration, and the composition employed.

The pharmaceutically acceptable carrier or vehicle can be solid or particulate, so that the compositions are, for example, in tablet or powder form. The carrier(s) can be liquid. In addition, the carrier(s) can be particulate.

The composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of a compound of the invention and/or antibody drug conjugate thereof that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound of the invention and/or antibody drug conjugate thereof such that a suitable dosage will be obtained. Typically, this amount is at least about 0.01% of a compound of the invention and/or antibody drug conjugate thereof by weight of the composition. In an exemplary embodiment, pharmaceutical compositions are prepared so that a parenteral dosage unit contains from about 0.01% to about 2% by weight of the amount of a compound of the invention and/or antibody drug conjugate thereof.

For intravenous administration, the composition can comprise from about 0.01 to about 100 mg of a compound of the invention and/or antibody drug conjugate thereof per kg of the patient's body weight. In one aspect, the composition can include from about 1 to about 100 mg of a compound of the invention and/or antibody drug conjugate thereof per kg of the patient's body weight. In another aspect, the amount administered will be in the range from about 0.1 to about 25 mg/kg of body weight of a compound of the invention and/or antibody drug conjugate thereof.

Generally, the dosage of a compound of the invention and/or antibody drug conjugate thereof administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight.

A compound of the invention and/or antibody drug conjugate thereof can be administered by any convenient route, for example by infusion or bolus injection. Administration can be systemic or local. Various delivery systems are known, e.g., encapsulation in liposomes, microparticles, microcapsules, capsules, etc., and can be used to administer a compound of the invention and/or antibody drug conjugate thereof. In certain embodiments, more than one compound of the invention and/or antibody drug conjugate thereof is administered to a patient.

In specific embodiments, it can be desirable to administer one or more compounds of the invention and/or antibody drug conjugates thereof locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In yet another embodiment, the compound of the invention and/or antibody drug conjugate thereof can be delivered in a controlled release system, such as but not limited to, a pump or various polymeric materials can be used. In yet another embodiment, a controlled-release system can be placed in proximity of the target of the compound of the invention and/or antibody drug conjugate thereof, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which a compound or antibody drug conjugate thereof is administered. Such pharmaceutical carriers can be liquids, such as water and oils, including those of petroleum, animal, vegetable or synthetic origin. The carriers can be saline, and the like. In addition, auxiliary, stabilizing and other agents can be used. In one embodiment, when administered to a patient, the compound or conjugate and pharmaceutically acceptable carriers are sterile. Water is an exemplary carrier when the compound or conjugate are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

The present compositions can take the form of solutions, pellets, powders, sustained-release formulations, or any other form suitable for use. Other examples of suitable pharmaceutical carriers are described in "Remington's Pharmaceutical Sciences" by E. W. Martin.

In an embodiment, the compound of the invention and/or antibody drug conjugate thereof are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a compound of the invention and/or antibody drug conjugate thereof is to be administered by infusion, it can be dispensed, for example, with an infusion bottle containing sterile pharmaceutical grade water or saline. Where the compound of the invention and/or antibody drug conjugate thereof is administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer.

Therapeutics Uses of Compounds and Antibody Drug Conjugates Thereof

Another aspect of the invention relates to a method of using the compounds of the invention and antibody drug conjugates thereof for treating cancer.

The compounds of the invention and/or antibody drug conjugates thereof are useful for inhibiting the multiplication of a tumor cell or cancer cell, causing apoptosis in a tumor or cancer cell, or for treating cancer in a patient. The compounds of the invention and/or antibody drug conjugates thereof can be used accordingly in a variety of settings for the treatment of animal cancers. Said conjugates can be used to deliver a compound of the invention to a tumor cell or cancer cell. Without being bound by theory, in one embodiment, the antibody of the conjugate binds to or associates with a cancer-cell or a tumor-cell-associated antigen, and the conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. In certain embodiments, once inside the cell, one or more specific peptide sequences are enzymatically or hydrolytically cleaved by one or more tumor cell or cancer cell-associated proteases, resulting in release of a compound of the invention from the conjugate. The released compound of the invention is then free to migrate within the cell and induce cytotoxic or cytostatic activities. The conjugate also can be cleaved by an intracellular protease to release a compound of the invention. In an alternative embodiment, the compound of the invention is cleaved from conjugate outside the tumor cell or cancer cell, and the compound of the invention subsequently penetrates the cell.

In certain embodiments, the conjugates provide conjugation-specific tumor or cancer drug targeting, thus reducing general toxicity of the compounds of the invention.

In another embodiment, the antibody unit binds to the tumor cell or cancer cell.

In another embodiment, the antibody unit binds to a tumor cell or cancer cell antigen which is on the surface of the tumor cell or cancer cell.

In another embodiment, the antibody unit binds to a tumor cell or cancer cell antigen which is an extracellular matrix protein associated with the tumor cell or cancer cell.

The specificity of the antibody unit for a particular tumor cell or cancer cell can be important for determining those tumors or cancers that are most effectively treated.

Particular types of cancers that can be treated with a compound of the invention and/or antibody drug conjugate thereof, include but are not limited to, carcinomas of the bladder, breast, cervix, colon, endometrium, kidney, lung, esophagus, ovary, prostate, pancreas, skin, stomach, and testes; and blood born cancers including but not limited to leukemias and lymphomas.

Multi-Modality Therapy for Cancer.

Cancers, including, but not limited to, a tumor, metastasis, or other disease or disorder characterized by uncontrolled cell growth, can be treated or inhibited by administration of a compound of the invention and/or antibody drug conjugate thereof.

In other embodiments, methods for treating cancer are provided, including administering to a patient in need thereof an effective amount of a compound of the invention and/or antibody drug conjugate thereof and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. A compound of the invention and/or antibody drug conjugate thereof can be administered to a patient that has also undergone surgery as treatment for the cancer.

In some embodiments, the patient also receives an additional treatment, such as radiation therapy. In a specific embodiment, the compound of the invention and/or antibody drug conjugate thereof is administered concurrently with the chemotherapeutic agent or with radiation therapy. In another specific embodiment, the chemotherapeutic agent or radiation therapy is administered prior or subsequent to administration of a compound of the invention and/or antibody drug conjugate thereof.

A chemotherapeutic agent can be administered over a series of sessions. Any one or a combination of the chemotherapeutic agents, such a standard of care chemotherapeutic agent(s), can be administered.

Additionally, methods of treatment of cancer with a compound of the invention and/or antibody drug conjugate thereof are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

The compounds of the invention and/or antibody drug conjugates thereof can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stein cells are harvested and purged of all cancer cells, the animal's remaining bone-marrow cell population is then eradicated via the administration of a high dose of a compound of the invention and/or antibody drug conjugate thereof with or without accompanying high dose radiation therapy, and the stem cell graft is infused back into the animal. Supportive care is then provided while bone marrow function is restored and the patient recovers.

The invention is further described in the following examples, which are in not intended to limit the scope of the invention.

Exemplification of Payloads and Linker-Payloads

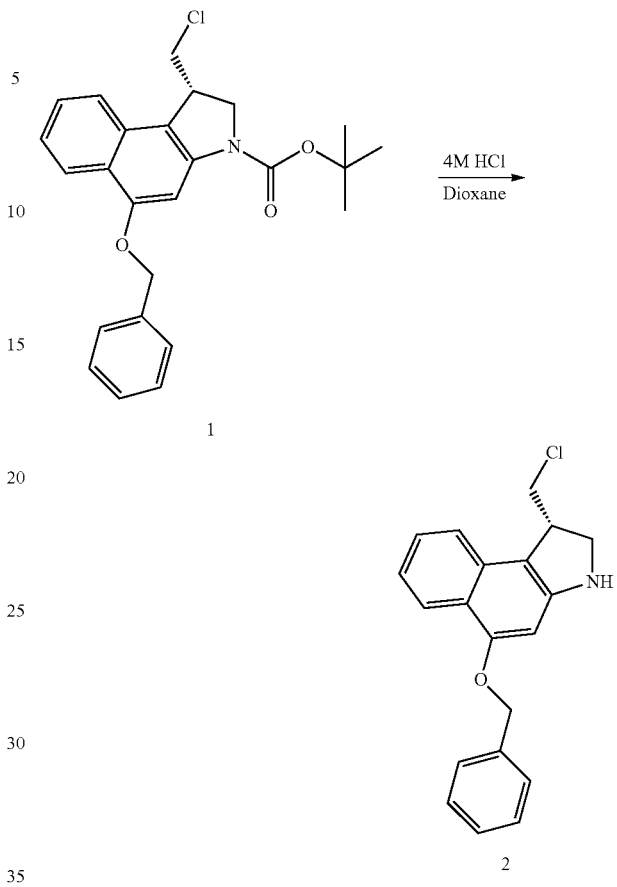

Compound 2 is a commercially known compound see PCT Int. Appl., 2005112919, 1 Dec. 2005

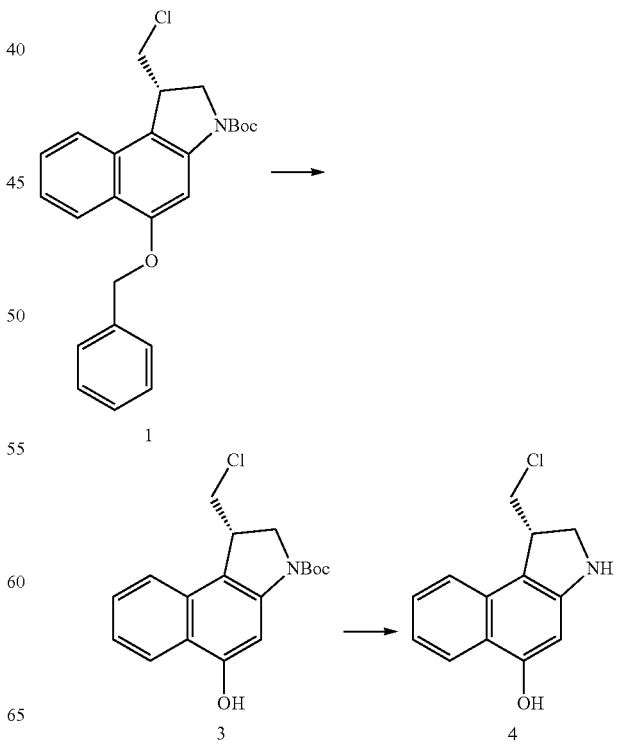

Preparation of tert-butyl(S)-1-(chloromethyl)-5-hydroxy-1,2-dihydro-3H-benzo[e]indole-3-carboxylate (3)

A solution of tert-Butyl(S)-5-(benzyloxy)-1-(chloromethyl)-1,2-dihydro-3H-benzo[e]indole-3-carboxylate (4 g, 9 mmol) in THF (250 mL) was added Pd—C (0.7 g) at 40° C. Then aqueous HCOONH4 (9.5 mL, 25%) was added portionwise and the reaction mixture was stirred at 40° C. for 1 hours. The reaction mixture was filtered and the filtrate was concentrated to dryness. The resulting residue was dissolved in ethyl acetate (250 mL) and washed with H$_2$O (20 mL), dried over Na2SO4, concentrated to dryness to give 3 as gray solid (2.9 g, 90%).

Preparation of (S)-1-(chloromethyl)-2,3-dihydro-1H-benzo[e]indol-5-ol (4)

To a round bottom flask containing 3 (820 mg, 2.46 mmol), 4 M HCl in dioxane (36 mL, 140 mmol) was added. The reaction was allowed to stir at room temperature. Reaction was reduced down and then placed underneath vacuum (belt pump) providing 4 (684 mg, 100%) as a gray solid.

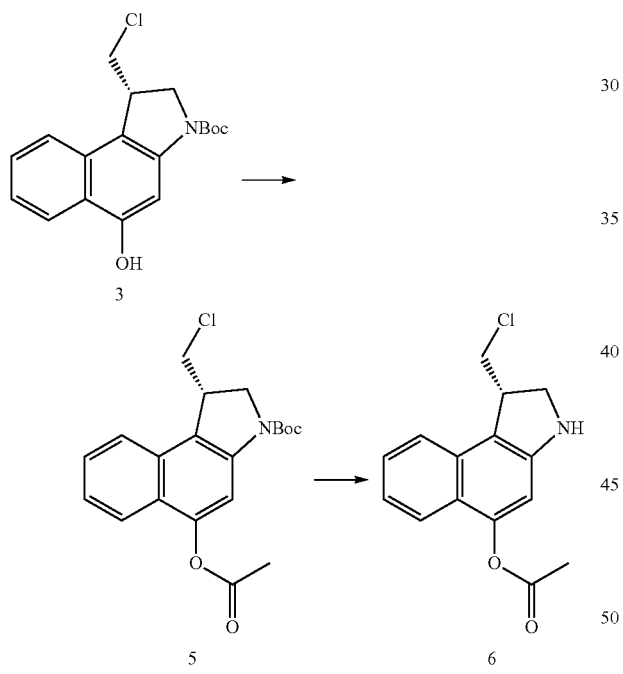

Preparation of tert-butyl(S)-5-acetoxy-1-(chloromethyl)-1,2-dihydro-3H-benzo[e]indole-3-carboxylate (5)

Acetyl chloride (0.1 mL, 1.4 mmol) was added to a solution of (S)-tert-butyl 1-(chloromethyl)-5-hydroxy-1H-benzo[e]indole-3(2H)-carboxylate [3] (230 mg, 0.7 mmol) in CH$_2$Cl$_2$ (6 mL) at 0° C., followed by pyridine (0.11 mL, 1.4 mmol). The mixture was stirred at 0° C. for 2 min, and then at room temperature for 1 h. The mixture was concentrated, and the residue was treated with EtOAc and water, extracted with EtOAc. The combined organic phases were washed with water and brine, dried over MgSO4. The solvent was removed under vacuo to give 5 as light yellow solid (235 mg, 91%). LC-MS (Protocol B): m/z 398.3 [M+H].

Preparation of (S)-1-(chloromethyl)-2,3-dihydro-1H-benzo[e]indol-5-yl acetate (6)

To a round bottom flask containing (S)-tert-butyl-5-acetoxy-1-(chloromethyl)-1H-benzo[e]indole-3(2H)-carboxylate (375 mg, 0.998 mM), 10 mL of 4M HCl in dioxane (40 mM) was added. The reaction was allowed to stir at room temperature and then solvent removed in vacuo providing 6 (312 mg, 100%).

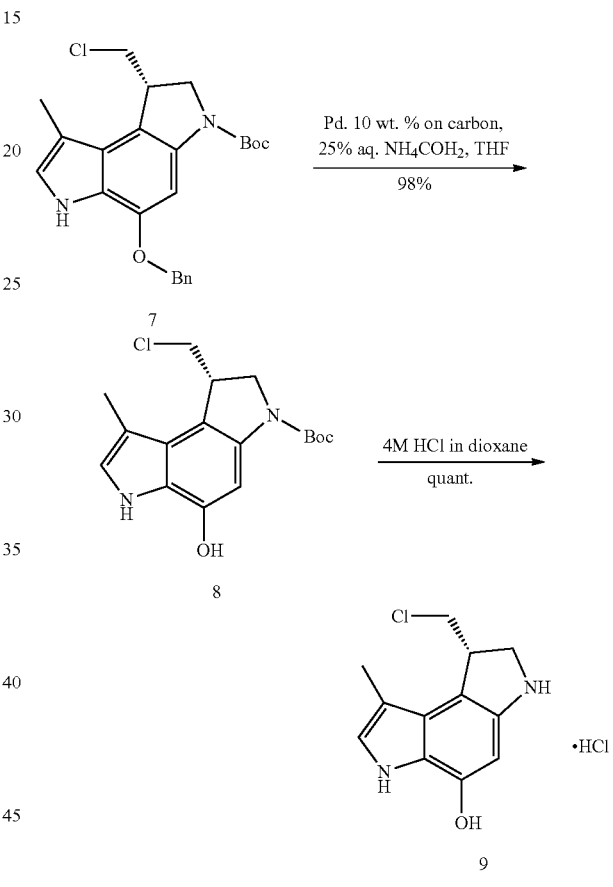

Preparation of tert-butyl-(1S)-1-(chloromethyl)-5-hydroxy-8-methyl-1,6-dihydropyrrolo[3,2-e]indole-3(2H)-carboxylate (8)

To a stirring solution of 7 (see J. Am. Chem. Soc. 1987, 109, 6837-6838) (12.2 g, 28.6 mmol) in 200 mL of THF at 0° C., Palladium 10 wt. % on carbon (4 g) was added followed by slow dropwise addition of 30 mL of 25% ammonium formate in water. The reaction was allowed to stir at 0° C. for ~90 minutes. Reaction was diluted with ether followed by the addition of sodium sulfate. The reaction was filtered through a thin pad of celite, which was then washed twice with ether. The organics where combined and then reduced down before being placed underneath vacuum yielding 7 (9.65 g, quantitative) as light gray solid. LC-MS (Protocol B): m/z 337.2 [M+H]$^+$, retention time=1.81 minutes.

Preparation of (S)-8-(chloromethyl)-1-methyl-3,6,7,8-tetrahydropyrrolo[3,2-e]indol-4-ol

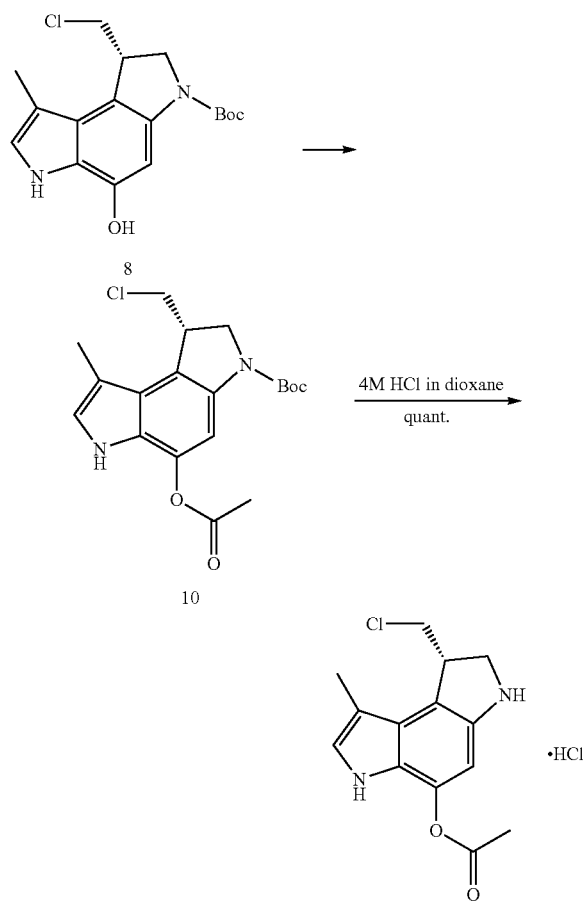

Step 1: Synthesis of Tert-Butyl (1S)-5-(acetyloxy)-1-(chloromethyl)-8-methyl-1,6-dihydropyrrolo[3,2-e]indole-3(2H)-carboxylate (188). To a stirring solution of 43 (1.99 g, 5.91 mmol) in 30 mL of dichloromethane at 0° C., acetyl chloride (0.462 mL, 6.50 mmol) was added followed immediately by pyridine (0.714 mL, 8.86 mmol). The reaction was allowed to stir at 0° C. for ~10 minutes. Reaction was reduced down onto silica. Silica chromatography was then preformed (gradient: 0%-15% acetone in heptanes). Appropriate test tubes where concentrated and placed underneath high vacuum to produce 10 (2.13 g, 95%) as a light brown solid. LC-MS (Protocol B): m/z 401.1 [M+Na]$^+$, retention time=1.93 minutes.

Step 2

Synthesis of (8S)-8-(chloromethyl)-1-methyl-3,6,7,8-tetrahydropyrrolo[3,2-e]indol-4-yl acetate hydrochloric acid salt (189). To a round bottom flask containing 10 (606 mg, 1.60 mmol), 4M HCl in dioxane (24 mL, 96 mmol) was added. The reaction was allowed to stir at room temperature for 90 minutes. Reaction was reduced down and then placed underneath high vacuum producing 11 (589 mg, quantitative) as a light green solid. LC-MS (Protocol B): m/z 279.1 [M+H]$^+$, retention time=0.72 minutes.

General Procedure A

To a stirring solution of the mono or diacid, in THF, dichloromethane, or a mixture of both at 0° C., oxalyl chloride (1-2.5 eq.) was added followed by a catalytic amount of DMF. The reaction allowed to stir at 0° C. for several minutes before being allowed to warm to room temperature, and then stir at room temperature for 30 minutes to several hours. The reaction was then concentrated in vacuo. In some cases the crude material was then azeotroped one to several times with heptane, or other relevant solvent or solvents. Crude material was then dried over high vacuum before being used in the next step.

General Procedure B

To a stirring solution of the amine (2-2.5 eq.) in THF, dichloromethane, or a mixture of both at 0° C. (or in some cases other relevant solvent or solvents), the acid chloride, or diacid chloride was added followed by pyridine (3-6 eq.), triethylamine (3-6 eq.), or other relevant base (3-6 eq.). The reaction allowed to stir at 0° C. for a few seconds to several minutes before being allowed to warm to room temperature, and then stir at room temperature for 10 minutes to several hours. The reaction was then concentrated in vacuo. In some cases the crude material was then azeotroped one to several times with heptane, or other relevant solvent or solvents. In most cases the crude material was then purified by a described method such as silica chromatography or medium pressure reverse phase C18 chromatography.

Preparation of (S)-furan-2,5-diylbis(((S)-1-(chloromethyl)-5-hydroxy-1H-benzo[e]indol-3(2H)-yl)methanone) (13)

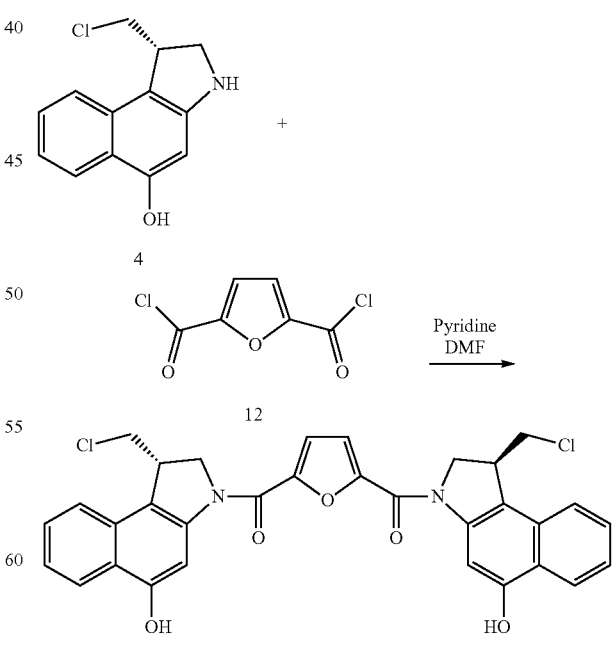

4 was dissolved in DMF (0.75 mL), was added pyridine (13 μL) and a solution of 12 (8 mg) in DMF (0.2 mL, 0.168 mmol), and the resulting solution was stirred at room temperature for overnight. The mixture was diluted with DCM, and washed with water and brine, and dried over MgSO$_4$. The crude was purified by flash chromatography in silica gel (DCM/MOH=0-10%) to give the product 13 as green solid (8 mg, 30%). LC-MS: m/z 587.4 [M+H], retention time=1.0 min. $^1$H NMR (400 MHz, DMSO-d$_6$), δ 10.50 (s), 8.14 (d), 7.95 (s), 7.88 (d), 7.55 (t), 7.50 (s), 7.40 (t), 4.78 (m), 4.58 (d), 4.25 (s), 4.02 (d), 3.92 (m).

Preparation of (S)-((1R,3S)-cyclohexane-1,3-diyl)bis(((S)-1-(chloromethyl)-5-hydroxy-1H-benzo[e]indol-3(2H)-yl)methanone) (16)

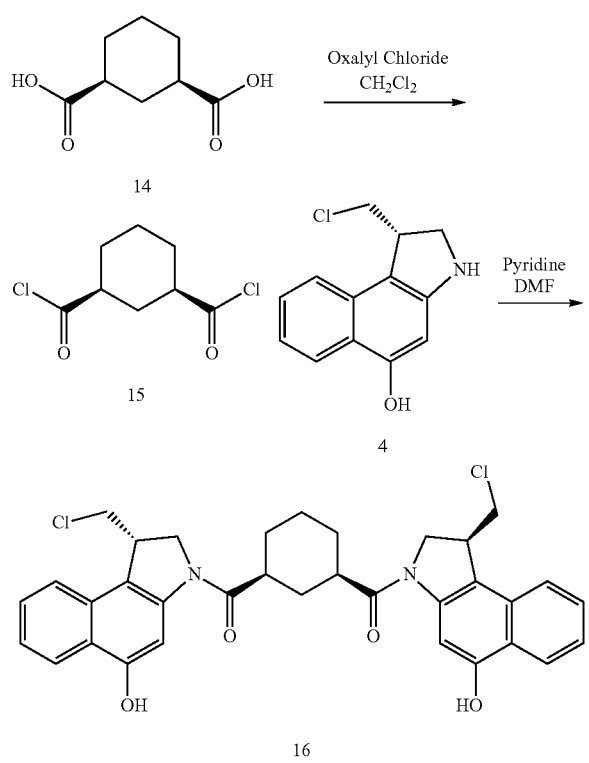

Step 1

Cis-cyclohexane-1,3-dicarboxylic acid (14, 10 mg, 0.058 mmol) was dissolved in THF (2 mL), added oxalyl chloride (2M in CH$_2$Cl$_2$, 0.09 mL, 0.17 mmol) and DMF (2 drops) at 0° C. The mixture was stirred at 0° C. for 5 min, then at room temperature for 1 h. Concentrated in vacuo to give the corresponding acid chloride 15 as off-white solid, which was used in next step without further purification.

Step 2

The above compound 15 was dissolved in DMF (2 ml) at 0° C., added (S)-1-(chloromethyl)-2,3-dihydro-1H-benzo[e]indol-5-ol HCl salt (4, 25 mg, 0.093 mmol), followed by pyridine (0.029 mL, 0.36 mmol). The mixture was stirred at room temperature for overnight. DMF was removed under reduced pressure, and the residue was purified by ISCO using MeOH/DCM (0-20%) to give the product 16 as dark blue solid (8.5 mg, 31%). LC-MS: m/z 603.4 [M+H], retention time=1.03 min. $^1$H NMR (400 MHz, DMSO-d$_6$), δ 10.36 (s), 8.09 (d), 8.03 (s), 7.80 (t), 7.53 (t), 7.33 (t), 4.44 (m), 4.33 (d), 4.18 (s), 4.02 (m), 3.85 (m), 2.88 (m), 2.04-1.90 (m), 1.74 (q), 1.52-1.45 (m).

Preparation of (S)-pyridine-2,6-diylbis(((S)-1-(chloromethyl)-5-hydroxy-1H-benzo[e]indol-3(2H)-yl)methanone) (18)

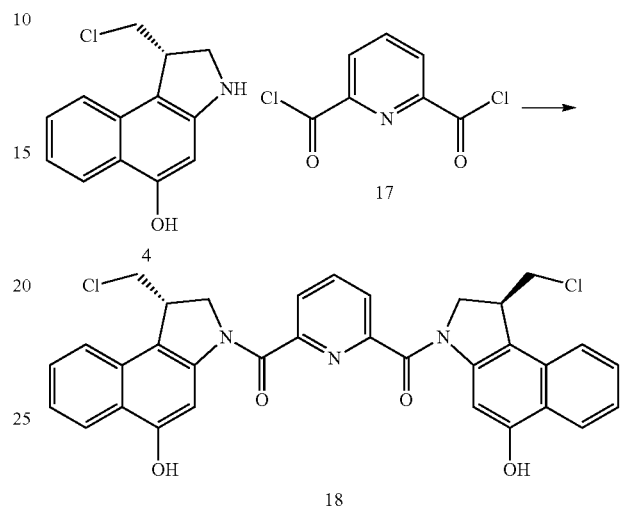

(S)-1-(chloromethyl)-2,3-dihydro-1H-benzo[e]indol-5-ol (4) (13.5 mg, HCl salt, 0.05 mmol) was dissolved in DMF (2 mL), and pyridine (8 mg, 0.10 mmol) was added, followed by 2,6-pyridinedicarbonyl dichloride (8, 5 mg, 0.025 mmol). The mixture was stirred at room temperature for 2 h. The crude was purified by ISCO using MeOH/DCM (0-10%) to give the product as green solid, which was washed with MeOH to give the product 18 as grey solid (10 mg, 67%). LC-MS: m/z 598.1 [M+H], retention time=1.0 min. $^1$H NMR (400 MHz, DMSO-d$_6$), δ 10.51 (s), 8.29 (t), 8.13 (d), 8.02 (s), 7.82 (d), 7.52 (t), 7.38 (t), 4.63 (s), 4.19-4.10 (m), 3.96 (m), 3.84 (m).

Preparation of (S)-1,3-phenylenebis(((S)-1-(chloromethyl)-5-hydroxy-1H-benzo[e]indol-3(2H)-yl)methanone) [20]

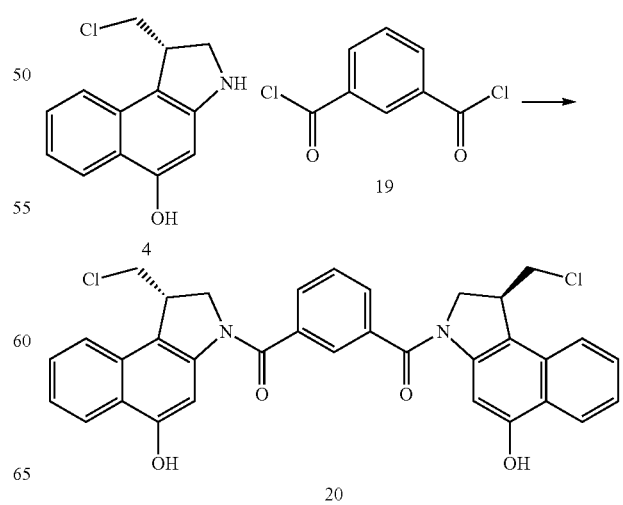

(S)-1-(chloromethyl)-2,3-dihydro-1H-benzo[e]indol-5-ol (4) (27 mg, HCl salt, 0.1 mmol) was dissolved in DMF (2 mL), and pyridine (0.024 mL, 0.29 mmol) was added, followed by isophthalic acid chloride (19, 10 mg, 0.05 mmol). The mixture was stirred at room temperature for overnight. The solvent was removed, and the residue was purified by ISCO using MeOH/DCM (0-10%) to give the product 20 as grey solid (20 mg, 68%). LC-MS (Protocol B): m/z 597.2 [M+H], retention time=0.99 min. $^1$H NMR (400 MHz, DMSO-$d_6$), δ 10.47 (s), 8.13 (d), 7.96 (s), 7.84 (d), 7.72 (t), 7.52 (t), 7.37 (t), 4.44 (s), 4.08 (s), 3.97 (s), 3.86 (s).

Preparation of (S)-3,3'-thiobis(1-((S)-1-(chloromethyl)-5-hydroxy-1H-benzo[e]indol-3(2H)-yl)propan-1-one) (23)

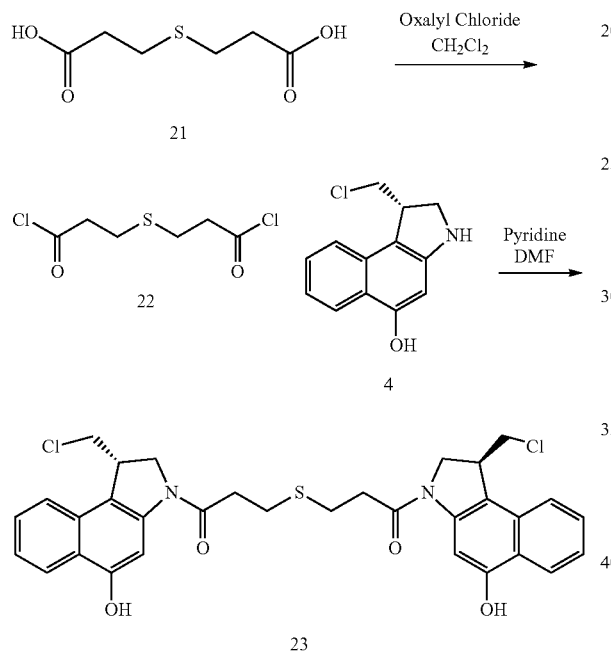

Step 1

3,3'-thiodipropanoic acid (21, 8 mg, 0.04 mmol) was dissolved in THF (2 mL), added oxalyl chloride (2M in $CH_2Cl_2$, 0.4 mL, 0.2 mmol) and DMF (2 drops) at 0° C. The mixture was stirred at 0° C. for 5 min, then at room temperature for 1 h. Concentrated in vacuo to give the corresponding acid chloride 22 that was used in next step without further purification.

Step 2

The above compound 22 was dissolved in DMF (2 ml) at 0° C., added (S)-1-(chloromethyl)-2,3-dihydro-1H-benzo[e]indol-5-ol HCl salt (6) (25 mg, 0.09 mmol), followed by pyridine (0.022 mL, 0.27 mmol). The mixture was stirred at room temperature for overnight. DMF was removed under reduced pressure, and the residue was purified by ISCO using MeOH/DCM (0-10%) to give the product 23 as off-white solid (15 mg, 50%). LC-MS (Protocol B): m/z 609.1 [M+H], retention time=1.0 min. $^1$H NMR (400 MHz, DMSO-$d_6$), δ 10.36 (s), 8.09 (d), 7.99 (s), 7.79 (d), 7.50 (t), 7.33 (t), 4.37 (m), 4.19 (m), 3.99 (d), 3.82 (m), 2.90-2.82 (m).

Preparation of (S)-pyridine-3,5-diylbis(((S)-1-(chloromethyl)-5-hydroxy-1H-benzo[e]indol-3(2H)-yl)methanone) (26)

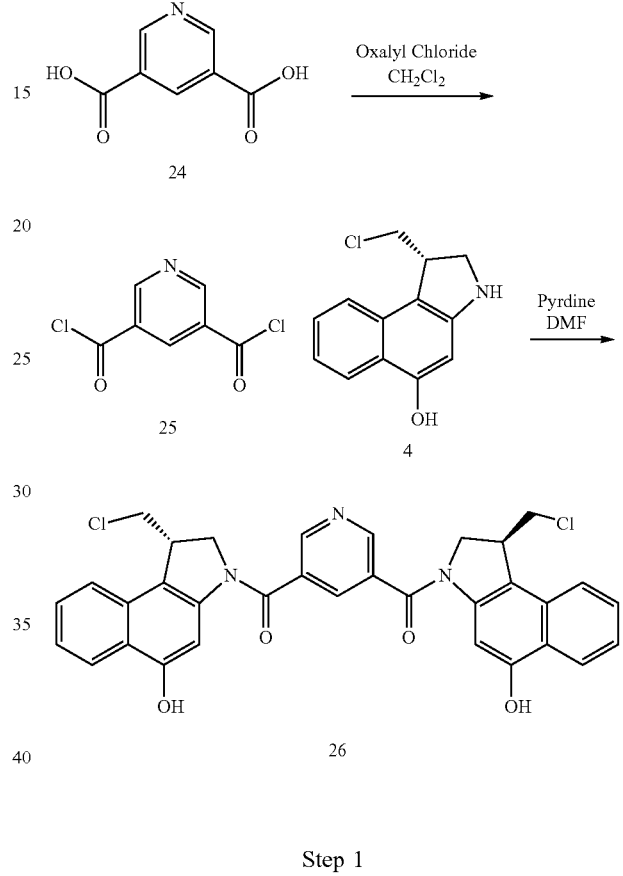

Step 1

Pyridine-3,5-dicarboxylic acid (24, 7 mg, 0.04 mmol) was added 2 mL of DCM, followed by 2M oxalyl chloride (0.2 mL, 0.4 mmol), and DMF (2 drops). The clear solution was stirred at room temperature for 2 h, and concentrated to give the corresponding acid chloride 25 as yellow solid.

Step 2

The above solid 25 was dissolved in DMF (0.2 mL), and the solution was added to a solution of (S)-1-(chloromethyl)-2,3-dihydro-1H-benzo[e]indol-5-ol HCl salt (4)(25 mg, 0.09 mmol) in DMF (1 mL), followed by pyridine (0.02 mL, 0.25 mmol). The mixture was stirred at room temperature for overnight. The solvent was removed in vacuo, and the residue was purified by using ISCO (MeOH/DCM=0-10%) to give the product 26 as grey solid (20 mg, 80%). LC-MS (Protocol B): m/z 598.1 [M+H], retention time=0.95 min. $^1$H NMR (400 MHz, DMSO-$d_6$), δ 10.55 (s), 9.00 (s), 8.2 (s), 7.97 (s), 7.84 (d), 7.53 (t), 7.36 (t), 4.50 (s), 4.10 (s), 3.98 (s), 3.86 (s).

Preparation of (S)-thiophene-2,5-diylbis(((S)-1-(chloromethyl)-5-hydroxy-1H-benzo[e]indol-3(2H)-yl)methanone) (29) and (S)-5-(1-(chloromethyl)-5-hydroxy-2,3-dihydro-1H-benzo[e]indole-3-carbonyl)thiophene-2-carboxylic acid (30)

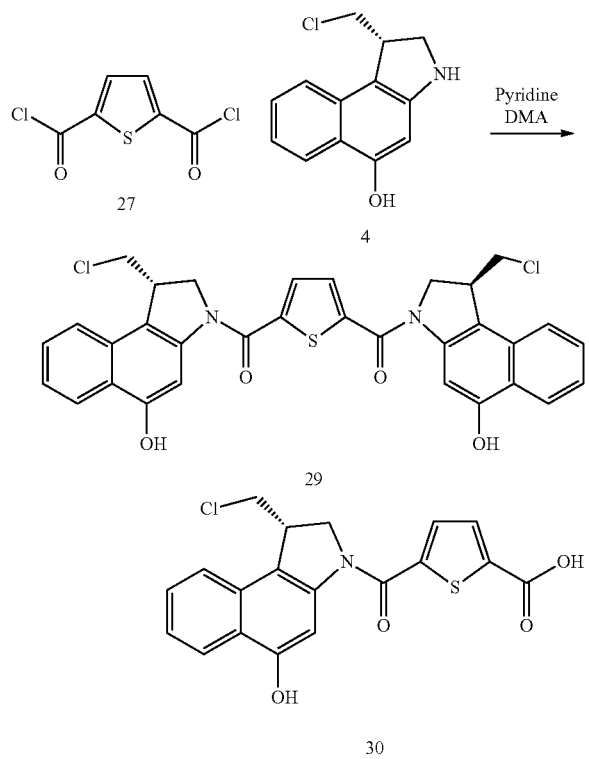

(S)-1-(chloromethyl)-2,3-dihydro-1H-benzo[e]indol-5-ol [4] (102 mg, HCl salt, 0.38 mmol) was dissolved in DMA (2 mL), and pyridine (0.061 mL, 0.76 mmol) was added, followed by thiophene-2,5-dicarbonyl dichloride (27, 40 mg, 0.19 mmol). The mixture was stirred at room temperature for 2 h. The crude was purified by Gilson HPLC (0.02% TFA) to give two products:

(S)-thiophene-2,5-diylbis(((S)-1-(chloromethyl)-5-hydroxy-1H-benzo[e]indol-3(2H)-yl)methanone)(29) as yellow solid (60 mg, 52%). LC-MS (Protocol B): m/z 603.0 [M+H], retention time=1.99 min. $^1$H NMR (400 MHz, DMSO-d$_6$), δ 10.48 (s), 8.14 (d), 7.86 (m), 7.55 (t), 7.40 (t), 4.78 (t), 4.44 (d), 4.23 (s), 4.03 (d), 3.91 (m).

(S)-5-(1-(chloromethyl)-5-hydroxy-2,3-dihydro-1H-benzo[e]indole-3-carbonyl)thiophene-2-carboxylic acid (30) as green solid (23 mg, 31%). LC-MS (Protocol B): m/z 388.1 [M+H], retention time=0.82 min. $^1$H NMR (400 MHz, MeOD-d$_4$), δ 8.23 (d), 7.82 (m), 7.71 (s), 7.55 (t), 7.40 (t), 4.64 (m), 4.53 (d), 4.15 (t), 4.01 (dd), 3.74 (m).

Preparation of (S)-(1H-pyrrole-2,5-diyl)bis(((S)-1-(chloromethyl)-5-hydroxy-1H-benzo[e]indol-3(2H)-yl)methanone) (32)

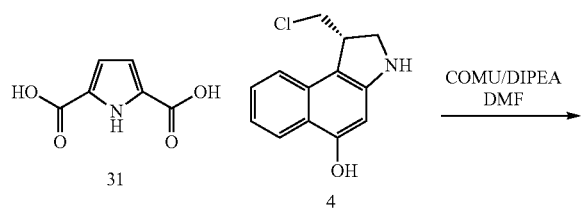

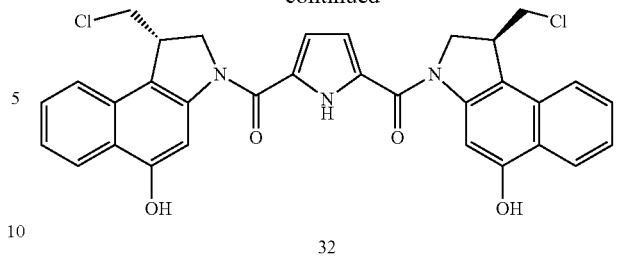

DIPEA (33 mg, 0.25 mmol) was added to a solution of 1H-pyrrole-2,5-dicarboxylic acid (31, 10 mg, 0.064 mmol) in DMF (1.5 mL), followed by (S)-1-(chloromethyl)-2,3-dihydro-1H-benzo[e]indol-5-ol [4] (38 mg, HCl salt, 0.14 mmol) and COMU (82 mg, 0.19 mmol), and the mixture was stirred at room temperature for overnight. The crude was purified by Gilson HPLC (ACN/water, 0.02% TFA) to give the product 32 as yellow solid (5 mg, 10%). LC-MS (Protocol B): m/z 586.3 [M+H], retention time=2.04 min. $^1$H NMR (400 MHz, DMSO-d$_6$), δ 11.66 (s), 10.44 (s), 8.13 (d), 7.92 (s), 7.86 (d), 7.55 (t), 7.38 (t), 5.76 (s), 4.71 (t), 4.44 (d), 4.22 (s), 4.03 (d), 3.88 (m).

Preparation of (S)-thiophene-2,4-diylbis(((S)-1-(chloromethyl)-5-hydroxy-1H-benzo[e]indol-3(2H)-yl)methanone) (35)

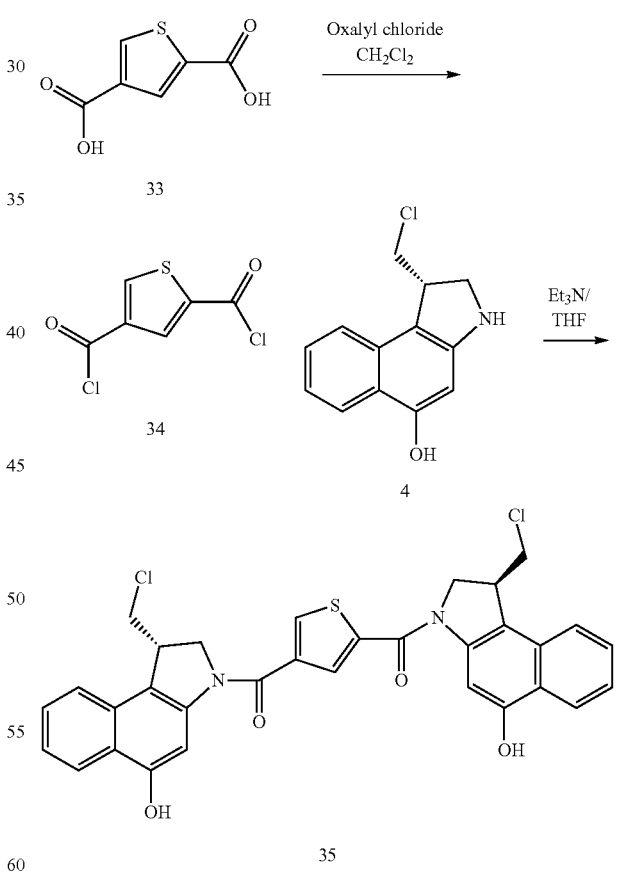

Step 1

2,4-Thiophenedicarboxylic acid (33, 100 mg, 0.58 mmol) was dissolved in THF (5 mL), cooled to 0° C. with ice bath. Oxalyl chloride (0.75 mL, 2M in CH$_2$Cl$_2$, 1.5 mmol) was added, followed by 2 drops of DMF. The resulting mixture was allowed to warm to room temperature, and stirred for 1 h. Some white precipitates can be observed during this period. The mixture was concentrated in vacuo to give thiophene-2,4-dicarbonyl dichloride (34) as off-white solid (122 mg, 100%).

Step 2

(S)-1-(chloromethyl)-2,3-dihydro-1H-benzo[e]indol-5-ol [4] (81 mg, HCl salt, 0.3 mmol) was dissolved in THF (3 mL), and added Et$_3$N (0.125 mL, 0.9 mmol) at 0 C, followed by a solution of thiophene-2,4-dicarbonyl dichloride (24, 31.4 mg, 0.15 mmol) in CH$_2$Cl$_2$ (1 mL). The mixture was stirred at 0° C. for 5 min, and then stirred at room temperature for 2 h. The reaction mixture was reduced down, and the residue was treated with MeOH, and the resulting yellow solid was collected by filtration to give the crude product. The crude was purified by Gislon HPLC (ACN/water, 0.02% TFA) to give the product 35 as yellow solid (40 mg, 44%). LC-MS (Protocol B): m/z 603.3 [M+H], retention time=1.96 min. $^1$H NMR (400 MHz, DMSO-d$_6$), δ 10.46 (d), 8.41 (s), 8.13 (d), 8.05 (s), 7.87 (t), 7.54 (t), 7.39 (m), 4.81 (t), 4.61 (s), 4.46 (d), 4.21 (m), 4.18 (m), 4.00 (m), 3.98-3.86 (m).

Preparation of (S)-(1-methyl-1H-pyrrole-2,5-diyl) bis(((S)-1-(chloromethyl)-5-hydroxy-1H-benzo[e] indol-3(2H)-yl)methanone) (38)

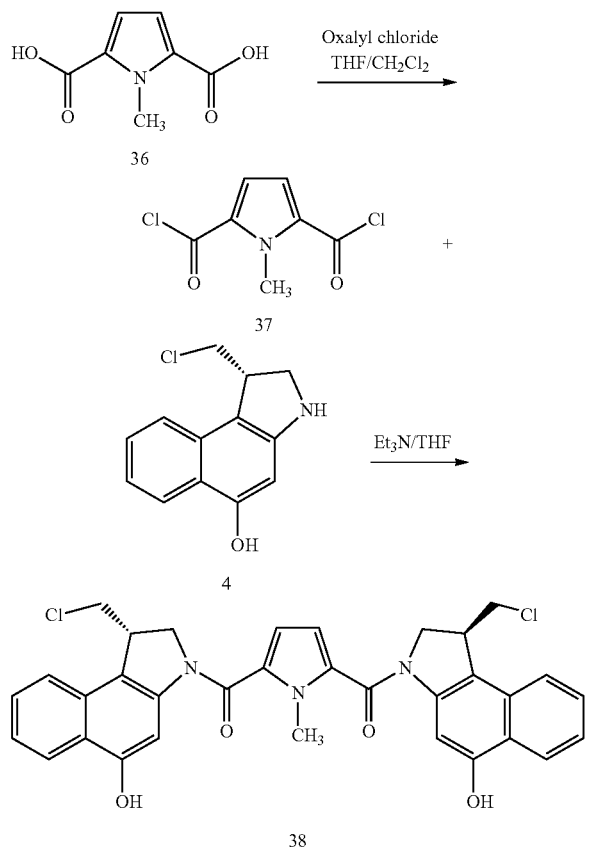

Step 1

1-Methyl-1H-pyrrole-2,5-dicarboxylic acid (36, 20 mg, 0.12 mmol) was dissolved in THF (2 mL), added oxalyl chloride (2M in CH$_2$Cl$_2$, 0.18 mL, 0.35 mmol) and DMF (2 drops) at 0° C. The mixture was stirred at 0° C. for 5 min, then at room temperature for 1 h. Concentrated in vacuo to give the corresponding acid chloride 37 as off-white solid, which was used in next step without further purification.

Step 2

The above compound 37 was dissolved in THF (2 ml) at 0° C., added (S)-1-(chloromethyl)-2,3-dihydro-1H-benzo[e]indol-5-ol HCl salt [4] (65 mg, 0.24 mmol), followed by Et$_3$N (0.1 mL, 0.71 mmol). The mixture was stirred at 0° C. for 5 min, then at room temperature for 1 h. The mixture was concentrated in vacuo, and the residue was purified by Gilson HPLC (0.02% TFA) to give the product 38 as off-white solid (31 mg, 44%). LC-MS: m/z 600.5 [M+H], retention time=1.04 min. $^1$H NMR (400 MHz, DMSO-d$_6$), δ 10.44 (s), 8.13 (d), 7.84 (d), 7.75 (s), 7.53 (t), 7.38 (t), 6.78 (s), 4.60 (t), 4.30 (d), 4.08 (s), 4.02 (d), 3.9 (s), 3.87 (d).

Preparation of 3-Amino-1,5-bis-((S)-1-chloromethyl-5-hydroxy-1,2-dihydro-enzo[e]indol-3-yl)-pentane-1,5-dione (40)

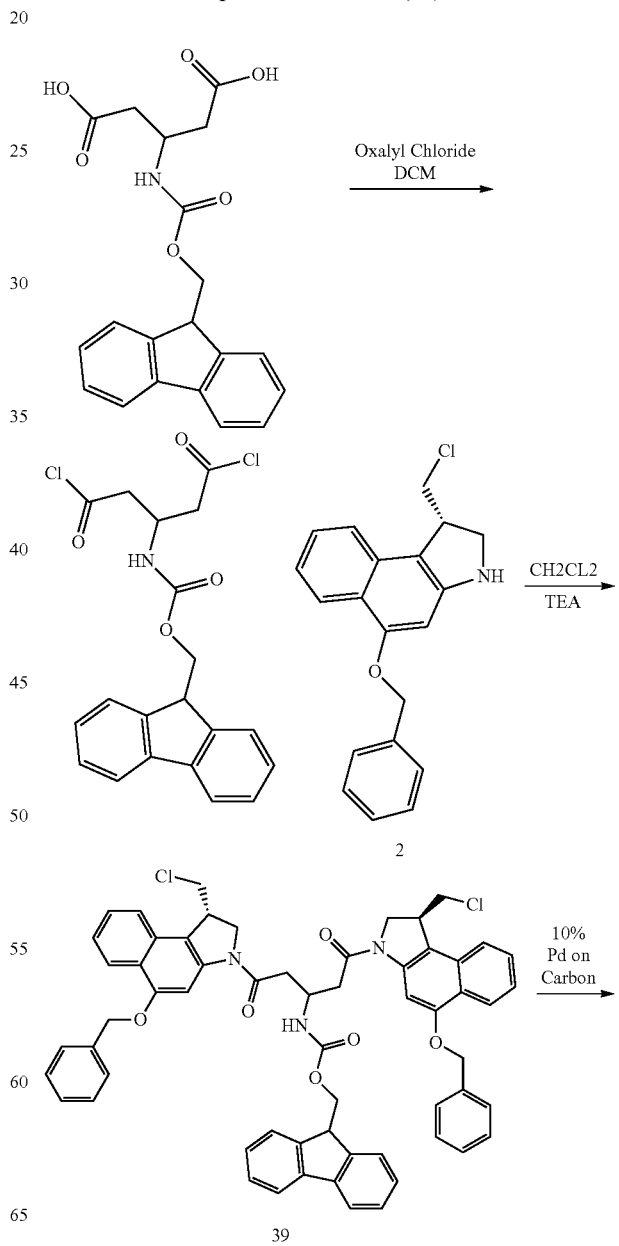

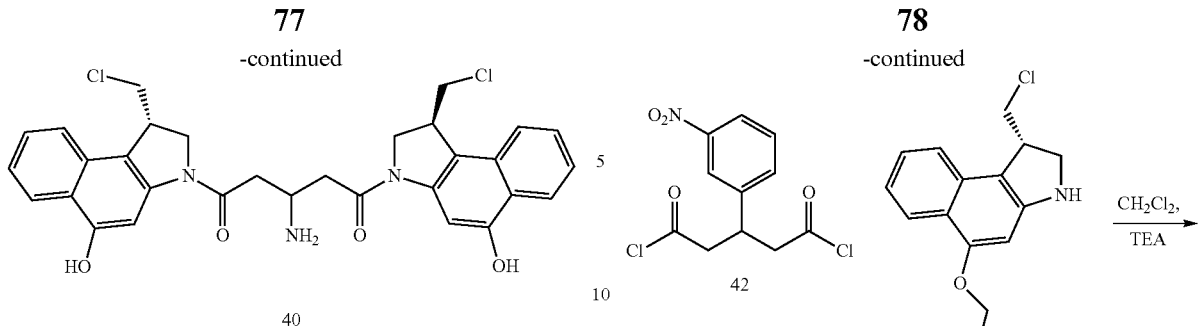

40

Step 1

In a round bottom flask purged with N₂, containing 3-(9H-Fluoren-9-ylmethoxycarbonylamino)-pentanedioic acid (918 mg, 2.48 mmol) in 20 mL of anhydrous dichloromethane was added Oxalyl Chloride (5.22 mmol, 0.469 mL). To this solution was added 1 drop of N,N-dimethylformamide. The reaction mixture was stirred for 3 hours and concentrated in vacuo to a crude residue. The residue was taken up in dichloromethane (10 mL) and added drop wise to a round bottom flask containing (2) (1610 mg, 4.97 mmol) in 25 mL of dichloromethane and triethylamine (2.08 mL). The crude reaction mixture was concentrated in vacuo and taken back up in 25 mL of dichloromethane and transferred to a separation funnel. Washed organic layer with 1M HCl (3×), Water (3×), and Brine (2×). Dried organic layer over sodium sulfate, filtered and concentrated the filtrate to a crude solid. Silica chromatography was then preformed (Gradient: 0%-100% ethyl acetate in heptanes) producing (39) (2.103 g, 86%) as a pale white solid. LC-MS (Protocol B): m/z 982 [M+H⁺], retention time=2.81 minutes.

Step 2

A stirring solution of 39, {3-((S)-5-Benzyloxy-1-chloromethyl-1,2-dihydro-benzo[e]indol-3-yl)-1-[2-((S)-5-benzyloxy-1-chloromethyl-1,2-dihydro-benzo[e]indol-3-yl)-2-oxo-ethyl]-3-oxo-ropyl}-carbamic acid 9H-fluoren-9-ylmethyl ester, (92 mg, 0.104 mmol) in 10 mL of tetrahydrofuran under nitrogen was cooled to 0 C using an ice bath. Palladium 10 wt. % on activated carbon (16 mg, 0.15 mmol) was then added followed by the slow drop wise addition of 1 mL of 25% ammonium formate in water. The reaction was allowed to stir at 0 C. for 5 hours. The reaction was then filtered through a pad of celite and the filtrate was then concentrated in vacuo. The crude residue was taken up in dichloromethane and washed with water. The dichloromethane layer was concentrated and 2 mL of 1 M HCl (aq) was added and concentrated. The residue was taken up in ethyl acetate and the solids were filtered to afford 40 as a white solid (52 mg, 51%). LC-MS (Protocol B): m/z 578 [M+H⁺], retention time=1.42 minutes.

Preparation of 3-(3-Amino-phenyl)-1,5-bis-((S)-1-chloromethyl-5-hydroxy-1,2-dihydro-benzo[e]indol-3-yl)-pentane-1,5-dione (44)

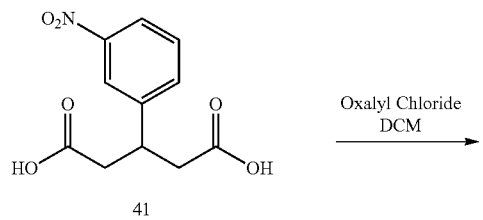

41

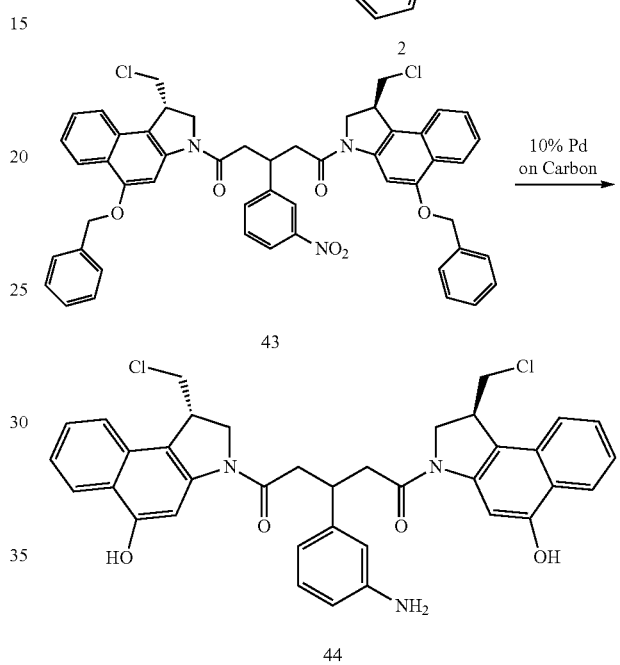

Step 1

In a round bottom flask purged with N₂, containing 3-(3-Nitro-phenyl)-pentanedioic acid (3, 330 mg, 1.30 mmol) in 15 mL of anhydrous dichloromethane was added Oxalyl Chloride (2.6 mmol, 0.24 mL). To this solution was added 1 drop of N,N-dimethylformamide. The reaction mixture was stirred for 3 hours and concentrated in vacuo to afford 42 as a white solid (378 mg, 1.30 mmol, quantitative).

Step 2

In a round bottom flask containing 2 (124 mg, 0.344 mmol) in 15 mL of dichloromethane was added 3-(3-Nitrophenyl)-pentanedioyl dichloride (42) (42 mg, 0.172 mmol). Triethylamine (0.08 mL) was then added and the system was stirred for 1 hour at room temperature. The crude reaction mixture was concentrated in vacuo and taken back up in 25 mL of dichloromethane and transferred to a separation funnel. Washed organic layer with 1M HCl (3×), Water (3×), and Brine (2×). Dried organic layer over Sodium Sulfate, filtered and concentrated the filtrate to a crude solid. The crude solid was taken up in 10% MeOH in EtOAc and the white solids were filtered to give desired product 43 (120 mg, 0.172 mmol, 80%). LC-MS (Protocol B): m/z 864 [M+H⁺], retention time=2.75 minutes.

Step 3

A stirring solution of 43 (85 mg, 0.098 mmol) in 10 mL of tetrahydrofuran under nitrogen was cooled to 0 C using an ice bath. Palladium 10 wt. % on activated carbon (16 mg, 0.15 mmol) was then added followed by the slow drop wise addition of 2 mL of 25% ammonium formate in water. The reaction was allowed to stir at 0 C. for 5 hours. The reaction was then filtered through a pad of celite and the filtrate was then concentrated in vacuo. The crude residue was taken up in dichloromethane and washed with water. The dichloromethane layer was concentrated and 2 mL of 1 M HCl (aq) was added and concentrated. The residue was taken up in ethyl acetate and the solids were filtered to afford (44) as a white solid. (35 mg, 52%). LC-MS: m/z 654 [M+H⁺], retention time=1.93 minutes.

Preparation of 3-(4-Amino-phenyl)-1,5-bis-((S)-1-chloromethyl-5-hydroxy-1,2-dihydro-benzo[e]indol-3-yl)-pentane-1,5-dione 48

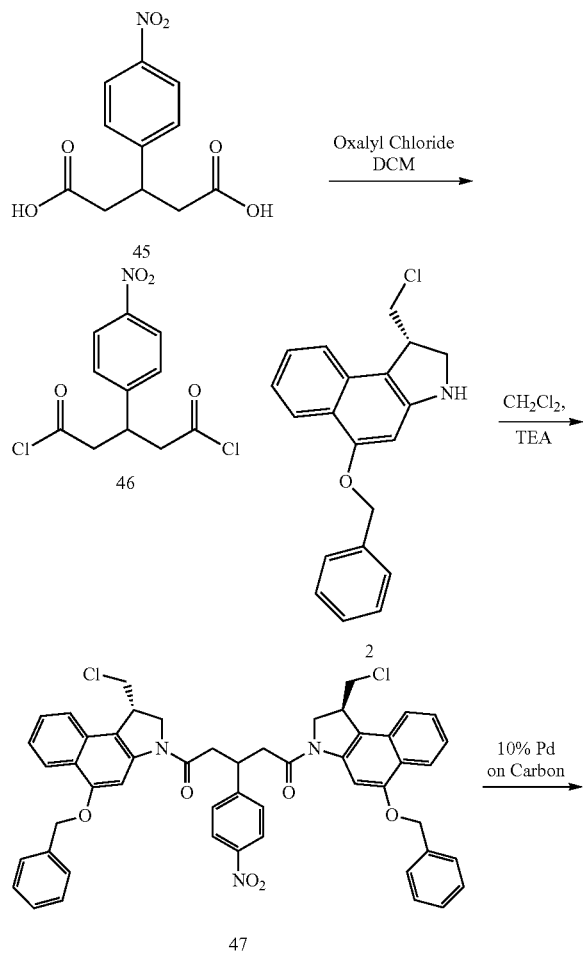

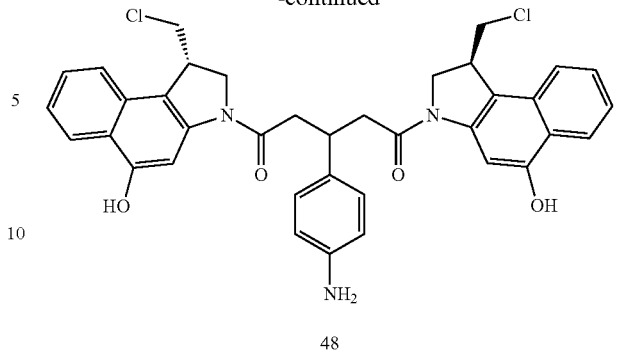

48

Step 1

In a round bottom flask purged with N₂, containing 3-(4-Nitro-phenyl)-pentanedioic acid (45, 110 mg, 0.434 mmol) in 5 mL of anhydrous DCM was added Oxalyl Chloride (0.911 mmol, 0.082 mL). To this solution was added 1 drop of N,N-dimethylformamide. The reaction mixture was stirred for 3 hours and concentrated in vacuo to afford (46) as a white solid (125 mg, 0.434 mmol, quantitative). LCMS, taken in methanol: m/z 282.0 [M+H⁺, for bis methanolysis product]. retention time=1.38 minutes. (7) (Commercial and Literature Known: Tetrahedron, 63(39), 9741-9745; 2007

Step 2

In a round bottom flask containing 2 (111 mg, 0.344 mmol) in 15 mL of dichloromethane was added 3-(4-Nitrophenyl)-pentanedioyl dichloride (46) (50 mg, 0.172 mmol). Triethylamine (0.144 mL) was then added and the system was stirred for 1 hour at room temperature. The crude reaction mixture was concentrated in vacuo and taken back up in 25 mL of dichloromethane and transferred to a separation funnel. Washed organic layer with 1M HCl (3×), Water (3×), and Brine (2×). Dried organic layer over Sodium Sulfate, filtered and concentrated the filtrate to a crude solid. The crude solid was taken up in 10% MeOH in EtOAc and the white solids were filtered to give desired product (47) (101 mg, 0.115 mmol, 68%). LC-MS: m/z 864 [M+H⁺], retention time=2.72 minutes.

Step 3

(10). A stirring solution of (47), 3-(4-nitro-phenyl)-1,5-bis-((S)-1-chloromethyl-5-hydroxy-1,2-dihydro-benzo[e]indol-3-yl)-pentane-1,5-dione (90 mg, 0.1 mmol) in 10 mL of tetrahydrofuran under nitrogen was cooled to 0 C using an ice bath. Palladium 10 wt. % on activated carbon (17 mg, 0.16 mmol) was then added followed by the slow drop wise addition of 1 mL of 25% ammonium formate in water. The reaction was allowed to stir at 0 C. for 5 hours. The reaction was then filtered through a pad of celite and the filtrate was then concentrated in vacuo. The crude residue was taken up in dichloromethane and washed with water. The dichloromethane layer was concentrated and 2 mL of 1 M HCl (aq) was added and concentrated. The residue was taken up in ethyl acetate and the solids were filtered to afford 48 as a white solid. (44 mg, 61%). LC-MS: m/z 654 [M+H⁺], retention time=1.73 minutes.

Preparation of Acetic acid (S)-3-{2-[2-((S)-5-acetoxy-1-chloromethyl-1,2-dihydro-benzo[e]indol-3-yl)-2-oxo-ethylamino]-acetyl}-1-chloromethyl-2,3-dihydro-1H-benzo[e]indol-5-1 ester (53)
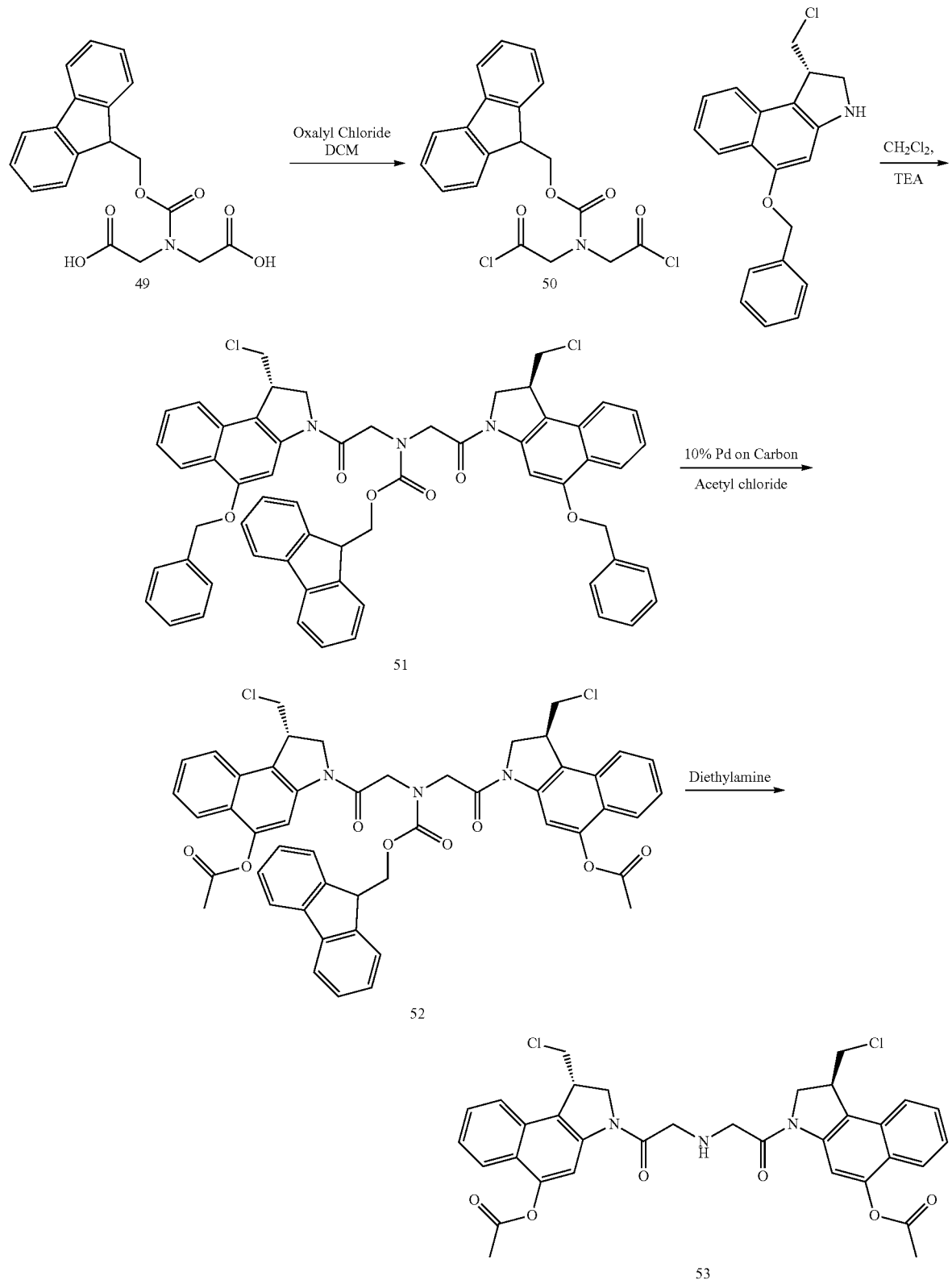

Step 1

In a round bottom flask purged with N₂, containing 3 [Carboxymethyl-(9H-fluoren-9-ylmethoxycarbonyl)-amino]-acetic acid (49, 300 mg, 0.844 mmol) in 5 mL of anhydrous DCM was added Oxalyl Chloride (1.94 mmol, 0.175 mL). To this solution was added 1 drop of N,N-dimethylformamide. The reaction mixture was stirred for 3 hours and concentrated in vacuo to afford (50) as a white solid (330 mg, 0.844 mmol, quantitative). LCMS, taken in methanol: m/z 384.0 [M+H$^+$, for bis methanolysis product]. Retention time=1.91 minutes.

Step 2

In a round bottom flask containing 2 (76 mg, 0.21 mmol) in 5 mL of dichloromethane, was added 50 (41 mg, 0.105 mmol). Triethylamine (0.088 mL) was then added and the system was stirred for 1 hour at room temperature. The crude reaction mixture was concentrated in vacuo and taken back up in 25 mL of dichloromethane and transferred to a separation funnel. Washed organic layer with 1M HCl (3×), Water (3×), and Brine (2×). Dried organic layer over Sodium Sulfate, filtered and concentrated the filtrate to a crude solid. Silica chromatography was then preformed (Gradient: 0%-75% Ethyl Acetate in heptanes) producing (51) (91 mg, 90%) as a pale white solid. LC-MS: m/z 966 [M+H$^+$], retention time=2.91 minutes.

Step 3

A stirring solution of 51 (40 mg, 0.041 mmol0) in 10 mL of tetrahydrofuran under nitrogen was cooled to 0 C using an ice bath. Palladium 10 wt. % on activated carbon (10 mg, 0.09 mmol) was then added followed by the slow drop wise addition of 1 mL of 25% ammonium formate in water. The reaction was allowed to stir at 0 C. for 5 hours. The reaction was then filtered through a pad of celite and the filtrate was then concentrated in vacuo. The crude residue was taken up in dichloromethane and acetyl chloride (1 mL) was added and the reaction was then concentrated in vacuo. The residue was taken back up in 15 mL of dichloromethane and transferred to a separation funnel. Washed organic layer with 1M HCl (3×), water (3×), and brine (2×). Dried organic layer over sodium sulfate, filtered and concentrated the filtrate to a crude solid. Silica chromatography was then preformed (Gradient: 0%-100% Ethyl Acetate in Heptanes) producing (52) (27 mg, 76%) as a white solid. LC-MS: m/z 870 [M+H$^+$], retention time=2.51 minutes.

Step 4

In a round-bottom flask equipped with a stir bar containing 52 (25 mg, 0.29 mmol) was added 5 mL of dichloromethane and 5 mL of diethyl amine. The solution was stirred for 3 hours. The reaction mixture was concentrated in vacuo and taken up in 50% dichloromethane and heptane and concentrated in vacuo again. This was repeated 3 times. The crude solid was taken up in 50% tetrahydrofuran and 1 M HCl (aq). The white solids was taken up in ether and filtered to afford (15) as a white solid (14 mg, 70%). LC-MS: m/z 648 [M+H$^+$], retention time=1.78 minutes.

Preparation of 3-(4-Amino-phenyl)-N,N-bis-[2-((S)-1-chloromethyl-5-hydroxy-1,2-dihydro-benzo[e]indol-3-yl)-2-oxo-ethyl]-propionamide (56)

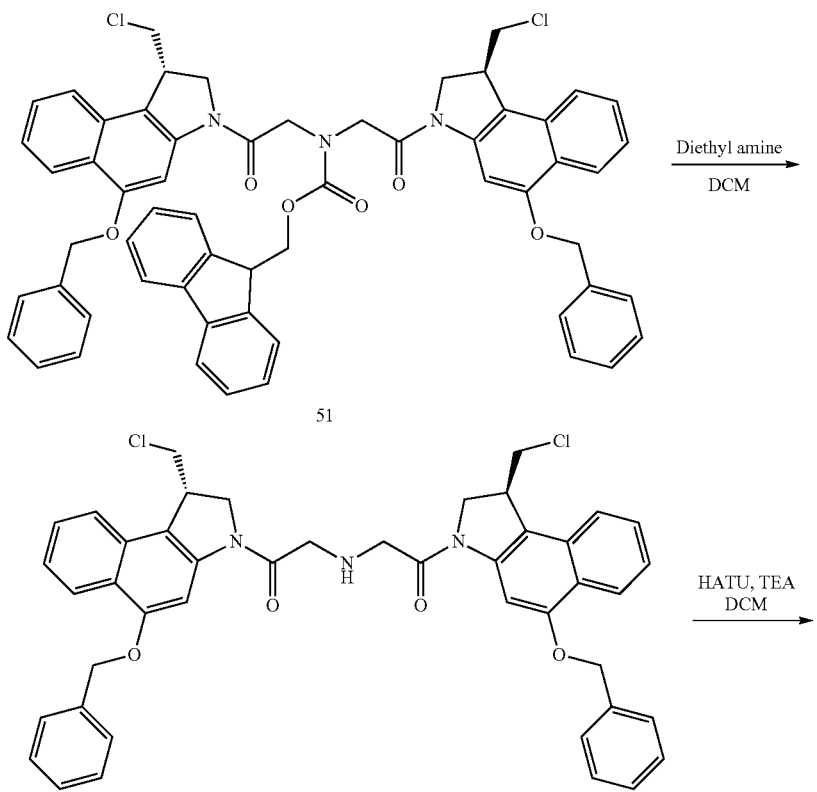

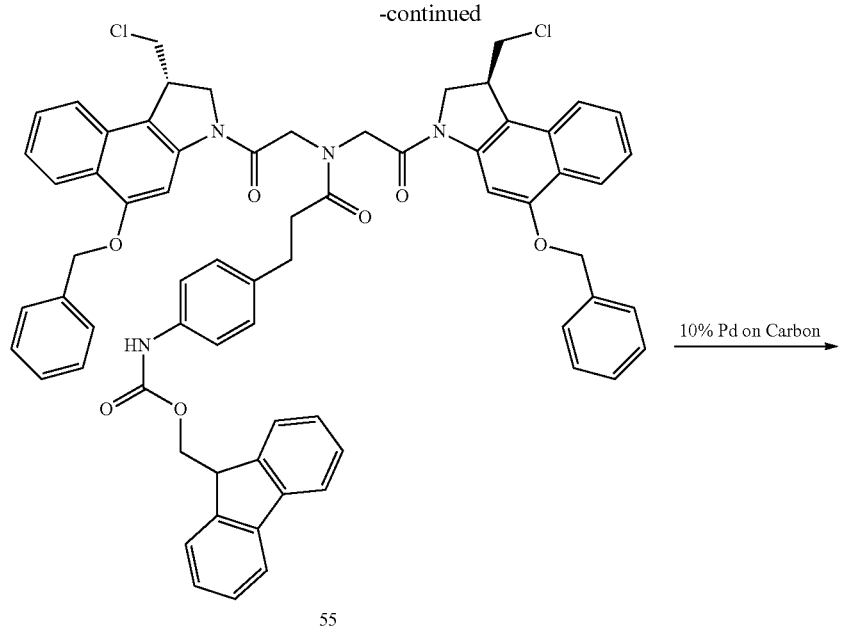

55

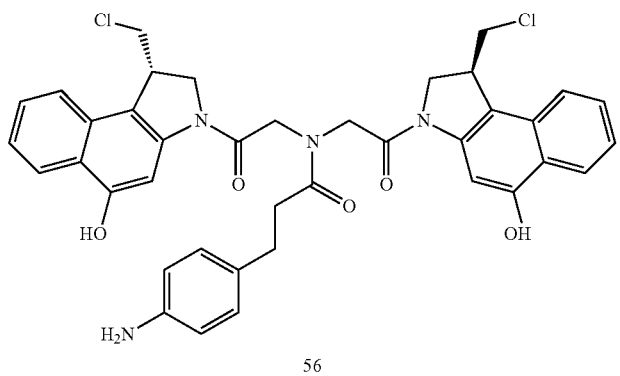

56

Step 1

In a round-bottom flask equipped with a stir bar containing 51 (300 mg, 0.310 mmol) was added 5 mL of dichloromethane and 5 mL of diethyl amine. The solution was stirred for 3 hours. The reaction mixture was concentrated in vacuo and taken up in 50% dichloromethane and heptane and concentrated in vacuo again. This was repeated 3 times to afford (54) as a white solid. (216 mg, 93%). LC-MS: m/z 744 [M+H$^+$], retention time=2.26 minutes.

Step 2

In a round bottom flask purged with $N_2$, containing 54 (100 mg, 0.134 mmol) in 5 mL of anhydrous dichloromethane was 3-[4-(9H-Fluoren-9-ylmethoxycarbonylamino)-phenyl]-propionic acid (52 mg, 0.134 mmol). To this solution was added (Dimethylamino)-N,N-dimethyl(3H-[1,2,3]triazolo[4,5-b]pyridine-3-yloxy)methaniminium hexafluorophosphate (52 mg, 0.134 mmol) and triethylamine (0.05 mL). The reaction mixture was stirred for 3 hours and concentrated in vacuo to a crude residue. The residue was taken back up in 25 mL of dichloromethane and transferred to a separation funnel. Washed organic layer with 1M HCl (3×), Water (3×), and Brine (2×). Dried organic layer over Sodium Sulfate, filtered and concentrated the filtrate to a crude solid. Silica chromatography was then preformed (Gradient: 0%-100% ethyl acetate in heptanes) producing (55) (130 mg, 87%) as a pale white solid. LC-MS: m/z 1113 [M+H$^+$], retention time=2.771 minutes.

Step 3

A stirring solution of 55 (115 mg, 0.103 mmol) in 10 mL of tetrahydrofuran under nitrogen was cooled to 0 C using an ice bath. Palladium 10 wt. % on activated carbon (10 mg, 0.1 mmol) was then added followed by the slow drop wise addition of 1 mL of 25% ammonium formate in water. The reaction was allowed to stir at 0 C. for 5 hours. The reaction was then filtered through a pad of celite and the filtrate was then concentrated in vacuo. The crude residue was taken up in dichloromethane and washed with water. The dichloromethane layer was concentrated and 2 mL of 1 M HCl (aq) was added and concentrated. The residue was taken up in ethyl acetate and the solids were filtered to afford (56) as a white solid. (26 mg, 34%). LC-MS: m/z 711 [M+H$^+$], retention time=1.6 minutes.

Preparation of [(S)-1-((S)-1-Chloromethyl-5-hydroxy-1,2-dihydro-benzo[e]indole-3-carbonyl)-4-((S)-1-chloromethyl-5-hydroxy-1,2-dihydro-benzo[e]indol-3-yl)-4-oxo-butyl]-carbamic acid 9H-fluoren-9-ylmethyl ester

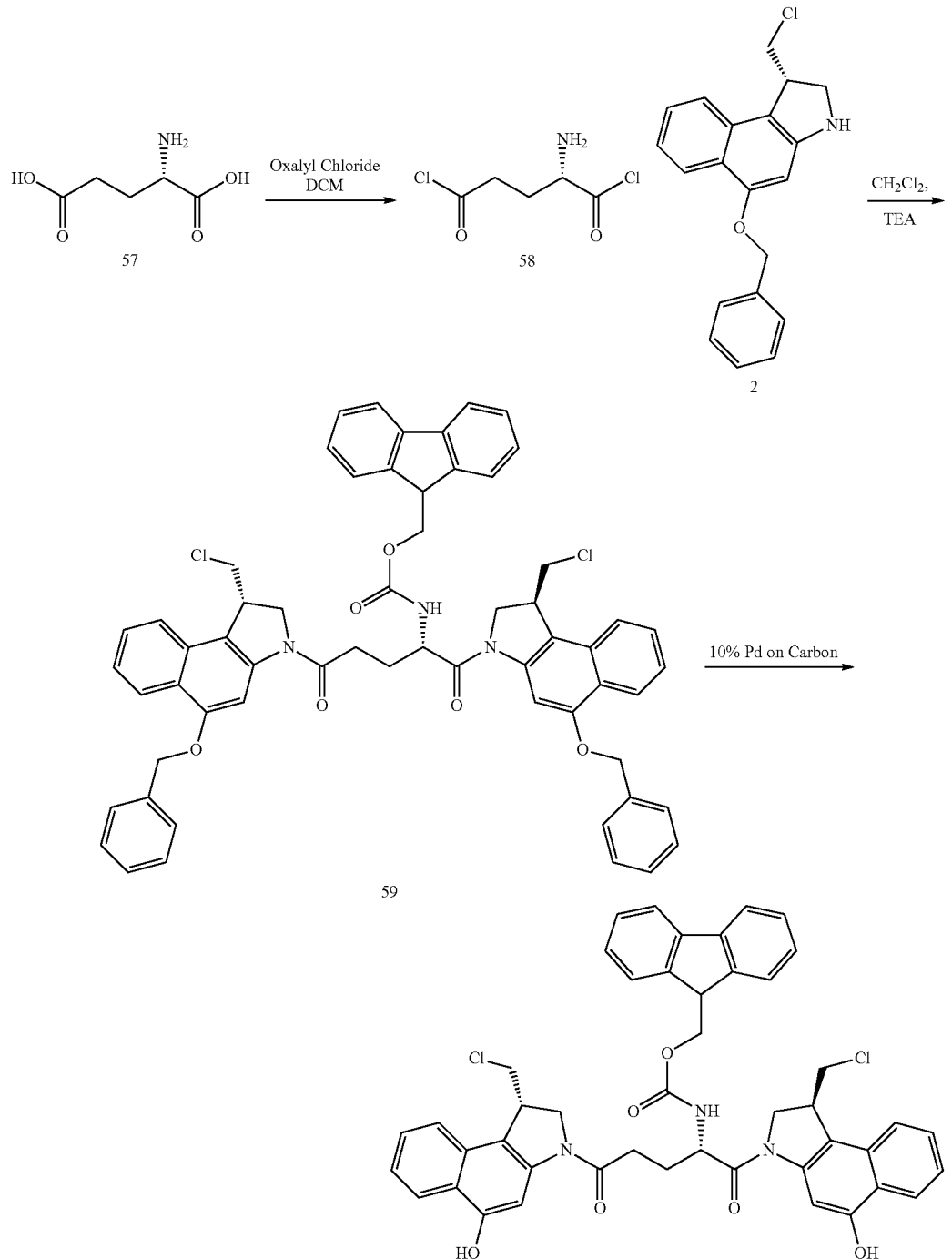

Step 1

In a round bottom flask purged with $N_2$, containing (S)-2-(9H-Fluoren-9-ylmethoxycarbonylamino)-pentanedioic acid 57 (400 mg, 1.08 mmol) in 15 mL of anhydrous dichloromethane was added Oxalyl Chloride (2.27 mmol, 0.205 mL). To this solution was added 1 drop of N,N-dimethylformamide. The reaction mixture was stirred for 3 hours and concentrated in vacuo to a crude residue 58. The residue was taken up in dichloromethane (10 mL) and added drop wise to a round bottom flask containing 2 (700 mg, 2.17 mmol) in 10 mL of dichloromethane and triethylamine (0.905 mL). The crude reaction mixture was concentrated in vacuo and taken back up in 25 mL of dichloromethane and transferred to a separation funnel. Washed organic layer with 1M HCl (3×), Water (3×), and Brine (2×). Dried organic layer over Sodium Sulfate, filtered and concentrated the filtrate to a crude solid. Silica chromatography was then preformed (Gradient: 0%-100% ethyl acetate in heptanes) producing (59) (260 mg, 24%) as a pale white solid. LC-MS: m/z 980 [M+H$^+$], retention time=2.84 minutes.

Step 2

A stirring solution of (59), (250 mg, 0.255 mmol) in 10 mL of tetrahydrofuran under nitrogen was cooled to 0 C using an ice bath. Palladium 10 wt. % on activated carbon (64 mg, 12.8 mmol) was then added followed by the slow drop wise addition of 2.1 mL of 25% ammonium formate in water. The reaction was allowed to stir at 0 C. for 30 min. The reaction was then filtered through a pad of celite and the filtrate was then concentrated in vacuo. The crude residue was taken up in dichloromethane and washed with water. Silica chromatography was then preformed (Gradient: 0%-100% ethyl acetate in heptanes) producing (60) (121 mg, 59%) as a pale white solid. LC-MS: m/z 800 [M+H$^+$], retention time=2.25 minutes.

Preparation of (S)-1-Chloromethyl-5-hydroxy-1,2-dihydro-benzo[e]indole-3-carboxylic acid [3-((S)-1-chloromethyl-5-hydroxy-1,2-dihydro-benzo[e]indol-3-yl)-3-oxo-propyl]-amide (31). A stirring solution of (65)

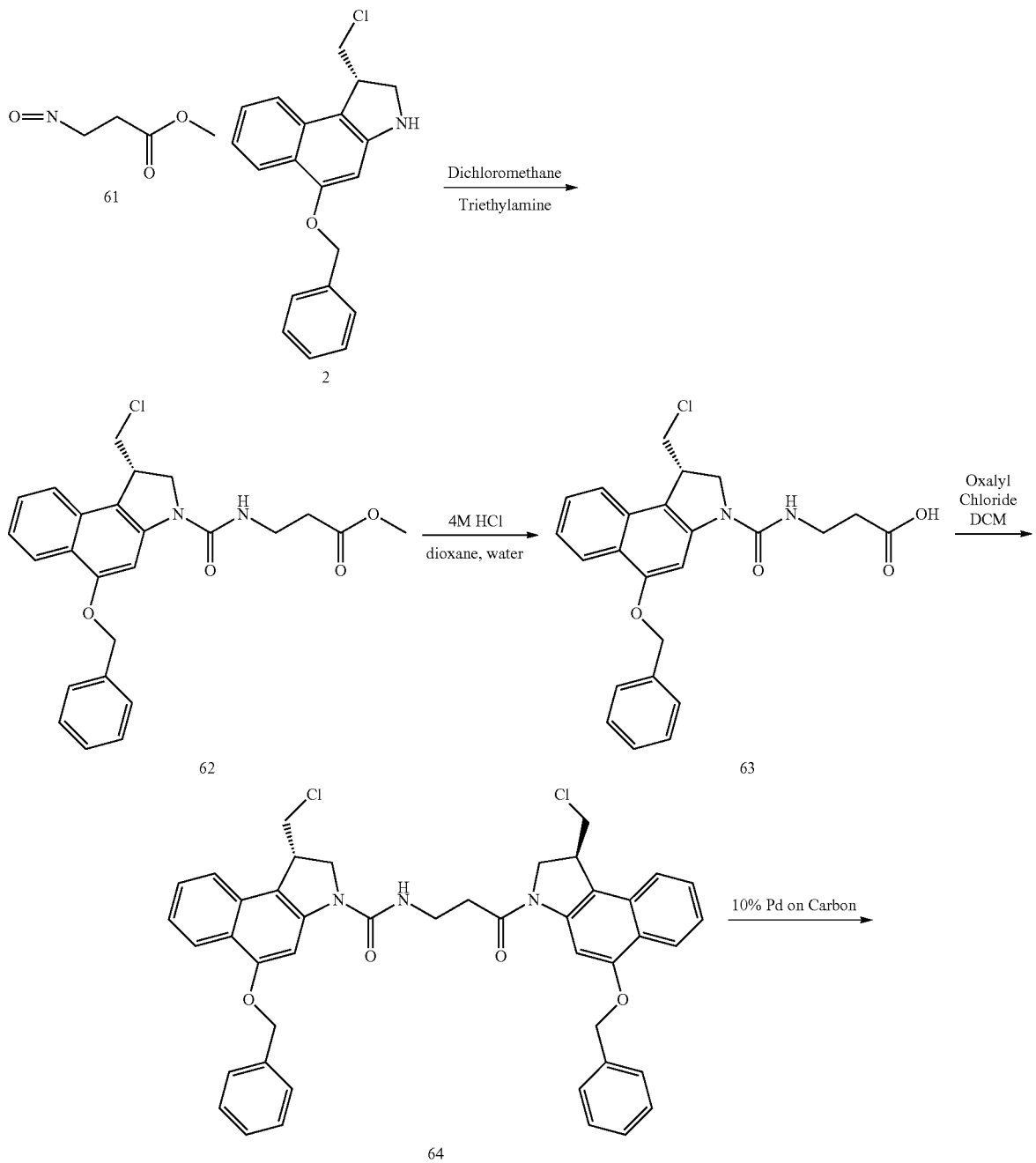

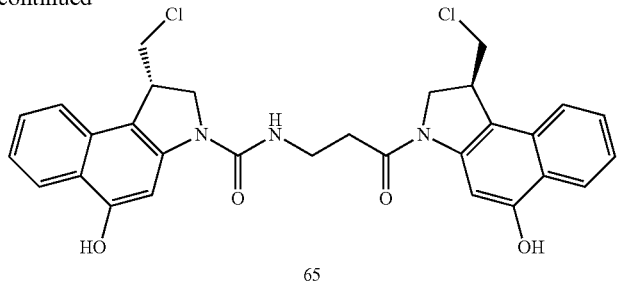

65

Step 1

To a round bottom flask containing (2)(200 mg, 0.555 mmol) in dichloromethane (10 mL) was added drop wise, 3-Isocyanato-propionic acid methyl ester 61 (79 mg, 0.555 mmol) and triethylamine (0.5 mL). The reaction was stirred for 3 hours. The crude reaction mixture was concentrated in vacuo and taken back up in 25 mL of dichloromethane and transferred to a separation funnel. Washed organic layer with 1M HCl (3×), Water (3×), and Brine (2×). Dried organic layer over Sodium Sulfate, filtered and concentrated the filtrate to a crude solid. Silica chromatography was then preformed (Gradient: 0%-100% ethyl acetate in heptanes) producing (62) (0.231 mg, 89%) as a pale white solid. LC-MS: m/z 467 [M+H$^+$], retention time=2.11 minutes. NMR yes

Step 2

In a round-bottom flask equipped with a stir bar containing 62 (230 mg, 0.493 mmol) was added 5 mL of 1M HCl (aq) in 5 mL of tetrahydrofuran. The solution was stirred for 3 hours at 70° C. The reaction mixture was concentrated in vacuo and taken up in 50% dichloromethane in heptane and concentrated in vacuo. This was repeated 3 times to afford (63)(180 mg, 83%) as a white solid upon concentrating. LC-MS: m/z 439 [M+H$^+$], retention time=1.83 minutes.

Step 3

In a round bottom flask purged with N$_2$, containing (63) (110 mg, 0.250 mmol) in 5 mL of anhydrous DCM was added Oxalyl Chloride (0.250 mmol, 0.02 mL). To this solution was added 1 drop of N,N-dimethylformamide. The reaction mixture was stirred for 3 hours and concentrated in vacuo to a crude residue. The residue was taken up in dichloromethane (10 mL) and added drop wise to a round bottom flask containing 2 (90 mg, 0.250 mmol) in 10 mL of dichloromethane and triethylamine (0.5 mL). The crude reaction mixture was concentrated in vacuo and taken back up in 15 mL of dichloromethane and transferred to a separation funnel. Washed organic layer with 1M HCl (3×), Water (3×), and Brine (2×). Dried organic layer over Sodium Sulfate, filtered and concentrated the filtrate to a crude solid. Silica chromatography was then preformed (Gradient: 0%-100% ethyl acetate in heptanes) producing (64) (80 g, 43%) as a pale white solid. LC-MS: m/z 744 [M+H$^+$], retention time=2.60 minutes.

Step 4

64 (75 mg, 0.100 mmol) in 10 mL of tetrahydrofuran under nitrogen was cooled to 0 C using an ice bath. Palladium 10 wt. % on activated carbon (25 mg, 0.24 mmol) was then added followed by the slow drop wise addition of 1 mL of 25% ammonium formate in water. The reaction was allowed to stir at 0 C. for 5 hours. The reaction was then filtered through a pad of celite and the filtrate was then concentrated in vacuo. The crude residue was taken up in dichloromethane and washed with water. The dichloromethane layer was concentrated and 2 mL of 1 M HCl (aq) was added and concentrated. The residue was taken up in ethyl acetate and the solids were filtered to afford (65 as a white solid. (15 mg, 26%). LC-MS: m/z 564 [M+H$^+$], retention time=1.88 minutes.

Preparation of (1S,1'S)-3,3'-(1H-pyrrole-2,5-dicarbonyl)bis(1-(chloromethyl)-2,3-dihydro-1H-benzo[e]indole-5,3-diyl)diacetate [68]

Step 1

1H-pyrrole-2,5-dicarboxylic acid (32, 50 mg, 0.3 mmol) was dissolved in THF (5 mL) at 0° C., oxalyl chloride (0.4 mL, 2M in CH$_2$Cl$_2$, 0.8 mmol) was added, followed by 2 drops of DMF. The mixture was stirred at 0° C. for 5 min, then room temperature for 2 h. Concentrated in vacuo to give 1H-pyrrole-2,5-dicarbonyl dichloride (33) as a yellow solid, which used in the next step without further purification.

Step 2

It was dissolved in THF (12 mL) at 0° C., 1H-pyrrole-2,5-dicarbonyl dichloride (33, from step 2) was added, followed by Et$_3$N (0.28 mL). The mixture was stirred at 0° C. for 5 min, the room temperature for 3 h. The mixture was concentrated in vacuo, and the residue was treated with MeOH to give a grey solid. The solid was collected by filtration to give the crude product as grey solid. The crude was purified by Gilson HPLC (ACN/water, 0.02% TFA) to give the pure product (1S,1'S)-3,3'-(1H-pyrrole-2,5-dicarbonyl)bis(1-(chloromethyl)-2,3-dihydro-1H-benzo[e]indole-5,3-diyl)diacetate as off-white solid (34, 60 mg, 30%). LC-MS: m/z 670.4 [M+H], retention time=2.20 min. $^1$H NMR (400 MHz, DMSO-d$_6$), δ 11.77 (s), 8.17 (s), 8.06 (d), 7.92 (d), 7.65 (t), 7.52 (t), 4.80 (t), 4.5 (d), 4.41 (s), 4.10 (d), 4.02 (m), 2.10 (s).

Preparation of (1S,1'S)-3,3'-(thiazole-2,5-dicarbonyl)bis(1-(chloromethyl)-2,3-dihydro-1H-benzo[e]indole-5,3-diyl)diacetate [71]

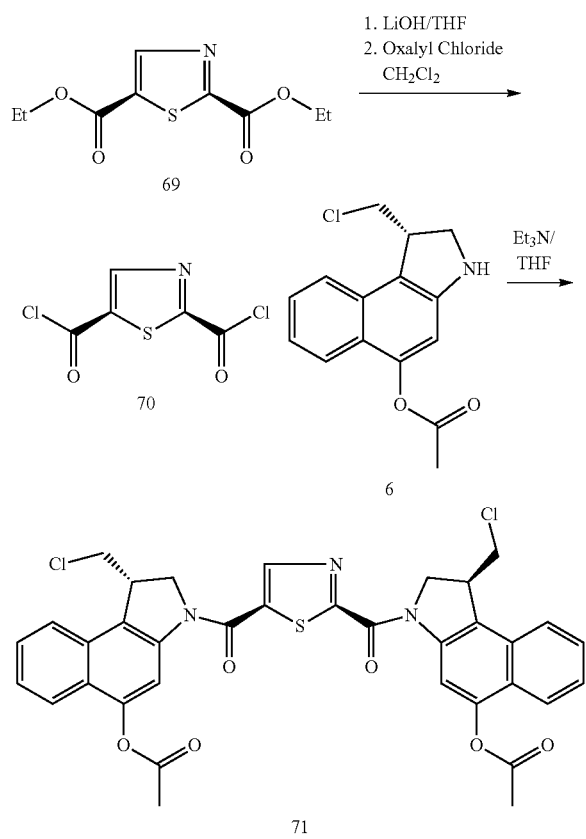

Step 1

Diethyl thiazole-2,5-dicarboxylate (35, 348 mg, 1.5 mmol) was dissolved in THF (10 mL), added a solution of LiOH.H$_2$O (383 mg, 9.0 mmol) in water (5 mL) at 0° C. The mixture was stirred at 0° C. for 30 min, then room temperature for 4 h. Concentrated in vacuo to remove THF, and residue was acidified by addition of 1M HCl aq solution to pH around 4-5. The resulting solid was collected by filtration to give the thiazole-2,5-dicarboxylic acid as white solid (63 mg, 24%). Thiazole-2,5-dicarboxylic acid (20 mg, 0.12 mmol) was dissolved in THF (2 mL), added oxalyl chloride (0.18 mL, 2M in DCM) at 0° C., followed by 2 drops of DMF. The mixture was stirred at 0° C. for 5 min, then at room temperature for 1 h. Concentrated in vacuo to give the corresponding acid chloride 70 as white solid.

Step 2

The yellow solid 5 was suspended in THF (3 mL), added the acid chloride from step 2, followed by Et$_3$N (0.05 mL, 0.4 mmol) at 0° C. The mixture was stirred at 0° C. for 5 min, and then room temperature for 1 h. The reaction mixture was concentrated in vacuo, and the residue was purified by Gilson HPLC to give the desired compound 71 as yellow solid (3.6 mg, 3.9%). LC-MS: m/z 688.5 [M+H], retention time=2.27 min. $^1$H NMR (400 MHz, DMSO-d$_6$), δ 8.81 (s), 8.41 (s), 8.27 (s), 8.16 (m), 8.04 (m), 7.74 (m), 7.64 (m), 5.25 (d), 4.94 (q), 4.53 (m), 4.21-4.08 (m), 2.63 (s).

Preparation of acetic acid (S)-3-[5-((S)-5-acetoxy-1-chloromethyl-1,2-dihydro-benzo[e]indole-3-carbonyl)-1-methyl-1H-pyrazole-3-carbonyl]-1-chloromethyl-2,3-dihydro-1H-benzo[e]indol-5-yl ester (74)

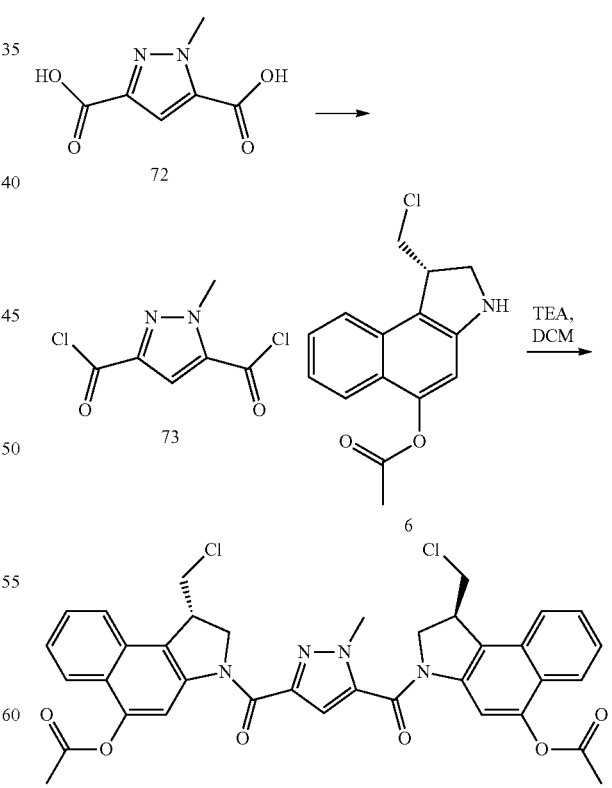

In a round bottom flask purged with N$_2$, containing 1-Methyl-1H-pyrazole-3,5-dicarboxylic acid 38 (20 mg, 0.12 mmol) in 5 mL of anhydrous dichloromethane was added oxalyl chloride (0.248 mmol, 0.022 mL). To this solution was added 1 drop of N,N-dimethylformamide. The reaction mixture was stirred for 3 hours and concentrated in vacuo to a crude residue 73. 73 was taken up in dichloromethane (10 mL) and added drop wise to a round bottom flask containing Acetic acid(S)-1-chloromethyl-2,3-dihydro-1H-benzo[e]indol-5-yl ester (5, 73 mg, 0.236 mmol) in 5 mL of dichloromethane and triethylamine (2.08 mL). The crude reaction mixture was concentrated in vacuo and taken back up in 25 mL of dichloromethane and transferred to a separation funnel. Washed organic layer with 1M HCl (3×), Water (3×), and Brine (2×). Dried organic layer over Sodium Sulfate, filtered and concentrated the filtrate to a crude solid. Silica chromatography was then preformed (Gradient: 0%-100% ethyl acetate in heptanes) producing (74) (12 mg, 15%) as a pale white solid. LC-MS: m/z 6852 [M+H$^+$], retention time=2.21 minutes.

Preparation of 7-azabicyclo[2.2.1]heptane-1,4-diyl-bis[carbonyl(1S)-1-(chloromethyl)-1,2-dihydro-3H-benzo[e]indole-3,5-diyl]diacetate 79

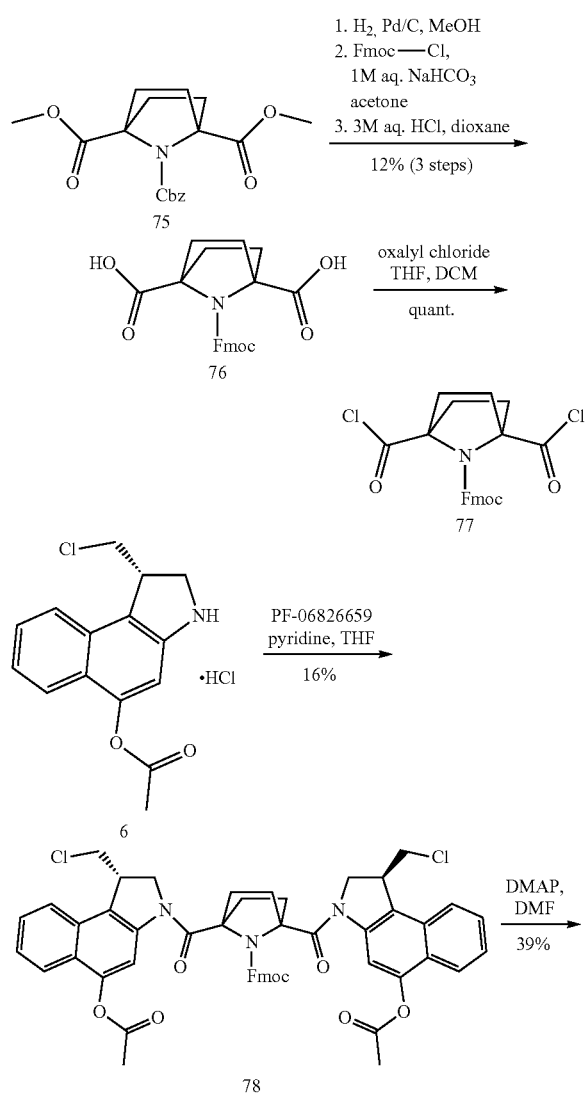

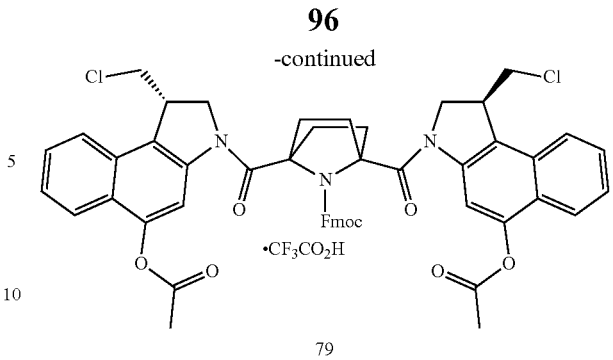

79

Step 1

A mixture of 7-benzyl 1,4-dimethyl 7-azabicyclo[2.2.1]heptane-1,4,7-tricarboxylate (3.20 g, 9.21 mmol) [prepared as described in Chem. Eur. J. 2012, 18, 1127-1141] in the presence of Pd/C (10%, 1000 mg) was hydrogenated at the pressure of a balloon at room temperature for ~2 hours. The reaction was filtered through a pad of celite and the cake was washed with a solution of 40 mL of methanol and 40 mL of dichloromethane. The organics were combined and concentrated in vacuo to afford a light yellow solid. The a stirring solution of this crude solid in 40 mL of acetone at 0° C., aq. NaHCO$_3$ (1 M, 65 mL, 64.6 mmol) was added followed by the drop wise addition of Fmoc-Cl (3.34 g, 12.9 mmol) as a solution in 40 mL of acetone. The reaction was diluted with 100 mL of water and extracted with ethyl acetate (100 mL, 3×). The organics where combined was with water, brine, dried over sodium sulfate, and concentrated in vacuo. Silica gel chromatography was then preformed (Gradient: 12.5% to 17% ethyl acetate in petroleum ether). Appropriate test tubes where combined and concentrated in vacuo yielding a white solid. Crude material was then suspended in aq. HCl (3 M, 60 mL) and 80 mL of dioxane. The reaction was heated to reflux and then allowed to stir at reflux for ~16 hours. The reaction was then concentrated in vacuo to remove most of the dioxane. The aq. phase was then extracted with ethyl acetate (100 mL, 2×). The organics where combined, washed with brine, dried over sodium sulfate, and concentrated in vacuo. Silica gel chromatography was then preformed (Gradient: 8.3% to 25% methanol in dichloromethane). Appropriate test tubes where combined and concentrated in vacuo and then purified again by preparative HPLC (method M, using gradient 50% B to 80% B over 30 minutes, then 95% over 5 minutes) to provide 76 (400 mg, 12%, 3 steps) as a white solid. $^1$H NMR (400 MHz, DMSO-d$_6$): δ 7.81-7.79 (d, 2H), 7.72-7.71 (d, 2H), 7.42-7.38 (m, 2H), 7.34-7.31 (m, 2H), 4.35-4.33-7.33 (d, 2H), 4.22-4.19 (m, 1H), 2.28-2.26 (d, 4H), 1.93-1.91 (d, 2H).

Step 2

Following general procedure A using 76 (90 mg, 0.40 mmol), oxalyl chloride (0.033 mL, 0.39 mmol), THF (8 mL) and 1 drop of DMF, 77 was prepared as an off white solid (79 mg, quant.). Crude 77 was used immediately in the next step as is.

Step 3

Following general procedure B using 6 (103 mg, 0.331 mmol), 77 (70 mg, 0.16 mmol), pyridine (0.051 mL, 0.63 mmol) and THF (12 mL) crude material was prepared. The reaction concentrated in vacuo dissolved in DMSO and injected onto a 12 g C18 pre-column (which was previously equilibrated with acetonitrile and then water, with 0.02% TFA in each phase). Material was purified by medium pressure reverse phase C18 chromatography (Gradient: 30% to 95% acetonitrile in water with 0.02% TFA in each phase). Appropriate test tubes where concentrated using a genevac producing 78 (23 mg, 16%) as a light brown solid. LC-MS (Protocol B): m/z 922.0 [M+H]$^+$, retention time=2.59 minutes.

Step 4

To a stirring solution of 78 (17.9 mg, 0.019 mmol) in 1.0 mL of DMF, DMAP (47.4 mg, 0.388 mmol) was added. The reaction was allowed to stir at room temperature for ~60 minutes. Crude reaction was injected onto a 5 g C18 pre-column (which was previously equilibrated with acetonitrile and then water, with 0.02% TFA in each phase). Material was purified by medium pressure reverse phase C18 chromatography (Gradient: 30% to 95% acetonitrile in water with 0.02% TFA in each phase). Appropriate test tubes where concentrated using a genevac producing 79 (6.1 mg, 39%) as a light brown solid. LC-MS (Protocol B): m/z 700.1 [M+H]$^+$, retention time=1.47 minutes. $^1$H NMR (400 MHz, DMSO-d$_6$): δ 10.26-10.17 (m, 2H), 8.28-8.24 (m, 2H), 8.11-8.06 (d, 2H), 8.00-7.95 (d, 2H), 7.71-7.64 (t, 2H), 7.60-7.53 (t, 2H), 4.56-4.37 (m, 6H), 4.18-4.05 (m, 4H), 2.83-2.59 (m, 8H), 2.49-2.37 (m, 6H).

Preparation of (1S,4S)-bicyclo[2.1.1]hexane-1,4-diylbis[carbonyl(1S)-1-(chloromethyl)-1,2-dihydro-3H-benzo[e]indole-3,5-diyl]diacetate 82

Step 1

Following general procedure A using bicyclo[2.1.1]hexane-1,4-dicarboxylic acid 80 (30 mg, 0.18 mmol), oxalyl chloride (0.0303 mL, 0.353 mmol), THF (4 mL) and 1 drop of DMF, 81 was prepared as an off white solid (39 mg, quant.). Crude 81 was used immediately in the next step as is.

Step 2

Following general procedure B using 6 (106 mg, 0.338 mmol), 81 (35 mg, 0.17 mmol), pyridine (0.0545 mL, 0.676 mmol) and THF (8 mL), and purification using medium pressure reverse phase C18 chromatography (Gradient: 10% to 75% acetonitrile in water with 0.02% TFA in each phase), 82 (52 mg, 45%) was produced as a white solid. LC-MS (Protocol B): m/z 685.2 [M+H]$^+$, retention time=2.16 minutes. $^1$H NMR (400 MHz, DMSO-d$_6$): δ 8.23 (s, 2H), 8.03-7.99 (d, 2H), 7.92-7.87 (d, 2H), 7.63-7.57 (t, 2H), 7.51-7.44 (t, 2H), 4.47-4.25 (m, 6H), 4.13-3.98 (m, 4H), 2.47 (s, 6H), 2.27-2.07 (m, 8H).

Preparation of bicyclo[2.2.2]octane-1,4-diylbis[carbonyl(1S)-1-(chloromethyl)-8-methyl-1,6-dihydropyrrolo[3,2-e]indole-3,5(2H)-diyl]diacetate 85

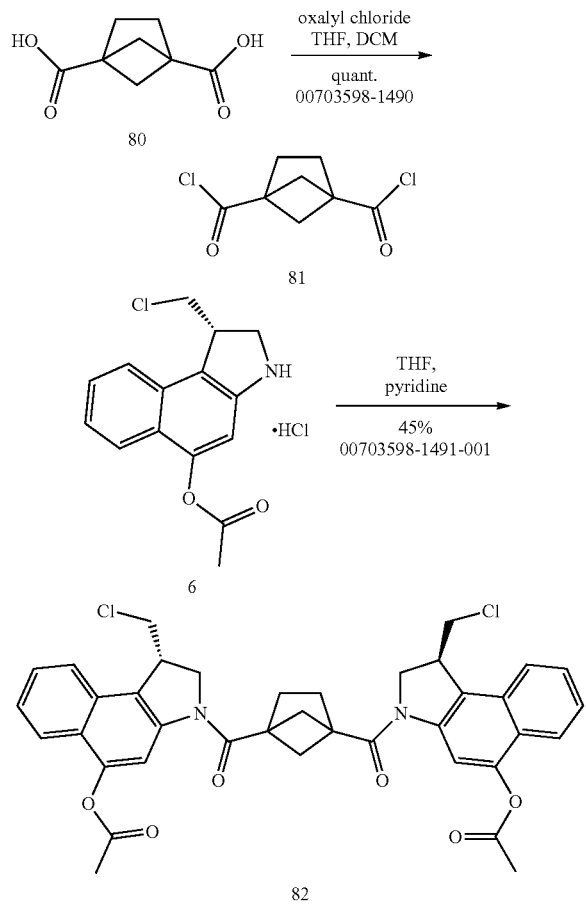

Step 1

Following general procedure A using bicyclo[2.2.2]octane-1,4-dicarboxylic acid 83 (16 mg, 0.081 mmol), oxalyl chloride (0.015 mL, 0.17 mmol), THF (5 mL) and 1 drop of DMF, 84 was prepared as an off white solid (19 mg, quant.). Crude 84 was used immediately in the next step as is.

Step 2

Following general procedure B using 189 (50.9 mg, 0.145 mmol), 84 (17.0 mg, 0.0723 mmol), pyridine (0.0233 mL, 0.289 mmol) and THF (4 mL), and purification using medium pressure reverse phase C18 chromatography (Gradient: 10% to 75% acetonitrile in water with 0.02% TFA in each phase), 85 (21.6 mg, 32%) was produced as a white solid. LC-MS (Protocol B): m/z 719.3 [M+H]+, retention time=2.27 minutes. ¹H NMR (400 MHz, DMSO-d₆): δ 11.00 (s, 2H), 7.79 (s, 2H), 7.19 (s, 2H), 4.68-4.62 (m, 2H), 4.27-4.19 (m, 2H), 4.06-3.94 (m, 4H), 3.65-3.57 (m, 2H), 2.42-2.32 (m, 12H), 2.12-1.96 (m, 12H).

Preparation of bicyclo[2.2.1]heptane-1,4-diylbis[carbonyl(1S)-1-(chloromethyl)-8-methyl-1,6-dihydropyrrolo[3,2-e]indole-3,5(2H)-diyl]diacetate 88

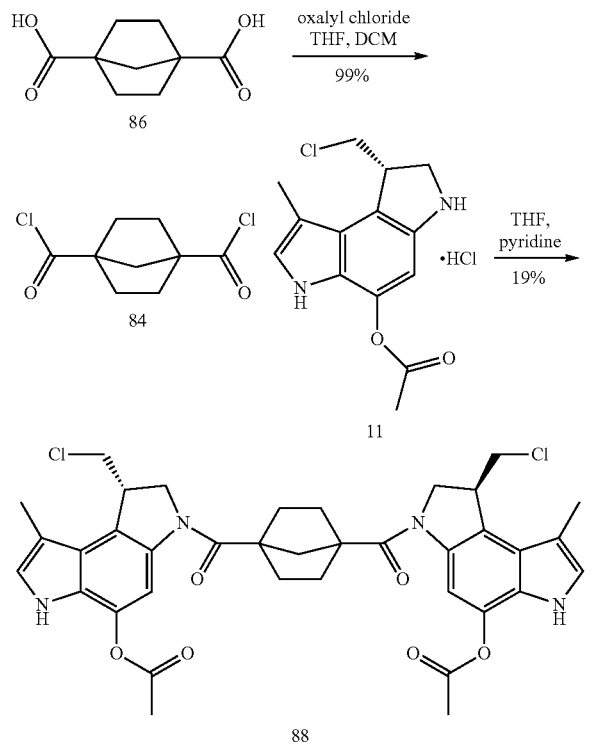

Step 1

Following general procedure A using bicyclo[2.2.1]heptane-1,4-dicarboxylic acid 86 (16 mg, 0.087 mmol), oxalyl chloride (0.016 mL, 0.18 mmol), THF (5 mL) and 1 drop of DMF, 87 was prepared as an off white solid (19 mg, 99%). Crude 87 was used immediately in the next step as is.

Step 2

Following general procedure B using 189 (54.1 mg, 0.154 mmol), 87 (17.0 mg, 0.0769 mmol), pyridine (0.0248 mL, 0.308 mmol) and THF (4 mL), and purification using medium pressure reverse phase C18 chromatography (Gradient: 10% to 75% acetonitrile in water with 0.02% TFA in each phase), 88 (13.6 mg, 19%) was produced as an light brown solid. LC-MS (Protocol B): m/z 705.3 [M+H]+, retention time=2.32 minutes. ¹H NMR (400 MHz, DMSO-d₆): δ 11.02 (s, 2H), 7.82 (s, 2H), 7.19 (s, 2H), 4.50-4.45 (d, 2H), 4.26-4.16 (m, 2H), 4.10-4.02 (m, 2H), 3.98-3.92 (m, 2H), 3.65-3.58 (m, 2H), 2.41-2.33 (m, 12H), 2.22-2.03 (m, 10H).

Preparation of bicyclo[1.1.1]pentane-1,3-diylbis[carbonyl(1S)-1-(chloromethyl)-8-methyl-1,6-dihydropyrrolo[3,2-e]indole-3,5(2H)-diyl]diacetate 91

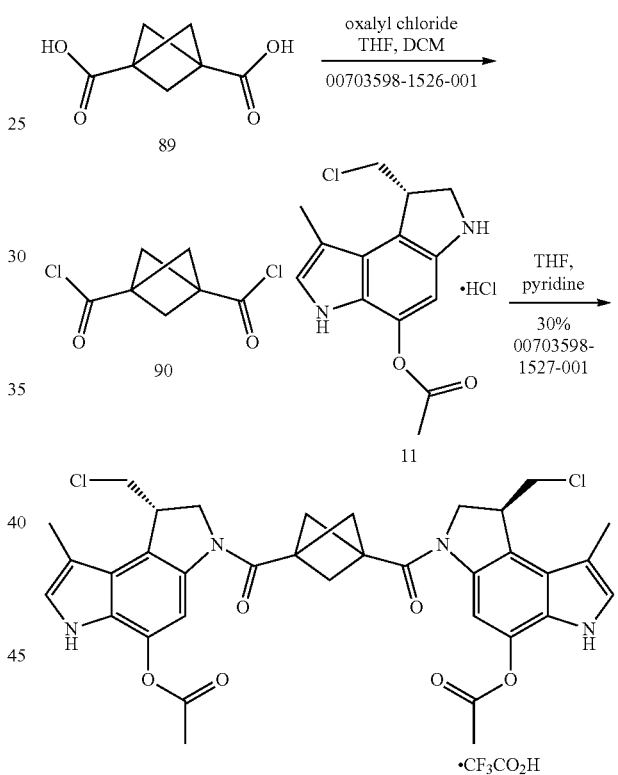

Step 1

Following general procedure A using bicyclo[1.1.1]pentane-1,3-dicarboxylic acid 89 (31 mg, 0.20 mmol), oxalyl chloride (0.025 mL, 0.40 mmol), THF (8 mL) and 1 drop of DMF, 90 was prepared as an off white solid (40 mg, quant.). Crude 90 was used immediately in the next step as is.

Step 2

Following general procedure B using 189 (142 mg, 0.404 mmol), 90 (39 mg, 0.20 mmol), pyridine (0.065 mL, 0.81 mmol) and THF (12 mL), and purification using medium pressure reverse phase C18 chromatography (Gradient: 10% to 75% acetonitrile in water with 0.02% TFA in each phase), 91 (45.5 mg, 30%) was produced as an light gray solid. LC-MS (Protocol B): m/z 677.2 [M+H]$^+$, retention time=1.89 minutes. $^1$H NMR (400 MHz, DMSO-d$_6$): δ 11.04 (s, 2H), 7.78 (s, 2H), 7.20 (s, 2H), 4.47-4.39 (m, 2H), 4.36-4.26 (m, 2H), 4.18-4.08 (m, 2H), 4.03-3.94 (m, 2H), 3.77-3.66 (m, 2H), 2.56 (s, 6H), 2.41-2.31 (m, 12H).

Preparation of (8S)-6-[(3-{[(1S)-5-(acetyloxy)-1-(chloromethyl)-8-methyl-1,6-dihydropyrrolo[3,2-e]indol-3(2H)-yl]carbonyl}bicyclo[1.1.1]pent-1-yl)acetyl]-8-(chloromethyl)-1-methyl-3,6,7,8-tetrahydropyrrolo[3,2-e]indol-4-yl acetate 97

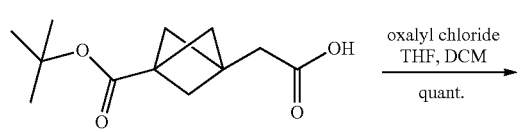

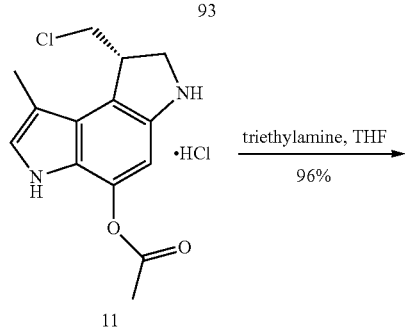

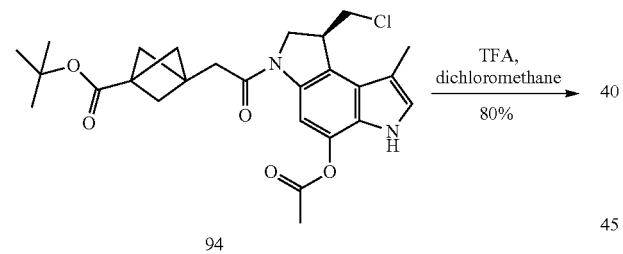

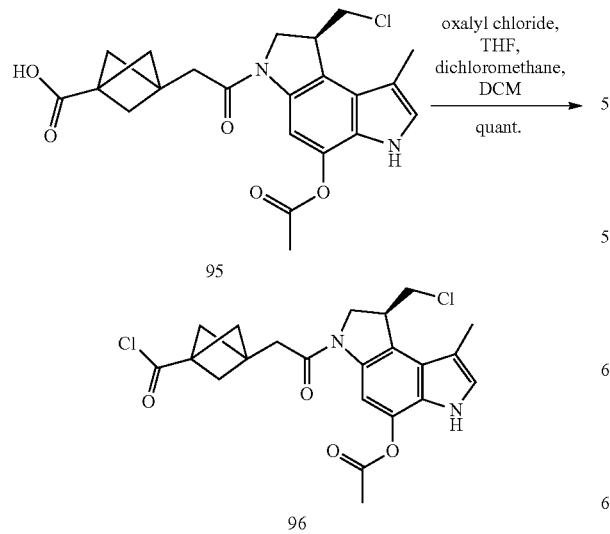

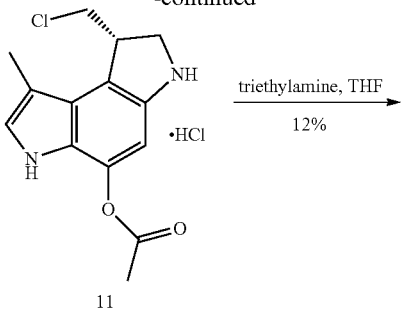

Step 1

Following general procedure A using 3-(2-tert-butoxy-2-oxoethyl)bicyclo[1.1.1]pentane-1-carboxylic acid 92 [prepared as described in Bioorg. Med. Chem. 2009, 17, 242-250.] (90 mg, 0.40 mmol), oxalyl chloride (0.041 mL, 0.477 mmol), THF (8 mL) and 1 drop of DMF, 93 was prepared as an off white solid (103 mg, quant.). Crude 93 was used immediately in the next step as is.

Step 2

Following general procedure B using 11 (141 mg, 0.40 mmol), 93 (98 mg, 0.40 mmol), triethylamine (0.168 mL, 1.20 mmol) and THF (30 mL), and purification using silica gel chromatography (Gradient: 0% to 35% acetone in heptane), 94 (188 mg, 96%) was produced as an off white solid. LC-MS (Protocol B): m/z 487.2 [M+H]$^+$, retention time=2.04 minutes.

Step 3

To a stirring solution of 94 (184 mg, 0.378 mmol), in 8 mL of dichloromethane, TFA (4.0 mL, 52 mmol) was added. The reaction was allowed to stir at room temperature for ~45 minutes. Reaction was concentrated in vacuo and placed underneath high vacuum producing 95 (164 mg, 80%) as a light gray solid, which was used in the next step without purification. LC-MS (Protocol B): m/z 431.7 [M+H]$^+$, retention time=1.39 minutes.

Step 4

Following general procedure A using 95 (55 mg, 0.101 mmol), oxalyl chloride (0.0104 mL, 0.121 mmol), THF (3 mL), dichloromethane (1 mL) and 1 drop of DMF, 96 was prepared as an off white solid (46 mg, quant.). Crude 96 was used immediately in the next step as is.

Step 5

Following general procedure B using 11 (31.3 mg, 0.089 mmol), 96 (40 mg, 0.089 mmol), pyridine (0.0215 mL, 0.267 mmol) and THF (8.0 mL), and purification using medium pressure reverse phase C18 chromatography (Gradient: 10% to 70% acetonitrile in water with 0.02% TFA in each phase), 97 (10.1 mg, 12%) was produced as an light gray solid. LC-MS (Protocol B): m/z 691.3 [M+H]$^+$, retention time=1.93 minutes. $^1$H NMR (400 MHz, DMSO-d$_6$): δ 11.02 (s, 2H), 7.86-7.72 (d, 2H), 7.19 (s, 2H), 4.43-4.36 (m, 1H), 4.28-4.14 (m, 3H), 4.13-4.05 (m, 2H), 3.96-3.89 (m, 2H), 3.68-3.60 (m, 2H), 2.89-2.82 (m, 2H), 2.73-2.66 (m, 2H), 2.40-2.30 (m, 12H), 2.24-2.15 (m, 6H).

Preparation of tert-butyl(1S)-8-amino-5-(benzyloxy)-1-(chloromethyl)-1,2-dihydro-3H-benzo[e]indole-3-carboxylate 99 and tert-butyl(1R)-8-amino-5-(benzyloxy)-1-(chloromethyl)-1,2-dihydro-3H-benzo[e]indole-3-carboxylate 98

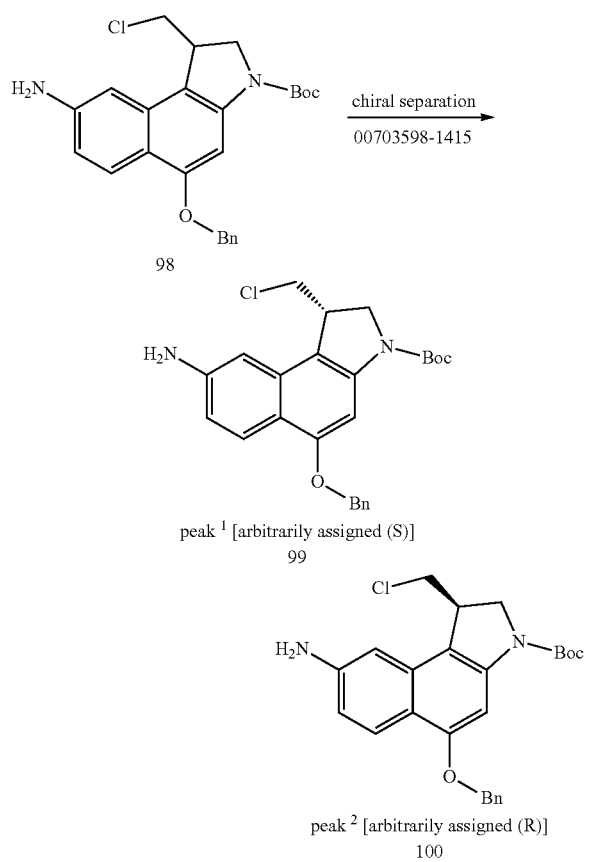

98 tert-butyl 8-amino-5-(benzyloxy)-1-(chloromethyl)-1,2-dihydro-3H-benzo[e]indole-3-carboxylate [prepared using the chemistry described in J. Med. Chem. 2012, 55, 5878-5886] was separated using supercritical fluid chromatography (method L1). Peak 1 was concentrated in vacuo yielding 99 (385 mg) was arbitrarily assigned as (S). LC-MS (Protocol B): m/z 439.1 [M+H]$^+$, retention time=2.34 minutes. Peak 2 was concentrated in vacuo yielding 100 (401 mg) was arbitrarily assigned as (R). LC-MS (Protocol B): m/z 439.1 [M+H]$^+$, retention time=2.34 minutes.

Preparation of tert-butyl(1R)-8-(acetylamino)-5-(acetyloxy)-1-(chloromethyl)-1,2-dihydro-3H-benzo[e]indole-3-carboxylate 102

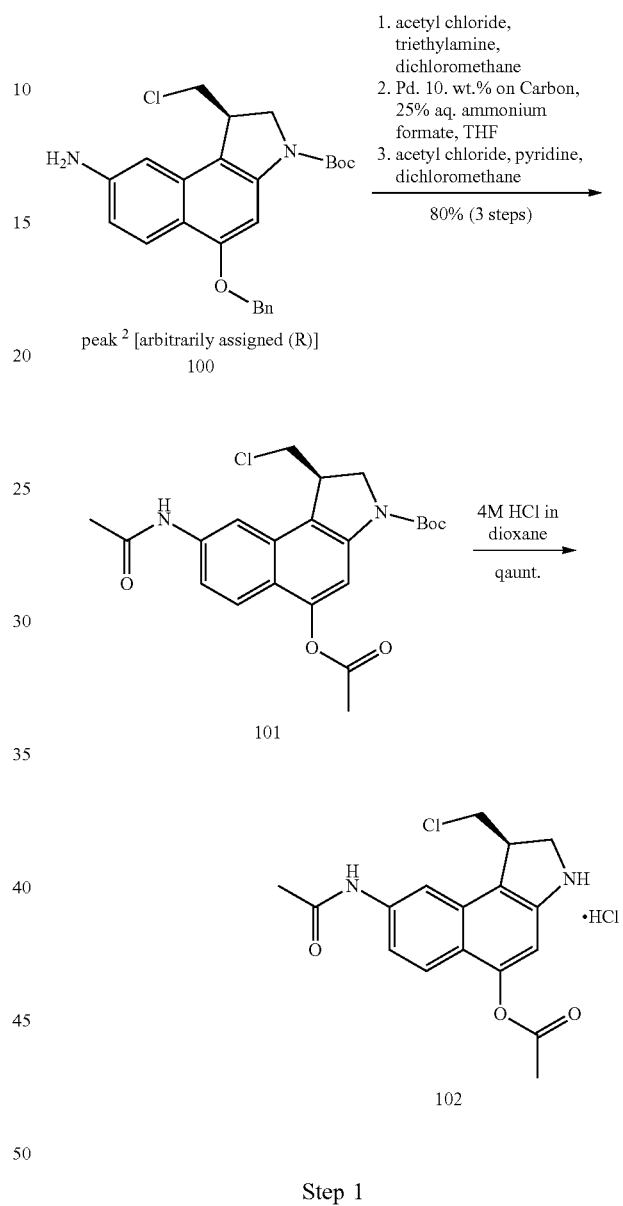

Step 1

To a stirring solution of 99 (60 mg, 0.14 mmol) in 6 mL of dichloromethane at 0° C., acetyl chloride (0.015 mL, 0.206 mmol) was added followed by triethylamine (0.029 mL, 0.206 mmol). The reaction was allowed to stir at 0° C. for ~1 minute and then allowed to warm to room temperature. The reaction was allowed to stir at room temperature for ~25 minutes. Reaction was diluted with dichloromethane and then transferred to a separatory funnel. The organic layer was separated, and then washed with 1 N HCl, and then water. The organic layer was dried over sodium sulfate, filtered and then concentrated in vacuo producing an orange solid. To a stirring solution of crude material in 4 mL of THF at 0° C., Pd. 10 wt. % on carbon (45 mg) was added followed by a solution of 25% ammonium formate aq. (0.3 mL). The reaction was allowed to stir at 0° C. for ~4 hours. Reaction was diluted with THF and ether. Sodium sulfate was added and the reaction was filtered through a thin pad of celite. Organics where concentrated in vacuo and placed underneath high vacuum producing a light brown solid. To a stirring solution of crude material in 6 mL of dichloromethane at 0° C., acetyl chloride (0.015 mL, 0.211 mmol) was added followed by pyridine (0.017 mL, 0.211 mmol). The reaction was allowed to stir at 0° C. for ~1 minute and then allowed to warm to room temperature. The reaction was allowed to stir at room temperature for ~25 minutes. Reaction was concentrated in vacuo. Silica gel chromatography was then preformed (Gradient: 0% to 45% acetone in heptane). Appropriate test tubes where combined and concentrated in vacuo yielding 101 (49 mg, 80%, 3 steps) as an off white solid. LC-MS (Protocol B): m/z 455.9 [M+Na]$^{+23}$, retention time=2.05 minutes.

Step 2

To a round bottom flask containing 101 (45 mg, 0.10 mmol), 4M HCl in dioxane (6.0 mL, 24 mmol) was added. The reaction was allowed to stir at room temperature for ~2 hours. Reaction was concentrated in vacuo and placed underneath high vacuum producing 102 (42 mg, quant.) as a dark brown solid. LC-MS (Protocol B): m/z 333.0 [M+H]$^+$, retention time=1.65 minutes.

Preparation of tert-butyl(1S)-8-(acetylamino)-5-(acetyloxy)-1-(chloromethyl)-1,2-dihydro-3H-benzo[e]indole-3-carboxylate 103

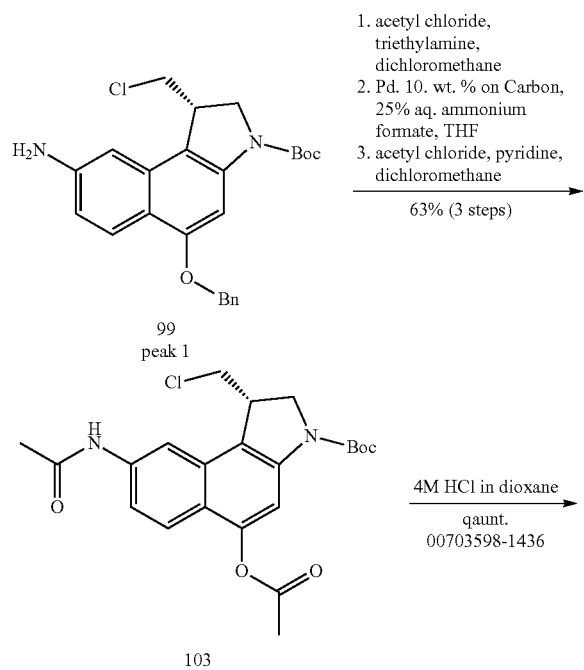

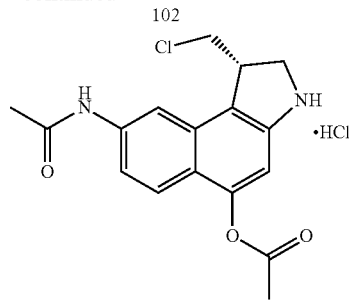

(S) stereochemistry was arbitrarily assigned (peak 1)

Step 1

To a stirring solution of 99 (65 mg, 0.15 mmol) in 6 mL of dichloromethane at 0° C., acetyl chloride (0.016 mL, 0.22 mmol) was added followed by triethylamine (0.031 mL, 0.22 mmol). The reaction was allowed to stir at 0° C. for ~1 minute and then allowed to warm to room temperature. The reaction was allowed to stir at room temperature for ~25 minutes. Reaction was diluted with dichloromethane and then transferred to a separatory funnel. The organic layer was separated, and then washed with 1 N HCl, and then water. The organic layer was dried over sodium sulfate, filtered and then concentrated in vacuo producing an orange solid. To a stirring solution of crude material in 4 mL of THF at 0° C., Pd. 10 wt. % on carbon (45 mg) was added followed by a solution of 25% ammonium formate aq. (0.5 mL). The reaction was allowed to stir at 0° C. for ~4 hours. Reaction was diluted with THF and ether. Sodium sulfate was added and the reaction was filtered through a thin pad of celite. Organics where concentrated in vacuo and placed underneath high vacuum producing a light brown solid. To a stirring solution of crude material in 8 mL of dichloromethane at 0° C., acetyl chloride (0.015 mL, 0.21 mmol) was added followed by pyridine (0.017 mL, 0.21 mmol). The reaction was allowed to stir at 0° C. for ~1 minute and then allowed to warm to room temperature. The reaction was allowed to stir at room temperature for ~25 minutes. Reaction was concentrated in vacuo. Silica gel chromatography was then preformed (Gradient: 0% to 25% acetone in heptane). Appropriate test tubes where combined and concentrated in vacuo yielding 103 (39.1 mg, 63%, 3 steps) as a white solid. LC-MS (Protocol B): m/z 455.0 [M+Na]$^{+23}$, retention time=2.00 minutes.

Step 2

To a round bottom flask containing 103 (37 mg, 0.085 mmol), 4M HCl in dioxane (4.0 mL, 16 mmol) was added. The reaction was allowed to stir at room temperature for ~2 hours. Reaction was concentrated in vacuo and placed underneath high vacuum producing 104 (34 mg, quant.) as a green solid. LC-MS (Protocol B): m/z 333.0 [M+H]$^+$, retention time=1.41 minutes.

Preparation of (1S)-3-{[3-(chlorocarbonyl)bicyclo[1.1.1]pent-1-yl]carbonyl}-1-(chloromethyl)-2,3-dihydro-1H-benzo[e]indol-5-yl 107

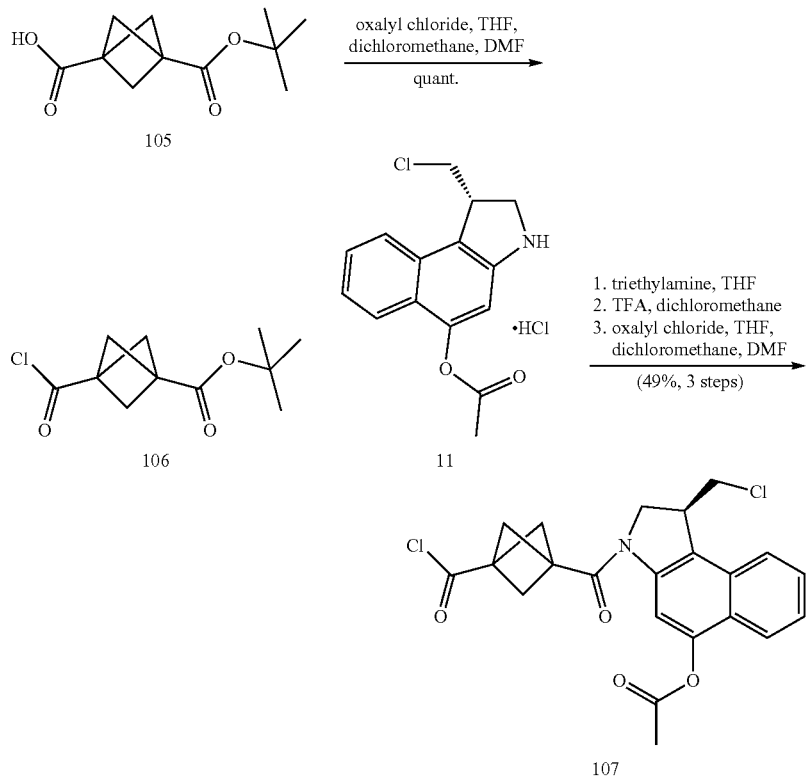

Step 1

Following general procedure A using 3-(tert-butoxycarbonyl)bicyclo[1.1.1]pentane-1-carboxylic acid 105 (212 mg, 1.0 mmol), oxalyl chloride (0.094 mL, 1.10 mmol), THF (3 mL), dichloromethane (6 m) and 1 drop of DMF, 105 was prepared as an off white solid (235 mg, quant.). Crude 105 was used immediately in the next step as is.

Step 2

Following general procedure B using 11 (311 mg, 0.997 mmol), 105 (230 mg, 0.997 mmol), triethylamine (0.292 mL, 2.09 mmol) and THF (20 mL), and purification using silica gel chromatography (Gradient: 10% to 75% acetone in heptane). Appropriate test tubes where combined and concentrated in vacuo producing a white solid. To a stirring solution of crude material in 10 mL of dichloromethane, TFA (5.0 mL, 65 mmol) was added. The reaction was allowed to stir at room temperature for ~90 minutes. Reaction was concentrated in vacuo. Material was dissolved with dichloromethane, transferred to a separatory funnel and then washed with 1N HCl aq., brine, and water. Organic layer was dried over sodium sulfate, filtered, and then concentrated in vacuo before being placed underneath high vacuum producing a white solid. Using this crude material and following general procedure A with oxalyl chloride (0.010 mL, 0.121 mmol), THF (4 mL), dichloromethane (2 mL) and 1 drop of DMF, 107 was prepared as a white solid (52 mg, 49%, 3 steps). Crude 107 was used immediately in the next step as is.

Preparation of (1R)-8-(acetylamino)-3-[(3-{[(1S)-5-(acetyloxy)-1-(chloromethyl)-1,2-dihydro-3H-benzo[e]indol-3-yl]carbonyl}bicyclo[1.1.1]pent-1-yl)carbonyl]-1-(chloromethyl)-1,2-dihydro-3H-benzo[e]indol-5-yl acetate 108

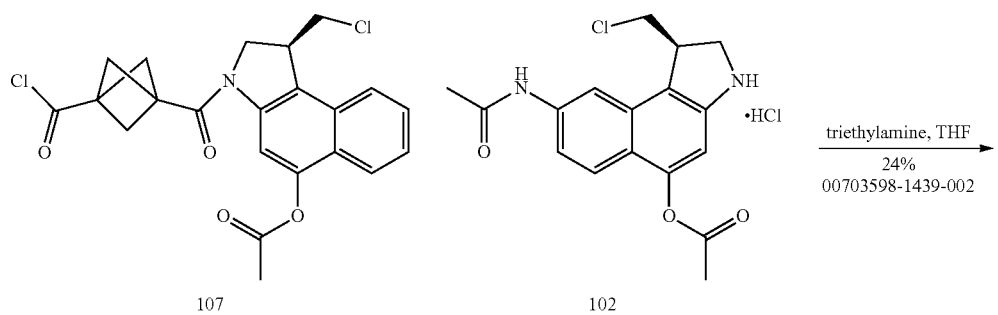

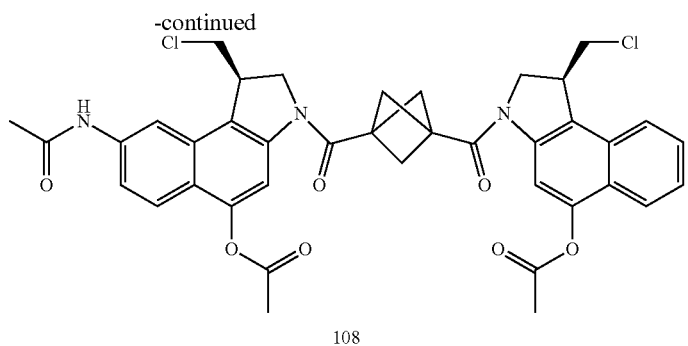

108

Following general procedure B using 107 (21 mg, 0.057 mmol), 102 (24.6 mg, 0.057 mmol), triethylamine (0.024 mL, 0.171 mmol) and THF (6 mL), and preparative HPLC purification (method H1 108 (5.8 mg, 14%) was produced as a off white solid. LC-MS (Protocol B): m/z 728.1 [M+H]+, retention time=2.12 minutes.

Preparation of (1S)-3-[(3-{[(1S)-8-(acetylamino)-5-(acetyloxy)-1-(chloromethyl)-1,2-dihydro-3H-benzo[e]indol-3-yl]carbonyl}bicyclo[1.1.1]pent-1-yl)carbonyl]-1-(chloromethyl)-2,3-dihydro-1H-benzo[e]indol-5-yl acetate 109

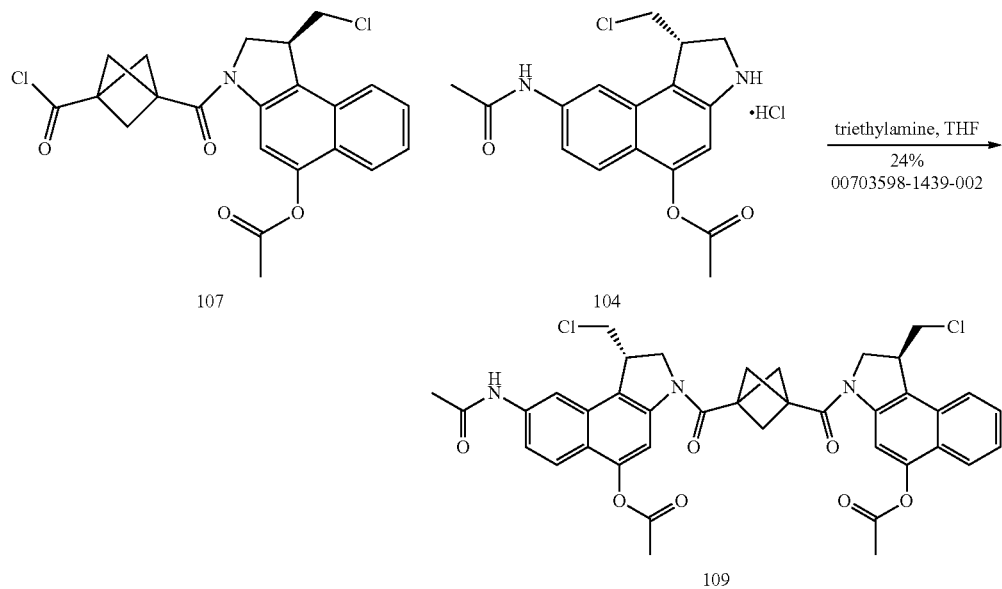

109

Following general procedure B using 107 (29.4 mg, 0.068 mmol), 104 (25 mg, 0.068 mmol), triethylamine (0.028 mL, 0.028 mmol) and THF (8 mL), and purification using medium pressure reverse phase C18 chromatography (Gradient: 10% to 75% acetonitrile in water with 0.02% TFA in each phase), 109 (11.8 mg, 24%) was produced as a white solid. LC-MS (Protocol B): m/z 728.0 [M+H]+, retention time=2.13 minutes. $^1$H NMR (400 MHz, DMSO-$d_6$): δ 10.25 (s, 1H), 8.27 (s, 1H), 8.20 (s, 1H), 8.06 (s, 1H), 8.04-7.98 (m, 1H), 7.92-7.80 (m, 2H), 7.63-7.55 (m, 2H), 7.50-7.45 (m, 1H), 4.56-4.33 (m, 5H), 4.29-4.17 (m, 1H), 4.16-3.94 (m, 4H), 2.62 (s, 6H), 2.48-2.43 (m, 6H), 2.11 (s, 3H).

Preparation of Acetic acid (S)-3-[5-((S)-5-amino-1-chloromethyl-1,2-dihydro-benzo[e]indole-3-carbonyl)-thiophene-2-carbonyl]-1-chloromethyl-2,3-dihydro-1H-benzo[e]indol-5-yl ester 115

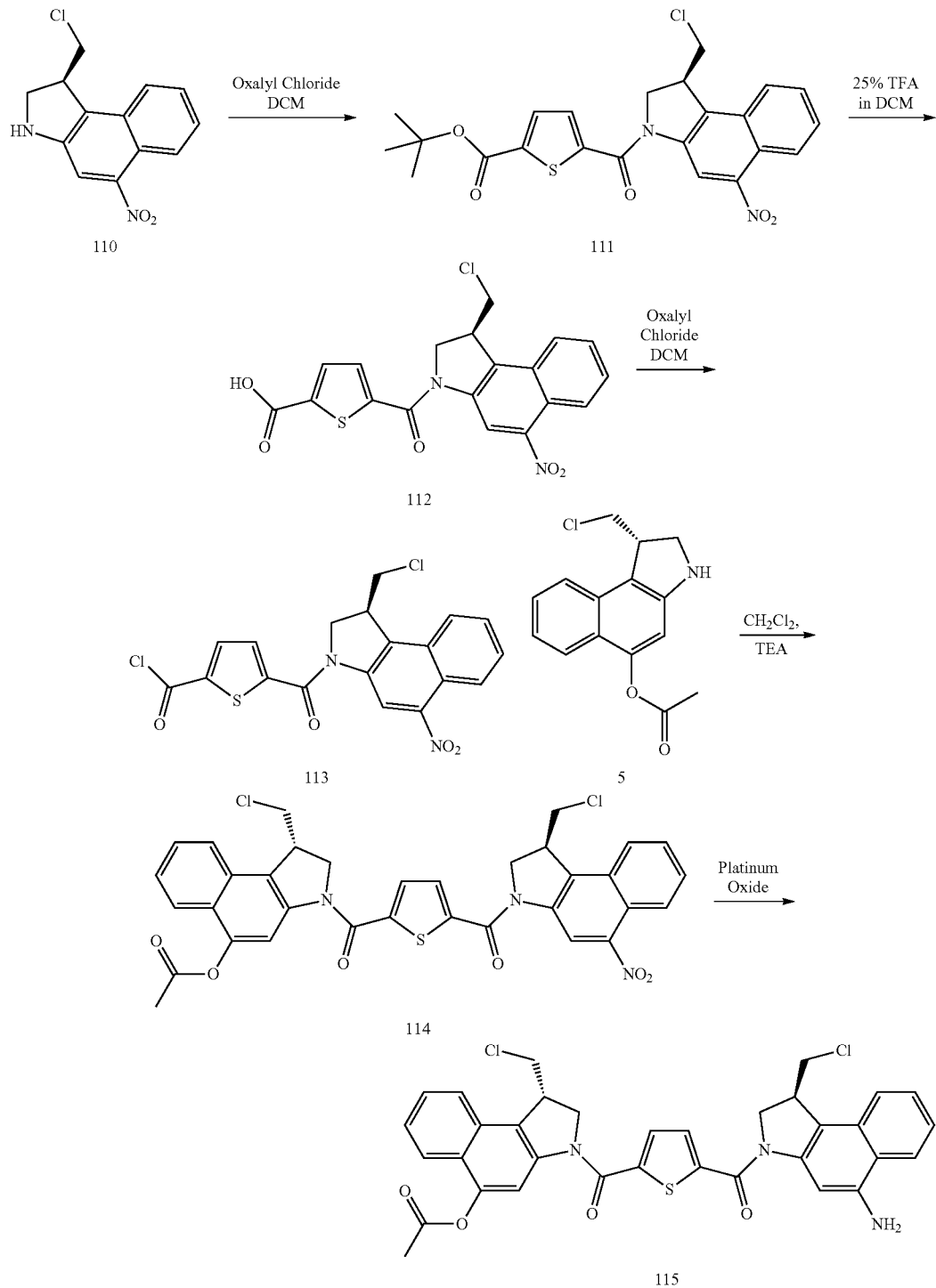

Step 1

In a round bottom flask purged with $N_2$, containing Thiophene-2,5-dicarboxylic acid mono-tert-butyl ester (152 mg, 0.66 mmol) in 5 mL of anhydrous DCM was added Oxalyl Chloride (0.66 mmol, 0.066 mL). To this solution was added 1 drop of N,N-dimethylformamide. The reaction mixture was stirred for 3 hours and concentrated in vacuo to a crud residue. The residue was then added to a round bottom flask containing 110 (200 mg, 0.66 mmol) in 15 mL of anhydrous dichloromethane. The reaction was stirred for 2 hours. The residue was diluted with 15 mL of dichloromethane and transferred to a separation funnel. Washed organic layer with 1M HCl (3×), Water (3×), and Brine (2×). Dried organic layer over Sodium Sulfate, filtered and concentrated to a crude solid. Silica chromatography was then preformed (Gradient: 0%-100% Ethyl Acetate in Heptanes) producing 111 (185 mg, 58%) as a yellow solid. LC-MS: m/z 473 [M+H$^+$], retention time=2.25 minutes.

Step 2

111 was added 10 mL of 25% trifluoro acidic acid in dichloromethane. The reaction was stirred for 30 min. The crude reaction mixture was concentrated in vacuo to afford 112 as a yellow solid. LC-MS: m/z 416 [M+H$^+$], retention time=1.65 minutes.

Step 3

In a round bottom flask purged with N$_2$, containing 112 (100 mg, 0.24 mmol) in 5 mL of anhydrous DCM was added Oxalyl Chloride (0.24 mmol, 0.02 mL). To this solution was added 1 drop of N,N-dimethylformamide. The reaction mixture was stirred for 3 hours and concentrated in vacuo to afford 113 as a yellow solid (100 mg, 0.24 mmol, quantitative). LCMS, taken in methanol: m/z 282.0 [M+H$^+$, for methanolysis product]. retention time=1.95 minutes.

Step 4

In a round bottom flask containing 5, 28 mg, 0.092 mmol) in 5 mL of dichloromethane was added 113 (40 mg, 0.092 mmol). Triethylamine (0.088 mL) was then added and the system was stirred for 1 hour at room temperature. The crude reaction mixture was concentrated in vacuo and taken back up in 25 mL of dichloromethane and transferred to a separation funnel. Washed organic layer with 1M HCl (3×), Water (3×), and Brine (2×). Dried organic layer over Sodium Sulfate, filtered and concentrated the filtrate to a crude solid. Silica chromatography was then preformed (Gradient: 0%-100% Ethyl Acetate in heptanes) producing 114 (40 mg, 64%) as a yellow solid. LC-MS: m/z 674 [M+H$^+$], retention time=2.25 minutes.

Step 5

In a Parr flask containing 114 (30 mg, 0.044 mmol) in 15 mL of anhydrous tetrahydrofuran was added Platinum Oxide (5 mg, 0.02 mmol). The system was capped with a rubber septum and hydrogenation occurred under H$_2$ at 50 Psi for 3 hours. After 3 hours hours the Parr flask was purged with N$_2$ and the crude reaction was filtered thru a plug of celite using ethyl acetate. The filtrate containing the desired crude product was then concentrated. Silica chromatography was then preformed (Gradient: 0%-100% ethyl acetate in heptanes) producing 115 (15 mg, 50%) as a yellow solid. LC-MS: m/z 644 [M+H$^+$], retention time=2.06 minutes.

Preparation of ((S)-1-Chloromethyl-5-hydroxy-1,2-dihydro-benzo[e]indol-3-yl)-[5-((S)-1-chloromethyl-5-hydroxy-8-methyl-1,6-dihydro-2H-pyrrolo[3,2-e]indole-3-carbonyl)-thiophen-2-yl]methanone 117

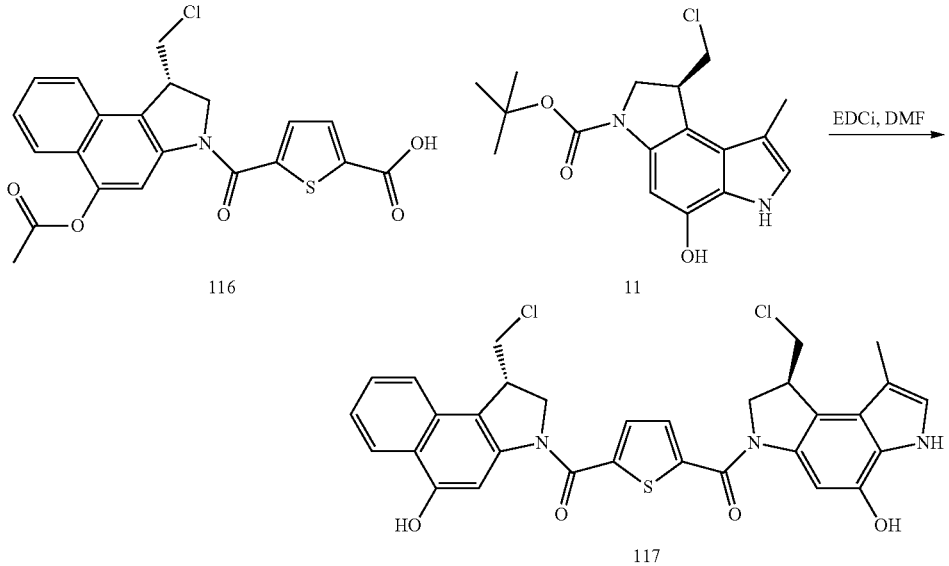

In a round-bottom flask equipped with a stir bar containing 11 (34 mg, 0.1 mmol) was taken up in N,N-dimethylformamide (5 mL) and added drop wise to a round bottom flask containing 5-((S)-5-Acetoxy-1-chloromethyl-1,2-dihydro-benzo[e]indole-3-carbonyl)-thiophene-2-carboxylic acid (42, 44 mg, 0.1 mmol), 3-(Ethyliminomethyleneamino)-N,N-dimethylpropan-1-amine (59 mg, 0.3 mmol) and sodium bicarbonate (36 mg, 0.4 mmol) in 5 mL of N,N-dimethylformamide). The reaction was stirred for 30 min. 3 mL of 1 M HCl (aq) was added and the crude reaction mixture was concentrated in vacuo. Reverse phase chromatography was then preformed (Gradient: 0%-65% acetonitrile in water) producing 117 (15 mg, 24%) as a pale white solid. LC-MS: m/z 604 [M−H$^-$], retention time=1.93 minutes Preparation of (S)-1-(chloromethyl)-3-(5-((S)-1-(chloromethyl)-5-hydroxy-2,3-dihydro-1H-benzo[e]indole-3-carbonyl)thiophene-2-carbonyl)-2,3-dihydro-1H-benzo[e]indol-5-yl methyl carbonate 119

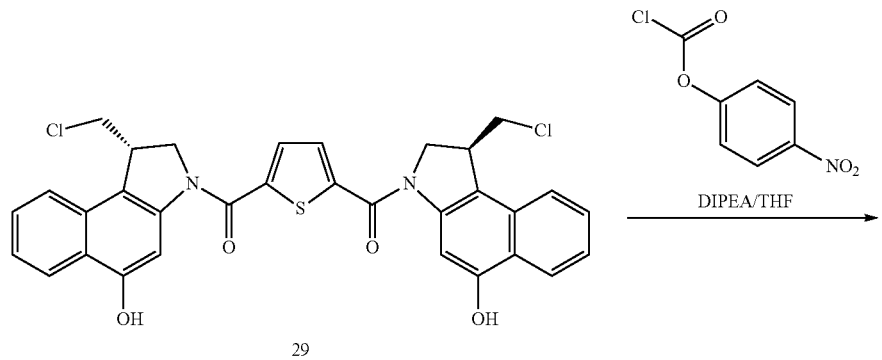

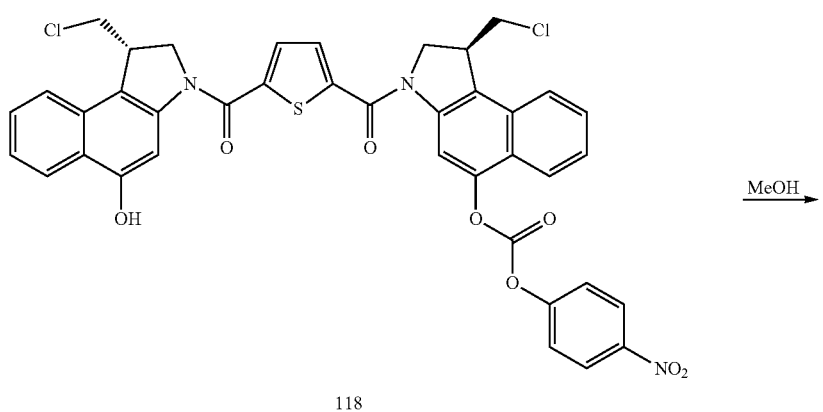

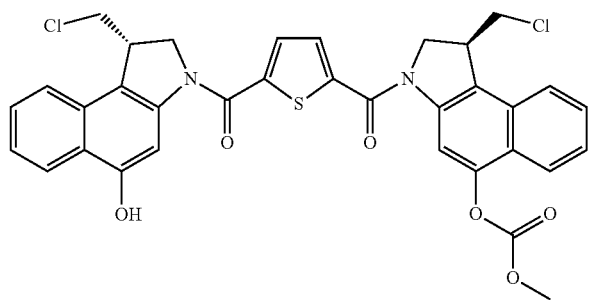

A solution of 4-nitrophenyl chloroformate (11 mg, 0.054 mmol) in THF (1 mL) was added to a solution of 29 (27 mg, 0.045 mmol) in THF (3 mL) and DIPEA (0.032 mL, 0.18 mmol) at 0° C. The mixture was stirred at 0° C. for 2 h, and stirred at room temperature for overnight. LC-MS showed the corresponding mono-PNP carbonate 118 was formed. To the reaction mixture, methanol (1 mL) was added. After being stirred for 5 min, it was concentrated in vacuo, and the residue was purified by Gilson HPLC (CAN/water, 0.02% TFA) to give the product 119 as off-white solid (5 mg, 20%). LC-MS: m/z 660.7 [M+H], retention time=1.06 min. $^1$H NMR (400 MHz, CDCl$_3$), δ 8.53 (d), 7.80 (m), 7.72 (d), 7.45 (m), 7.34 (m), 4.72 (m), 4.62 (d), 4.30 (m), 4.11 (t), 4.04 (s), 3.86 (d), 3.71 (d), 3.47 (t), 3.24 (m).

Preparation of (S)-1-(chloromethyl)-3-(5-((S)-1-(chloromethyl)-5-hydroxy-2,3-dihydro-1H-benzo[e]indole-3-carbonyl)thiophene-2-carbonyl)-2,3-dihydro-1H-benzo[e]indol-5-yl(2-(dimethylamino)ethyl)carbamate 123
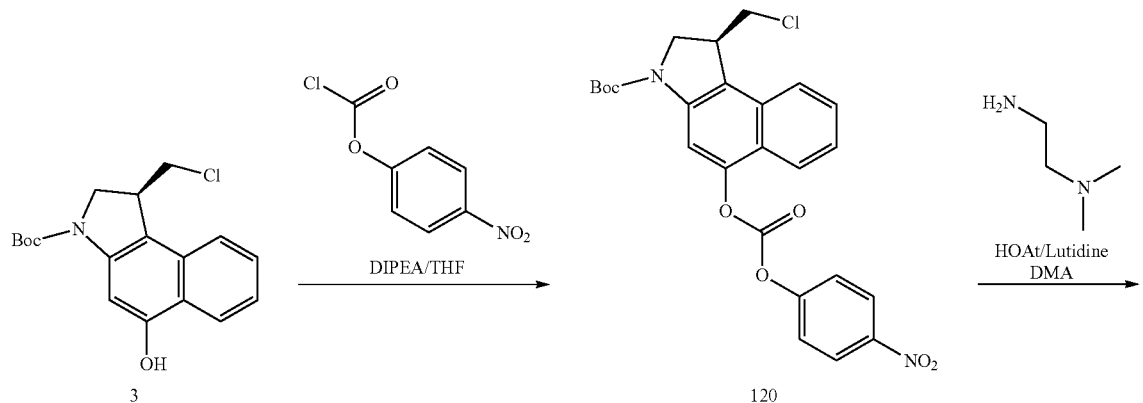
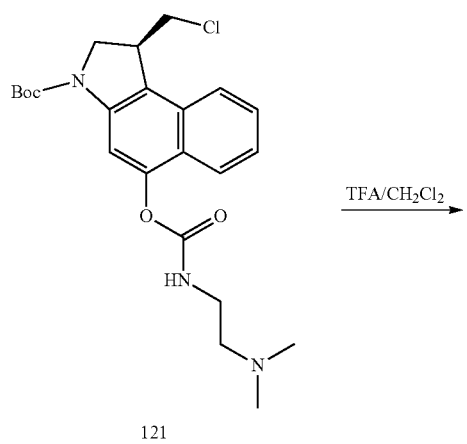
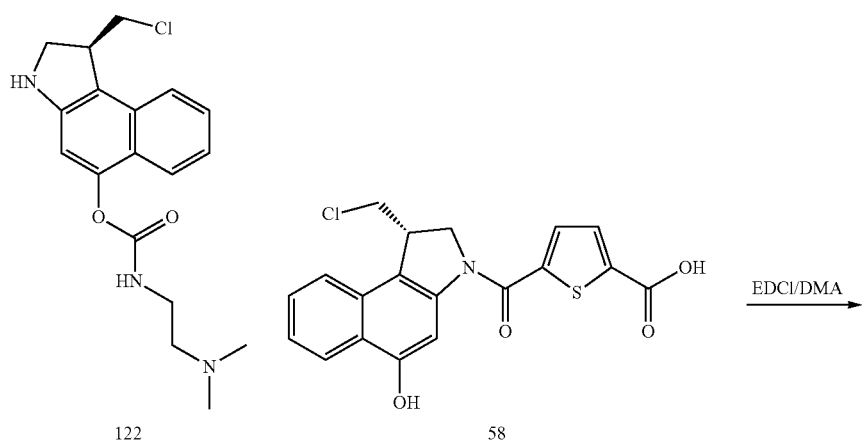

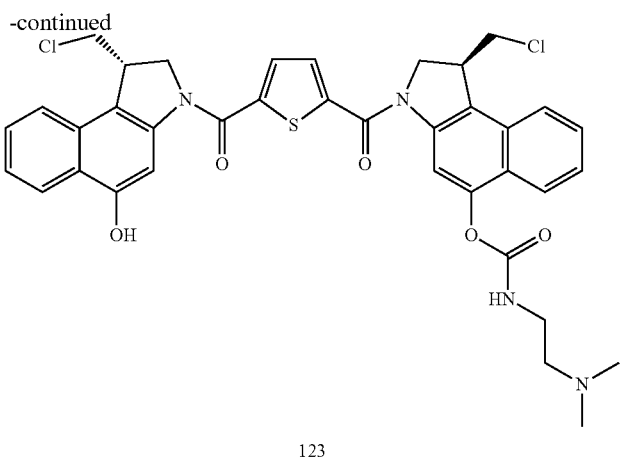

Step 1

A solution of 4-nitrophenyl chloroformate (164 mg, 0.78 mmol) in THF (1 mL) was added to a solution of 3 (200 mg, 0.60 mmol) in THF (6 mL) and DIPEA (0.315 mL, 1.8 mmol) at 0° C., and the mixture was stirred at room temperature for 2 h. Concentrated and the residue was treated with EA and water, extracted with EA, washed with water and brine. Dried over MgSO4, the solvent was removed in vacuo to give the PNP carbonate 120 as yellow form (300 mg, 100%). LC-MS: m/z 399.0 [M+H], retention time=2.37 min.

Step 2

N,N-dimethylethylenediamine (35 mg, 0.4 mmol) was added to a solution of the above PNP carbonate 120 (100 mg, 0.2 mmol) in DMA (3 mL), followed by lutidine (0.07 mL, 0.6 mmol) and HOAt (14 mg, 0.1 mmol). The mixture was stirred at room temperature for 4 h. the mixture was subjected to purification by Gilson HPLC (ACN/water, 0.02% TFA) to give the carbamate (S)-tert-butyl 1-(chloromethyl)-5-(((2-(dimethylamino)ethyl)carbamoyl)oxy)-1H-benzo[e]indole-3(2H)-carboxylate 121 as yellow glass (86 mg, 77%). LC-MS: m/z 448.1 [M+H], retention time=0.70 min.

Step 3

The above compound 121 (38 mg, 0.067 mmol) was treated with TFA (0.5 mL) and CH$_2$Cl$_2$ (2 mL) for 2 h, then concentrated in vacuo to give the corresponding deprotected amine 122 which was dissolved in DMA (3 mL). To this solution, it was added (S)-5-(1-(chloromethyl)-5-hydroxy-2,3-dihydro-1H-benzo[e]indole-3-carbonyl)thiophene-2-carboxylic acid [58] (26 mg, 0.067 mmol), followed by EDO (27 mg, 0.14 mmol), and the mixture was stirred at room temperature for overnight. The crude was purified by Gilson HPLC (ACN/water, 0.02% TFA) to give 123 (4.5 mg, 8%). LC-MS: m/z 717.4 [M+H], retention time=1.38 min. $^1$H NMR (400 MHz, CDCl$_3$), δ 8.24 (d), 8.0 (d), 7.75 (d), 7.64 (s), 7.55-7.34 (m), 4.62 (m), 4.13 (t), 4.05 (t), 3.94 (t), 3.64 (t), 3.57-3.45 (m), 3.33 (s), 3.25 (s), 2.89 (s).

Preparation of (S)-1-(chloromethyl)-3-(5-((S)-1-(chloromethyl)-5-hydroxy-2,3-dihydro-1H-benzo[e]indole-3-carbonyl)thiophene-2-carbonyl)-2,3-dihydro-1H-benzo[e]indol-5-ylmethyl(2-(methylamino)ethyl)carbamate 126

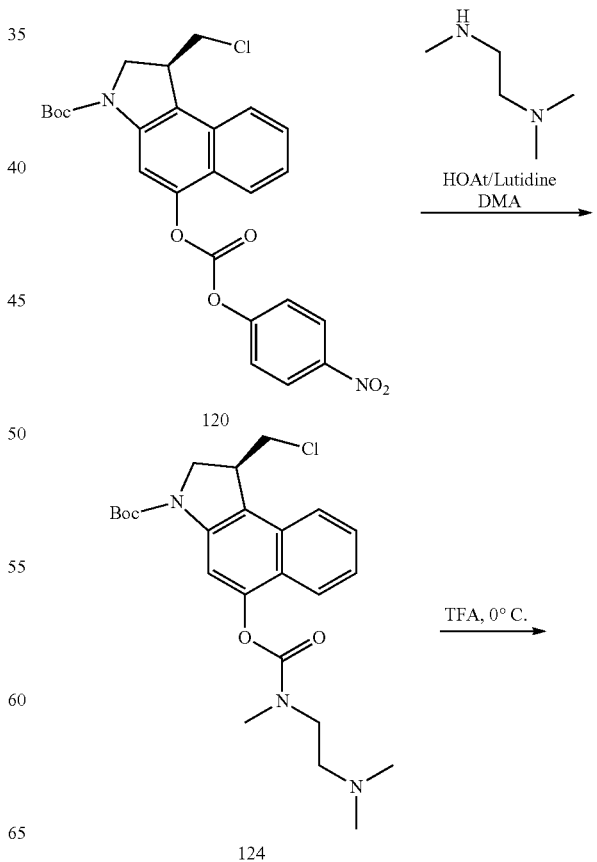

121

-continued

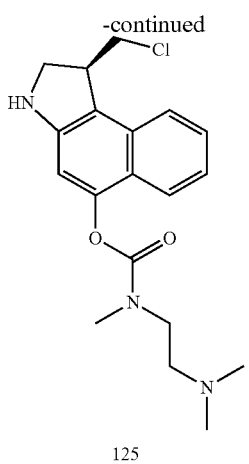

125

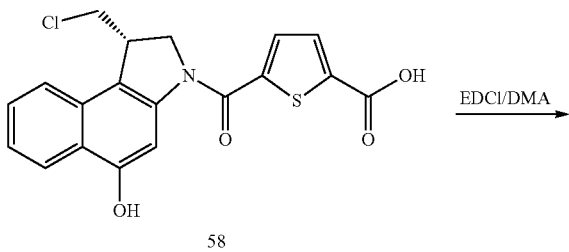

58  EDCl/DMA →

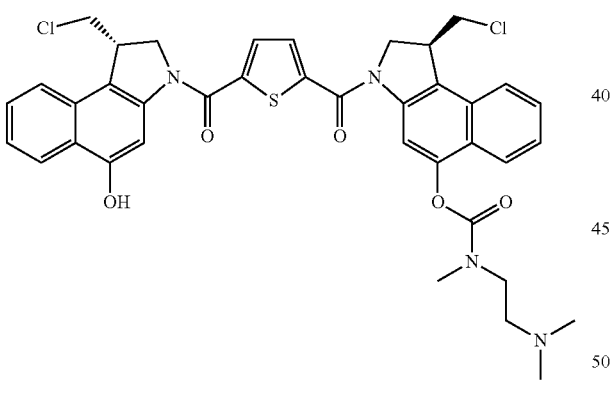

126

122

Step 1

To the above solution of 120, N,N,N-trimethylethylenediamine (222 mg, 0.28 mmol) was added, followed by lutidine (0.37 mL, 3.2 mmol) and HOAt (29 mg, 0.2 mmol). The mixture was stirred at room temperature for 1 h. The mixture was concentrated, and the residue was diluted with ethyl acetate, washed with brine, dried over MgSO4. The crude reaction product was purified by ISCO using MeOH/DCM (0-20%) to give the 124 as white foam (245 mg, 50%). LC-MS: m/z 462.2 [M+H], retention time=1.45 min.

Step 2

The above compound 124 (40 mg, 0.087 mmol) was treated with pre-cooled TFA (1 mL) at 0° C. for 10 min. TFA was removed under vacuo to give the corresponding deprotected amine 125, which was dissolved in DMF (3 mL). To this solution, it was added (S)-5-(1-(chloromethyl)-5-hydroxy-2,3-dihydro-1H-benzo[e]indole-3-carbonyl)thiophene-2-carboxylic acid [58] (34 mg, 0.087 mmol), followed by MCI (35 mg, 0.17 mmol), and the mixture was stirred at room temperature for overnight. The crude was purified by Gilson HPLC (ACN/water, 0.02% TFA) to give the product 126 as off-white solid (25 mg, 39%). LC-MS: m/z 731.1 [M+H], retention time=1.71 min. $^1$H NMR (400 MHz, DMSO-$d_6$), δ 10.49 (s), 8.26 (s), 8.14 (d), 7.98 (d), 7.88 (d), 7.66 (t), 7.77 (t), 7.40 (t), 4.89 (t), 4.78 (t), 4.55 (d), 4.43 (d), 4.23 (s), 4.08-3.91 (m), 3.73 (s), 3.50 (s), 3.40 (s), 3.26 (s), 2.89 (m).

Preparation of bicyclo[1.1.1]pentane-1,3-diylbis{[(1S)-5-amino-1-(chloromethyl)-1,2-dihydro-3H-benzo[e]indol-3-yl]methanone} 130

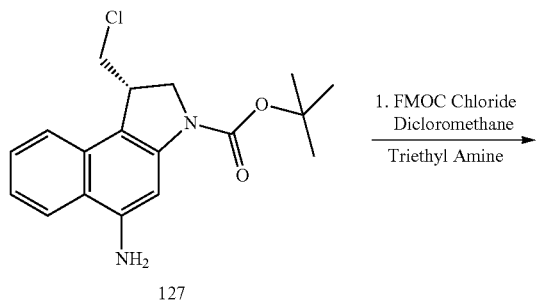

127

1. FMOC Chloride
   Dicloromethane
   ──────────────→
   Triethyl Amine

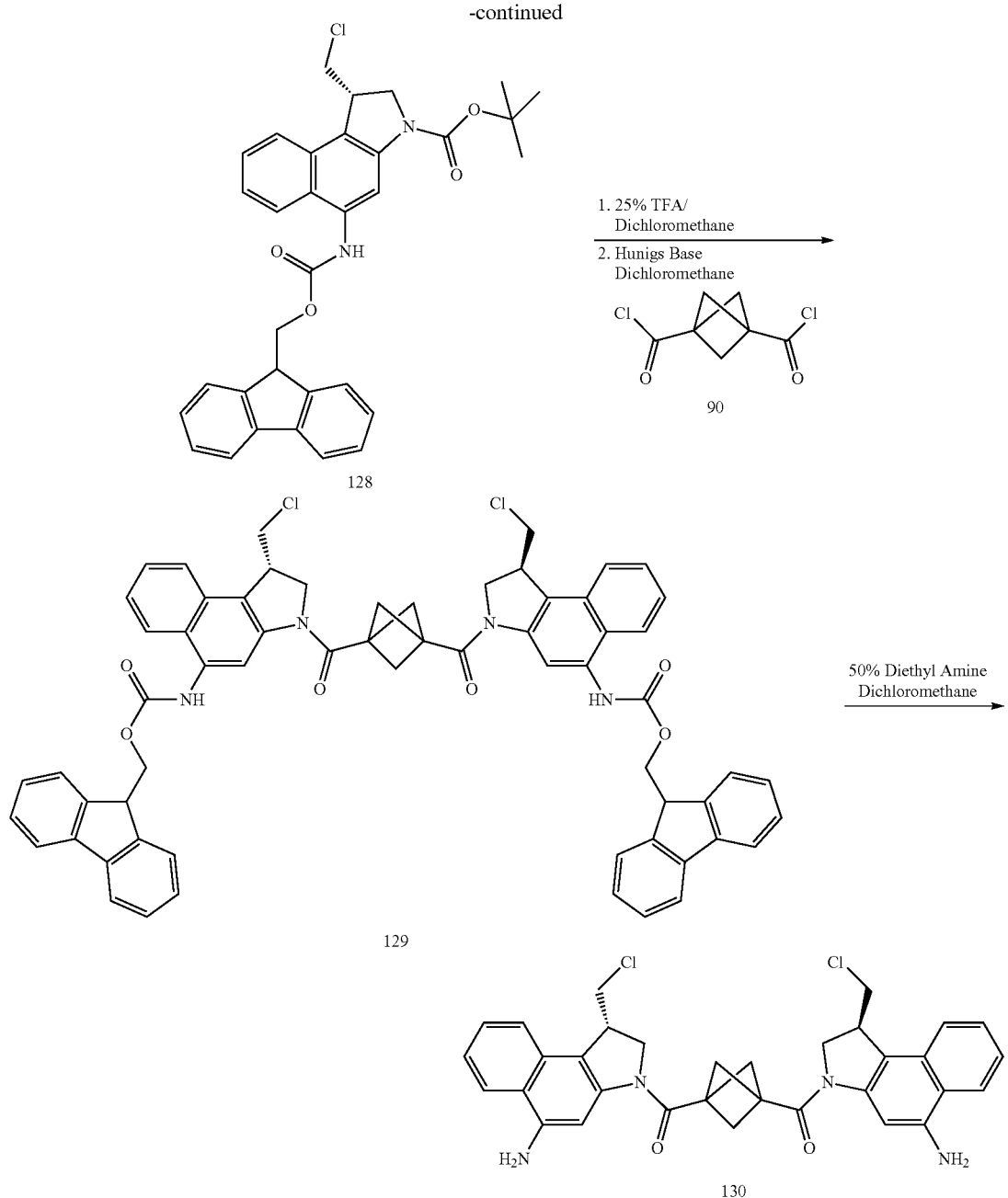

Step 1

In a round bottom flask equipped with a stir bar Fluorenylmethyloxycarbonyl chloride (560 mg, 2.1 mmol) was added 5 mL of anhydrous DCM and purged the system with Nitrogen. 127 (800 mg, 2.1 mmol) was added followed by TEA (0.3 mL, 2.1 mmol). The system was let to stir for 5 hours. The crude reaction mixture was taken up in Ethyl Acetate and transferred to a separatory funnel. Washed organic layer with 1M HCl (3×), Water (3×), Sodium Bicarbonate and Brine (2×). Dried organic layer over Sodium Sulfate, filtered and concentrated the filtrate to a crude residue. The crude product was purified by silica gel chromatography (Gradient: 0% to 100% Ethyl Acetate in Heptane) to give 128 as a yellow solid (1.096 g, 91%). LC-MS (Protocol B): m/z 455 [M-Boc]⁺, retention time=2.58 minutes.

Step 2

In a round-bottom flask equipped with a stir bar containing 128 (1000 mg, 1.96 mmol) was added 15 mL of 25% TFA in DCM. The solution was stirred for 30 mins. The reaction mixture was concentrated under vacuum and taken up in 50% DCM and Heptane and concentrated under vacuum. This was repeated 3 times (to remove excess TFA) to give a white solid upon concentrating. This white solid was added to a stirring solution of bicyclo[1.1.1]pentane-1, 3-dicarbonyl dichloride 90 in 10 mL of anhydrous DCM.

The reaction was stirred for 1 hour and concentrated to a crude glass. The crude reaction mixture was taken up in Ethyl Acetate and transferred to a separatory funnel. Washed organic layer with 1M HCl (3×), Water (3×), Sodium Bicarbonate and Brine (2×). Dried organic layer over Sodium Sulfate, filtered and concentrated the filtrate to a crude residue. The crude product was purified by silica gel chromatography (Gradient: 0% to 100% Ethyl Acetate in Heptane) to 129 as a yellow solid (250 mg, 12%). LC-MS (Protocol B): m/z 1030.7 [M−H]⁻, retention time=2.29 minutes.

Step 3

In a round-bottom flask equipped with a stir bar containing of bis(9H-fluoren-9-ylmethyl) (bicyclo[1.1.1]pentane-1,3-diylbis{carbonyl[(1S)-1-(chloromethyl)-1,2-dihydro-3H-benzo[e]indole-3,5-diyl]})biscarbamate 129 (20 mg, 0.19 mmol) was added 10 mL of 1:1 DCM in DEA. The solution was stirred for 3 hours. The reaction mixture was concentrated under vacuum and taken up in 50% DCM in Heptane and concentrated under vacuum. This was repeated 3 times (to remove excess DEA) to give a white solid upon concentrating. The crude product was purified by silica gel chromatography (Gradient: 0% to 10% Methanol in DCM) to give 130 as a yellow solid (4 mg, 30%). LC-MS (Protocol B): m/z 585.1 [M+H]⁺, retention time=1.99 minutes.

Preparation of (1S)-1-(chloromethyl)-3-[(4-{[(1S)-1-(chloromethyl)-5-hydroxy-1,2-dihydro-3H-benzo[e]indol-3-yl]carbonyl}bicyclo[2.2.1]hept-1-yl)carbonyl]-2,3-dihydro-1H-benzo[e]indol-5-yl acetate 134

Step 1

Following general procedure A using 4-(methoxycarbonyl)bicyclo[2.2.1]heptane-1-carboxylic acid 131 (75 mg, 0.38 mmol), oxalyl chloride (0.032 mL, 0.378 mmol), THF (1.5 mL), dichloromethane (1.5) and 1 drop of DMF, 132 was prepared as a white oil and solid mix (85 mg, quant.). Crude 132 was used immediately in the next step as is.

Step 2

Following general procedure B using 2 (125 mg, 0.346 mmol), 132 (75 mg, 0.35 mmol), pyridine (0.112 mL, 1.38 mmol), dichloromethane (2 mL) and THF (6 mL), and purification using silica gel chromatography (Gradient: 0% to 25% acetone in heptane) appropriate test tubes where combined and concentrated in vacuo to produce a white solid. To a stirring solution of crude material in 6 mL of THF, lithium hydroxide (52.9 mg, 2.21 mmol) dissolved in 1.5 mL of water was added. The reaction was allowed to stir at room temperature for ~3.5 hours. The reaction was concentrated to a smaller volume, transferred to a separatory funnel, and diluted with dichloromethane. The reaction was washed with 1N HCl. The aq. layer was washed once with dichloromethane. The organic layers where combined, washed with brine, water, dried over sodium sulfate, filtered, and then concentrated in vacuo before being placed underneath high vacuum. Following general procedure A using crude material, oxalyl chloride (0.024 mL, 0.281 mmol), THF (4.0 mL), dichloromethane (4.0 mL) and 1 drop of DMF, 133 was prepared as a white oil and solid mix (85 mg, quant.). Crude 133 was used immediately in the next step as is.

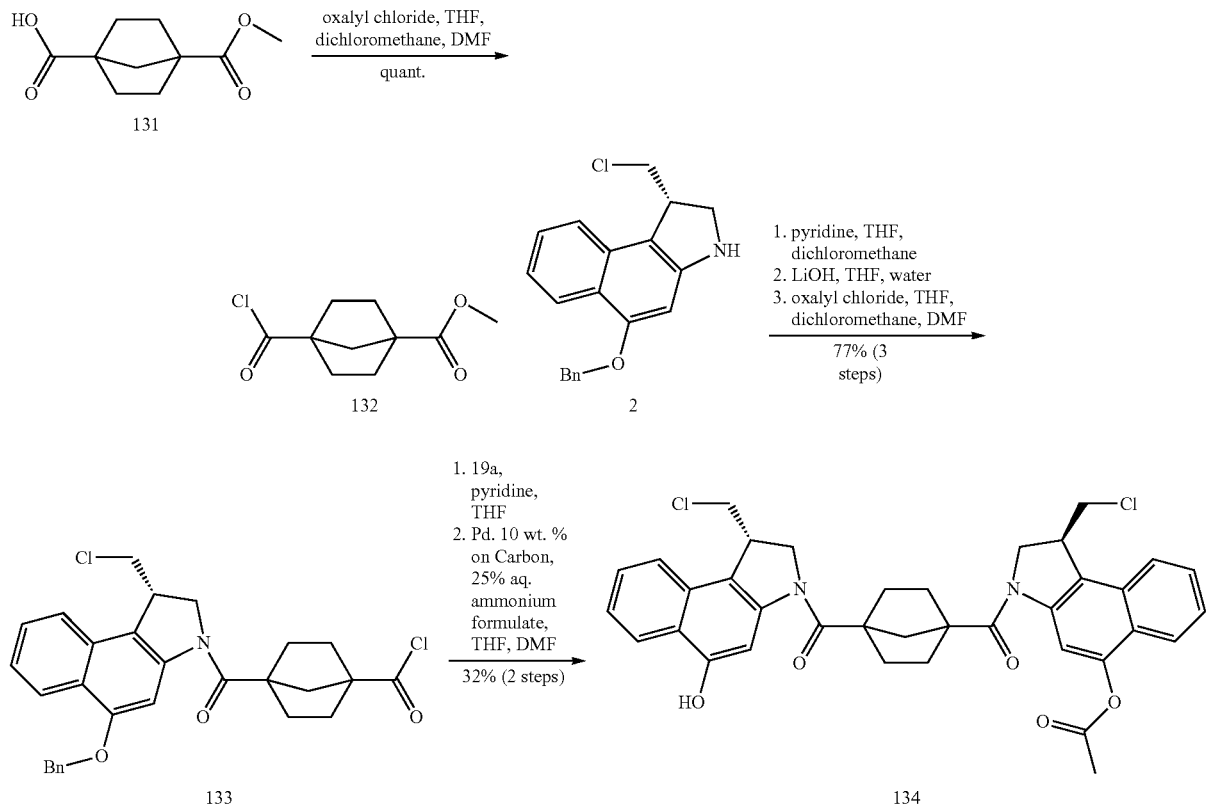

Step 3

Following general procedure B using 19a (79.9 mg, 0.256 mmol), 133 (130 mg, 0.256 mmol), pyridine (0.103 mL, 1.28 mmol), and THF (6 mL) a crude light pink solid was produced after concentrating this reaction in vacuo. To a stirring solution of crude material in 3 mL of DMF and 1 mL of THF at 0° C., Pd. 10 wt. % on carbon (100 mg) was added followed by a solution of 25% ammonium formate aq. (0.4 mL). The reaction was allowed to stir at 0° C. for ~90 minutes. Reaction was filtered through a C18 plug which was washed with a 70%/30% solution of acetonitrile and water with 0.02% TFA in each phase. Material was reduced down using a genevac producing 134 (54 mg, 32%, 2 steps) as a light gray solid. LC-MS (Protocol B): m/z 657.1 [M+H]$^+$, retention time=2.10 minutes. $^1$H NMR (400 MHz, DMSO-d$_6$): δ 10.32 (s, 1H), 8.24 (s, 1H), 8.11-8.07 (s, 1H), 8.02-7.96 (m, 2H), 7.91-7.86 (d, 1H), 7.83-7.78 (d, 1H), 7.63-7.57 (m, 1H), 7.52-7.45 (m, 2H), 7.36-7.30 (m, 1H), 4.54-4.38 (m, 3H), 4.35-4.27 (m, 2H), 4.16-4.05 (m, 2H), 4.02-3.90 (m, 2H), 3.80-3.73 (m, 1H), 2.47 (s, 3H), 2.26-2.03 (m, 10H).

Preparation of (3bR,4aS,3b'R,4a'S)-6,6'-(bicyclo[1.1.1]pentane-1,3-diyldicarbonyl)bis(3-methyl-4,4a,5,6-tetrahydrocyclopropa[c]pyrrolo[3,2-e]indol-8(1H)-one)

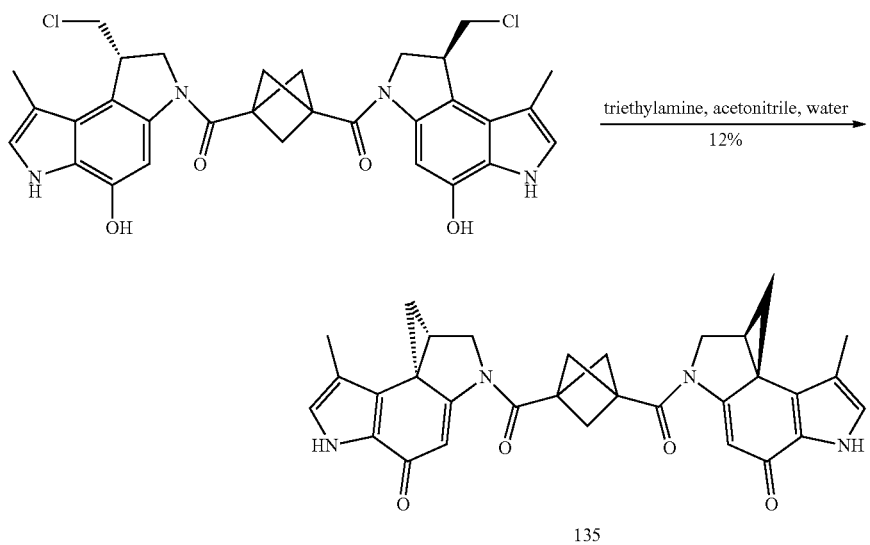 [SMILES: Cc1c[nH]c2c(O)cc3c(c12)[C@H](CCl)CN3C(=O)C12CC(C(=O)N3C[C@@H](CCl)c4c3cc(O)c3[nH]cc(C)c43)(C1)C2 ; Cc1c[nH]c2c1[C@@]13C[C@@H]1CN(C(=O)C14CC(C(=O)N5C[C@H]6C[C@@]67C5=CC(=O)c5[nH]cc(C)c57)(C1)C4)C3=CC2=O]

To a mixture of 109 (21 mg, 0.026 mmol) in 2 mL of acetonitrile, triethylamine (0.40 mL, 2.9 mmol) was added followed by 0.4 mL of water. The reaction was allowed to stir at room temperature for ~40 minutes. Reaction was concentrated in vacuo. Silica gel chromatography was then preformed (Gradient: 0% to 10% methanol in dichloromethane). Appropriate test tubes where combined and concentrated in vacuo yielding 135 (1.6 mg, 12%) as a light brown solid. LC-MS (Protocol B): m/z 521.3 [M+H]$^+$, retention time=1.28 minutes. $^1$H NMR (400 MHz, DMSO-d$_6$): δ 11.47 (s, 2H), 6.85 (s, 4H), 4.29-4.22 (m, 2H), 4.17-4.10 (m, 2H), 3.19-3.09 (m, 2H), 1.97 (s, 6H), 1.93-1.87 (m, 2H), 1.27-1.22 (m, 2H).

Preparation of (1aS,9bR,1a'S,9b'R)-3,3'-(thiene-2,5-diyldicarbonyl)bis(1,1a,2,3-tetrahydro-5H-benzo[e]cyclopropa[c]indol-5-one)

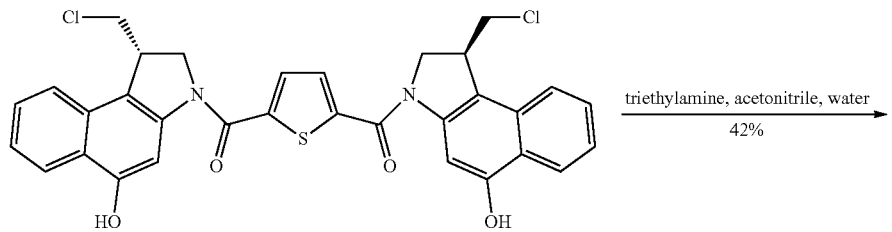

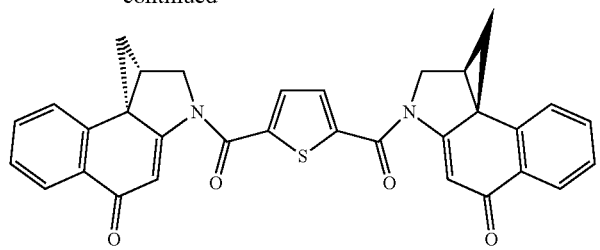

136

To a mixture of 57 (44 mg, 0.073 mmol) in 3 mL of acetonitrile, triethylamine (0.40 mL, 2.9 mmol) was added followed by 0.4 mL of water. The reaction was allowed to stir at room temperature for ~40 minutes. Reaction was concentrated in vacuo. Silica gel chromatography was then preformed (Gradient: 0% to 5% methanol in dichloromethane). Appropriate test tubes where combined and concentrated in vacuo yielding 136 (16.3 mg, 39%) as a light brown solid. LC-MS (Protocol B): m/z 531.1 [M+H]$^+$, retention time=1.55 minutes. $^1$H NMR (400 MHz, DMSO-d$_6$): δ 8.05-8.01 (d, 2H), 7.80 (s, 2H), 7.65-7.59 (t, 2H), 7.48-7.43 (t, 2H), 7.28-7.23 (d, 2H), 6.76 (s, 2H), 4.57-4.51 (m, 2H), 4.34-4.26 (m, 2H), 1.85-1.76 (m, 4H).

Preparation of (1S)-1-(chloromethyl)-3-[(3-{[(1S)-1-(chloromethyl)-5-hydroxy-1,2-dihydro-3H-benzo[e]indol-3-yl]carbonyl}bicyclo[1.1.1]pent-1-yl)carbonyl]-2,3-dihydro-1H-benzo[e]indol-5-yl methyl 2,3,4-tri-O-acetyl-beta-D-glucopyranosiduronate 141

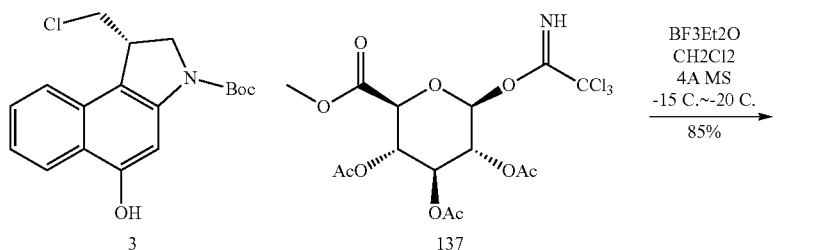

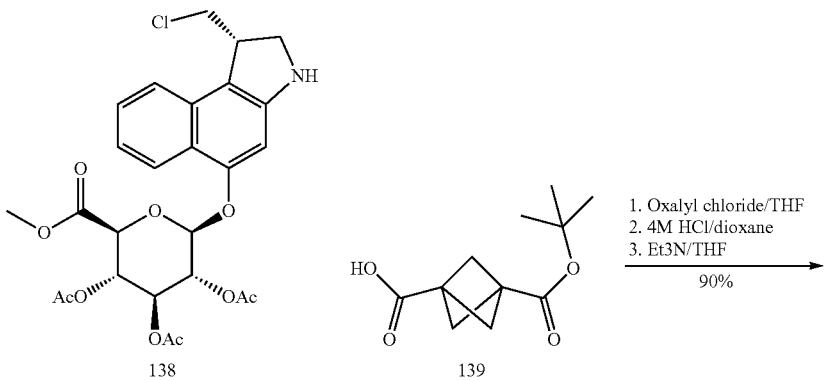

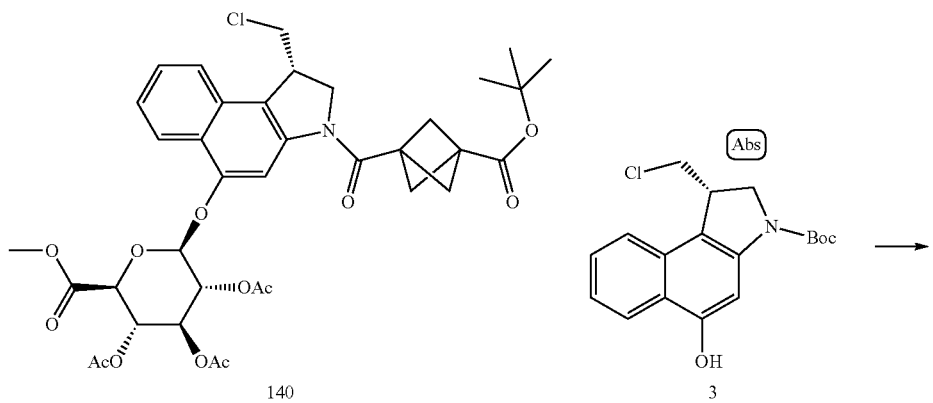

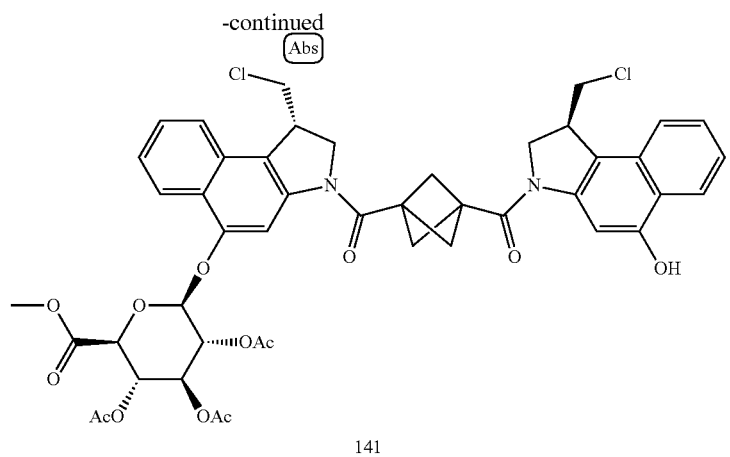

141

140 (464 mg, 0.6 mmol) was dissolved in DCM (4 mL), added TFA (2 mL), and the mixture was sealed for 2 h. The mixture was concentrated in vacuo to give the corresponding acid LC-MS (Protocol B): 688.0 [M+H]+, retention time 0.98 min. It was dissolved in THF (8 mL), cooled to 0 C, added oxalyl chloride (0.9 mL, 2M in DCM), followed by 2 drops of DMF. The mixture was stirred at 0 C for 5 min, then at rt for 50 min. Concentrated in vacuo to give the corresponding acid chloride.

LC-MS: 702.1 (1.05 min at Larry, the peak of the corresponding Me ester);

4 was dissolved in THF (10 mL), cooled to 0 C, added the above acid chloride, followed by Et3N (0.5 mL, 4.0 mmol). The mixture was stirred at 0 C for 30 min. The mixture was diluted with EA, washed with water and brine, dried over MgSO4. Solvent was removed under reduced pressure, and the residue was treated with MeOH. The resulting solid was collected by filtration to give 141 as green solid (414 mg, 73.5%). LC-MS (Protocol B): 903.2 [M+H]+, retention time 1.11 min.

TABLE 1

| | Additional Payloads | | |
|---|---|---|---|
| ID | Structure | Method of synthesis | M/S |
| 142 | | 68 | 759.5 [M + H]+ |
| 143 | | 68 | 747.4 [M + H]+ |

TABLE 1-continued

Additional Payloads

| ID | Structure | Method of synthesis | M/S |
|---|---|---|---|
| 144 | 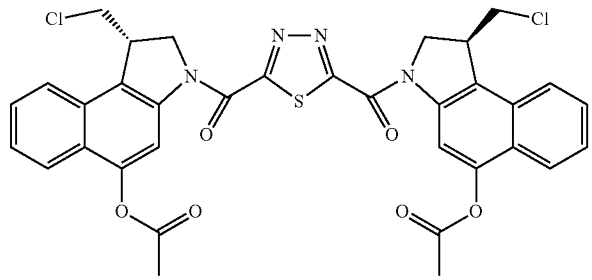 [SMILES: CC(=O)Oc1cc2c(c3ccccc13)[C@H](CCl)CN2C(=O)c1nnc(C(=O)N2C[C@@H](CCl)c3c2cc(OC(C)=O)c2ccccc32)s1] | 68 | 689.4 [M + H]+ |
| 145 | 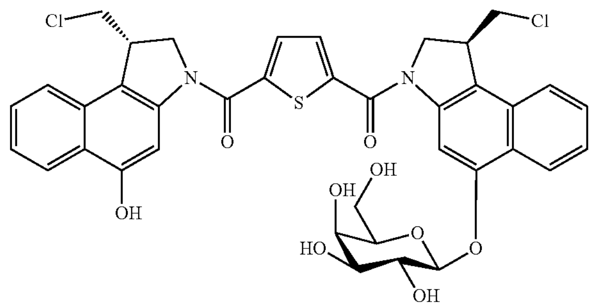 | 141 | 765.1 [M + H]+ |
| 146 | 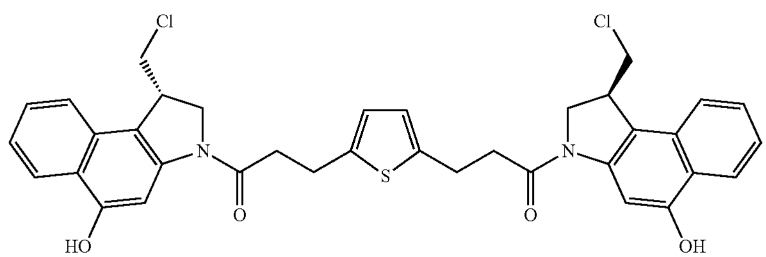 [SMILES: O=C(CCc1ccc(CCC(=O)N2C[C@@H](CCl)c3c2cc(O)c2ccccc32)s1)N1C[C@@H](CCl)c2c1cc(O)c1ccccc21] | 60 | 659.2 [M + H]+ |
| 147 | 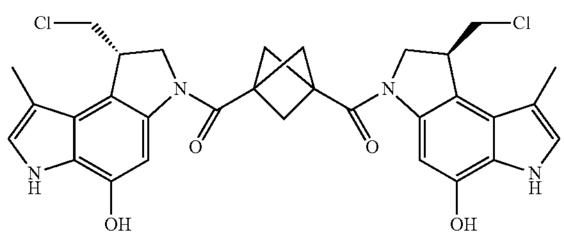 [SMILES: Cc1c[nH]c2c(O)cc3c(c12)[C@H](CCl)CN3C(=O)C12CC(C(=O)N3C[C@@H](CCl)c4c3cc(O)c3[nH]cc(C)c43)(C1)C2] | 60 | 593.2 [M + H]+ |
| 148 | 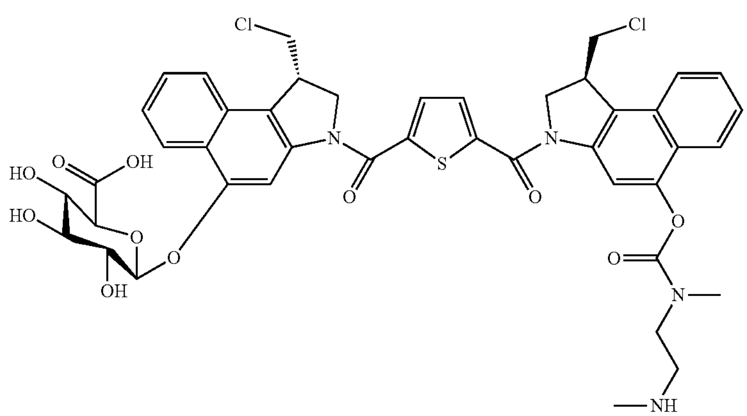 | 141 | 893.2 [M + H]+ |

TABLE 1-continued

Additional Payloads

| ID | Structure | Method of synthesis | M/S |
|----|-----------|---------------------|-----|
| 149 | 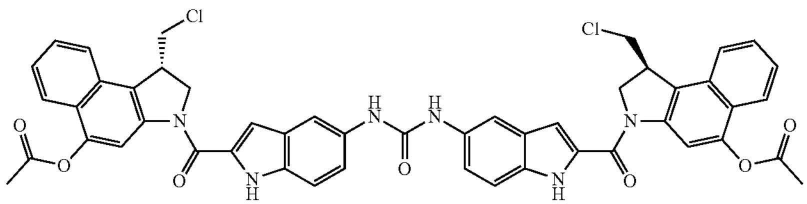 [SMILES: CC(=O)Oc1cc2c(c3ccccc13)[C@H](CCl)CN2C(=O)c1cc2cc(NC(=O)Nc3ccc4[nH]c(C(=O)N5C[C@@H](CCl)c6c5cc(OC(C)=O)c5ccccc65)cc4c3)ccc2[nH]1] | 68 | 893.2 [M + H]+ |
| 151 | 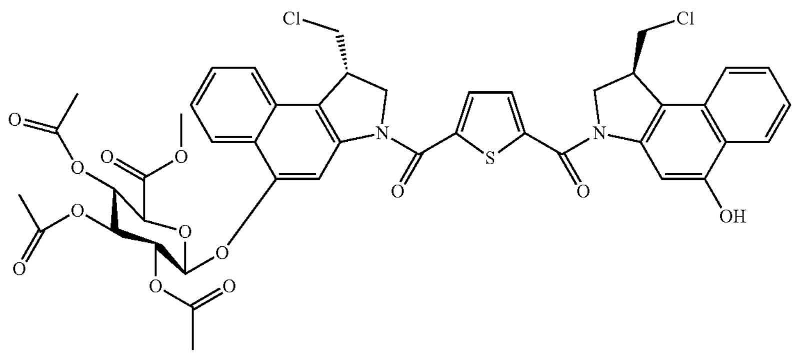 | 141 | 919.2 [M + H]+ |
| 152 | 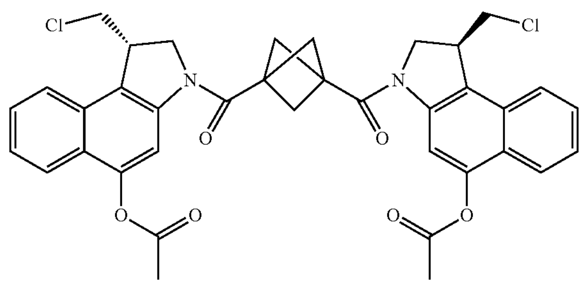 [SMILES: CC(=O)Oc1cc2c(c3ccccc13)[C@H](CCl)CN2C(=O)C12CC(C(=O)N3C[C@@H](CCl)c4c3cc(OC(C)=O)c3ccccc43)(C1)C2] | 68 | 671.2 [M + H]+ |
| 153 | 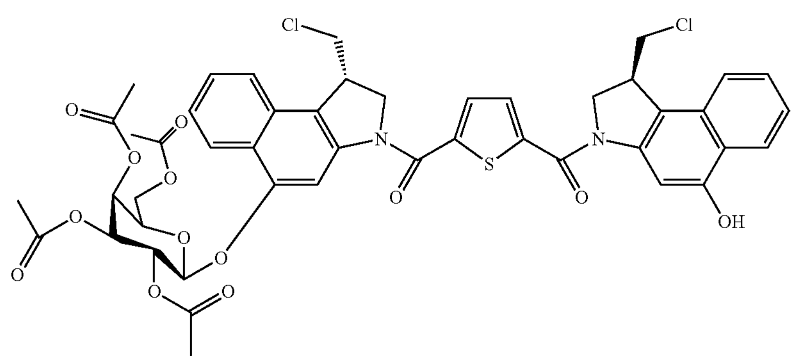 | 141 | 933.2 [M + H]+ |
| 154 | 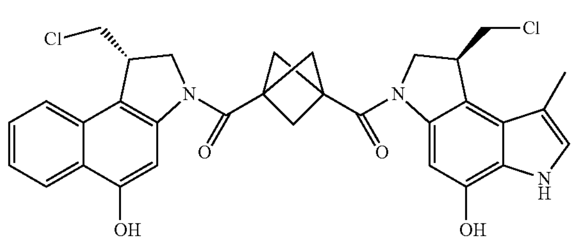 [SMILES: Cc1c[nH]c2c(O)cc3c(c12)[C@H](CCl)CN3C(=O)C12CC(C(=O)N3C[C@@H](CCl)c4c3cc(O)c3ccccc43)(C1)C2] | 60 | 590.2 [M + H]+ |

TABLE 1-continued
Additional Payloads
| ID | Structure | Method of synthesis | M/S |
|---|---|---|---|
| 155 | 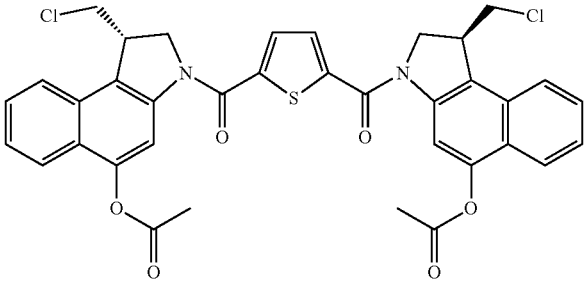 [SMILES: CC(=O)Oc1cc2c(c3ccccc13)[C@H](CCl)CN2C(=O)c1ccc(C(=O)N2C[C@@H](CCl)c3c2cc(OC(C)=O)c2ccccc32)s1] | 68 | 687.1 [M + H]+ |
| 156 | 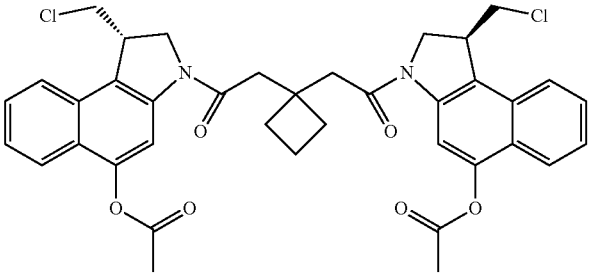 [SMILES: CC(=O)Oc1cc2c(c3ccccc13)[C@H](CCl)CN2C(=O)CC1(CC(=O)N2C[C@@H](CCl)c3c2cc(OC(C)=O)c2ccccc32)CCC1] | 68 | 687.2 [M + H]+ |
| 157 | 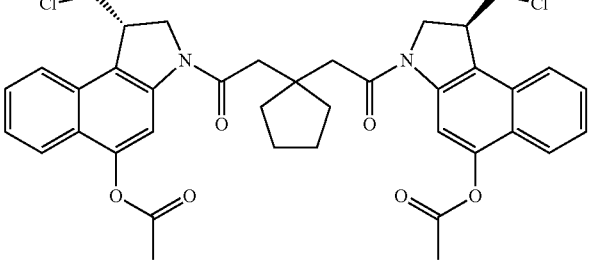 | 68 | 701.2 [M + H]+ |
| 158 | 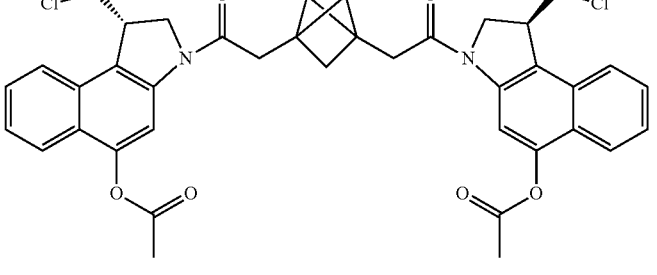 | 68 | 700.6 [M + H]+ |
| 159 | 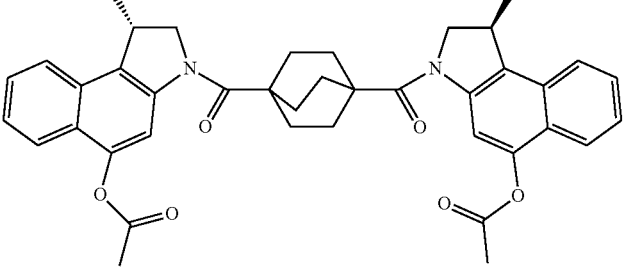 | 68 | 713.2 [M + H]+ |

TABLE 1-continued

Additional Payloads

| ID | Structure | Method of synthesis | M/S |
|---|---|---|---|
| 160 | 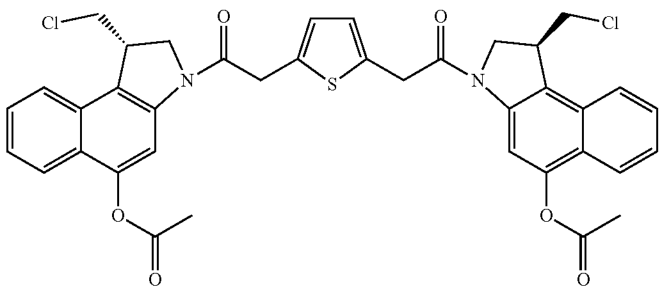 [SMILES: CC(=O)Oc1cc2c(c3ccccc13)[C@H](CCl)CN2C(=O)Cc1ccc(CC(=O)N2C[C@@H](CCl)c3c2cc(OC(C)=O)c2ccccc32)s1] | 68 | 715.1 [M + H]+ |
| 161 | 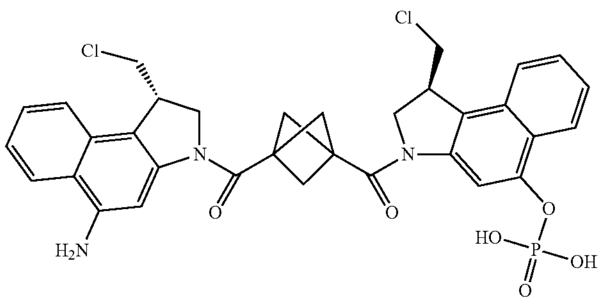 [SMILES: Nc1cc2c(c3ccccc13)[C@H](CCl)CN2C(=O)C12CC(C(=O)N3C[C@@H](CCl)c4c3cc(OP(=O)(O)O)c3ccccc43)(C1)C2] | 65 | 666.1 [M + H]+ |
| 162 | 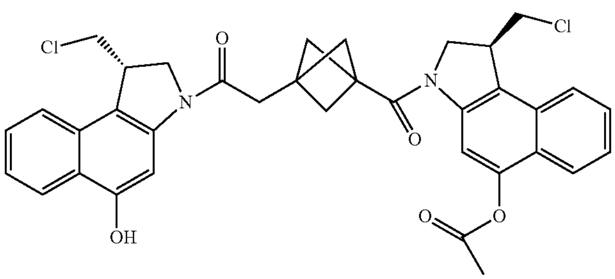 [SMILES: CC(=O)Oc1cc2c(c3ccccc13)[C@H](CCl)CN2C(=O)C12CC(CC(=O)N3C[C@@H](CCl)c4c3cc(O)c3ccccc43)(C1)C2] | 134 | 643.2 [M + H]+ |
| 163 | 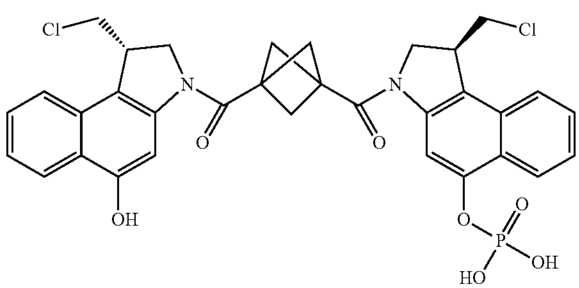 [SMILES: O=C(N1C[C@@H](CCl)c2c1cc(O)c1ccccc21)C12CC(C(=O)N3C[C@@H](CCl)c4c3cc(OP(=O)(O)O)c3ccccc43)(C1)C2] | 65 | 667.1 [M + H]+ |
| 164 | 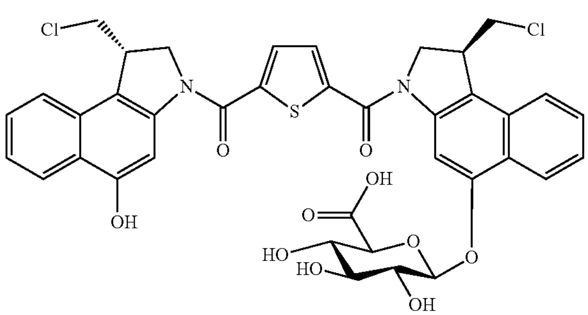 | 141 | 779.1 [M + H]+ |

TABLE 1-continued

Additional Payloads

| ID | Structure | Method of synthesis | M/S |
|---|---|---|---|
| 165 | 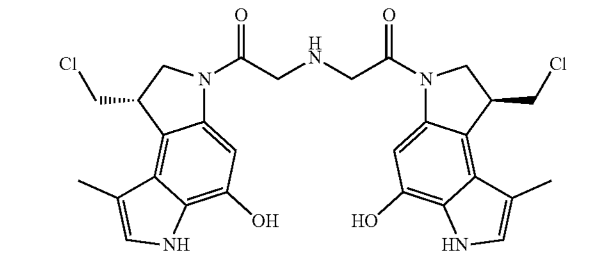 [SMILES: Cc1c[nH]c2c(O)cc3c(c12)[C@H](CCl)CN3C(=O)CNCC(=O)N1C[C@@H](CCl)c2c1cc(O)c1[nH]cc(C)c21] | 60 | 570.2 [M + H]+ |
| 166 | 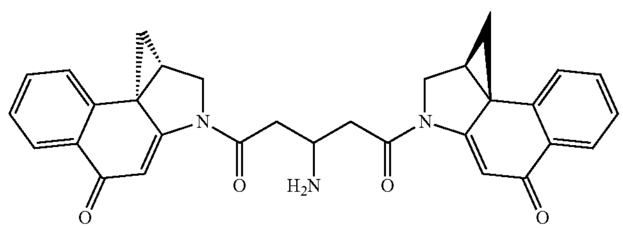 [SMILES: NC(CC(=O)N1C[C@H]2C[C@@]23C1=CC(=O)c1ccccc13)CC(=O)N1C[C@H]2C[C@@]23C1=CC(=O)c1ccccc13] | 135 | 506.2 [M + H]+ |
| 167 | 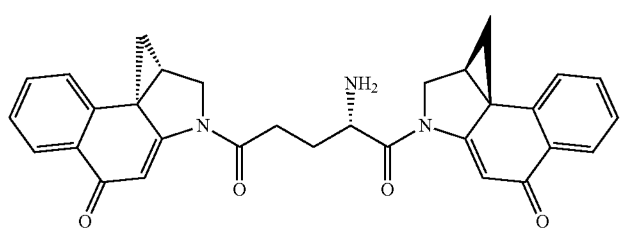 [SMILES: N[C@@H](CCC(=O)N1C[C@H]2C[C@@]23C1=CC(=O)c1ccccc13)C(=O)N1C[C@H]2C[C@@]23C1=CC(=O)c1ccccc13] | 135 | 506.2 [M + H]+ |
| 168 | 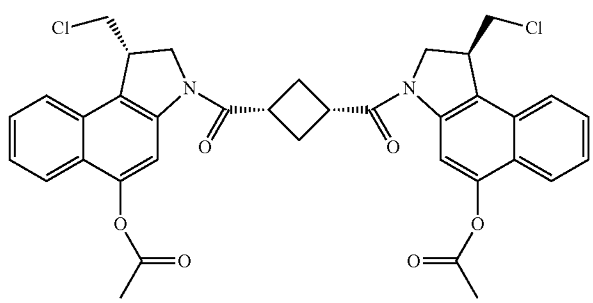 [SMILES: CC(=O)Oc1cc2c(c3ccccc13)[C@H](CCl)CN2C(=O)[C@H]1C[C@@H](C(=O)N2C[C@@H](CCl)c3c2cc(OC(C)=O)c2ccccc32)C1] | 68 | 659.2 [M + H]+ |
| 169 | 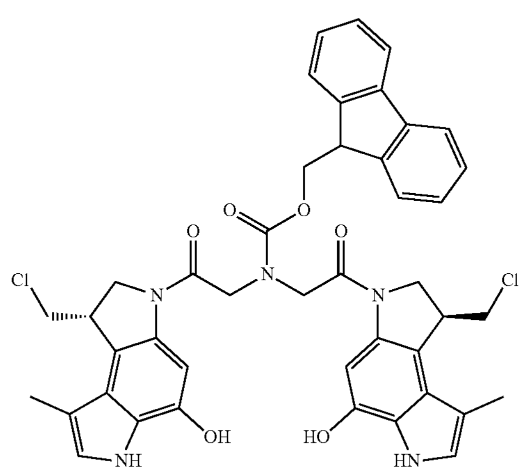 [SMILES: Cc1c[nH]c2c(O)cc3c(c12)[C@H](CCl)CN3C(=O)CN(CC(=O)N1C[C@@H](CCl)c2c1cc(O)c1[nH]cc(C)c21)C(=O)OCC1c2ccccc2-c2ccccc21] | 60 | 792.2 [M + H]+ |

TABLE 1-continued

Additional Payloads

| ID | Structure | Method of synthesis | M/S |
|---|---|---|---|
| 170 | 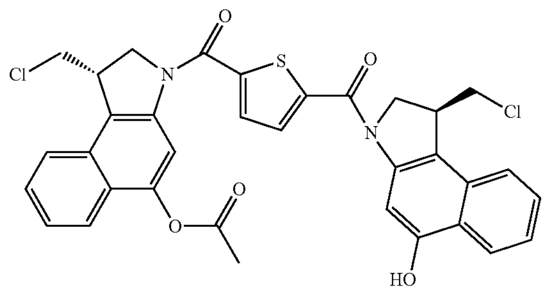 [SMILES: CC(=O)Oc1cc2c(c3ccccc13)[C@H](CCl)CN2C(=O)c1ccc(C(=O)N2C[C@@H](CCl)c3c2cc(O)c2ccccc32)s1] | 134 | 645.0 [M + H]+ |
| 171 | 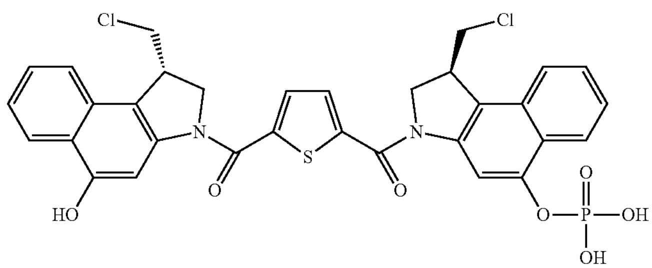 [SMILES: O=C(c1ccc(C(=O)N2C[C@@H](CCl)c3c2cc(OP(=O)(O)O)c2ccccc32)s1)N1C[C@@H](CCl)c2c1cc(O)c1ccccc21] | 196 | 683.1 [M + H]+ |
| 172 | 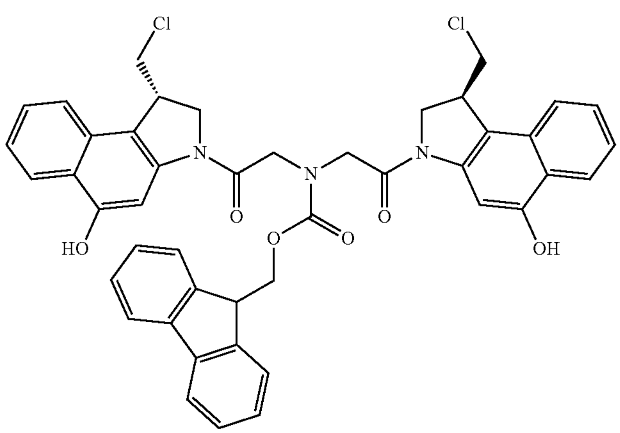 [SMILES: O=C(OCC1c2ccccc2-c2ccccc21)N(CC(=O)N1C[C@@H](CCl)c2c1cc(O)c1ccccc21)CC(=O)N1C[C@@H](CCl)c2c1cc(O)c1ccccc21] | 60 | 786.4 [M + H]+ |
| 173 | 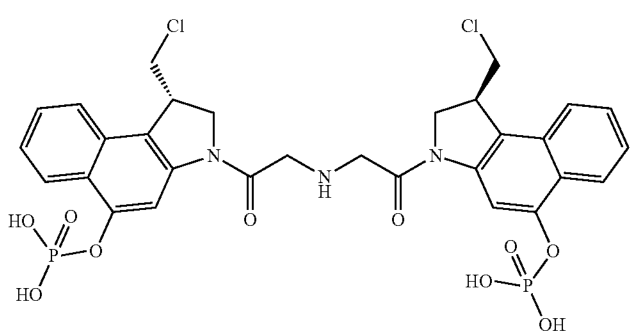 [SMILES: O=C(CNCC(=O)N1C[C@@H](CCl)c2c1cc(OP(=O)(O)O)c1ccccc21)N1C[C@@H](CCl)c2c1cc(OP(=O)(O)O)c1ccccc21] | 184 | 724.3 [M + H]+ |

TABLE 1-continued

Additional Payloads

| ID | Structure | Method of synthesis | M/S |
|---|---|---|---|
| 174 | 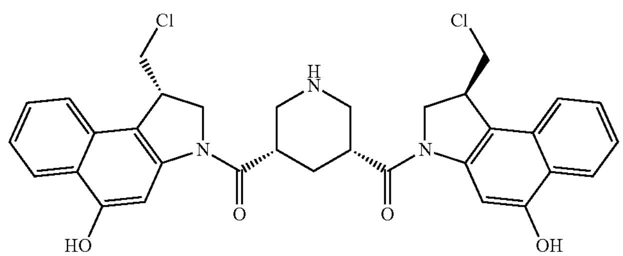 [SMILES: O=C([C@@H]1CNC[C@H](C(=O)N2C[C@@H](CCl)c3c2cc(O)c2ccccc32)C1)N1C[C@@H](CCl)c2c1cc(O)c1ccccc21] | 60 | 604.4 [M + H]+ |
| 175 | 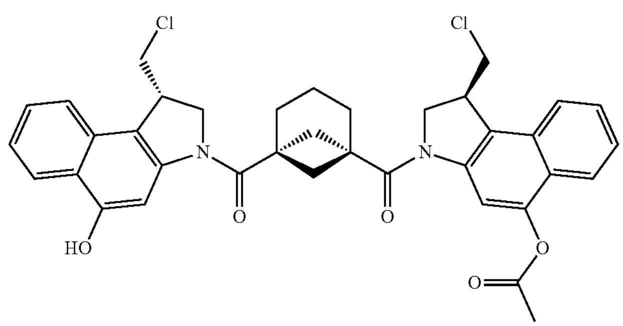 [SMILES: CC(=O)Oc1cc2c(c3ccccc13)[C@H](CCl)CN2C(=O)[C@]12CCC[C@](C(=O)N3C[C@@H](CCl)c4c3cc(O)c3ccccc43)(C1)C2] | 134 | 657.2 [M + H]+ |
| 176 | 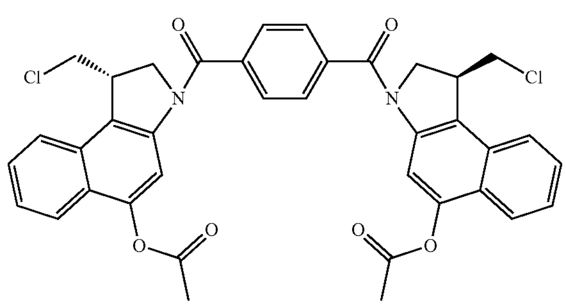 [SMILES: CC(=O)Oc1cc2c(c3ccccc13)[C@H](CCl)CN2C(=O)c1ccc(C(=O)N2C[C@@H](CCl)c3c2cc(OC(C)=O)c2ccccc32)cc1] | 68 | 681.2 [M + H]+ |
| 177 | 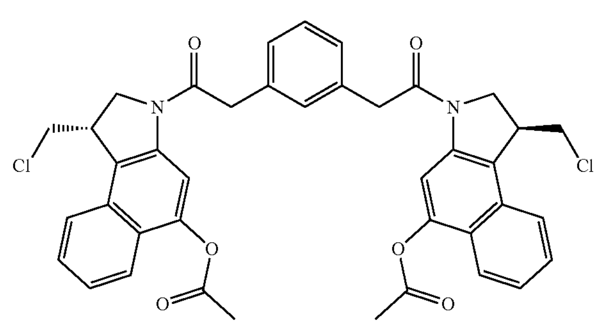 [SMILES: CC(=O)Oc1cc2c(c3ccccc13)[C@H](CCl)CN2C(=O)Cc1cccc(CC(=O)N2C[C@@H](CCl)c3c2cc(OC(C)=O)c2ccccc32)c1] | 68 | 709.2 [M + H]+ |

TABLE 1-continued

Additional Payloads

| ID | Structure | Method of synthesis | M/S |
|---|---|---|---|
| 178 | 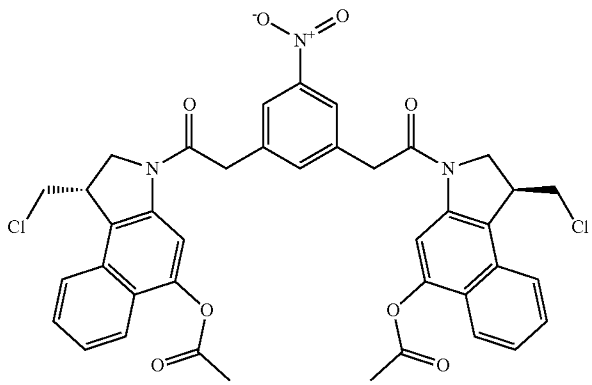 | 68 | 754.4 [M + H]+ |
| 179 | 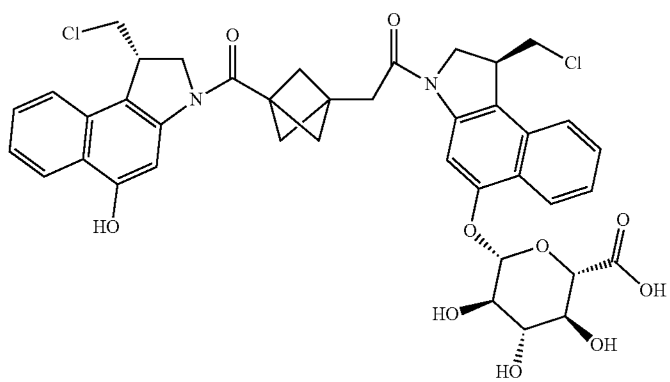 [SMILES: O=C(O)[C@H]1O[C@@H](Oc2cc3c(c4ccccc24)[C@H](CCl)CN3C(=O)CC23CC(C(=O)N4C[C@@H](CCl)c5c4cc(O)c4ccccc54)(C2)C3)[C@H](O)[C@@H](O)[C@@H]1O] | 141 | 777.3 [M + H]+ |
| 180 | 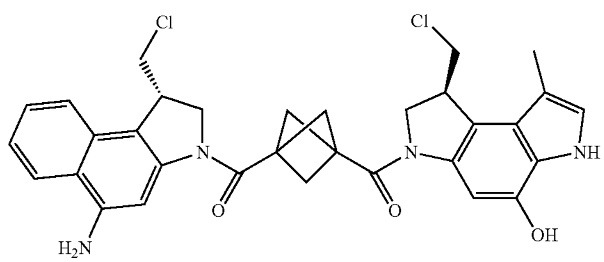 [SMILES: Cc1c[nH]c2c(O)cc3c(c12)[C@H](CCl)CN3C(=O)C12CC(C(=O)N3C[C@@H](CCl)c4c3cc(N)c3ccccc43)(C1)C2] | 68 | 590.5 [M + H]+ |
| 181 | 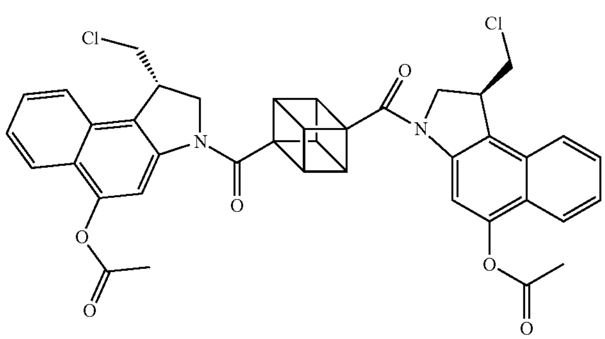 [SMILES: CC(=O)Oc1cc2c(c3ccccc13)[C@H](CCl)CN2C(=O)C12C3C4C1C1C2C3C41C(=O)N1C[C@@H](CCl)c2c1cc(OC(C)=O)c1ccccc21] | 68 | 707.3 [M + H]+ |

149

Names of Table 1 compounds are provided below:

TABLE 2

Additional Payloads, IUPAC names

142 3,4-dihydro-2H-thieno[3,4-b][1,4]dioxepine-6,8-diylbis[carbonyl(1S)-1-(chloromethyl)-1,2-dihydro-3H-benzo[e]indole-3,5-diyl] diacetate
143 (3,4-dimethoxythiene-2,5-diyl)bis[carbonyl(1S)-1-(chloromethyl)-1,2-dihydro-3H-benzo[e]indole-3,5-diyl] diacetate
144 1,3,4-thiadiazole-2,5-diylbis[carbonyl(1S)-1-(chloromethyl)-1,2-dihydro-3H-benzo[e]indole-3,5-diyl] diacetate
145 ((S)-1-(chloromethyl)-5-(((2S,3R,4S,5R,6R)-3,4,5-trihydroxy-6-(hydroxymethyl)tetrahydro-2H-pyran-2-yl)oxy)-1,2-dihydro-3H-benzo[e]indol-3-yl)(5-((S)-1-(chloromethyl)-5-hydroxy-2,3-dihydro-1H-benzo[e]indole-3-carbonyl)thiophen-2-yl)methanone
146 3,3'-thiene-2,5-diylbis{1-[(1S)-1-(chloromethyl)-5-hydroxy-1,2-dihydro-3H-benzo[e]indol-3-yl]propan-1-one}
147 bicyclo[1.1.1]pentane-1,3-diylbis{[(1S)-1-(chloromethyl)-5-hydroxy-8-methyl-1,6-dihydropyrrolo[3,2-e]indol-3(2H)-yl]methanone}
148 (2S,3S,4S,5R,6S)-6-(((S)-1-(chloromethyl)-3-(5-((S)-1-(chloromethyl)-5-((methyl(2-(methylamino)ethyl)carbamoyl)oxy)-2,3-dihydro-1H-benzo[e]indole-3-carbonyl)thiophene-2-carbonyl)-2,3-dihydro-1H-benzo[e]indol-5-yl)oxy)-3,4,5-trihydroxytetrahydro-2H-pyran-2-carboxylic acid
149 (1S)-3-[(5-{[(2-{[(1S)-5-(acetyloxy)-1-(chloromethyl)-1,2-dihydro-3H-benzo[e]indol-3-yl]carbonyl}-1H-indol-5-yl)carbamoyl]amino}-1H-indol-2-yl)carbonyl]-1-(chloromethyl)-1,2-dihydro-3H-benzo[e]indol-5-yl acetate
150 thiene-2,5-diylbis{[(1S)-1-(chloromethyl)-5-hydroxy-8-methyl-1,6-dihydropyrrolo[3,2-e]indol-3(2H)-yl]methanone}
151 (2S,3R,4S,5S,6S)-2-(((S)-1-(chloromethyl)-3-(5-((S)-1-(chloromethyl)-5-hydroxy-2,3-dihydro-1H-benzo[e]indole-3-carbonyl)thiophene-2-carbonyl)-2,3-dihydro-1H-benzo[e]indol-5-yl)oxy)-6-(methoxycarbonyl)tetrahydro-2H-pyran-3,4,5-triyl triacetate
152 bicyclo[1.1.1]pentane-1,3-diylbis[carbonyl(1S)-1-(chloromethyl)-1,2-dihydro-3H-benzo[e]indole-3,5-diyl] diacetate
153 (2R,3S,4S,5R,6S)-2-(acetoxymethyl)-6-(((S)-1-(chloromethyl)-3-(5-((S)-1-(chloromethyl)-5-hydroxy-2,3-dihydro-1H-benzo[e]indole-3-carbonyl)thiophene-2-carbonyl)-2,3-dihydro-1H-benzo[e]indol-5-yl)oxy)tetrahydro-2H-pyran-3,4,5-triyl triacetate
154 [(1S)-1-(chloromethyl)-5-hydroxy-1,2-dihydro-3H-benzo[e]indol-3-yl](3-{[(1S)-1-(chloromethyl)-5-hydroxy-8-methyl-1,6-dihydropyrrolo[3,2-e]indol-3(2H)-yl]carbonyl}bicyclo[1.1.1]pent-1-yl)methanone
155 thiene-2,5-diylbis[carbonyl(1S)-1-(chloromethyl)-1,2-dihydro-3H-benzo[e]indole-3,5-diyl] diacetate
156 cyclobutane-1,1-diylbis[(1-oxoethane-2,1-diyl)(1S)-1-(chloromethyl)-1,2-dihydro-3H-benzo[e]indole-3,5-diyl] diacetate
157 cyclopentane-1,1-diylbis[(1-oxoethane-2,1-diyl)(1S)-1-(chloromethyl)-1,2-dihydro-3H-benzo[e]indole-3,5-diyl] diacetate
158 bicyclo[1.1.1]pentane-1,3-diylbis[(1-oxoethane-2,1-diyl)(1S)-1-(chloromethyl)-1,2-dihydro-3H-benzo[e]indole-3,5-diyl] diacetate
159 bicyclo[2.2.2]octane-1,4-diylbis[carbonyl(1S)-1-(chloromethyl)-1,2-dihydro-3H-benzo[e]indole-3,5-diyl] diacetate
160 thiene-2,5-diylbis[(1-oxoethane-2,1-diyl)(1S)-1-(chloromethyl)-1,2-dihydro-3H-benzo[e]indole-3,5-diyl] diacetate
161 (1S)-3-[(3-{[(1S)-5-amino-1-(chloromethyl)-1,2-dihydro-3H-benzo[e]indol-3-yl]carbonyl}bicyclo[1.1.1]pent-1-yl)carbonyl]-1-(chloromethyl)-2,3-dihydro-1H-benzo[e]indol-5-yl dihydrogen phosphate
162 (1S)-1-(chloromethyl)-3-[(3-{2-[(1S)-1-(chloromethyl)-5-hydroxy-1,2-dihydro-3H-benzo[e]indol-3-yl]-2-oxoethyl}bicyclo[1.1.1]pent-1-yl)carbonyl]-2,3-dihydro-1H-benzo[e]indol-5-yl acetate

150

TABLE 2-continued

Additional Payloads, IUPAC names

163 (1S)-1-(chloromethyl)-3-[(3-{[(1S)-1-(chloromethyl)-5-hydroxy-1,2-dihydro-3H-benzo[e]indol-3-yl]carbonyl}bicyclo[1.1.1]pent-1-yl)carbonyl]-2,3-dihydro-1H-benzo[e]indol-5-yl dihydrogen phosphate
164 (2S,3S,4S,5R,6S)-6-(((S)-1-(chloromethyl)-3-(5-((S)-1-(chloromethyl)-5-hydroxy-2,3-dihydro-1H-benzo[e]indole-3-carbonyl)thiophene-2-carbonyl)-2,3-dihydro-1H-benzo[e]indol-5-yl)oxy)-3,4,5-trihydroxytetrahydro-2H-pyran-2-carboxylic acid
165 2,2'-iminobis{1-[(1S)-1-(chloromethyl)-5-hydroxy-8-methyl-1,6-dihydropyrrolo[3,2-e]indol-3(2H)-yl]ethanone}
166 3-amino-1,5-bis[(1aS,9bR)-5-oxo-1a,2-dihydro-1H-benzo[e]cyclopropa[c]indol-3(5H)-yl]pentane-1,5-dione
167 (2S)-2-amino-1,5-bis[(1aS,9bR)-5-oxo-1a,2-dihydro-1H-benzo[e]cyclopropa[c]indol-3(5H)-yl]pentane-1,5-dione
168 cis-cyclobutane-1,3-diylbis[carbonyl(1S)-1-(chloromethyl)-1,2-dihydro-3H-benzo[e]indole-3,5-diyl] diacetate
169 9H-fluoren-9-ylmethyl bis{2-[(1S)-1-(chloromethyl)-5-hydroxy-8-methyl-1,6-dihydropyrrolo[3,2-e]indol-3(2H)-yl]-2-oxoethyl}carbamate
170 (1S)-1-(chloromethyl)-3-[(5-{[(1S)-1-(chloromethyl)-5-hydroxy-1,2-dihydro-3H-benzo[e]indol-3-yl]carbonyl}thiophen-2-yl)carbonyl]-2,3-dihydro-1H-benzo[e]indol-5-yl acetate
171 (1S)-1-(chloromethyl)-3-[(5-{[(1S)-1-(chloromethyl)-5-hydroxy-1,2-dihydro-3H-benzo[e]indol-3-yl]carbonyl}thiophen-2-yl)carbonyl]-2,3-dihydro-1H-benzo[e]indol-5-yl dihydrogen phosphate
172 9H-fluoren-9-ylmethyl bis{2-[(1S)-1-(chloromethyl)-5-hydroxy-1,2-dihydro-3H-benzo[e]indol-3-yl]-2-oxoethyl}carbamate
173 iminobis[(1-oxoethane-2,1-diyl)(1S)-1-(chloromethyl)-1,2-dihydro-3H-benzo[e]indole-3,5-diyl] bis[dihydrogen (phosphate)]
174 (3R,5S)-piperidine-3,5-diylbis{[(1S)-1-(chloromethyl)-5-hydroxy-1,2-dihydro-3H-benzo[e]indol-3-yl]methanone}
175 (1S)-1-(chloromethyl)-3-{[(1S,5S)-5-{[(1S)-1-(chloromethyl)-5-hydroxy-1,2-dihydro-3H-benzo[e]indol-3-yl]carbonyl}bicyclo[3.1.1]hept-1-yl]carbonyl}-2,3-dihydro-1H-benzo[e]indol-5-yl acetate
176 benzene-1,4-diylbis[carbonyl(1S)-1-(chloromethyl)-1,2-dihydro-3H-benzo[e]indole-3,5-diyl] diacetate
177 benzene-1,3-diylbis[(1-oxoethane-2,1-diyl)(1S)-1-(chloromethyl)-1,2-dihydro-3H-benzo[e]indole-3,5-diyl] diacetate
178 (5-nitrobenzene-1,3-diyl)bis[(1-oxoethane-2,1-diyl)(1S)-1-(chloromethyl)-1,2-dihydro-3H-benzo[e]indole-3,5-diyl] diacetate
179 (1S)-1-(chloromethyl)-3-[(3-{[(1S)-1-(chloromethyl)-5-hydroxy-1,2-dihydro-3H-benzo[e]indol-3-yl]carbonyl}bicyclo[1.1.1]pent-1-yl)acetyl]-2,3-dihydro-1H-benzo[e]indol-5-yl beta-D-glucopyranosiduronic acid
180 [(1S)-5-amino-1-(chloromethyl)-1,2-dihydro-3H-benzo[e]indol-3-yl](3-{[(1S)-1-(chloromethyl)-5-hydroxy-8-methyl-1,6-dihydropyrrolo[3,2-e]indol-3(2H)-yl]carbonyl}bicyclo[1.1.1]pent-1-yl)methanone
181 pentacyclo[4.2.0.0~2,5~.0~3,8~.0~4,7~]octane-1,4-diylbis[carbonyl(1S)-1-(chloromethyl)-1,2-dihydro-3H-benzo[e]indole-3,5-diyl] diacetate Preparation of 4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosanamido)benzyl bis(2-((S)-1-(chloromethyl)-5-(phosphonooxy)-1H-benzo[e]indol-3(2H)-yl)-2-oxoethyl)carbamate (186)

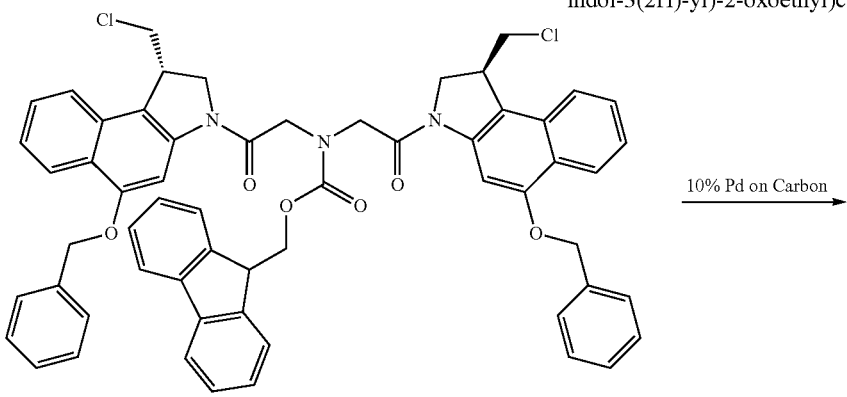

10% Pd on Carbon

-continued
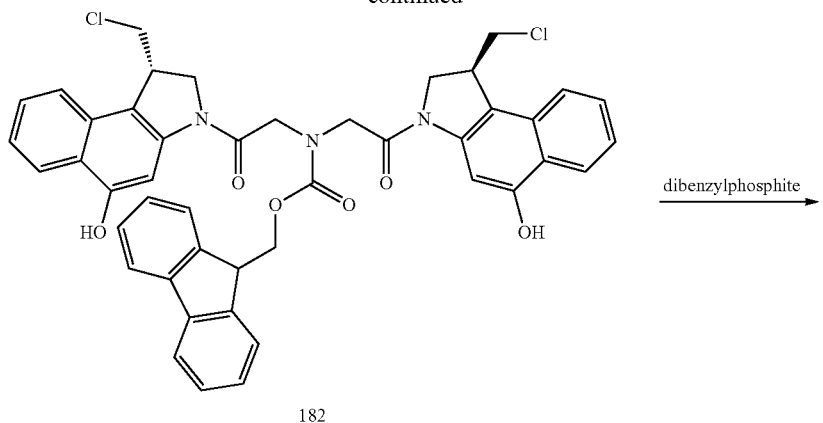
182
dibenzylphosphite →
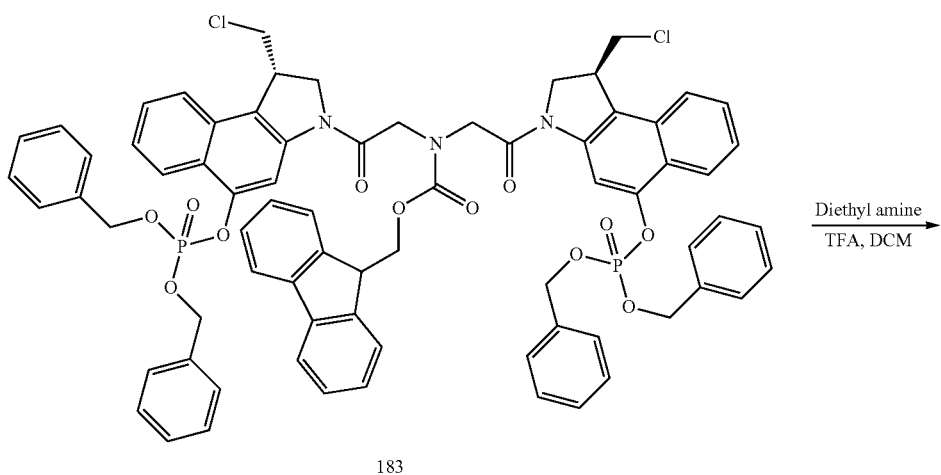
183
Diethyl amine
TFA, DCM →
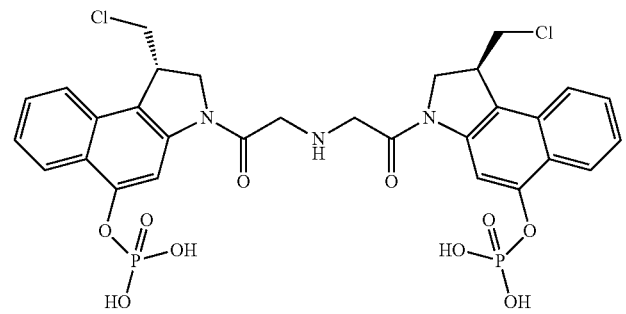
184

-continued

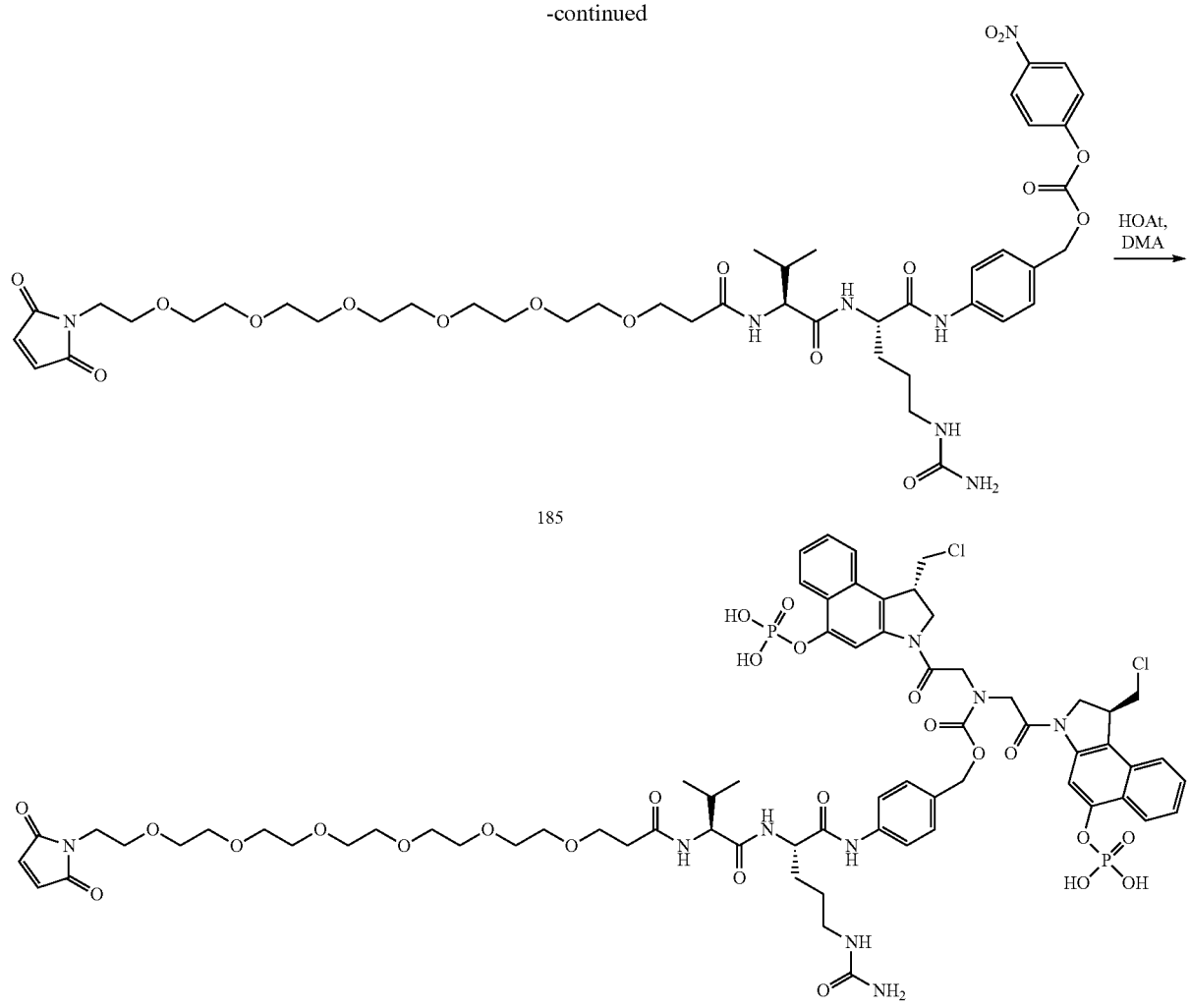

Step 1

A stirring solution of 51 (120 mg, 0.124 mmol) in 10 mL of tetrahydrofuran under nitrogen was cooled to 0 C using an ice bath. Palladium 10 wt. % on activated carbon (106 mg, 0.298 mmol) was then added followed by the slow drop wise addition of 1 mL of 25% ammonium formate in water. The reaction was allowed to stir at 0 C. for 5 hours. The reaction was then filtered through a pad of celite and the filtrate was then concentrated in vacuo. Silica chromatography was then preformed (Gradient: 0%-100% ethyl acetate in heptanes) producing 182 (35 mg, 36%) as a pale white solid. LC-MS: m/z 786 [M+H$^+$], retention time=2.22 minutes.

Step 2

To a stirring solution of 182 (274 mg, 0.348 mmol) in 10 mL of THF and 10 mL of acetonitrile, carbon tetrachloride (2.04 mL, 21.0 mmol) and Hunig's base (1.12 mL, 6.45 mmol) was added dibenzylphosphite (0.9 mL, 4.32 mmol) and DMAP (catalytic). The reaction was allowed to stir at room temperature for ~20 minutes. The crude reaction mixture was concentrated in vacuo and silica chromatography was then preformed (Gradient: 0%-100% ethyl acetate in heptanes) producing 183 (239 mg, 52%) as a pale white solid. LC-MS: m/z 1308 [M+H$^+$], retention time=2.70 minutes.

Step 3

In a round-bottom flask equipped with a stir bar containing 183 (200 mg, 0.153 mmol) was added 5 mL of dichloromethane and 5 mL of diethyl amine. The solution was stirred for 3 hours. The reaction mixture was concentrated in vacuo and taken up in 50% dichloromethane and heptane and concentrated in vacuo again. This was repeated 3 times. The crude residue was taken up in 10 mL of 25% trifluoro acetic acid in dichloromethane followed by thiophenol (1 mL). The reaction was stirred at room temperature for two days. The crude reaction mixture was concentrated in vacuo and silica chromatography was then preformed (Gradient: 0%-100% ethyl acetate in heptanes) producing 184 (60 mg, 47%) as a pale white solid. LC-MS: m/z 724 [M+H$^+$], retention time=1.02 minutes.

Step 4

To a round bottom flask containing 184 (75 mg, 0.1 mmol) was added 10 mL DMA and the system was purged with N₂. To this stirring solution was added 185 (99 mg, 0.104 mmol) followed by HOAt (416 mg, 0.104 mmol) and Hunigs base (1 drop). The system was stirred at 45° C. for 3 hours. The crude reaction mixture was concentrated in vacuo and reverse phase chromatography was then preformed producing 186 (34 mg, 21%) as a white solid. LC-MS: m/z 1546 [M+H⁺], retention time=1.23 minutes.

Preparation of (S)-3-(5-(chlorocarbonyl)thiophene-2-carbonyl)-1-(chloromethyl)-2,3-dihydro-1H-benzo[e]indol-5-yl acetate 191

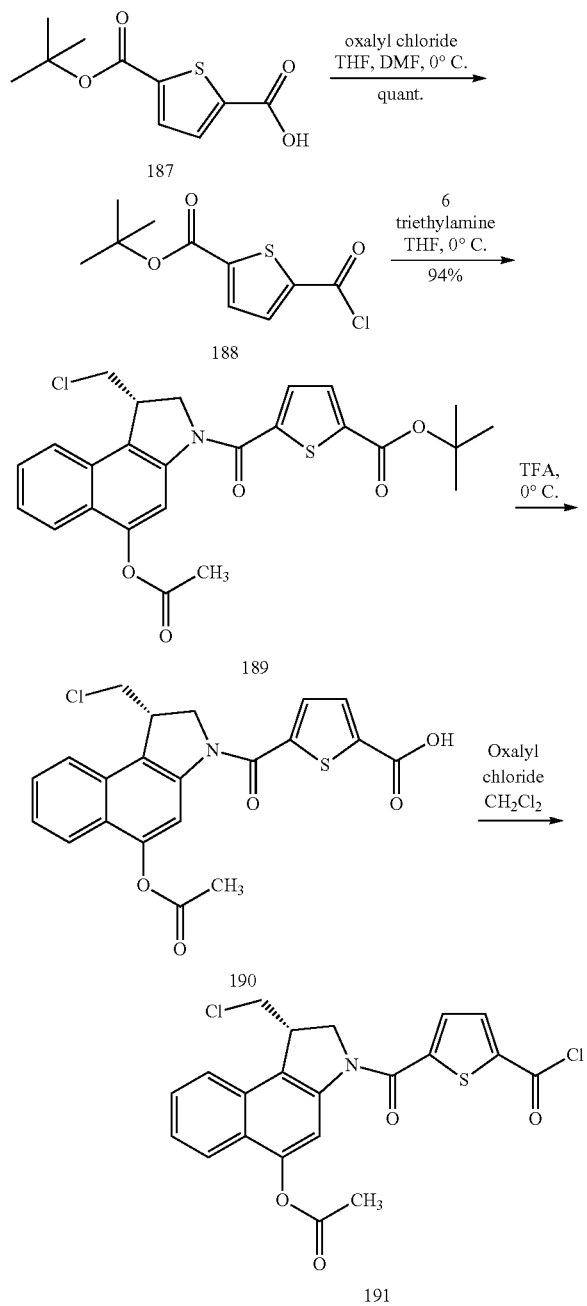

Step 1

To a stirring solution of 5-(tert-butoxycarbonyl)thiophene-2-carboxylic acid (187) in 20 mL of THF at 0° C., oxalyl chloride (0.677 mL, 7.88 mmol) was added followed by 1 drop of DMF. The reaction was allowed to stir at room temperature at 0° C. for ~1 minute and then allowed to warm to room temperature. The reaction was allowed to stir at room temperature for ~90 minutes. Reaction was reduced down and placed underneath high vacuum to produce 188 (1.67 g, quant.) as a white solid. Crude material was then immediately used in the next step.

Step 2

To a stirring solution mixture of 6 (1.54 g, 4.93 mmol) in 25 mL of THF at 0° C., triethylamine (1.38 mL, 9.87 mmol) was added followed immediately by the addition of 188 (1.46 g, 5.92 mmol) dissolved in 25 mL of THF. The reaction was allowed to stir at 0° C. for ~1 minute and then allowed to warm to room temperature while stirring. The reaction was then allowed to stir at room temperature for ~45 minutes. Reaction was reduced down onto silica. Silica chromatography was then preformed (gradient: 0%-100% acetone in heptanes). Appropriate test tubes where concentrated and placed underneath high vacuum to produce 189 (2.24 g, 94%) as brown solid. LC-MS (Protocol B): m/z 486.3 [M+H]⁺, retention time=2.19 minutes.

Step 3

189 (144 mg, 0.3 mmol) was treated with pre-cooled TFA (3 mL) at 0° C. for 30 min, then concentrated in vacuo to give the corresponding acid 190. LC-MS: m/z 430.3 [M+H], retention time=1.59 min. 190 was dissolved in THF (3 mL), oxalyl chloride (0.2 mL, 2M in CH₂Cl₂, 0.4 mmol) was added at 0° C., followed by 2 drops of DMF (cat), the mixture was stirred at 0° C. for 5 min, and then room temperature for 2 h. Concentrated in vacuo to give the 191 as yellow solid.

Preparation of (S)-dibenzyl(1-(chloromethyl)-2,3-dihydro-1H-benzo[e]indol-5-yl)phosphate (193)

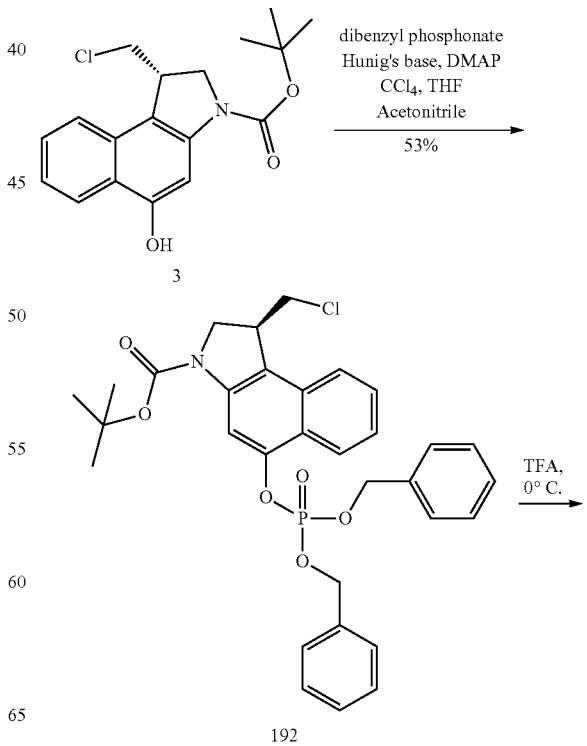

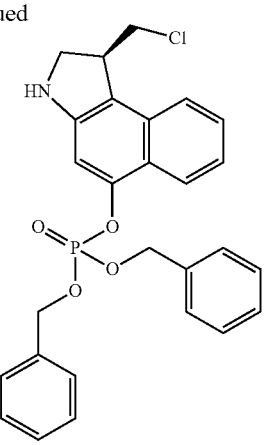

193

Step 1

To a stirring solution of 3 (889 mg, 2.66 mmol) in 20 mL of THF and 20 mL of acetonitrile, carbon tetrachloride (3.61 mL, 37.3 mmol) was added followed by Hunig's base (2.0 mL, 11.5 mmol), dibenzylphosphonate (3.65 mL, 16.5 mmol) and DMAP (65.1 mg, 0.533 mmol). The reaction was allowed to stir at room temperature for ~20 minutes. The reaction was concentrated to a smaller volume, diluted with a few mLs of DMSO and then injected onto a 25 g C18 pre-column (which was previously equilibrated with acetonitrile and then water, with 0.02% TFA in each phase). Material was purified by medium pressure reverse phase C18 chromatography (Gradient: 5% to 85% acetonitrile in water with 0.02% TFA in each phase) with the appropriate test tubes concentrated using a genevac producing 192 (839 mg, 53%) as a clear light brown oil/solid mix. LC-MS (Protocol B): m/z 595.3 [M+2H]', retention time=2.47 minutes.

Step 2

To a stirring solution of 192 (834 mg, 1.40 mmol) in 16 mL of dichloromethane, TFA (16 mL, 210 mmol) was added. The reaction was allowed to stir at room temperature for 1 minute and then immediately reduced down before being placed underneath high vacuum producing 193 (701 mg, quant.) as a green oil/solid mix. LC-MS (Protocol B): m/z 494.2 [M+H]$^+$, retention time=2.17 minutes.

Preparation of (1S)-3-(5-(((1S)-5-(((benzyloxy)(hydroxy)phosphoryl)oxy)-1-(chloromethyl)-2,3-dihydro-1H-benzo[e]indole-3-carbonyl)thiophene-2-carbonyl)-1-(chloromethyl)-2,3-dihydro-1H-benzo[e]indol-5-yl acetate and (S)-3-(5-(((S)-5-((bis(benzyloxy)phosphoryl)oxy)-1-(chloromethyl)-2,3-dihydro-1H-benzo[e]indole-3-carbonyl)thiophene-2-carbonyl)-1-(chloromethyl)-2,3-dihydro-1H-benzo[e]indol-5-yl acetate [195]

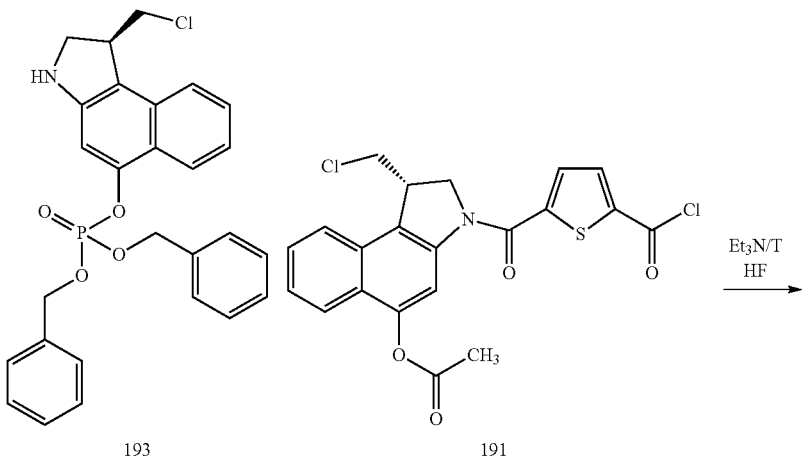

193                 191

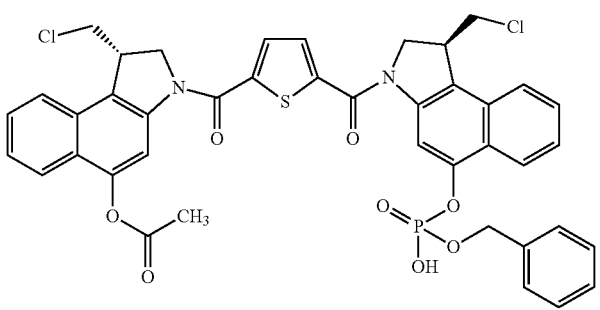

194

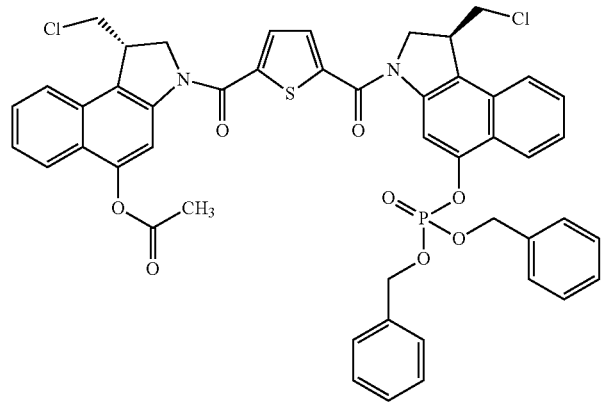

195

193 was dissolved in THF (3 ml) at 0° C., Et₃N (0.165 mL, 1.2 mmol) was added, followed by a solution of 191 in THF (2 mL). The mixture was stirred at 0° C. for 5 min, and room temperature for 2 h. The reaction mixture was concentrated in vacuo, and the residue was purified by Gilson HPLC (ACN/water, 0.02% TFA) to give two products 194 as yellow solid (50 mg, 21%). LC-MS: m/z 815.4 [M+H], retention time=0.96 min. ¹H NMR (400 MHz, DMSO-d₆), δ 8.42 (s), 8.16 (s), 8.07 (d), 8.02 (d), 7.94 (d), 7.90 (s), 7.64 (q), 7.54 (q), 7.10-7.29 (m), 5.14 (d), 4.86 (q), 4.52 (t), 4.42 (m), 4.11-4.00 (m) and 195 as green solid (50 mg, 19%). LC-MS: m/z 905.4 [M+H], retention time=2.43 min.

Preparation of (1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl 4-nitrophenyl carbonate (196)

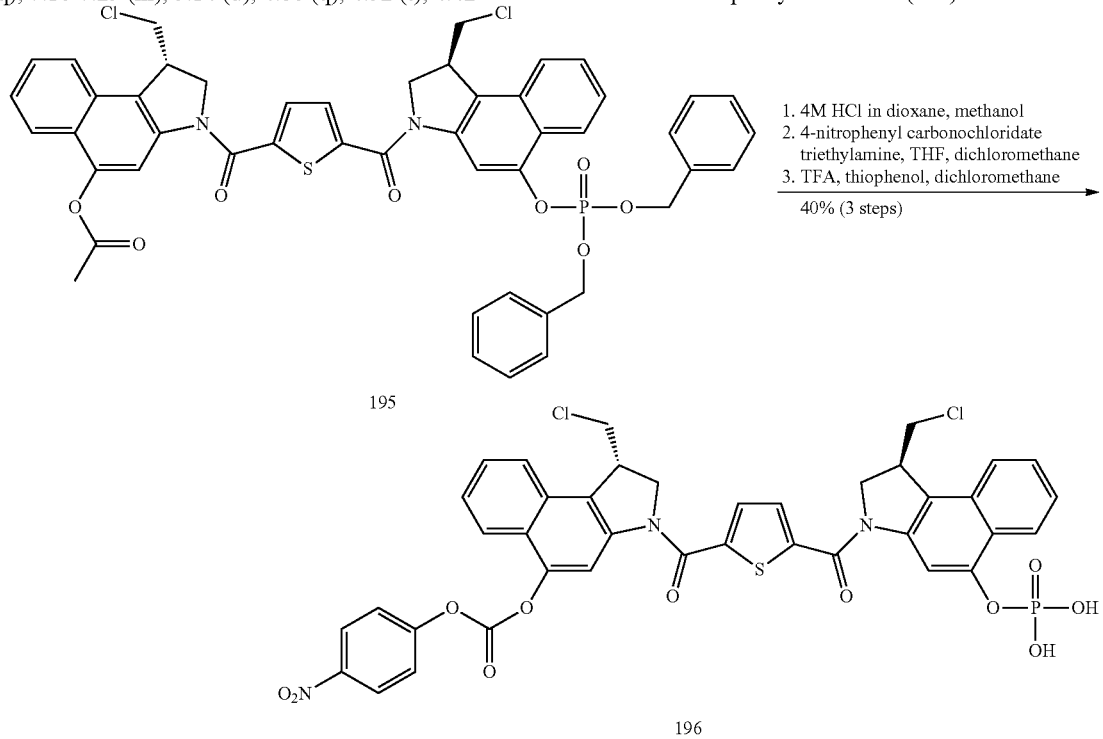

To a stirring mixture of 195 (200 mg, 0.221 mmol) in 8 mL of methanol, 4M HCl in dioxane (8.0 mL, 230 mmol) was added. The reaction was allowed to stir at room temperature for ~20 minutes. Reaction was reduced down. Crude material was taken up in 8 mL of THF and 8 mL of dichloromethane. To this stirring solution at 0° C., 4-nitrophenyl carbonochloridate (86.3 mg, 0.428 mmol) was added followed by triethylamine (0.179 mL, 1.28 mmol). The reaction was allowed to stir at 0° C. for ~1 minute and then allowed to warm to room temperature while stirring. The reaction was allowed to stir at room temperature for ~20 minutes. The reaction was reduced down and then placed underneath high vacuum. To a stirring mixture of crude material in 10 mL of dichloromethane, a solution of TFA (5 mL, 70 mmol) in 10 mL of dichloromethane was added followed by thiophenol (0.107 mL, 1.04 mmol). The reaction was allowed to stir at room temperature for ~6-7 hours. The reaction was concentrated to a smaller volume, diluted with a few mLs of DMSO and then injected onto a 25 g C18 pre-column (which was previously equilibrated with acetonitrile and then water, with 0.02% TFA in each phase). Material was purified by medium pressure reverse phase C18 chromatography (Gradient: 5% to 60% acetonitrile in water with 0.02% TFA in each phase) with the appropriate test tubes concentrated using a genevac producing 196 (71 mg, 40%) as a yellow solid. LC-MS (Protocol B): m/z 848.3 [M+H]⁺, retention time=1.78 minutes. ¹H NMR (400 MHz, DMSO-d₆) δ 8.51 (br s), 8.35-8.41 (m), 8.09-8.15 (m), 8.00, 7.97-8.02 (d), 7.87-7.93 (m), 7.80-7.86 (m), 7.67-7.73 (m), 7.58-7.65 (m), 7.50-7.55 (m), 4.80-4.93 (m), 4.42-4.58 (m), 4.31-4.37 (m), 3.96-4.15 (m).

Preparation of 4-((S)-2-((S)-2-((tert-butoxycarbonyl)amino)-3-methylbutanamido)-5-ureidopentanamido)benzyl(2-(((((S)-1-(chloromethyl)-3-(5-((S)-1-(chloromethyl)-5-(phosphonooxy)-2,3-dihydro-1H-benzo[e]indole-3-carbonyl)thiophene-2-carbonyl)-2,3-dihydro-1H-benzo[e]indol-5-yl)oxy)carbonyl)(2-methoxyethyl)amino)ethyl)(methyl)carbamate [198]
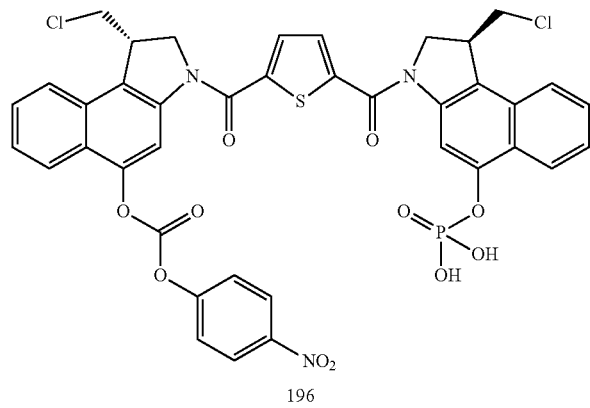
196
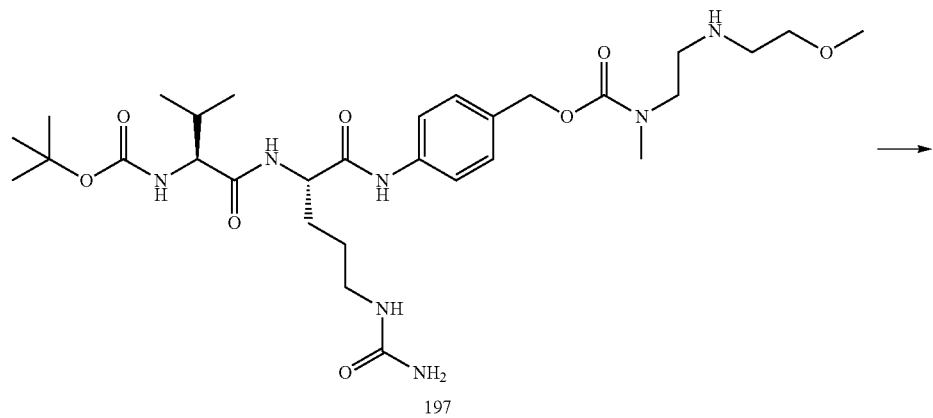
197
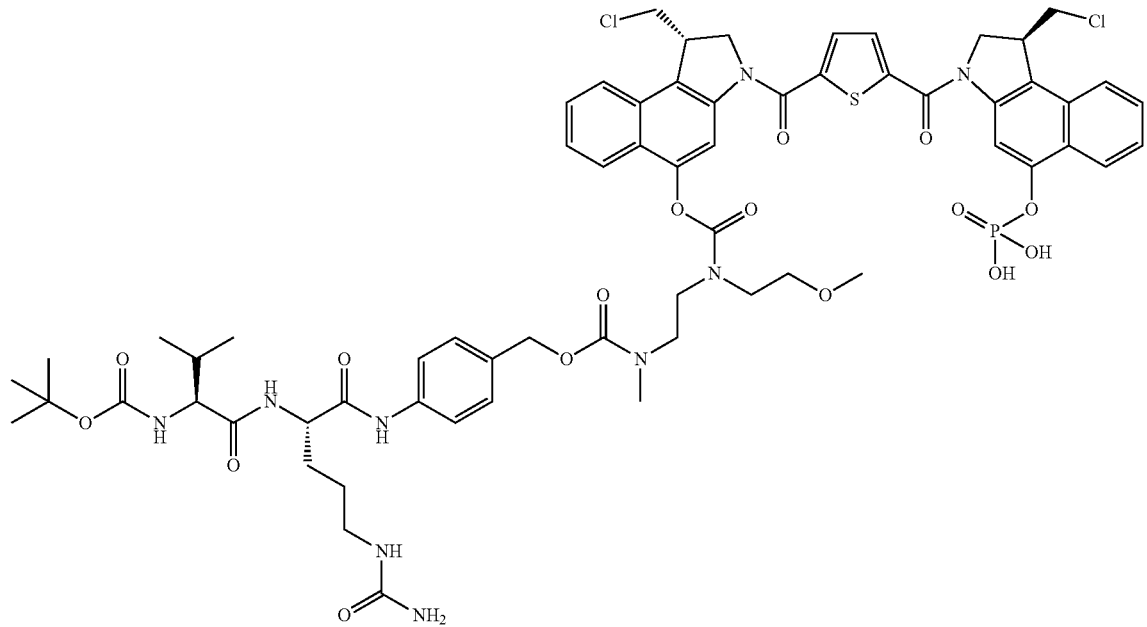
198

196 (15 mg, 0.018 mmol) was dissolved in DMF (1 mL), added a solution of 197 (17 mg, 0.023 mmol) in DMF (1 mL), followed by DIPEA (0.013 mL, 0.072 mmol) and lutidine (0.008 mL, 0.072 mmol), HOAt (2.6 mg). The mixture was stirred at rt for 30 min. The reaction was completed in 30 min observed by LC-MS. The crude was purified by Gilson HPLC (0.02% TFA) to give the product 198 as light yellow solid (13 mg, 53%). LC-MS: m/z 1346.8 [M+H], retention time=1.77 min. $^1$H NMR (400 MHz, DMSO-d$_6$), δ 8.39 (s), 8.15 (d), 8.01 (m), 7.89 (m), 7.63 (m), 7.53 (m), 7.45-7.23 (m), 6.73 (d), 5.98 (s), 5.07-4.95 (m), 4.84 (t), 4.51 (m), 4.49-4.60 (m), 4.08-3.95 (m), 3.84-3.63 (m), 3.00-2.89 (m), 1.68-1.59 (m), 0.85 (m).

Preparation of 4-((26S,29S)-1-bromo-26-isopropyl-2,24,27-trioxo-29-(3-ureidopropyl)-6,9,12,15,18,21-hexaoxa-3,25,28-triazatriacontanamido)benzyl (2-(((((S)-1-(chloromethyl)-3-(5-((S)-1-(chloromethyl)-5-(phosphonooxy)-2,3-dihydro-1H-benzo[e]indole-3-carbonyl)thiophene-2-carbonyl)-2,3-dihydro-1H-benzo[e]indol-5-yl)oxy)carbonyl)(2-methoxyethyl)amino)ethyl)(methyl)carbamate [201]

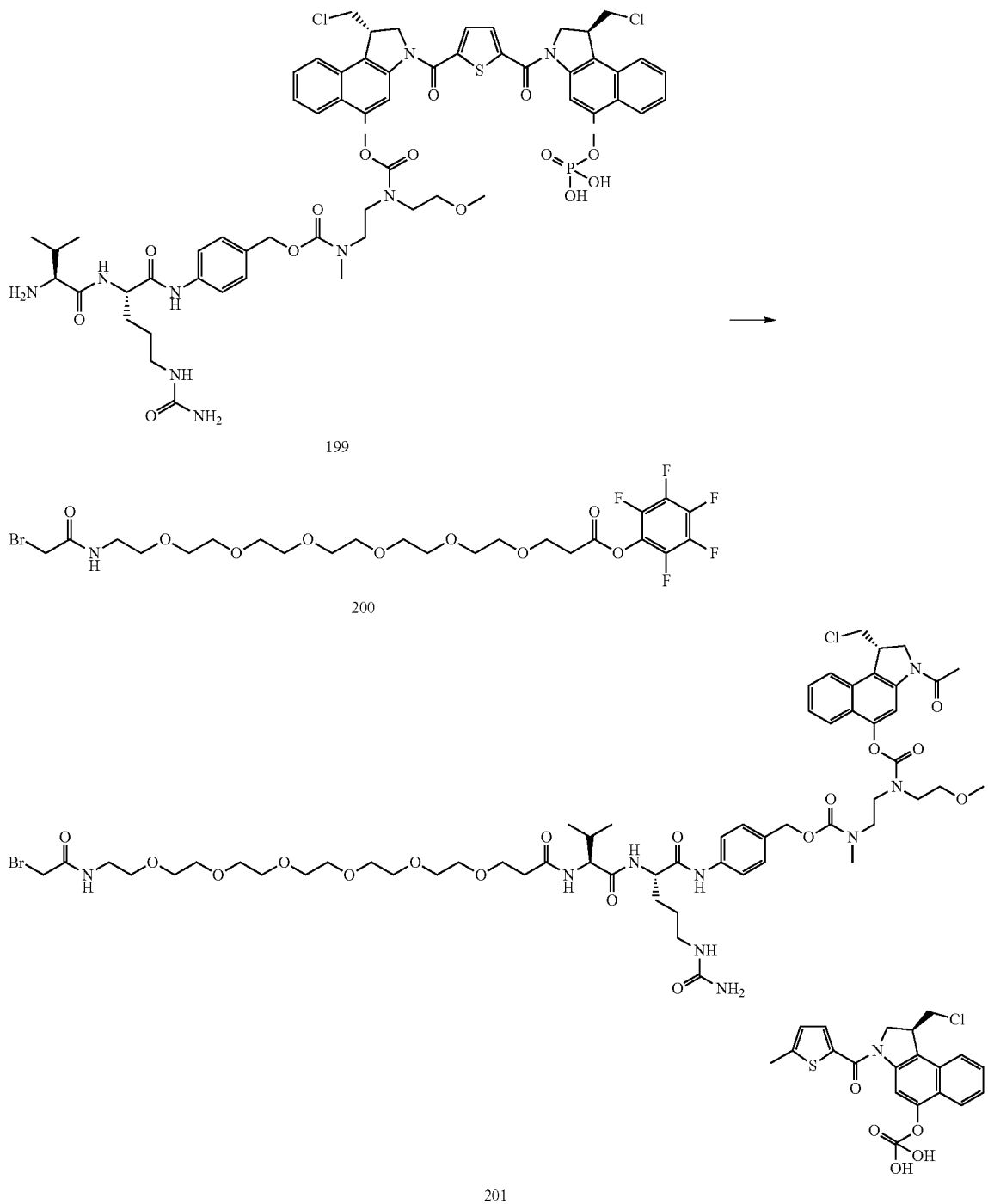

Step 1

198 (13 mg, 0.01 mmol) was treated with pre-cooled TFA (0° C., 2 mL) for 2 min, and concentrated in vacuo to give the product 199 as yellow solid (14 mg, TFA salt, 100%). LC-MS: m/z 1247.9 [M+H], retention time=1.57 min. $^1$H NMR (400 MHz, DMF-$d_7$), δ 10.13 (s), 8.65 (d), 8.45 (s), 8.17 (d), 7.95-7.85 (m), 7.65-7.22 (m), 5.04-4.97 (m), 4.81 (dd), 4.56 (s), 4.33 (d), 4.07-3.94 (m), 3.73-3.64 (m), 3.50 (s), 3.55-3.09 (m), 2.95-2.85 (m), 2.21 (dd), 1.76 (m), 1.62 (m), 1.46 (s), 0.99 (m).

Step 2

199 (5 mg, 0.004 mmol) was added to a solution of perfluorophenyl 1-bromo-2-oxo-6,9,12,15,18,21-hexaoxa-3-azatetracosan-24-oate 200 (3.8 mg, 0.006 mmol) in DMF (0.5 mL), followed by DIPEA (0.003 mL, 0.016 mmol). The mixture was stirred at room temperature for 1 h. The crude was purified by Gilson HPLC using ACN/water (0.02% TFA) to give the product 201 as yellow solid (3 mg, 40%). LC-MS: m/z 1704.0 [M+H], retention time=1.61 min. $^1$H NMR (400 MHz, DMSO-$d_6$), δ 9.88 (s), 8.30 (s), 8.24 (s), 8.06 (m), 7.91 (m), 7.81 (m), 7.54 (m), 7.47 (m), 7.43-7.13 (m), 5.91 (s), 4.98-4.85 (m), 4.76 (m), 4.43 (m), 4.30 (s), 4.14 (m), 4.00-3.90 (m), 3.52 (m), 3.16 (m), 2.92-2.86 (m), 2.31-2.25 (m), 1.90 (s), 1.52 (s), 1.34 (s), 1.32 (m), 0.78 (m).

Preparation of 4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosanamido)benzyl(2-(((((S)-1-(chloromethyl)-3-(5-((S)-1-(chloromethyl)-5-(phosphonooxy)-2,3-dihydro-1H-benzo[e]indole-3-carbonyl)thiophene-2-carbonyl)-2,3-dihydro-1H-benzo[e]indol-5-yl)oxy)carbonyl)(2-methoxyethyl)amino)ethyl)(methyl)carbamate [206]

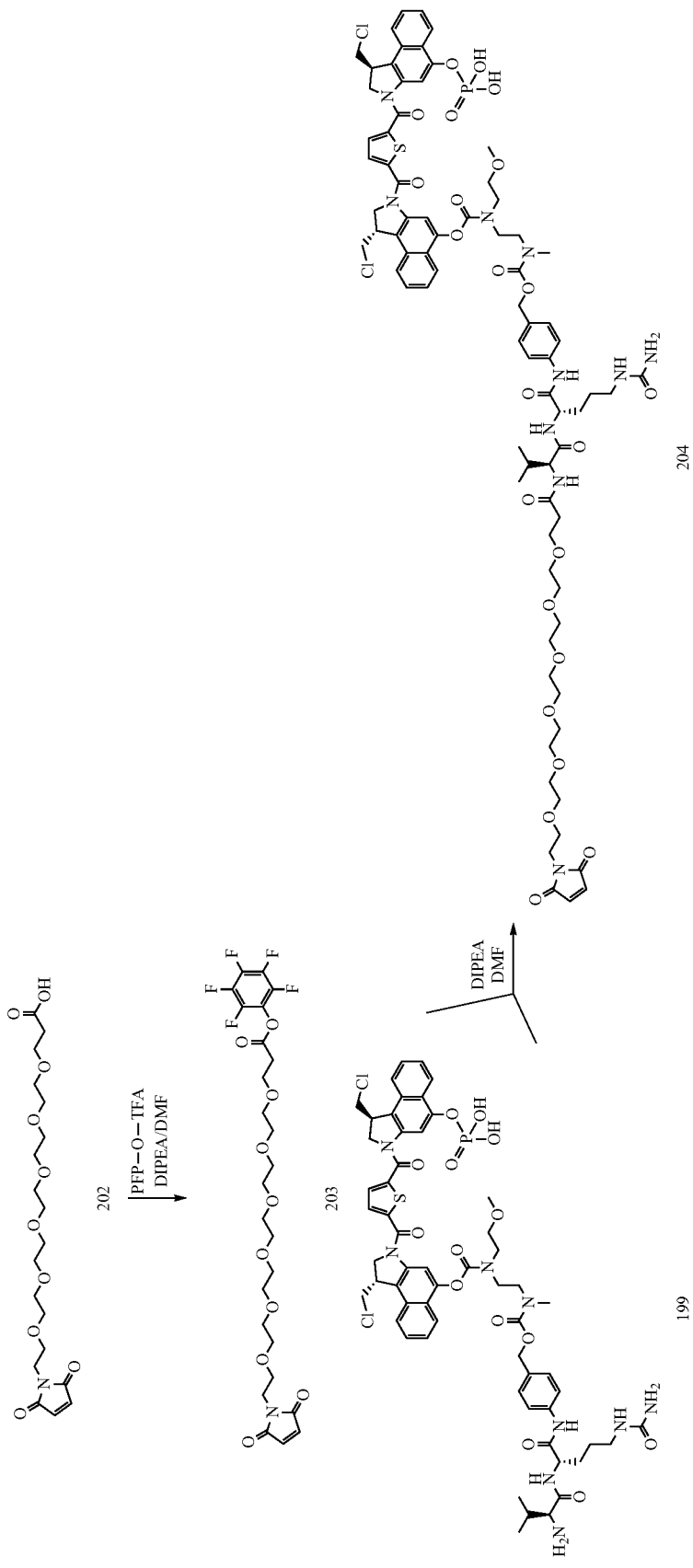

Step 1

202 (227 mg, 0.52 mmol) was dissolved in $CH_2Cl_2$ (2 mL) and DMF (2 mL), added PFP-O-TFA (0.19 mL, 1.05 mmol) and DIPEA (0.275 mL, 1.57 mmol). The mixture was stirred at room temperature for 2 h. Concentrated in vacuo, and the residue was purified by Gilson HPLC (0.02% TFA) to give the corresponding PFP ester 203 as yellow oil (34 mg, 11%). LC-MS: m/z 623.4 [M+Na], retention time=0.92 min.

Step 2

203 (3 mg, 0.005 mmol) was added to a solution of 199 (7 mg, 0.005 mmol) in DMF (0.3 mL), followed by DIPEA (0.005 mL, 0.03 mmol). The mixture was stirred at room temperature for 2 h. The reaction mixture was subjected to Gilson HPLC separation (0.02% TFA) to give the product 204 as yellow solid (4.6 mg, 60%). LC-MS: m/z 1664.1 [M+H], retention time=1.63 min. $^1$H NMR (400 MHz, DMSO-$d_6$), δ 8.39 (s), 8.14 (m), 8.10-7.99 (m), 7.63 (m), 7.55-7.5 (m), 7.48 (s), 7.02 (s), 6.52 (s), 5.99 (s), 5.07-4.95 (m), 4.84 (t), 4.52 (t), 4.38 (s), 4.24 (t), 4.08-3.99 (m), 3.61-3.48 (m), 3.00-2.89 (m), 2.68 (s), 2.34 (s), 0.86 (dd).

Preparation of 4-((23S,26S)-1-amino-23-isopropyl-21,24-dioxo-26-(3-ureidopropyl)-3,6,9,12,15,18-hexaoxa-22,25-diazaheptacosanamido)benzyl(2-(((((S)-1-(chloromethyl)-3-(5-((S)-1-(chloromethyl)-5-(phosphonooxy)-2,3-dihydro-1H-benzo[e]indole-3-carbonyl)thiophene-2-carbonyl)-2,3-dihydro-1H-benzo[e]indol-5-yl)oxy)carbonyl)(2-methoxyethyl)amino)ethyl)(methyl)carbamate [208]

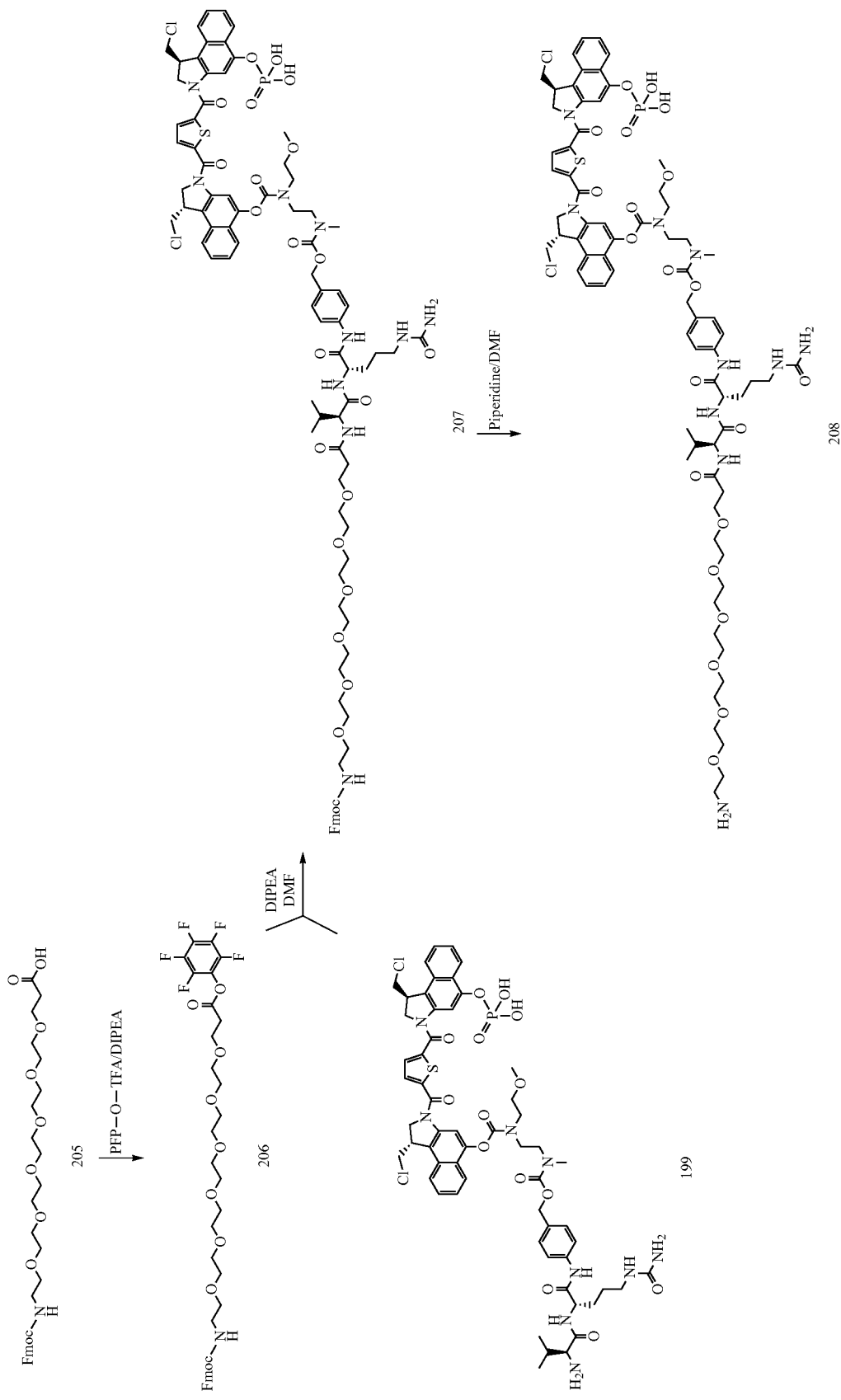

173
Step 1

205 (43 mg, 0.07 mmol) was dissolved in DMF (2 mL), added PFP-O-TFA (0.026 mL, 0.14 mmoL), followed by DIPEA (0.038 mL, 0.21 mmol). The mixture was stirred at room temperature for 2 h. The crude was purified by Gilson HPLC (0.02% TFA) to give the product 206 as colorless oil (39 mg, 72%). LC-MS: m/z 742.2 [M+H], retention time=2.17 min.

Step 2

199 (7 mg, 0.005 mmol) was dissolved in DMF (0.6 mL), added a solution of the above PFP ester 206 (3.7 mg, 0.005 mmol) in DCM (0.1 mL), followed by DIPEA (0.005 mL, 0.03 mmol). The mixture was stirred at rt for 1 h. Crude product 207: LC-MS: m/z 1805.3 [M+H], retention time=1.97 min.

174
Step 3

To the above reaction mixture 207, piperidine (0.02 mL, 0.2 mmol) was added, and the mixture was stirred at rt for 30 min. Concentrated in vacuo, and the crude was purified by Gilson HPLC (0.02% TFA) to give the product 208 as yellow solid (4.2 mg, TFA salt, 50%). LC-MS: m/z 1584.0 [M+H], retention time=1.54 min. $^1$H NMR (400 MHz, DMSO-$d_6$), δ 9.98 (s), 8.38 (s), 8.14 (m), 7.98 (m), 7.88 (m), 7.70 (s), 7.62 (m), 7.54 (m), 7.47 (m), 7.27 (m), 6.01 (s), 5.06-5.00 (m), 4.84 (m), 4.51 (m), 4.37 (m), 4.25 (m), 4.08 (m), 4.02 (m), 3.59 (m), 3.25 (m), 2.98 (m), 2.37 (m), 1.97 (s), 1.69 (s), 1.59 9 s), 1.39 (m), 0.86 (dd).

Preparation (1S)-1-(chloromethyl)-3-[(5-{[(1S)-1-(chloromethyl)-5-{[(4-nitrophenoxy)carbonyl]oxy}-1,2-dihydro-3H-benzo[e]indol-3-yl]carbonyl}thiophen-2-yl)carbonyl]-2,3-dihydro-1H-benzo[e]indol-5-yl acetate (211)

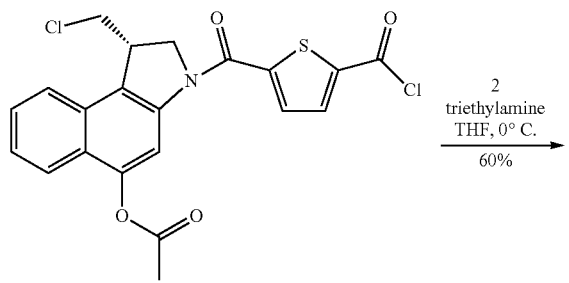

191

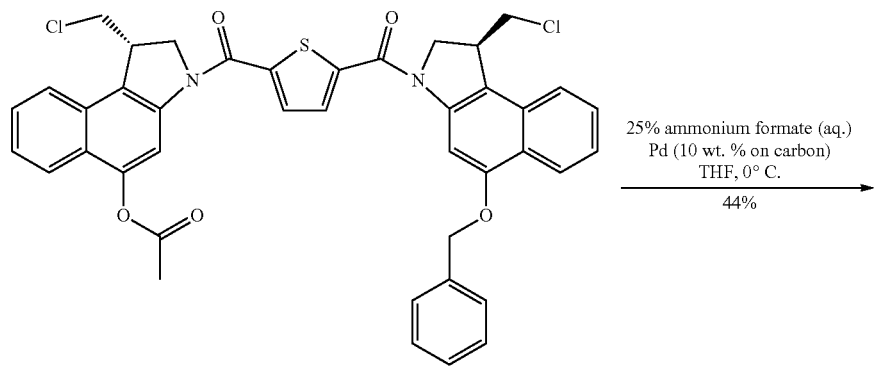

209

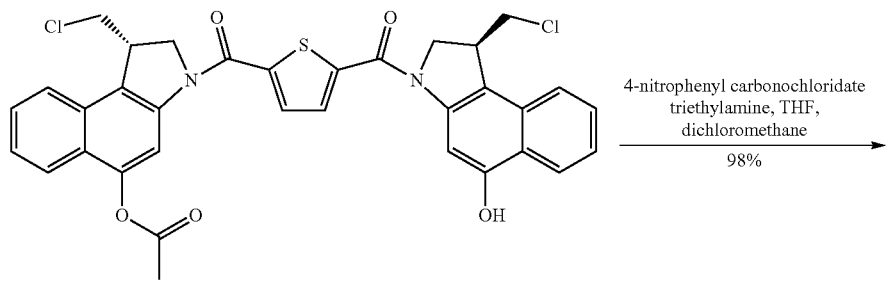

210

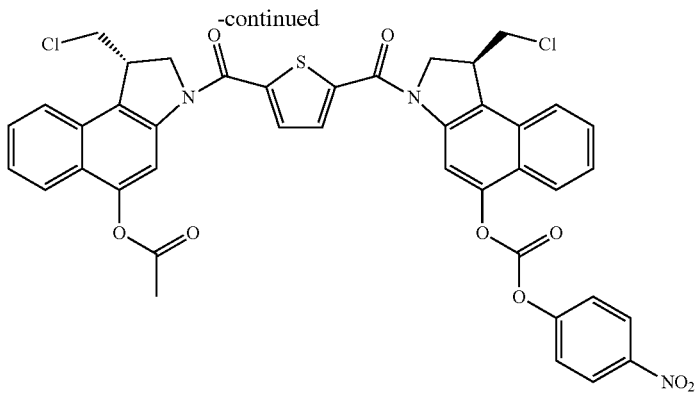

211

Step 1

To a stirring mixture of 2 (425 mg, 1.31 mmol) in 5 mL of THF under nitrogen at 0° C., triethylamine (0.333 mL, 2.39 mmol) was added followed immediately by 191 (535 mg, 1.19 mmol) dissolved in 5 mL of THF. The reaction was allowed to stir at 0° C. for 5 minutes and then allowed to warm to room temperature while stirring. The reaction was allowed to stir at room temperature for ~30 minutes. Reaction was then reduced down onto silica. Silica chromatography was then preformed (gradient: 5%-80% acetone in heptanes). Appropriate test tubes where concentrated and placed underneath high vacuum to produce 209 (530 mg, 60%) as a yellow solid. LC-MS (Protocol B): m/z 735.1 [M+H]$^+$, retention time=2.48 minutes.

Step 6

A stirring solution of 209 (610 mg, 0.829 mmol) in 15 mL of THF under nitrogen was cooled to 0° C. using an ice bath. Palladium 10 wt. % on activated carbon (203 mg) was then added followed by the slow dropwise addition of 2 mL of 25% ammonium formate in water. The reaction was allowed to stir at 0° C. for 12-24 hours. Reaction was diluted with ether followed by the addition of sodium sulfate. Reaction was filtered through celite, and the celite was washed twice with ether. The organics where combined and then reduced down. Residue was purified by medium pressure reverse phase C18 chromatography (Gradient: 5% to 80% acetonitrile in water with 0.02% TFA in each phase) with the appropriate test tubes concentrated using a genevac producing 210 (206 mg, 44%) as a yellow solid. LC-MS (Protocol B): m/z 645.0 [M+H]$^+$, retention time=2.08 minutes. $^1$H NMR (400 MHz, DMSO) δ 10.49 (br s), 8.13-8.18 (d), 8.05-8.10 (d), 7.93-7.97 (d), 7.83-7.91 (m), 7.63-7.69 (t), 7.53-7.58 (m), 7.38-7.43 (m), 4.83-4.92 (m), 4.74-4.82 (m), 4.50-4.55 (d), 4.39-4.47 (m), 4.20-4.27 (m), 4.01-4.15, 3.88-3.96 (m), 3.57-3.68 (m), 1.74-1.80, 1.36-1.39 (m).

Step 7

To a stirring solution of 210 (195 mg, 0.302 mmol) in 12 mL of dichloromethane and 8 mL THF at 0° C., 4-nitrophenyl carbonochloridate (122 mg, 0.604 mmol) was added followed by triethylamine (0.168 mL, 1.21 mmol). The reaction was allowed to stir at 0° C. for 5 minutes, and then allowed to warm to room temperature while stirring. Reaction was allowed to stir at room temperature for ~30 minutes. Reaction was reduced down. Residue was purified by medium pressure reverse phase C18 chromatography (Gradient: 5% to 85% acetonitrile in water with 0.02% TFA in each phase) with the appropriate test tubes concentrated using a genevac producing 211 (240 mg, 98%) as a yellow solid. LC-MS (Protocol B): m/z 810.3 [M+H]$^+$, retention time=2.35 minutes.

Preparation of N-[6-(2,5-dioxo-2,5-dihydro-1H-pyrrol-1-yl)hexanoyl]-L-valyl-N-[4-({[{2-[({[(1S)-3-[(5-{[(1S)-5-(acetyloxy)-1-(chloromethyl)-1,2-dihydro-3H-benzo[e]indol-3-yl]carbonyl}thiophen-2-yl)carbonyl]-1-(chloromethyl)-2,3-dihydro-1H-benzo[e]indol-5-yl]oxy}carbonyl)(methyl)amino] ethyl}(methyl)carbamoyl]oxy}methyl)phenyl]-N~5~-carbamoyl-L-ornithinamide (215)

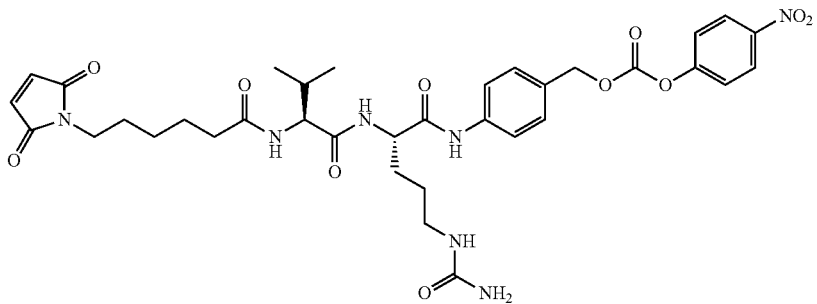

212

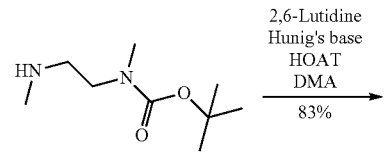

213

-continued

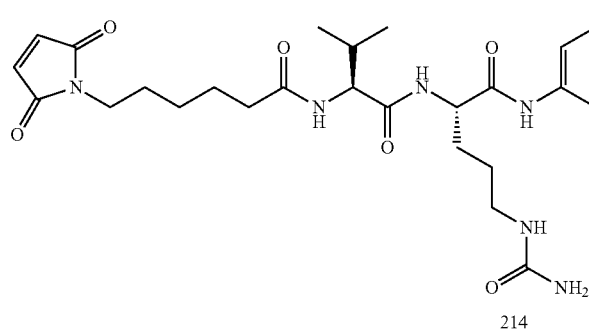
214

1. THF, dichloromethane
2. 211 Hunig's base HOAT DMA
24%

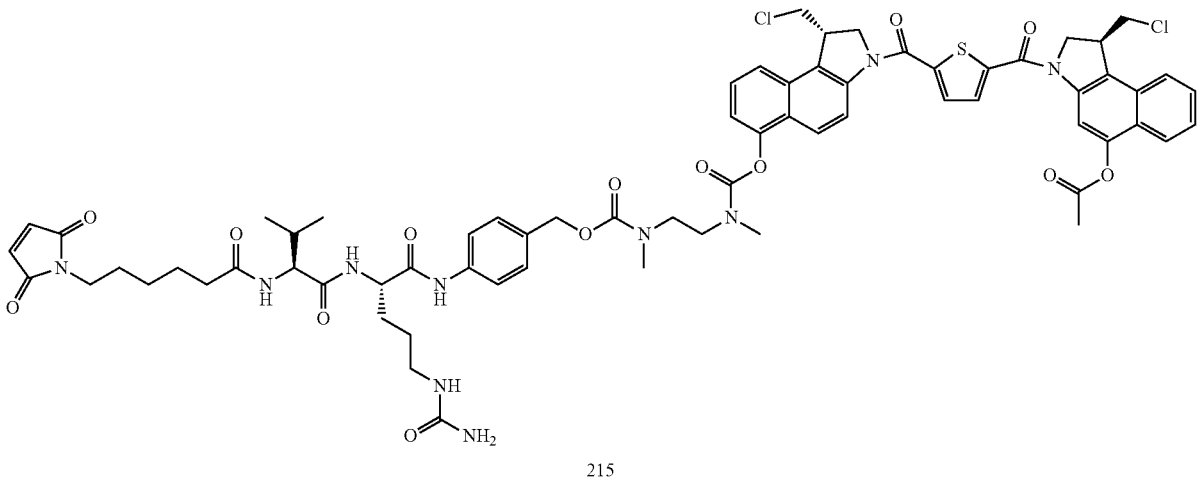
215

Step 1

To a stirring solution of 212 (750 mg, 1.02 mmol) and 213 tert-butyl methyl[2-(methylamino)ethyl]carbamate (192 mg, 1.02 mmol) in 6 mL of DMA, 2-6-Lutidine (0.236 mL, 2.03 mmol) was added followed by Hunig's base (0.354 mL, 2.03 mmol) and HOAT (69.1 mg, 0.5 mmol). Reaction was allowed to stir at room temperature for ~40 minutes. Reaction was injected onto a 25 g C18 pre-column (which was previously equilibrated with acetonitrile and then water, with 0.02% TFA in each phase) and then purified by medium pressure reverse phase C18 chromatography (Gradient: 5% to 45% acetonitrile in water with 0.02% TFA in each phase) with the appropriate test tubes concentrated using a genevac producing 214 (663 mg, 83%) as a white solid. LC-MS (Protocol B): m/z 787.3 [M+H]$^+$, retention time=1.45 minutes.

Step 2

To a stirring mixture of 214 (40.9 mg, 0.052 mmol) in 2 mL of dichloromethane, TFA (1 mL, 10 mmol) was added. Reaction was allowed to stir at room temperature for ~40 minutes. Reaction was reduced down and then placed underneath high vacuum. Crude material was taken up in 2 mL of DMA and to this stirring solution Hunig's base (0.03 mL, 0.17 mmol) was added followed by 2,6-Lutidine (0.02 mL, 0.17 mmol), HOAT (5.9 mg, 0.043 mmol), and then 211 (35 mg, 0.043 mmol) dissolved in 1 mL of DMA. Reaction was allowed to stir at room temperature for ~40 minutes. Reaction was injected onto a 5 g C18 pre-column (which was previously equilibrated with acetonitrile and then water, with 0.02% TFA in each phase) and then purified by medium pressure reverse phase C18 chromatography (Gradient: 5% to 60% acetonitrile in water with 0.02% TFA in each phase) with the appropriate test tubes concentrated using a genevac producing 215 (14.1 mg, 24%) as a yellow solid. LC-MS (Protocol B): m/z 1359.3 [M+3H]$^+$, retention time=2.01 minutes. HR-MS: m/z 1359.4549 [M+3H]$^+$.

Preparation of N-[1-(2,5-dioxo-2,5-dihydro-1H-pyrrol-1-yl)-21-oxo-3,6,9,12,15,18-hexaoxahenicosan-21-yl]-L-valyl-N~5~-carbamoyl-N-{4-[({methyl[2-(methylamino)ethyl]carbamoyl}oxy)methyl]phenyl}-L-ornithinamide (215)

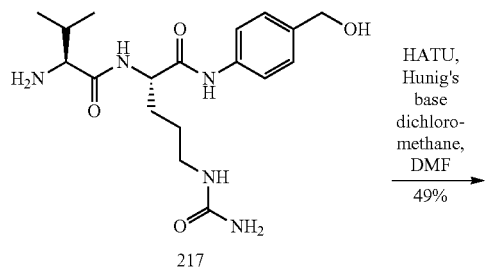
217

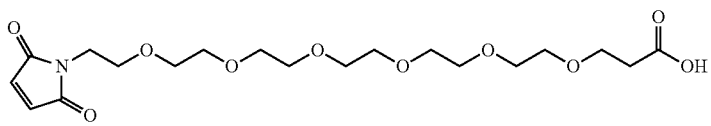
216

HATU, Hunig's base dichloromethane, DMF
49%

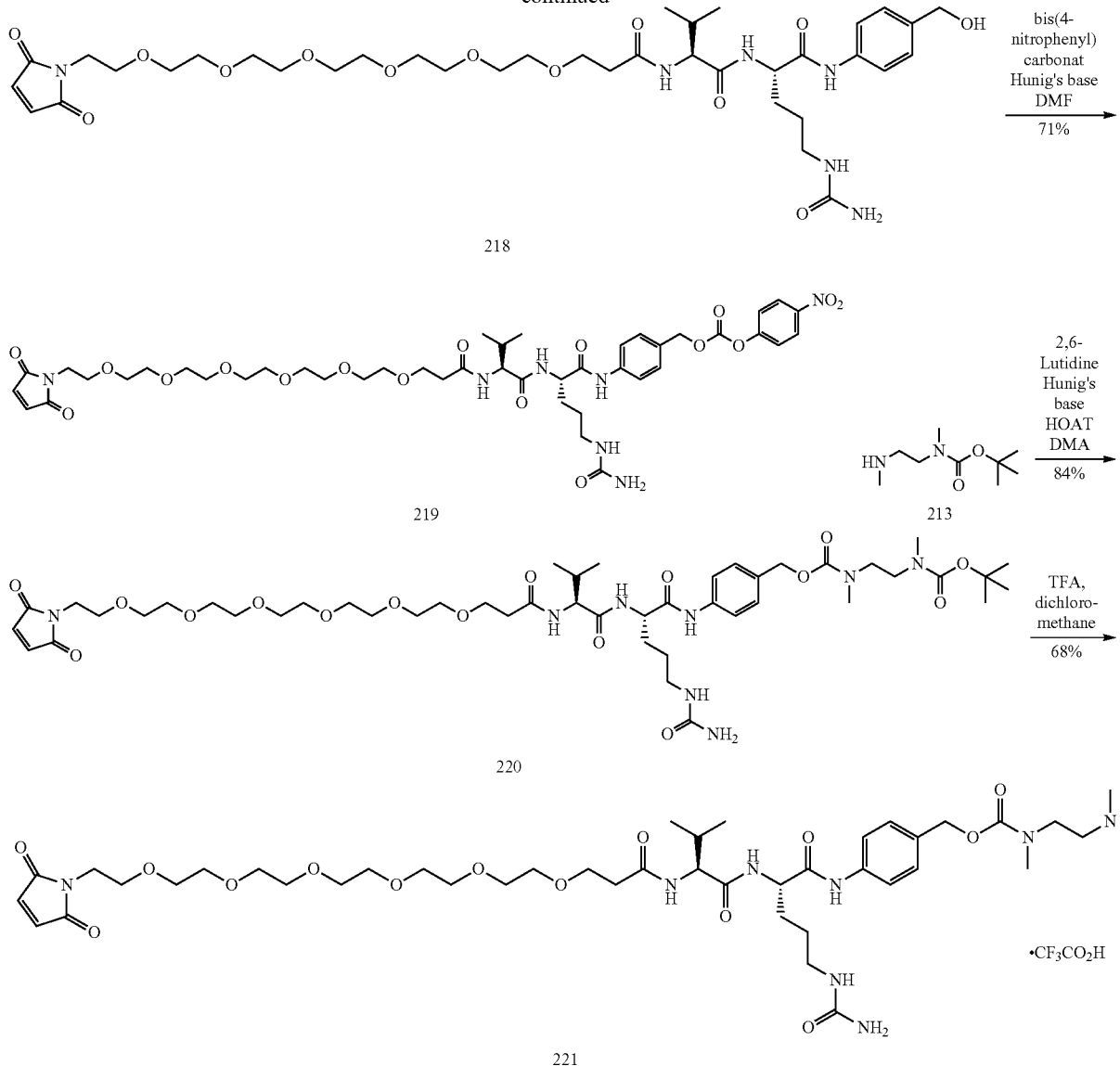

Step 1

To a round bottom flask containing 1-(2,5-dioxo-2,5-dihydro-1H-pyrrol-1-yl)-3,6,9,12,15,18-hexaoxahenicosan-21-oic acid, 216 (628 mg, 1.45 mmol), 20 mL of dichloromethane, 2 mL of DMF, HATU (501 mg, 1.32 mmol) and Hunig's base (0.92 mL, 5.3 mmol) was added. The reaction was allowed to stir at room temperature for 2 minutes before the addition of L-valyl-N~5~-carbamoyl-N-[4-(hydroxymethyl)phenyl]-L-ornithinamide, 217 (500 mg, 1.32 mmol). The reaction was allowed to stir at room temperature for ~90 minutes before being quenched through the addition of TFA. The reaction was concentrated to a smaller volume, diluted with a few mLs of DMSO and then injected onto a 25 g C18 pre-column (which was previously equilibrated with acetonitrile and then water, with 0.02% TFA in each phase). Material was purified by medium pressure reverse phase C18 chromatography (Gradient: 5% to 40% acetonitrile in water with 0.02% TFA in each phase) with the appropriate test tubes concentrated using a genevac producing 218 (514 mg, 49%) as a clear solid. LC-MS (Protocol B): m/z 795.5 [M+H]$^+$, retention time=1.01 minutes.

Step 2

To a stirring solution of 218 (210 mg, 0.264 mmol) and bis(4-nitrophenyl) carbonate (161 mg, 0.528 mmol) in 4 mL of DMF, Hunig's base (0.096 mL, 0.554 mmol) was added. The reaction was allowed to stir at room temperature for ~2 hours. The reaction was injected onto a 25 g C18 pre-column (which was previously equilibrated with acetonitrile and then water, with 0.02% TFA in each phase). Material was purified by medium pressure reverse phase C18 chromatography (Gradient: 5% to 55% acetonitrile in water with 0.02% TFA in each phase) with the appropriate test tubes concentrated using a genevac producing 219 (180 mg, 71%) as a solid. LC-MS (Protocol B): m/z 960.5 [M+H]$^+$, retention time=1.48 minutes.

Step 3

To a stirring solution of 219 (640 mg, 0.667 mmol) and 213 [prepared as described J. Med. Chem. 1992, 33, 559-567] (127 mg, 0.674 mmol) in 6 mL of DMA, 2,6-Lutidine (0.154 mL, 1.33 mmol) was added followed by Hunig's base (0.232 mL, 1.33 mmol) and HOAT (9.1 mg, 0.67 mmol). The reaction was allowed to stir at room temperature for ~15 minutes. The reaction was injected onto a 25 g C18 pre-column (which was previously equilibrated with acetonitrile and then water, with 0.02% TFA in each phase). Material was purified by medium pressure reverse phase C18 chromatography (Gradient: 5% to 40% acetonitrile in water with 0.02% TFA in each phase) with the appropriate test tubes concentrated using a genevac producing 220 (564 mg, 84%) as a wax like white solid. LC-MS (Protocol B): m/z 1009.7 $[M+H]^+$, retention time=1.43 minutes.

Step 4

To a stirring mixture of 220 (470 mg, 0.466 mmol) in 6 mL of dichloromethane, TFA (3.0 mL, 40 mmol) was added. The reaction was allowed to stir at room temperature for ~10 minutes. Reaction was reduced down. Residue was purified by medium pressure reverse phase C18 chromatography (Gradient: 5% to 30% acetonitrile in water with 0.02% TFA in each phase) with the appropriate test tubes concentrated using a genevac producing 221 (326 mg, 68%) as a white oil/solid mix. LC-MS (Protocol B): m/z 909.8 $[M+H]^+$, retention time=0.91 minutes.

Preparation of N-[1-(2,5-dioxo-2,5-dihydro-1H-pyrrol-1-yl)-21-oxo-3,6,9,12,15,18-hexaoxahenicosan-21-yl]-L-valyl-N-[4-({[{2-[({[(1S)-3-[(5-{[(1S)-5-(acetyloxy)-1-(chloromethyl)-1,2-dihydro-3H-benzo[e]indol-3-yl]carbon yl}thiophen-2-yl)carbonyl]-1-(chloromethyl)-2,3-dihydro-1H-benzo[e]indol-5-yl]oxy}carbonyl)(methyl)amino]ethyl}(methyl)carbamoyl]oxy}methyl)phenyl]-N~5~-carbamoyl-L-ornithinamide (222)

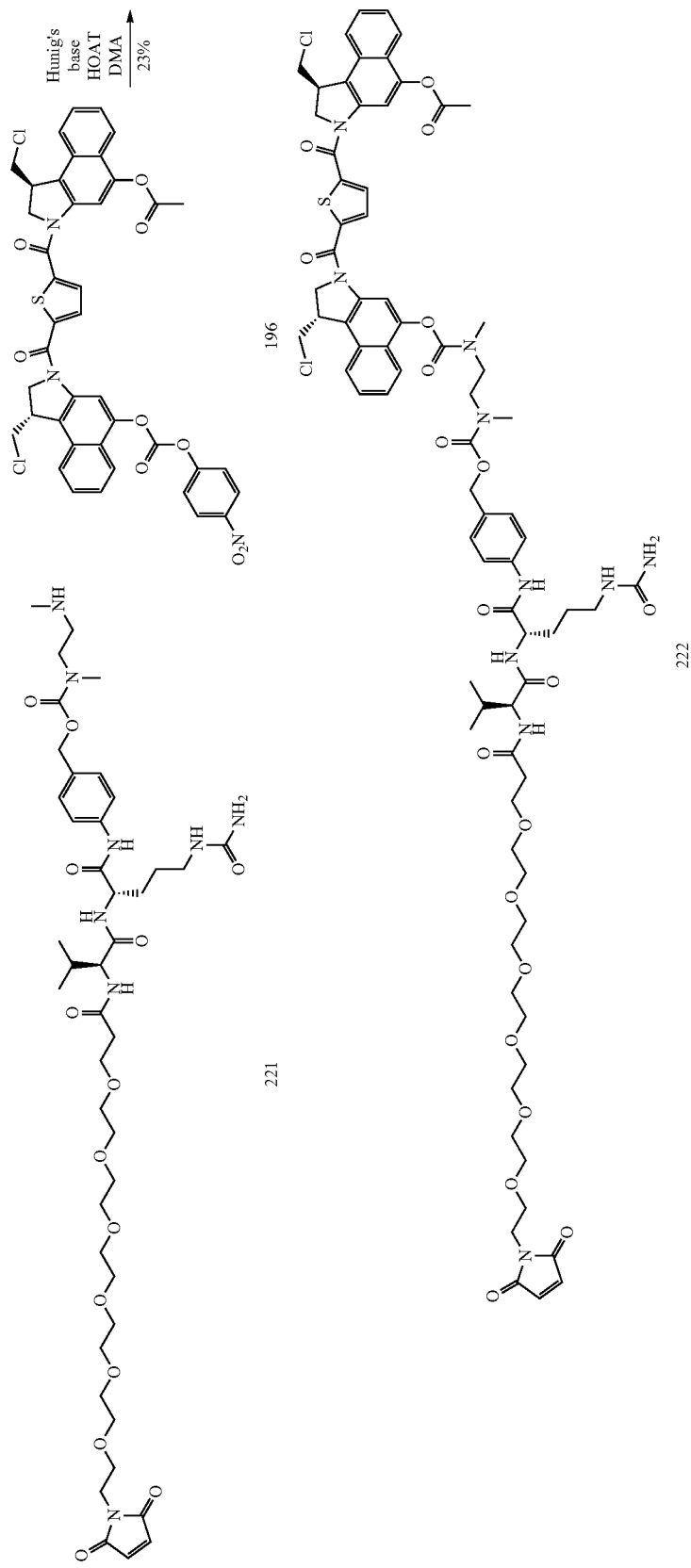

To a stirring mixture of 221 (50.1 mg, 0.05 mmol) in 1 mL of DMA and to this stirring solution, Hunig's base (0.03 mL, 0.172 mmol) was added followed by 2,6-Lutidine (0.02 mL, 0.172 mmol), HOAT (5.9 mg, 0.043 mmol), and 211 (35 mg, 0.043 mmol) dissolved in 1 mL of DMA. Reaction was allowed to stir at room temperature for ~40 minutes. Reaction was injected onto a 5 g C18 pre-column (which was previously equilibrated with acetonitrile and then water, with 0.02% TFA in each phase). Material was purified by medium pressure reverse phase C18 chromatography (Gradient: 5% to 60% acetonitrile in water with 0.02% TFA in each phase) with the appropriate test tubes concentrated using a genevac producing 222 (15.4 mg, 23%) as a yellow/white solid. LC-MS (Protocol B): m/z 1580.4 [M+2H]', retention time=1.95 minutes. HRMS: m/z 790.7923 [M+2H]'.

Preparation of N-[1-(2,5-dioxo-2,5-dihydro-1H-pyrrol-1-yl)-21-oxo-3,6,9,12,15,18-hexaoxahenicosan-21-yl]-L-valyl-N ~5~-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide (223)

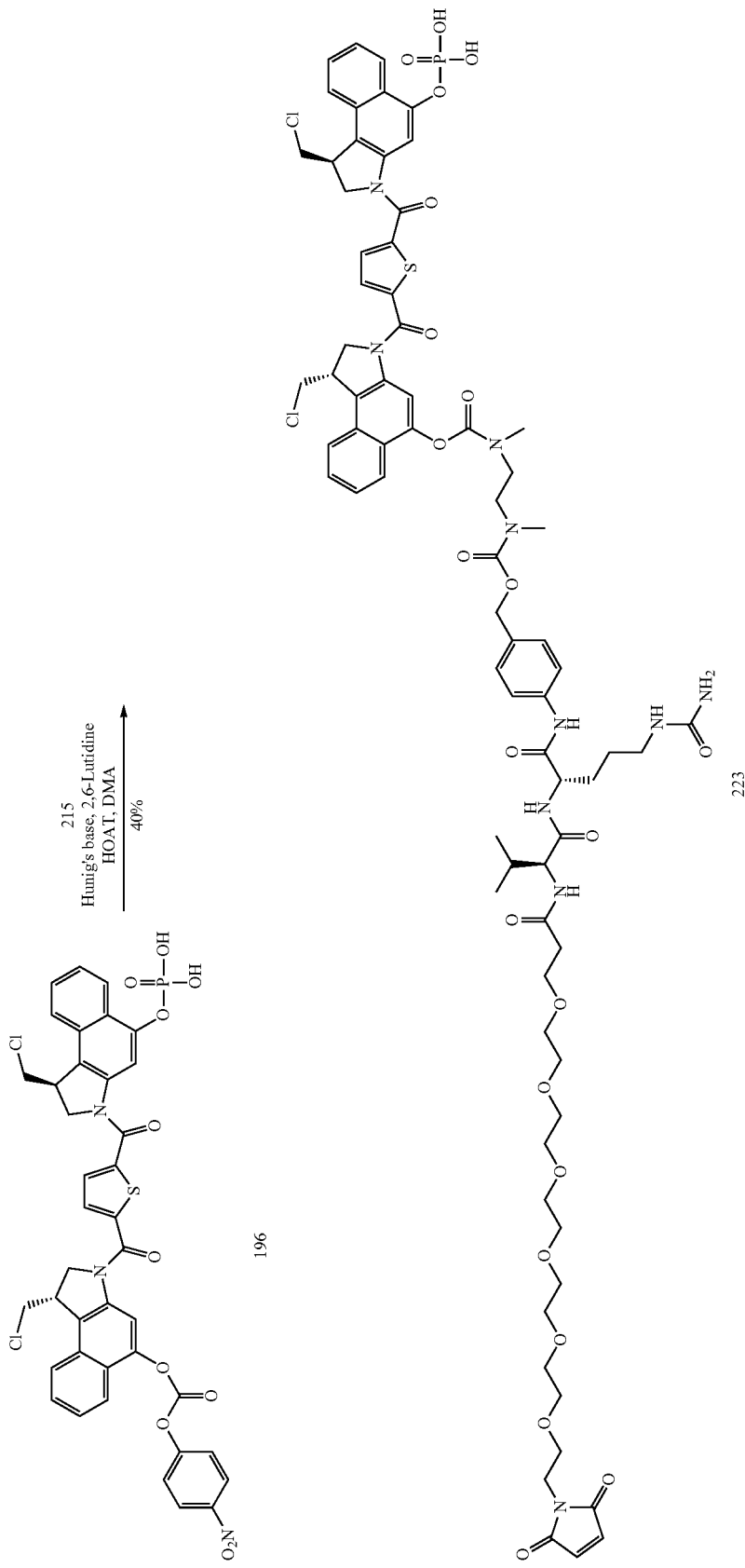

Step 1

To a stirring solution of 196 (29.8 mg, 0.035 mmol) in 0.5 mL of DMA, 221 (17.3 mg, 0.019 mmol) was added as a solution in 1.5 mL of DMA followed by the addition of Hunig's base (0.024 mL, 0.14 mmol), 2,6-Lutidine (0.016 mL, 0.14 mmol) and HOAT (4.8 mg, 0.035 mmol). The reaction was allowed to stir at room temperature for ~20 minutes. The reaction was injected onto a 5 g C18 pre-column (which was previously equilibrated with acetonitrile and then water, with 0.02% TFA in each phase). Material was purified by medium pressure reverse phase C18 chromatography (Gradient: 5% to 75% acetonitrile in water with 0.02% TFA in each phase) followed by preparative HPLC purification (method B) with the appropriate test tubes concentrated using a genevac producing 222 (22.6 mg, 40%) as a yellow solid. LC-MS (Protocol B): m/z 1619.9 [M+3H]', retention time=1.62 minutes. HPLC (Protocol D): retention time=9.339 minutes.

Preparation of methyl 3-(chlorocarbonyl)bicyclo[1.1.1]pentane-1-carboxylate (225)

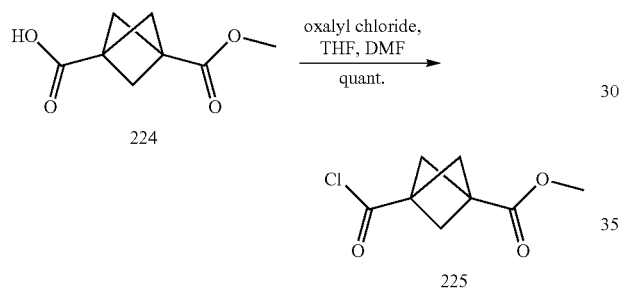

To a stirring solution of 224 in 12 mL of THF at 0° C., oxalyl chloride (0.381 mL, 4.44 mmol) was added followed by 1 drop of DMF. The reaction was allowed to stir at 0° C. for ~1 minute and then allowed to warm to room temperature while stirring. The reaction was allowed to stir at room temperature for ~30 minutes. Reaction was reduced down and then placed high vacuum producing 225 (701 mg, quantitative) as a white solid.

Preparation of (8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl 4-nitrophenyl carbonate trifluoroacetic acid salt 230

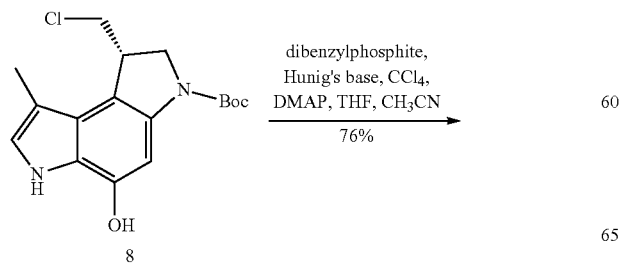

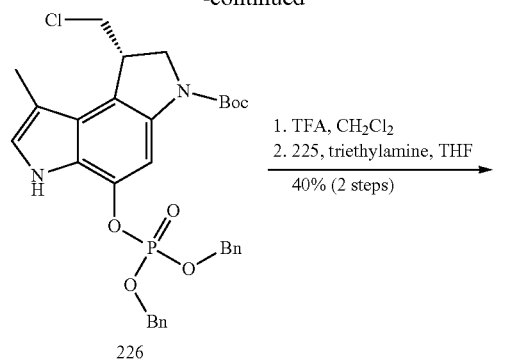

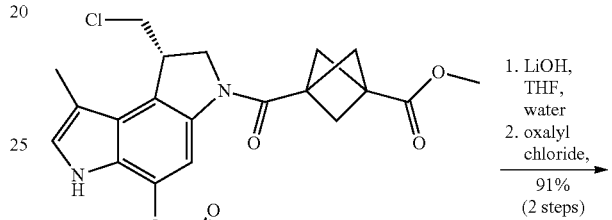

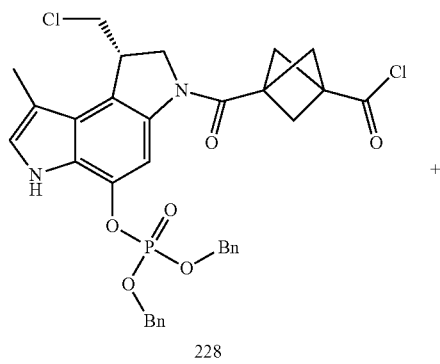

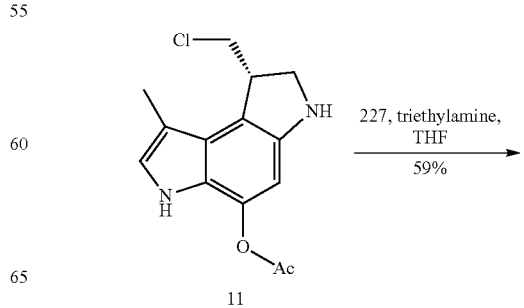

191

-continued

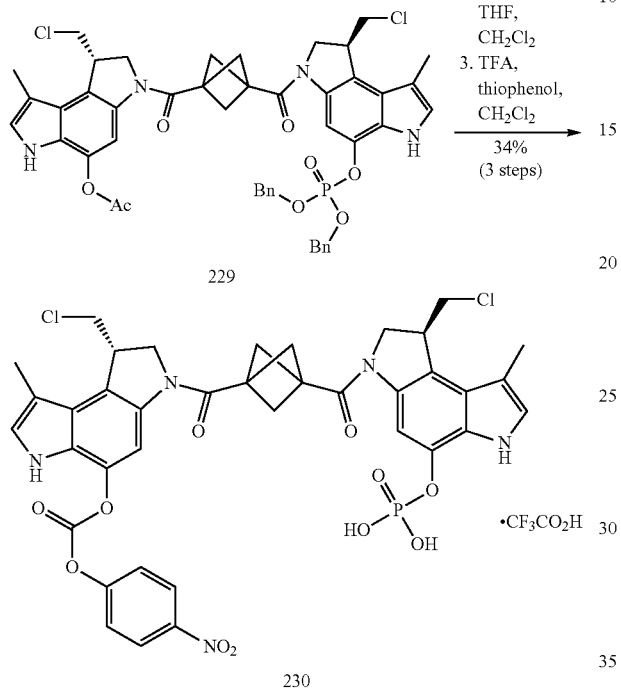

229

230

Step 1

To a stirring solution of 8 (4.5 g, 13.4 mmol) in 80 mL of THF and 80 mL of acetonitrile, carbon tetrachloride (18.1 mL, 187 mmol) was added followed by Hunig's base (9.31 mL, 53.4 mmol), dibenzylphosphite (17.7 mL, 80.2 mmol), and DMAP (326 mg, 2.67 mmol). The reaction was allowed to stir at room temperature for ~10 minutes. Reaction was reduced down onto silica. Silica chromatography was then preformed (gradient: 0%-20% acetone in heptanes). Appropriate test tubes where concentrated and placed underneath high vacuum to produce 226 (6.04 g, 76%) as a light yellow solid. LC-MS (Protocol B): m/z 614.3 [M+NH$_4$]', retention time=2.38 minutes.

Step 2

To a stirring solution of 226 (2.15 g, 3.60 mmol) in 24 mL of dichloromethane, TFA (24 mL, 310 mmol) was added. The reaction was allowed to stir at room temperature for ~60 seconds, immediately reduced down, and then placed underneath vacuum (belt pump). To a stirring solution of crude material (2.59 g, 3.57 mmol) in 15 mL of THF at 0° C., triethylamine (1.49 mL, 10.7 mmol) was added followed immediately by 225 (674 mg, 3.57 mmol) dissolved in 15 mL of THF was added. The reaction was allowed to stir at 0° C. for ~5 minutes and then allowed to warm to room temperature while stirring. The reaction was allowed to stir at room temperature for ~20 minutes. Reaction was reduced down onto silica. Silica chromatography was then preformed (gradient: 0%-30% acetone in heptanes). Appropriate test tubes where concentrated and placed underneath high vacuum to produce 227 (920 mg, 40%, 2 steps) as a white solid. LC-MS (Protocol B): m/z 649.2 [M+H]$^+$, retention time=2.04 minutes.

Step 3

To a stirring solution of 227 (895 mg, 1.38 mmol) in 16 mL of THF, lithium hydroxide (330 mg, 13.8 mmol) dissolved in 4 mL of water was added. The reaction was allowed to stir at room temperature for ~90 minutes. Dichloromethane was added followed by aqueous 1N HCl. Material was transferred to a separatory funnel. The organic layer was separated and the aqueous was washed twice with dichloromethane. The organic layers where combined, washed once with brine, water, dried over sodium sulfate, filtered, and then reduced down before being placed underneath high vacuum. Crude material was taken up in 15 mL of THF and 5 mL dichloromethane then cooled to 0° C. To this stirring solution at 0° C. oxalyl chloride (0.140 mL, 1.63 mmol) was added followed by 1 drop of DMF. The reaction was allowed to warm to room temperature and then stir at room temperature for ~60 minutes. Reaction was reduced down and then placed underneath high vacuum 228 (820 mg, 91%, 2 steps) as a light brown solid. Crude material was used as is in the next step.

Step 4

To a stirring solution of 11 (527 mg, 1.50 mmol) in 12 mL of THF at 0° C., triethylamine (0.348 mL, 2.50 mmol) was added followed immediately by 228 (816 mg, 1.25 mmol) dissolved in 12 mL of THF. The reaction was allowed to stir at 0° C. for ~5 minutes before being allowed to warm to room temperature while stirring. The reaction was allowed to stir at room temperature for ~30 minutes. Reaction was reduced down onto silica. Silica chromatography was then preformed (gradient: 0%-45% acetone in heptanes). Appropriate test tubes where concentrated and placed underneath high vacuum to produce 229 (660 mg, 59%) as a white solid. LC-MS (Protocol B): m/z 895.3 [M+H]$^+$, retention time=2.21 minutes.

Step 5

To a stirring solution of 229 (652 mg, 0.728 mmol) in 20 mL of methanol, 4M HCl in dioxane (20 mL, 80 mmol) was added. The reaction was allowed to stir at room temperature for ~24 minutes. Reaction was reduced and then placed underneath high vacuum. To a stirring solution of crude material in 16 mL of dichloromethane and 16 mL of THF at 0° C., p-nitrophenyl chloroformate (191 mg, 0.946 mmol) was added followed immediately by triethylamine (0.508 mL, 3.64 mmol). The reaction was allowed to stir at 0° C. for ~5 minutes and then allowed to warm to room temperature while stirring. The reaction was allowed to stir at room temperature for ~10 minutes. Reaction was reduced down. To a stirring solution of crude material in 12 mL of dichloromethane, a solution of TFA (12 mL, 160 mmol) in 12 mL of dichloromethane was added followed by the addition of thiophenol (0.745 mL, 7.28 mmol). The reaction was allowed to stir at room temperature for ~6 hours. Reaction was reduced down. Crude material was diluted with a few milliliters of DMSO and then injected onto a 25 g C18 pre-column (which was previously equilibrated with acetonitrile and then water, with 0.02% TFA in each phase). Material was purified by medium pressure reverse phase C18 chromatography (Gradient: 15% to 60% acetonitrile in water with 0.02% TFA in each phase) with the appropriate test tubes concentrated using a genevac producing 230 (267 mg, 34%, 3 steps) as a light yellow solid. LC-MS (Protocol B): m/z 838.3 [M+H]$^+$, retention time=1.68 minutes.

Preparation of N-[1-(2,5-dioxo-2,5-dihydro-1H-pyrrol-1-yl)-21-oxo-3,6,9,12,15,18-hexaoxahenicosan-21-yl]-L-valyl-N~5~-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide trifluoroacetic acid salt (231)

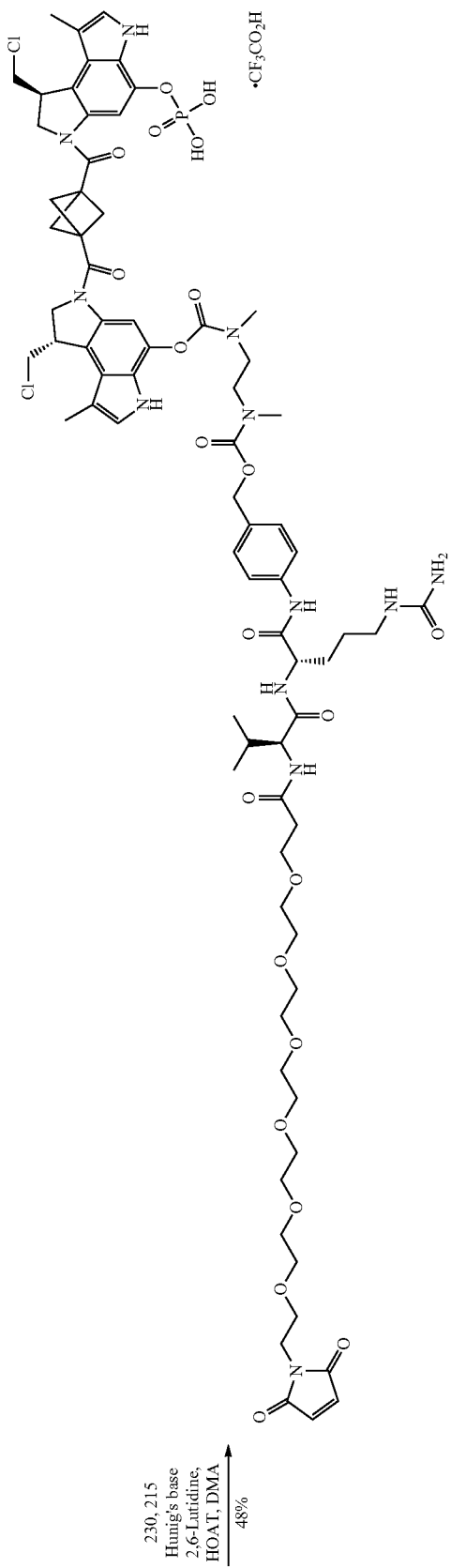

Step 1

To a 2 dram vial containing 230 (90 mg, 0.11 mmol) and 215 (121 mg, 0.118 mmol), 3.0 mL of DMA was added followed by Hunig's base (0.0748 mL, 0.429 mmol), 2,6-Lutidine (0.0497 mL, 0.429 mmol) and HOAT (14.7 mg, 0.108 mmol). The reaction was allowed to stir at room temperature for ~15 minutes. Crude reaction was injected onto a 12 g C18 pre-column (which was previously equilibrated with acetonitrile and then water, with 0.02% TFA in each phase). Material was purified by medium pressure reverse phase C18 chromatography (Gradient: 5% to 45% acetonitrile in water with 0.02% TFA in each phase) followed by a second purification by method H with the appropriate test tubes concentrated using a genevac producing 231 (117 mg, 60%) as a white solid. LC-MS (Protocol B): m/z 1607.8 [M+H]$^+$, retention time=1.60 minutes.

Preparation of N~2~-acetyl-N~6~-(tert-butoxycarbonyl)-L-lysyl-L-valyl-N~5~-carbamoyl-N-{4-[({methyl[2-(methylamino)ethyl]carbamoyl}oxy)methyl]phenyl}-L-ornithinamide trifluoroacetic acid salt (236)

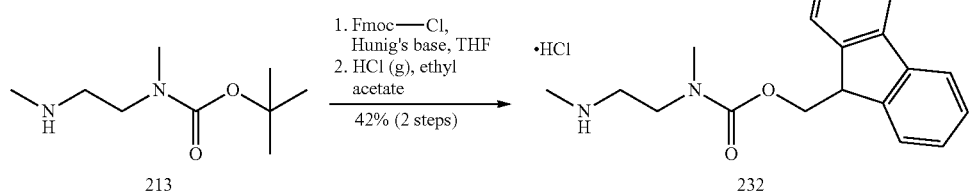

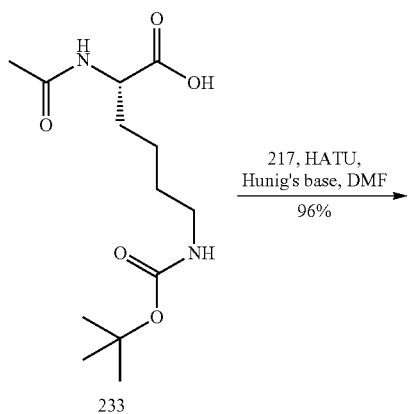

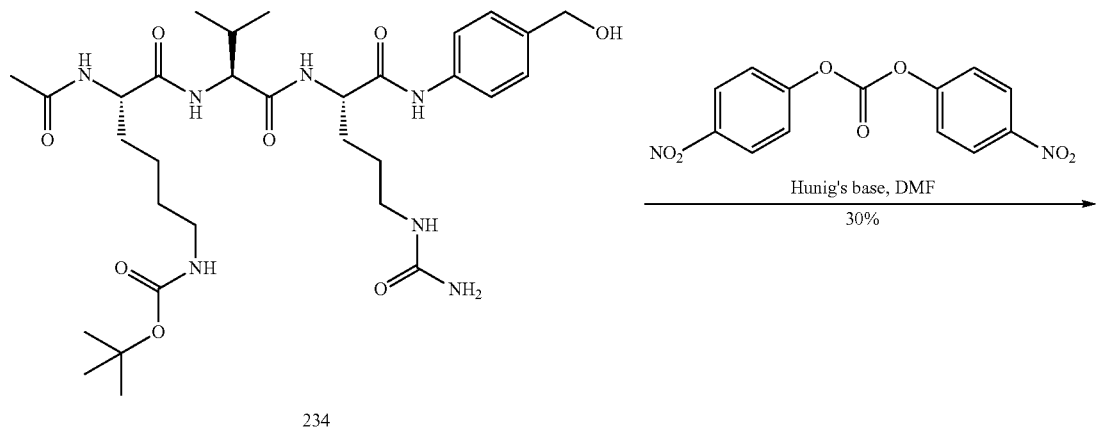

-continued

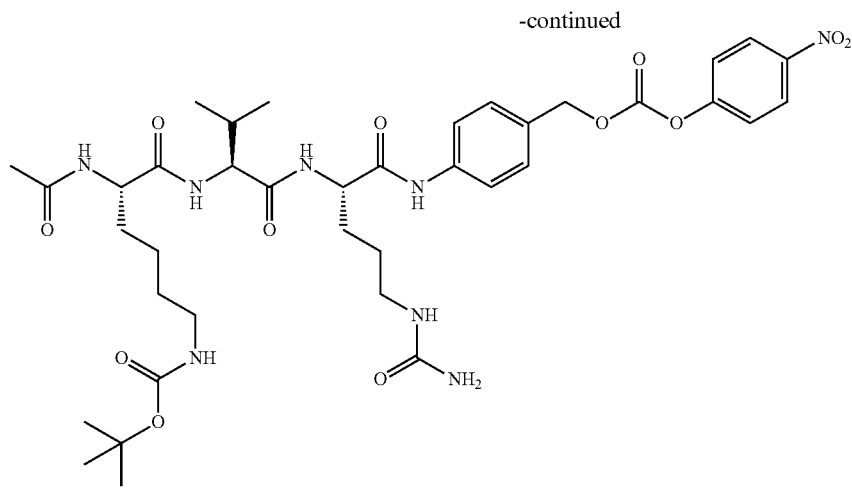

235

1. 231, Hunig's base, DMA
2. piperidine
───────────────────
89% (2 steps)

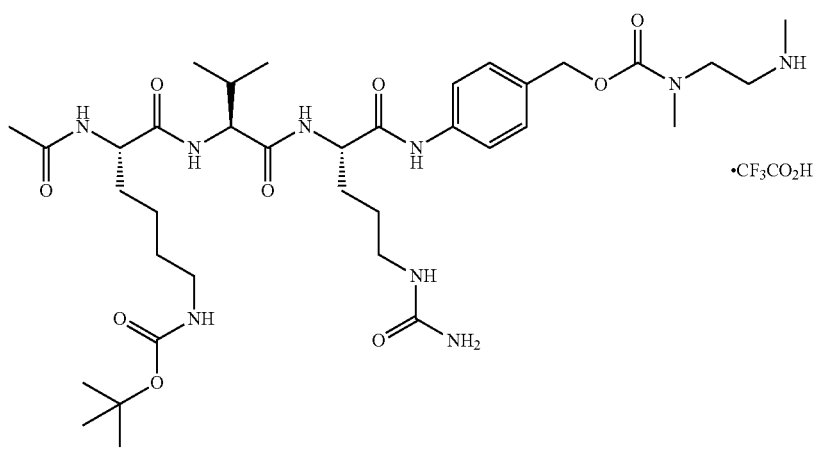

236

Step 1

To a stirring solution of compound 213 (16.0 g, 85.0 mmol) and Hunig's base (23 g, 178 mmol) in 450 mL of THF at 0° C., Fmoc-Cl (22 g, 85.0 mmol) was added drop wise as a solution in 450 mL of THF. The mixture was stirred at 0° C. for 10 minutes. The reaction was allowed to stir at room temperature overnight. The reaction was diluted with ethyl acetate and then washed with $NH_4Cl$ (aq) and brine. The organic layer separated, dried over $Na_2SO_4$ and reduced down. The residue was purified by silica chromatography (gradient: 2.5%-50% ethyl acetate in petroleum ether). Appropriate test tubes where concentrated. Material was dissolved in 150 mL of ethyl acetate followed by the addition of 150 mL of HCl in ethyl acetate. The reaction was allowed to stir at room temperature overnight. The reaction was concentrated and 300 mL of MTBE was added. The resulting precipitate was collected by filtration to provide 232 (10.4 g, 42%, 2 steps) as a white solid. $^1$H NMR (400 MHz, DMSO-$d_6$), δ 8.89 (br, 2H), 7.91 (d, 2H), 7.66 (d, 2H) 7.42 (m, 2H), 7.36 (m, 2H), 4.34 (m, 3H), 3.51 (m, 1H), 3.04 (m, 1H), 2.85 (s, 3H), 2.72 (m, 1H), 2.32 (m, 1H).

Step 2

To a solution of 217 (481 mg, 1.27 mmol) in 10 mL of DMF, 233 (366 mg, 1.27 mmol), HATU (660 mg, 1.65 mmol) and Hunig's base (0.302 mL, 1.6 mmol) where added. The reaction was allowed to stir at room temperature for ~30 minutes. The reaction was diluted with ethyl acetate which caused to solids to crash out. This slurry was allowed to stir for ~30 minutes. The solids were collected by filtration, rinsed with fresh ethyl acetate and dried under high vacuum to obtain 234 (797 mg, 97%) as a brown colored solid. LC-MS (Protocol B): m/z 650.3 $[M+H]^+$, retention time=0.64 minutes.

Step 3

To a solution of compound 234 (18.5 g, 28.5 mmol) in DMF (500 mL), bis(4-nitrophenyl) carbonate (9.54 g, 31.4 mmol) was added followed by Hunig's base (5.5 g, 42.8 mmol). The reaction was allowed to stir at room temperature for ~12 hours. The reaction was concentrated. The residue was purified by silica chromatography (gradient: 1%-10% methanol in dichloromethane to provide 235 (6.9 g, 29.7%) as a white solid. ¹H NMR (400 MHz, DMSO-d₆), δ 8.30 (d, 2H), 8.12 (d, 1H), 8.01 (d, 1H), 7.70 (d, 1H), 7.64 (d, 2H), 7.56 (d, 2H), 7.40 (d, 2H), 6.78 (m, 1H), 5.98 (m, 1H), 5.43 (s, 2H), 5.24 (s, 2H), 4.49 (m, 1H), 4.19 (m, 2H), 2.86 (m, 4H), 1.99 (m, 1H), 1.60 (m, 3H), 1.36 (m, 16H), 0.82 (m, 6H).

Step 4

To a stirring solution of 235 (500 mg, 0.605 mmol) and 232 (210 mg, 0.605 mmol) in 3.0 mL of DMA, Hunig's base (0.316 mL, 1.82 mmol) was added. The reaction was allowed to stir at room temperature for ~30 minutes. Piperidine (0.598 mL, 6.05 mmol) was then added to the reaction. The reaction was allowed to stir at room temperature for an additional ~15 minutes. Crude reaction was injected onto a 12 g C18 pre-column (which was previously equilibrated with acetonitrile and then water, with 0.02% TFA in each phase). Material was purified by medium pressure reverse phase C18 chromatography (Gradient: 5% to 35% acetonitrile in water with 0.02% TFA in each phase). Appropriate test tubes concentrated using a genevac producing 236 (475 mg, 89%, 2 steps) as a clear white solid. LC-MS (Protocol B): m/z 764.4 [M+H]⁺, retention time=1.03 minutes.

Preparation of N⁻²⁻-acetyl-L-lysyl-L-valyl-N⁻⁵⁻-carbamoyl-N-[4-({[(2-{[({(8S)-8-(chloromethyl)-6-[(3-{[(1S)-1-(chloro methyl)-8-methyl-5-(phosphonooxy)-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide trifluoroacetic acid salt (237)

To a 2 dram vial containing 230 (100 mg, 0.119 mmol) and 236 (115 mg, 0.131 mmol), DMF (2.0 mL) was added followed by Hunig's base (0.0831 mL, 0.477 mmol), 2,6-Lutidine (0.0552 mL, 0.477 mmol) and HOAT (16.2 mg, 0.119 mmol). The reaction was allowed to stir at room temperature for ~10 minutes. Reaction was reduced down. Dichloromethane (2 mL) was added to the crude sample. To this stirring mixture TFA (1.0 mL, 13 mmol) was added. The reaction was allowed to stir at room temperature for ~30 minutes. Reaction was reduced down. Crude material was dissolved in DMSO and injected onto a 12 g C18 pre-column (which was previously equilibrated with acetonitrile and then water, with 0.02% TFA in each phase). Material was purified by medium pressure reverse phase C18 chromatography (Gradient: 10% to 50% acetonitrile in water with 0.02% TFA in each phase) followed by a second purification by method G with the appropriate test tubes concentrated using a genevac producing 237 (55.8 mg, 27%) as a white solid. LC-MS (Protocol B): m/z 1362.8 [M+H]⁺, retention time=1.44 minutes. ¹H NMR (400 MHz, DMSO-d₆): δ 10.96-10.83 (m), 10.06-9.97 (m), 8.16-7.97 (m), 7.87-7.66 (m), 7.59-7.47 (m), 7.37-6.97 (m), 6.54 (s), 6.05 (s), 5.47 (s), 5.12-4.96 (m), 4.45-3.91 (m), 3.74-2.83 (m), 2.76-2.68 (m), 2.59-2.52 (m), 2.39-2.32 (m), 2.02-1.93 (m), 1.83 (s), 1.71-1.21 (m), 0.88-0.77 (m).

1. 230, 236 Hunig's base, 2,6-Lutidine, HOAT, DMF
2. TFA, CH₂Cl₂

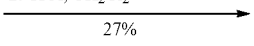

27%

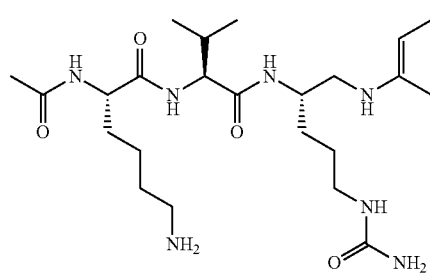

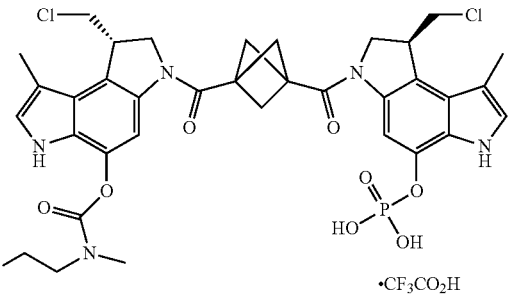

Preparation of 3-{[2-({[(2-{[({(1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl}oxy)carbonyl](methyl)amino}ethyl)(methyl)carbamoyl]oxy}methyl)phenyl]disulfanyl}-N-[6-(2,5-dioxo-2,5-dihydro-1H-pyrrol-1-yl)hexanoyl]-L-alanine (244)
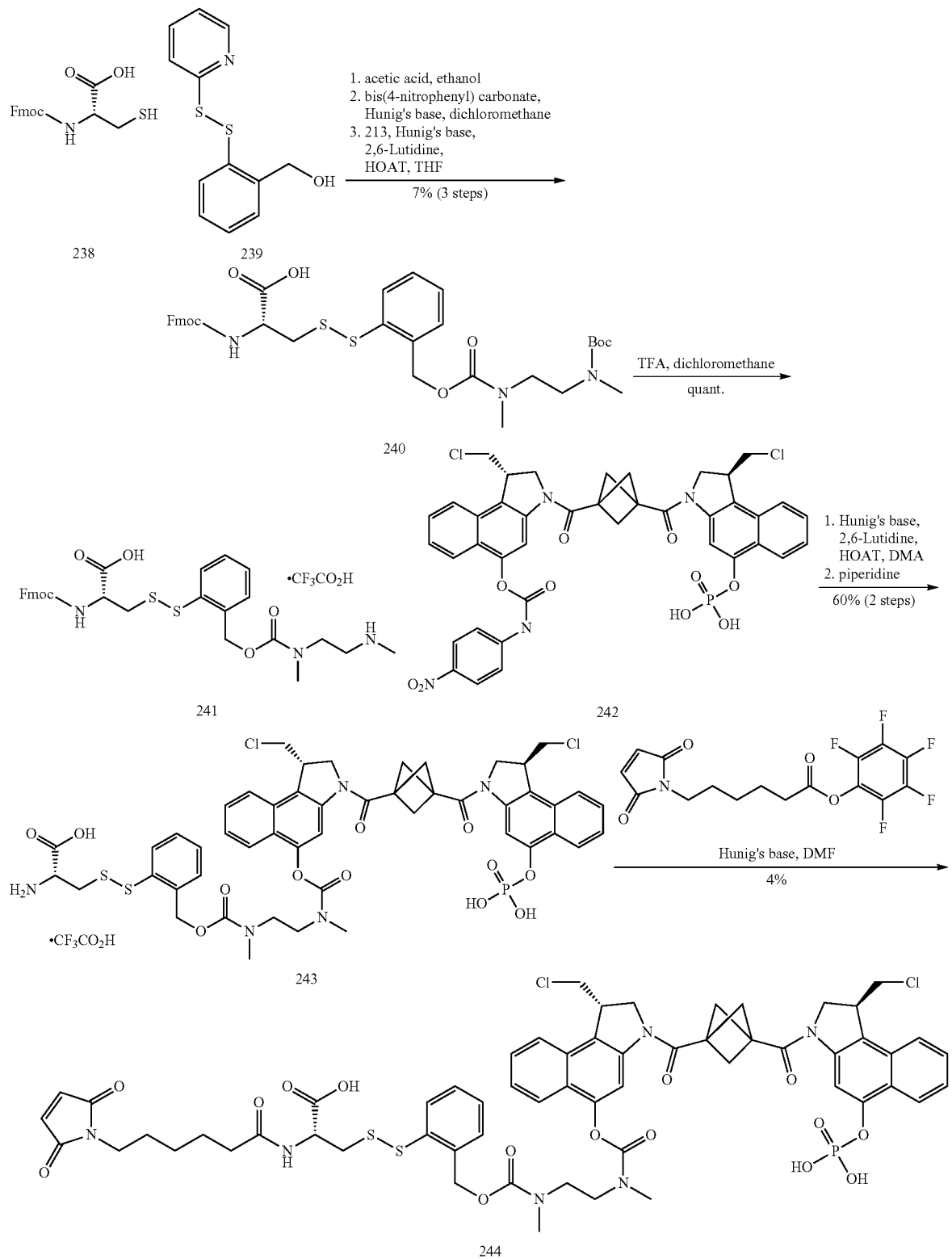

Step 1

To a stirring mixture of N-[(9H-fluoren-9-ylmethoxy)carbonyl]-L-cysteine 238 (17.9 g, 52.1 mmol) in dry ethanol (360 mL) at 0° C. acetic acid (2.41 g, 40.1 mmol) was added. Then a solution of [2-(pyridin-2-yldisulfanyl)phenyl]methanol 239 (10 g, 40.104 mmol) in dry ethanol (200 mL) was added to the reaction mixture at 0° C. The mixture was stirred at room temperature for 20 minutes. The reaction mixture was concentrated in vacuo producing yellow oil. The residue was purified by preparative HPLC (method M) producing a yellow gum (3.5 g). To a stirring solution of this crude material (2.5 g, 5.191 mmol) in dry dichloromethane (100 mL) at 0° C., bis(4-nitrophenyl) carbonate (1.9 g, 6.23 mmol) was added followed by Hunig's base (805 mg, 6.23 mmol). The mixture was stirred at 0° C. for ½ hour and then allowed to warm to room temperature. The reaction was allowed to stir at room temperature for ~23 hours. The reaction mixture was warmed to 30° C. and allowed to stir at 30° C. for ~18 hours. The reaction was warmed to 40° C. and allowed to stir at 40° C. for ~6 hours. The reaction mixture was washed with 1 M HCl (20 mL×2), brine, dried over sodium sulfate and concentrated in vacuo to give the residue (3.89 g) as yellow oil. The residue was purified by silica gel chromatography (Gradient: 0% to 4% methanol in dichloromethane) to produce a yellow solid (2.48 g). To a stirring solution of this crude material in THF (35 mL) at 0° C., 213 (635 mg, 3.37 mmol) was added followed by Hunig's base (793 mg, 6.14 mmol), 2,6-lutidine (657 mg, 6.14 mmol) and HOAT (41.8 mg, 0.307 mmol). The reaction mixture was allowed to warm to room temperature and then stir at room temperature for 40 minutes. The reaction mixture was diluted with ethyl acetate (200 mL), washed with 1 M HCl (30 mL, ×2), and brine. The organics where dried over sodium sulfate and concentrated in vacuo to give the crude product (3.6 g) as yellow oil. The crude product was purified by silica gel chromatography (Gradient: 0% to 4% methanol in dichloromethane) to give the product (2.35 g) as a yellow gum. The product was then purified by preparative HPLC using (method M, using gradient 50% B to 80% B over 30 minutes, then 95% over 5 minutes). The mixture was concentrated in vacuum and extracted with ethyl acetate (100 mL, ×3). The organic layers were combined, washed with brine, dried over sodium and concentrated in vacuo to give 240 (1.45 g, 7%, 3 steps) as a yellow gum. $^1$H NMR (400 MHz, DMSO-d$_6$): δ 7.91-7.89 (m, 3H), 7.74-7.72 (m, 3H), 7.44-7.31 (m, 7H), 5.14 (s, 2H), 4.34-4.24 (m, 4H), 3.31-3.29 (m, 3H), 3.10-3.09 (m, 1H), 3.04-3.02 (m, 1H), 2.86-2.82 (d, 3H), 2.75-2.73 (m, 2H), 2.67-2.50 (m, 2H), 1.38-1.31 (m, 9H).

Step 2

To a stirring solution of 240 (35 mg, 0.050 mmol) in 4 mL of dichloromethane, TFA (2 mL, 30 mmol) was added. The reaction was allowed to stir at room temperature for ~10 minutes. Reaction was concentrated in vacuo and placed underneath high vacuum to produce 241 as a white solid (40 mg, quant.). LC-MS (Protocol B): m/z 596.5 [M+H]$^+$, retention time=1.38 minutes.

Step 3

To a vial containing 241 (29.8 mg, 0.042 mmol) and 242 (1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl 4-nitrophenyl carbonate [prepared utilizing the chemistry described in the preparation of 229], (35.0 mg, 0.042 mmol), 2.0 mL of DMA was added followed immediately by Hunig's base (0.0293 mL, 0.168 mmol), 2,6-Lutidine (0.0195 mL, 0.168 mmol), and HOAT (5.72 mg, 0.042 mmol). The reaction was allowed to stir at room temperature for ~10 minutes. Piperidine (0.30 mL, 3 mmol) was then added to the reaction and the reaction was allowed to stir at room temperature for ~10 minutes. Crude reaction was injected onto a 12 g C18 pre-column (which was previously equilibrated with acetonitrile and then water, with 0.02% TFA in each phase). Material was purified by medium pressure reverse phase C18 chromatography (Gradient: 5% to 65% acetonitrile in water with 0.02% TFA in each phase) with the appropriate test tubes concentrated using a genevac producing 243 (30 mg, 60%) as a gray solid. LC-MS (Protocol B): m/z 838.3 [M+2H]', retention time=1.55 minutes.

Step 4

To a stirring solution of 243 (20 mg, 0.017 mmol) and pentafluorophenyl 6-(2,5-dioxo-2,5-dihydro-1H-pyrrol-1-yl)hexanoate (7.03 mg, 0.0186 mmol) in 1.5 mL of DMF, Hunig's base (0.0118 mL, 0.0677 mmol) was added. The reaction was allowed to stir at room temperature for ~15 minutes. Crude reaction was injected onto a 5 g C18 pre-column (which was previously equilibrated with acetonitrile and then water, with 0.02% TFA in each phase). Material was purified by medium pressure reverse phase C18 chromatography (Gradient: 20% to 70% acetonitrile in water with 0.02% TFA in each phase) followed by preparative HPLC purification (method 11) with the appropriate test tubes concentrated using a genevac producing 244 (0.8 mg, 4%) as a gray solid. LC-MS (Protocol D): m/z 630.8 [1/2 M+1H]$^+$, retention time=10.786 minutes.

Preparation of 3-{[4-({[(2-{[({(1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl}oxy) carbonyl](methyl)amino}ethyl)(methyl)carbamoyl]oxy}methyl)phenyl]disulfanyl]-N-[6-(2,5-dioxo-2,5-dihydro-1H-pyrrol-1-yl)hexanoyl]-L-alanine 250

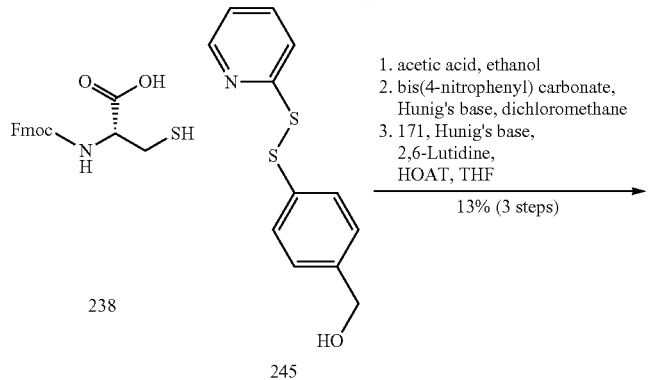

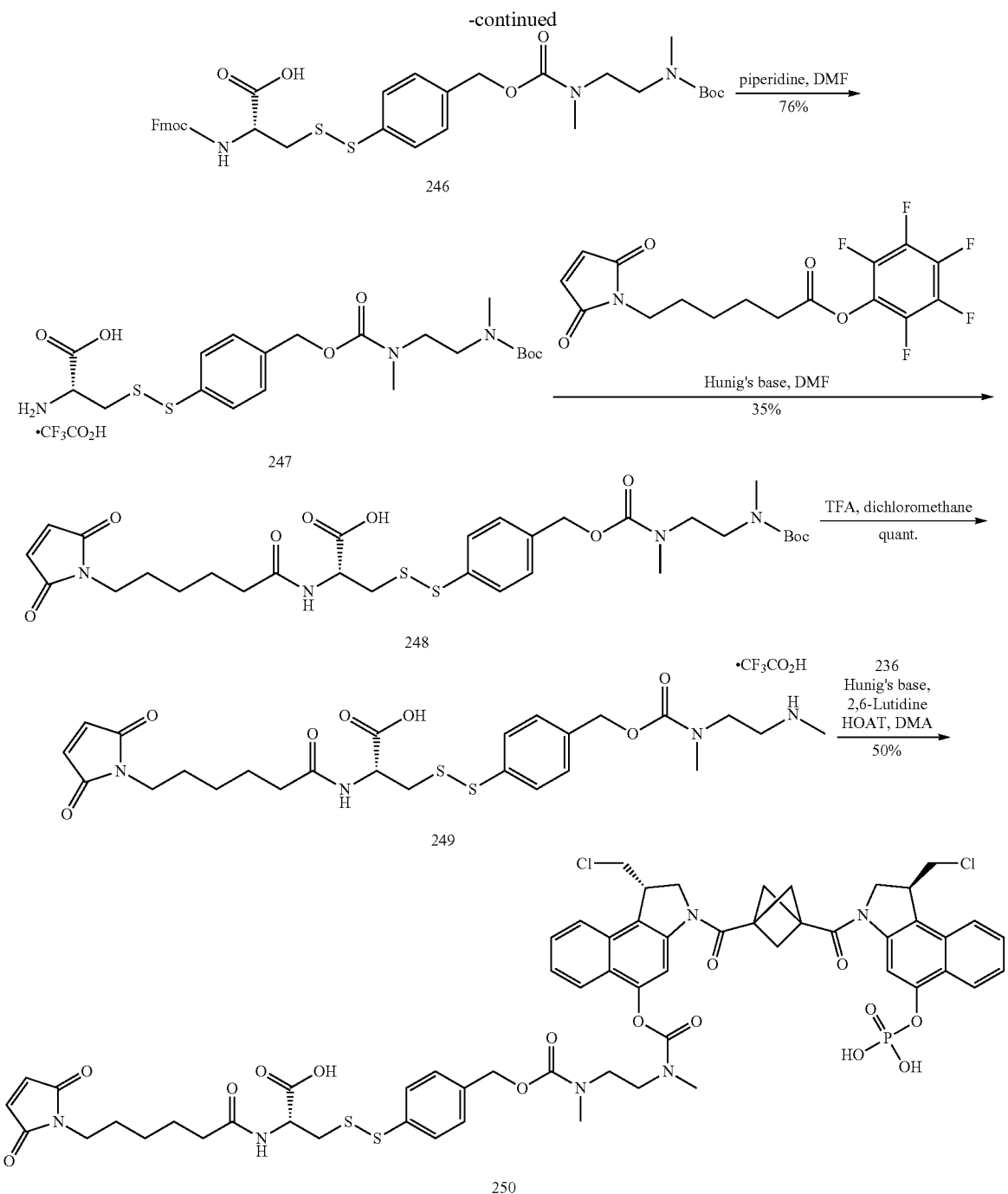

Step 1

To a stirring mixture of N-[(9H-fluoren-9-ylmethoxy)carbonyl]-L-cysteine 238 (11.6 g, 33.7 mmol) in dry ethanol (230 mL) at 0° C. acetic acid (1.93 g, 32.1 mmol) was added. Then a solution of [4-(pyridin-2-yldisulfanyl)phenyl]methanol 245 (10 g, 40.104 mmol) in dry ethanol (160 mL) was added to the reaction mixture at 0° C. The mixture was allowed to room to room temperature and then stirred at room temperature for 4 hours. The reaction mixture was concentrated in vacuo producing a yellow oil. The residue was purified by prep-HPLC (method M, using gradient 45% B to 75% B over 30 minutes, then 95% over 5 minutes) producing a yellow gum (8.5 g). To a stirring solution of this crude material (8.0 g, 16.61 mmol) in dry dichloromethane (320 mL) at 0° C., bis(4-nitrophenyl) carbonate (6.06 g, 19.9 mmol) was added followed by Hunig's base (2.58 g, 19.9 mmol). The mixture was stirred at 0° C. for 10 minutes and then allowed to warm to room temperature. The reaction was allowed to stir at room temperature for ~15 hours. Additional Bis(4-nitrophenyl) carbonate (1.52 g, 4.98 mmol) and Hunig's base (644 mg, 4.98 mmol, 0.3 eq) was then added to the reaction mixture. The reaction mixture was allowed to stir at room temperature for an additional 2 hours. The reaction mixture was washed with 1 M HCl (50 mL×2), brine, dried over sodium sulfate and concentrated in vacuo to give the residue (17.1 g) as yellow oil. The residue was purified by silica gel chromatography (Gradient: 0% to 7% methanol in dichloromethane) to produce a yellow oil. To a stirring solution of this crude material in THF (103 mL) at 0° C., 171 (1.89 g, 10.0 mmol) was added followed by Hunig's base (2.36 g, 18.2 mmol), 2,6-lutidine (1.96 g, 18.2 mmol) and HOAT (124 mg, 0.912 mmol). The reaction mixture was allowed to warm to room temperature and then stir at room temperature for 60 minutes. The reaction mixture was diluted with ethyl acetate (200 mL), washed with 1 M HCl (30 mL, ×2), and brine. The organics where dried over sodium sulfate and concentrated in vacuo to give the crude product (7.5 g) as yellow oil. The crude product was purified by silica gel chromatography (Gradient: 0% to 4% methanol in dichloromethane) to give the product (4.0 g) as a yellow gum. The product was then purified by (method M, using gradient 50% B to 80% B over 30 minutes, then 95% over 5 minutes). The mixture was concentrated in vacuo and extracted with ethyl acetate (100 mL, ×3). The organic layers were combined, washed with brine, dried over sodium and concentrated in vacuo to give 246 (3.0 g, 13%, 3 steps) as a white solid. $^1$H NMR (400 MHz, DMSO-$d_6$): δ 7.89-7.87 (d, 2H), 7.71-7.70 (d, 2H), 7.55-7.52 (m, 2H), 7.50-7.41 (m, 2H), 7.39-7.30 (m, 4H), 4.97 (s, 2H), 4.30-4.22 (m, 4H), 3.29 (br, 4H), 3.10-3.01 (m, 2H), 2.82-2.80 (d, 3H), 2.73 (s, 1H), 2.66 (s, 2H), 1.32-1.30 (d, 9H).

Step 2

To a stirring solution of 246 (499 mg, 0.717 mmol) in 4.0 DMF, piperidine (1.13 mL, 11.5 mmol) was added. The reaction was allowed to stir at room temperature for ~5 minutes. Crude reaction was injected onto a 12 g C18 pre-column (which was previously equilibrated with acetonitrile and then water, with 0.02% TFA in each phase). Material was purified by medium pressure reverse phase C18 chromatography (Gradient: 5% to 50% acetonitrile in water with 0.02% TFA in each phase) with the appropriate test tubes concentrated using a genevac producing 3-{[4-(4,7,10,10-tetramethyl-3,8-dioxo-2,9-dioxa-4,7-diazaundec-1-yl)phenyl]disulfanyl}-L-alanine 247 (320 mg, 76%) as a gray solid. LC-MS (Protocol B): m/z 474.5 [M+H]$^+$, retention time=1.19 minutes.

Step 3

To a stirring solution of 247 (140 mg, 0.238 mmol) and pentafluorophenyl 6-(2,5-dioxo-2,5-dihydro-1H-pyrrol-1-yl)hexanoate (98.9 mg, 0.262 mmol), 2 mL of DMF was added followed immediately by Hunig's base (0.124 mL, 0.715 mmol). The reaction was allowed to stir at room temperature for ~5 minutes. Crude reaction was injected onto a 12 g C18 pre-column (which was previously equilibrated with acetonitrile and then water, with 0.02% TFA in each phase). Material was purified by medium pressure reverse phase C18 chromatography (Gradient: 10% to 70% acetonitrile in water with 0.02% TFA in each phase) with the appropriate test tubes concentrated using a genevac producing N-[6-(2,5-dioxo-2,5-dihydro-1H-pyrrol-1-yl)hexanoyl]-3-{[4-(4,7,10,10-tetramethyl-3,8-dioxo-2,9-dioxa-4,7-diazaundec-1-yl)phenyl]disulfanyl}-L-alanine 248 (56 mg, 35%) as a clear solid. LC-MS (Protocol B): m/z 667.3 [M+H]$^+$, retention time=1.71 minutes.

Step 4

To a stirring solution of 248 (35 mg, 0.050 mmol) in 4 mL of dichloromethane, TFA (2 mL, 30 mmol) was added. The reaction was allowed to stir at room temperature for ~10 minutes. Reaction was concentrated in vacuo and placed underneath high vacuum to produce 249 as a white solid (40 mg, quant.).

Step 4

To a vial containing 249 (18.0 mg, 0.0264 mmol) and 242 (22.0 mg, 0.0264 mmol), 1.6 mL of DMA was added followed immediately by Hunig's base (0.0184 mL, 0.106 mmol), 2,6-Lutidine (0.0123 mL, 0.106 mmol), and HOAT (3.60 mg, 0.0264 mmol). The reaction was allowed to stir at room temperature for ~10 minutes. Crude reaction was injected onto a 12 g C18 pre-column (which was previously equilibrated with acetonitrile and then water, with 0.02% TFA in each phase). Material was purified by medium pressure reverse phase C18 chromatography (Gradient: 10% to 60% acetonitrile in water with 0.02% TFA in each phase) followed by preparative HPLC purification (method 12) with the appropriate test tubes concentrated using a genevac producing 250 (16.7 mg, 50%) as a white solid. LC-MS (Protocol B): m/z 1261.4 [M+3H]$^+$, retention time=1.71 minutes.

Preparation of N-[6-(2,5-dioxo-2,5-dihydro-1H-pyrrol-1-yl)hexanoyl]-L-valyl-N~5~-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide 255

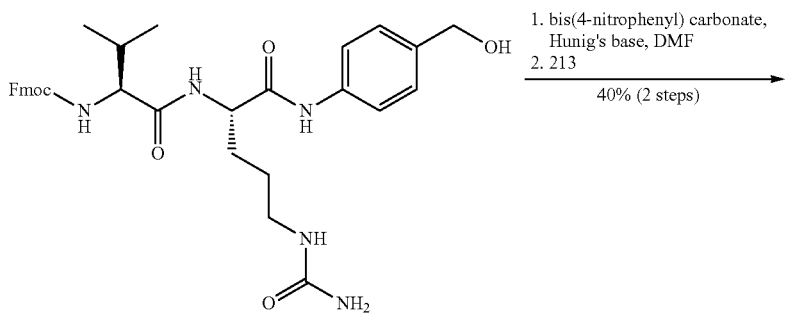

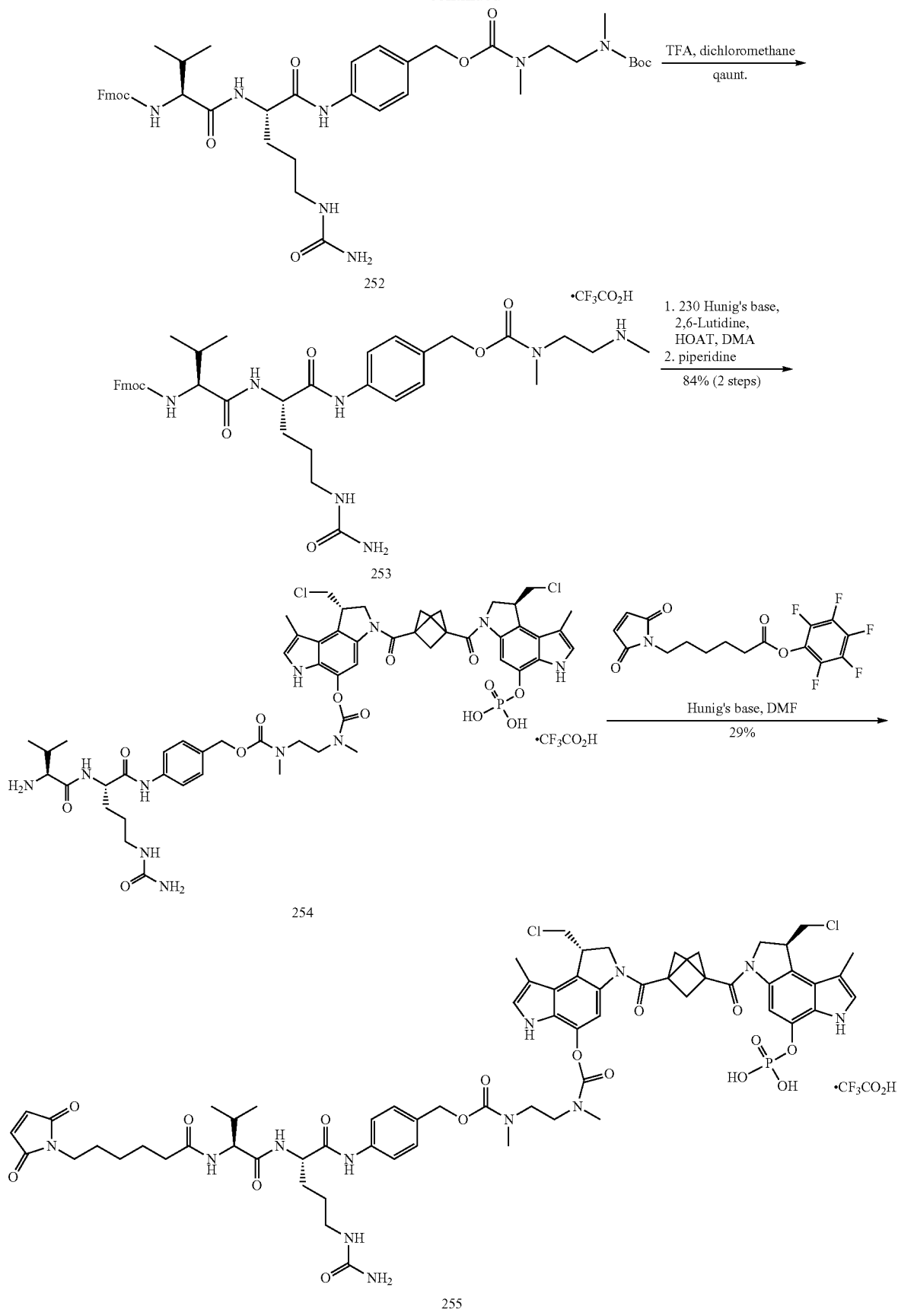

Step 1

N-[(9H-fluoren-9-ylmethoxy)carbonyl]-L-valyl-N~5~-carbamoyl-N-[4-(hydroxymethyl)phenyl]-L-ornithinamide 251 (725 mg, 1.2 mmol) was dissolved in 6 mL of DMF followed by sonication for ~10 minutes. A stir bar was then added and this solution was allowed to stir at room temperature. Bis(4-nitrophenyl)carbonate (403 mg, 1.33 mmol) was then added followed by Hunig's base (0.44 mL, 2.5 mmol). The reaction was allowed to stir at room temperature for ~5 hours. 213 (227 mg, 1.2 mmol) dissolved in 1 mL of DMF was added. The reaction was allowed to stir at room temperature for ~1 minute. Crude reaction was injected onto a 24 g C18 pre-column (which was previously equilibrated with acetonitrile and then water, with 0.02% TFA in each phase). Material was purified by medium pressure reverse phase C18 chromatography (Gradient: 5% to 60% acetonitrile in water with 0.02% TFA in each phase) with the appropriate test tubes concentrated using a genevac producing N-[(9H-fluoren-9-ylmethoxy)carbonyl]-L-valyl-N~5~-carbamoyl-N-[4-(4,7,10,10-tetramethyl-3,8-dioxo-2,9-dioxa-4,7-diazaundec-1-yl)phenyl]-L-ornithinamide 252 (395 mg, 40%, 2 steps) as a brown solid. LC-MS (Protocol B): m/z 816.7 [M+H]$^+$, retention time=1.88 minutes.

Step 2

To a stirring mixture of 252 (197 mg, 0.241 mmol) in 6 mL of dichloromethane, TFA (2 mL, 30 mmol) was added. The reaction was allowed to stir at room temperature for ~20 minutes. Reaction was concentrated in vacuo and placed underneath high vacuum producing N-[(9H-fluoren-9-ylmethoxy)carbonyl]-L-valyl-N~5~-carbamoyl-N-[4-(4,7,10,10-tetramethyl-3,8-dioxo-2,9-dioxa-4,7-diazaundec-1-yl)phenyl]-L-ornithinamide 253 (210 mg, quant.) as white and light brown solid. LC-MS (Protocol B): m/z 716.7 [M+H]$^+$, retention time=1.27 minutes.

Step 3

To a vial containing 230 (48 mg, 0.053 mmol) and 253 (52.4 mg, 0.063 mmol), 2.0 mL of DMA was added followed immediately by Hunig's base (0.036 mL, 0.211 mmol), 2,6-Lutidine (0.024 mL, 0.211 mmol), and HOAT (7.1 mg, 0.0525 mmol). The reaction was allowed to stir at room temperature for ~10 minutes. Piperidine (0.30 mL, 3 mmol) was then added and the reaction was allowed to stir at room temperature for ~10 minutes. Crude reaction was injected onto a 12 g C18 pre-column (which was previously equilibrated with acetonitrile and then water, with 0.02% TFA in each phase). Material was purified by medium pressure reverse phase C18 chromatography (Gradient: 10% to 50% acetonitrile in water with 0.02% TFA in each phase) with the appropriate test tubes concentrated using a genevac producing 254 (68 mg, 84%, 2 steps) as a light gray solid. LC-MS (Protocol B): m/z 1193.5 [M+2H]', retention time=1.46 minutes.

Step 4

To a stirring solution of 254 (30 mg, 0.020 mmol) and pentafluorophenyl 6-(2,5-dioxo-2,5-dihydro-1H-pyrrol-1-yl)hexanoate (8.11 mg, 0.0215 mmol) in 2.0 mL of DMF, Hunig's base (0.0136 mL, 0.0782 mmol) was added. The reaction was allowed to stir at room temperature for ~10 minutes. Crude reaction was injected onto a 5 g C18 pre-column (which was previously equilibrated with acetonitrile and then water, with 0.02% TFA in each phase). Material was purified by medium pressure reverse phase C18 chromatography (Gradient: 5% to 50% acetonitrile in water with 0.02% TFA in each phase) followed by a second preparative HPLC purification (method J1). Appropriate test tubes where concentrated using a genevac producing 255 (9.1 mg, 29%) as a light brown solid. LC-MS (Protocol B): m/z 1386.9 [M+2H]', retention time=1.60 minutes.

Preparation of N-(24-bromo-23-oxo-4,7,10,13,16,19-hexaoxa-22-azatetracosan-1-oyl)-L-valyl-N~5~-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide 257

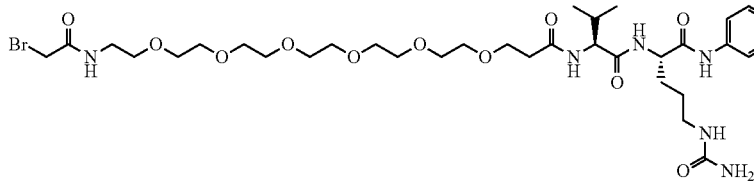

256
(WO 2014/068443)

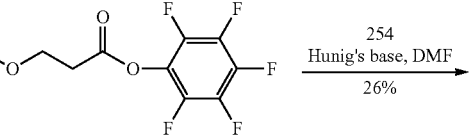

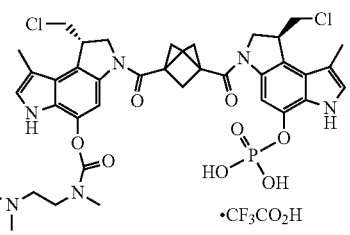

To a stirring solution of 254 (30 mg, 0.020 mmol) and pentafluorophenyl 1-bromo-2-oxo-6,9,12,15,18,21-hexaoxa-3-azatetracosan-24-oate 2556(13.8 mg, 0.0215 mmol) [prepared as described in WO2014/068443] in 2.0 mL of DMF, Hunig's base (0.0136 mL, 0.0782 mmol) was added. The reaction was allowed to stir at room temperature for ~40 minutes. Crude reaction was injected onto a 5 g C18 pre-column (which was previously equilibrated with acetonitrile and then water, with 0.02% TFA in each phase). Material was purified by medium pressure reverse phase C18 chromatography (Gradient: 5% to 50% acetonitrile in water with 0.02% TFA in each phase) followed by a second preparative HPLC purification (method K1). Appropriate test tubes where concentrated using a genevac producing 257 (10.8 mg, 26%) as a white solid. LC-MS (Protocol B): m/z 1649.7 [M+3H]', retention time=1.53 minutes.

Preparation of N-[(9H-fluoren-9-ylmethoxy)carbonyl]-L-valyl-N-[(1S)-3-[(3-carboxybicyclo[1.1.1]pent-1-yl)carbonyl]-1-(chloromethyl)-2,3-dihydro-1H-benzo[e]indol-5-yl]-L-alaninamide 261

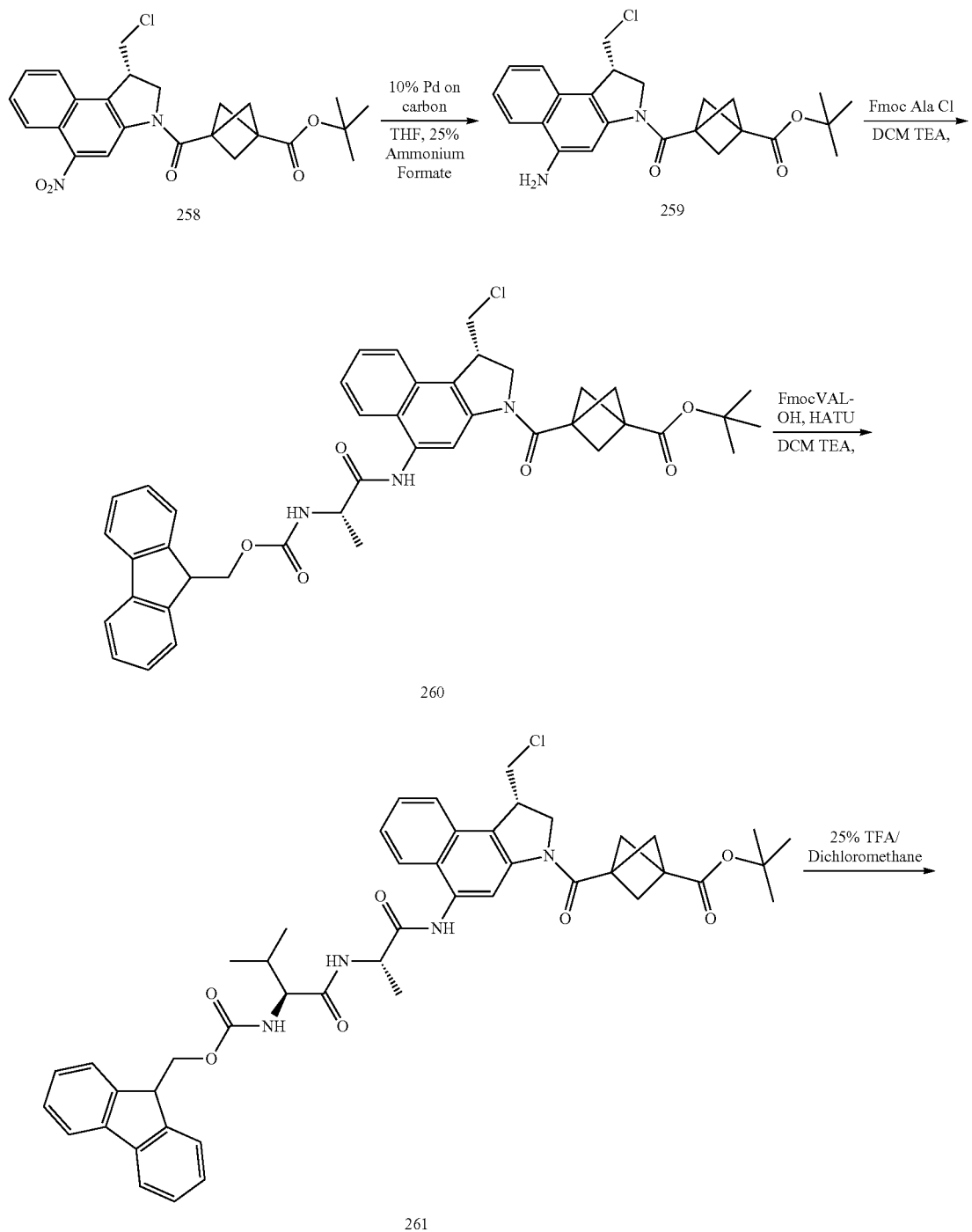

217 218
-continued

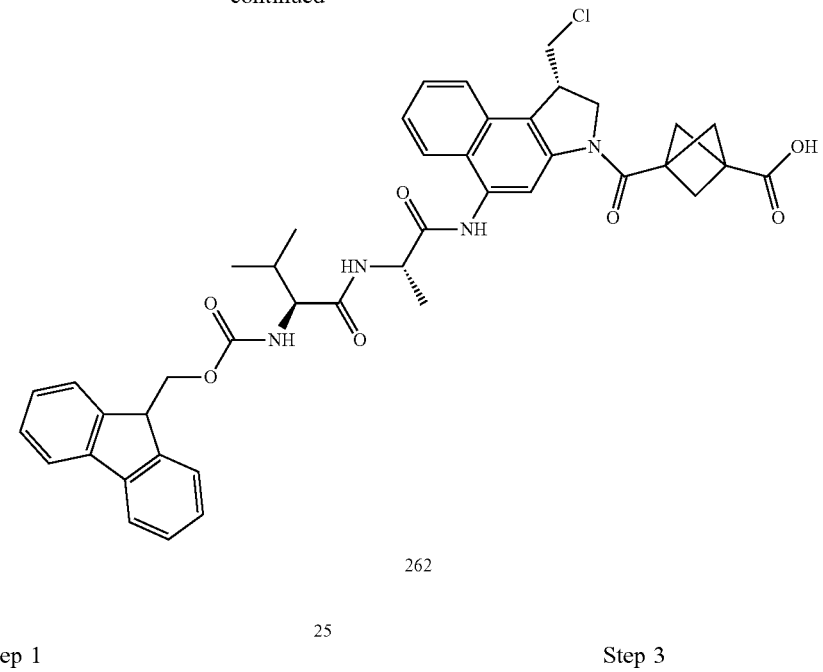

262

Step 1

A stirring solution of tert-butyl 3-{[(1S)-1-(chloromethyl)-5-nitro-1,2-dihydro-3H-benzo[e]indol-3-yl]carbonyl}bicyclo[1.1.1]pentane-1-carboxylate 258 (prepared similarly to 189) (980 mg, 2.14 mmol) in 7 mL of THF under nitrogen was cooled to 0 C using an ice bath. Palladium 10 wt. % on activated carbon (30 mg) was then added followed by the slow drop wise addition of 2 mL of 25% ammonium formate in water. The reaction was allowed to stir at 0 C. for 3 hours. Upon completion the reaction mixture was filtered through a pad of celite and the filtrate concentrated under vacuum. The crude products was purified by silica gel chromatography (Gradient: 0% to 10% MeOH in DCM) to give tert-butyl 3-{[(1S)-5-amino-1-(chloromethyl)-1,2-dihydro-3H-benzo[e]indol-3-yl]carbonyl}bicyclo[1.1.1]pentane-1-carboxylate 259 as a yellow solid (905 mg, 98%). LC-MS (Protocol B): m/z 427 [M+H]$^+$, retention time=1.92 minutes.

Step 2

A stirring solution of 259 (900, 2.11 mmol) in 5 mL of anhydrous DCM was added (9H-fluoren-9-yl)methyl(S)-(1-chloro-1-oxopropan-2-yl)carbamate (695 mg, 2.11 mmol) followed by drop wise addition of TEA (0.5 mL). The reaction was allowed to stir for 2 hours. Upon completion the reaction mixture was concentrated under vacuum. The crude products was purified by silica gel chromatography (Gradient: 0% to 100% Ethyl Acetate in Heptane) to give tert-butyl 3-{[(1S)-1-(chloromethyl)-5-({N-[(9H-fluoren-9-ylmethoxy)carbonyl]-L-alanyl}amino)-1,2-dihydro-3H-benzo[e]indol-3-yl]carbonyl}bicyclo[1.1.1]pentane-1-carboxylate 260 as a white solid (1.102 g, 73%). LC-MS (Protocol B): m/z 720 [M+H]$^+$, retention time=2.32 minutes.

Step 3

In a round-bottom flask equipped with a stir bar containing 260 (1000 mg, 1.388 mmol) was added 15 mL of 1:1 DCM in DEA. The solution was stirred for 3 hours. The reaction mixture was concentrated under vacuum and taken up in 50% DCM in Heptane and concentrated under vacuum again. This was repeated 3 times (to remove excess DEA) to give a crude white solid upon concentrating. This crude white solid was added to a round bottom flask containing (((9H-fluoren-9-yl)methoxy)carbonyl)-L-valine (471 mg, 1.38 mmol), and HATU (350 mg, 1.38 mmol) in 10 mL of anhydrous DCM. TEA (0.5 mL) was then added and the reaction was stirred at room temperature of 3 hours. Upon completion the reaction mixture was concentrated under vacuum. The crude products was purified by silica gel chromatography (Gradient: 0% to 100% Ethyl Acetate in Heptane) to give N-[(9H-fluoren-9-ylmethoxy)carbonyl]-L-valyl-N-[(1S)-3-{[3-(tert-butoxycarbonyl)bicyclo[1.1.1]pent-1-yl]carbonyl}-1-(chloromethyl)-2,3-dihydro-1H-benzo[e]indol-5-yl]-L-alaninamide 261 as a white solid (1.005 g, 88%). LC-MS (Protocol B): m/z 819 [M+H]$^+$, retention time=2.31 minutes.

Step 4

10 mL of 25% TFA in DCM was added to a round bottom flask containing 261 (1000 mg, 1.22 mmol). The reaction was stirred for 3 hours. The solution was stirred for 3 hours. The reaction mixture was concentrated under vacuum and taken up in 50% DCM and Heptane and concentrated under vacuum. This was repeated 3 times (to remove excess TFA) to give a 262 as a white solid upon concentrating (920 mg, 98%). LC-MS (Protocol B): m/z 763 [M+H]$^+$, retention time=1.88 minutes.

Preparation of N-[6-(2,5-dioxo-2,5-dihydro-1H-pyrrol-1-yl)hexanoyl]-L-valyl-N-{(1S)-1-(chloromethyl)-3-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-2,3-dihydro-1H-benzo[e]indol-5-yl}-L-alaninamide 266
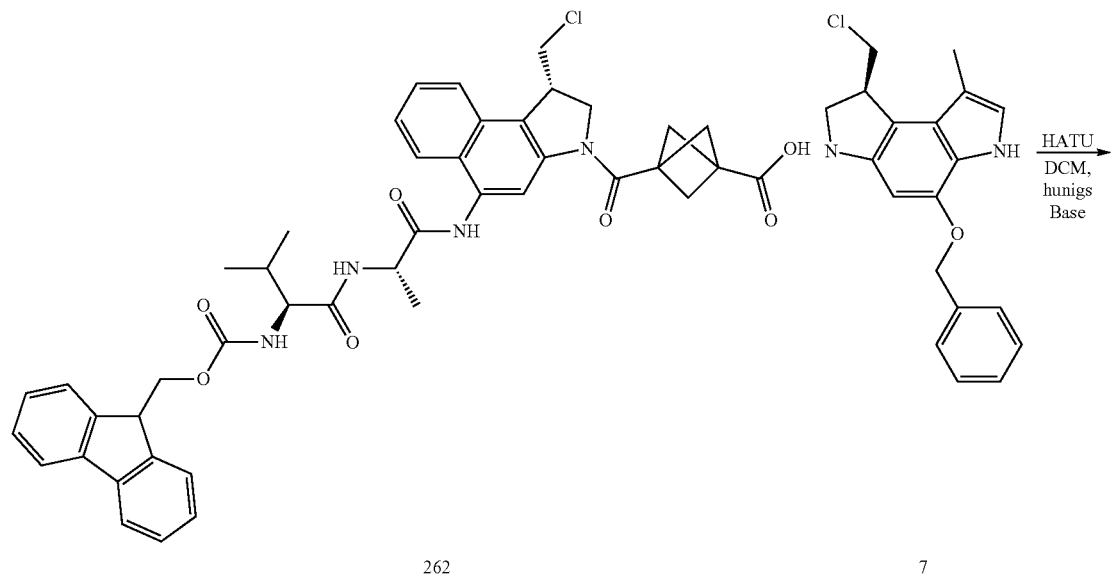
262
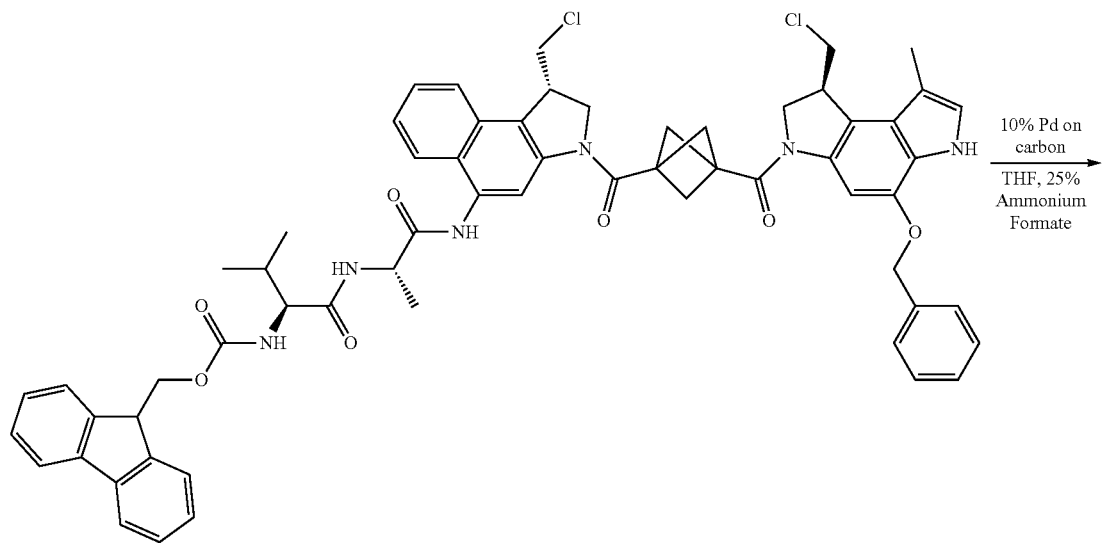
263

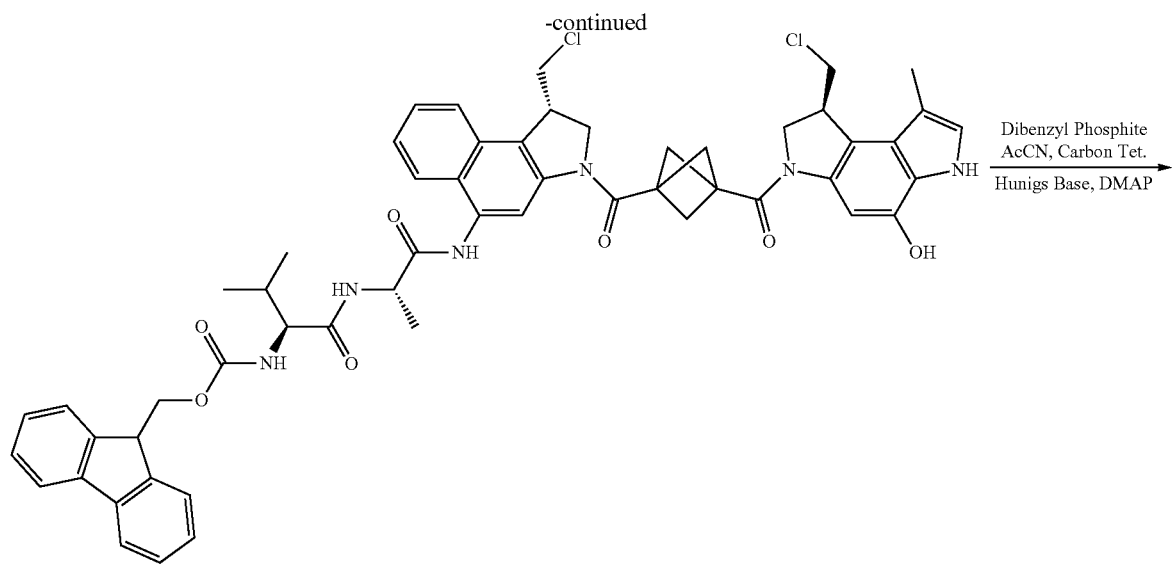
264
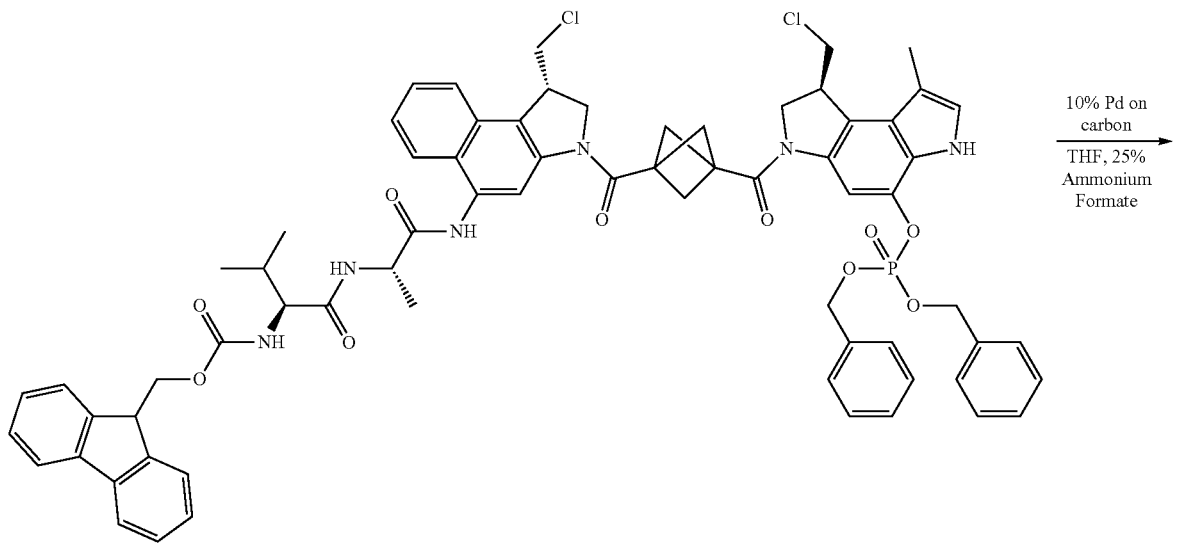
265
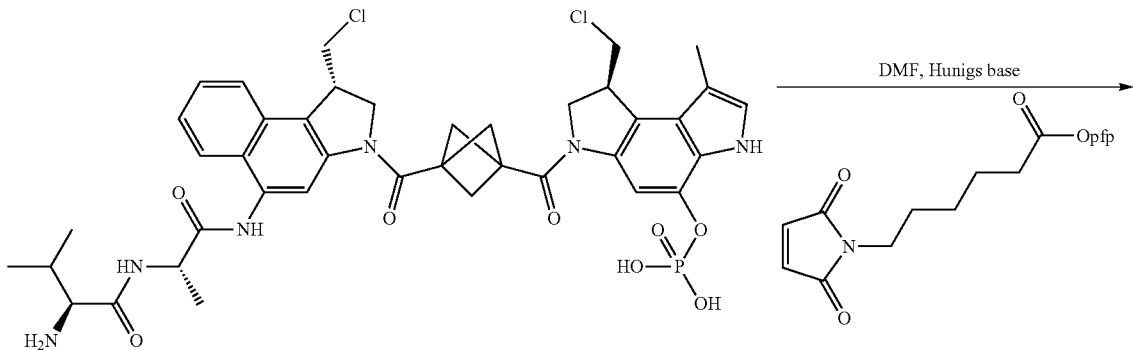
266

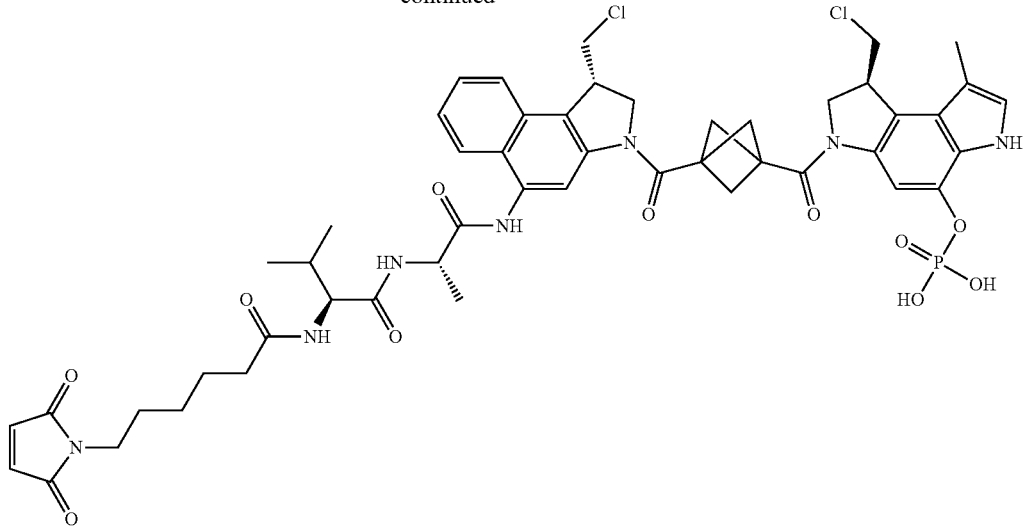

267

Step 1

In a round bottom flask containing N-[(9H-fluoren-9-ylmethoxy)carbonyl]-L-valyl-N-[(1S)-3-[(3-carboxybicyclo[1.1.1]pent-1-yl)carbonyl]-1-(chloromethyl)-2,3-dihydro-1H-benzo[e]indol-5-yl]-L-alaninamide 262 (580 mg, 0.76 mmol) in 5 mL of THF was added HATU (298 mg, 0.76 mmol). The solution mixture was stirred at room temperature for 30 min. (1S)-5-(benzyloxy)-1-(chloromethyl)-8-methyl-1,2,3,6-tetrahydropyrrolo[3,2-e]indole 7 was then added followed by 0.3 mL of Hunigs base. The reaction was stirred for 1 hour and concentrated to a crude glass. The crude reaction mixture was purified by silica gel chromatography (Gradient: 0% to 10% MeOH in DCM) to give Synthesis of N-[(9H-fluoren-9-ylmethoxy)carbonyl]-L-valyl-N-[(1S)-3-[(3-{[(1S)-5-{[bis(benzyloxy)phosphoryl]oxy}-1-(chloromethyl)-8-methyl-1,6-dihydropyrrolo[3,2-e]indol-3(2H)-yl]carbonyl}bicyclo[1.1.1]pent-1-yl)carbonyl]-1-(chloromethyl)-2,3-dihydro-1H-benzo[e]indol-5-yl]-L-alaninamide 263 as a white solid (723 mg, 98%). LC-MS (Protocol B): m/z 1071 [M+H]$^+$, retention time=2.45 minutes.

Step 2

A stirring solution of of 263 (100 mg, 0.932 mmol) in 7 mL of THF under nitrogen was cooled to 0 C using an ice bath. Palladium 10 wt. % on activated carbon (10 mg) was then added followed by the slow drop wise addition of 0.5 mL of 25% ammonium formate in water. The reaction was allowed to stir at 0 C. for 1 hour. Upon completion the reaction mixture was filtered through a pad of celite and the filtrate concentrated under vacuum. The crude products was purified by silica gel chromatography (Gradient: 0% to 10% MeOH in DCM) to give Synthesis of N-[(9H-fluoren-9-ylmethoxy)carbonyl]-L-valyl-N-{(1S)-1-(chloromethyl)-3-[(3-{[(1S)-1-(chloromethyl)-5-hydroxy-8-methyl-1,6-dihydropyrrolo[3,2-e]indol-3(2H)-yl]carbonyl}bicyclo[1.1.1]pent-1-yl)carbonyl]-2,3-dihydro-1H-benzo[e]indol-5-yl}-L-alaninamide 264 as a yellow solid (821 mg, 89%). %). LC-MS (Protocol B): m/z 981 [M+H]$^+$, retention time=2.16 minutes.

Step 3

To a stirring solution of of 264 (650 mg, 0.66 mmol) in 10 mL of THF and 10 mL of AcCN, carbon tetrachloride (2.04 mL, 21.0 mmol) was added followed by Hunig's base (1.12 mL, 6.45 mmol), dibenzylphosphite (694 mg, 2.65 mmol) and DMAP (catalytic). The reaction was allowed to stir at room temperature for 20 minutes. The reaction was concentrated to a crude glass. The crude reaction mixture was purified by silica gel chromatography (Gradient: 0% to 10% MeOH in DCM) to give N-[(9H-fluoren-9-ylmethoxy)carbonyl]-L-valyl-N-[(1S)-3-[(3-{[(1S)-5-{[bis(benzyloxy)phosphoryl]oxy}-1-(chloromethyl)-8-methyl-1,6-dihydropyrrolo[3,2-e]indol-3(2H)-yl]carbonyl}bicyclo[1.1.1]pent-1-yl)carbonyl]-1-(chloromethyl)-2,3-dihydro-1H-benzo[e]indol-5-yl]-L-alaninamide 265 as a white glass (502 mg, 66%). LC-MS (Protocol B): m/z 1243 [M+H]$^+$, retention time=2.46 minutes.

Step 4

A stirring solution of 264 (100 mg, 0.932 mmol) in 7 mL of THF under nitrogen was cooled to 0 C using an ice bath. Palladium 10 wt. % on activated carbon (10 mg) was then added followed by the slow drop wise addition of 0.5 mL of 25% ammonium formate in water. The reaction was allowed to stir at 0 C. for 1 hour. Upon completion the reaction mixture was filtered through a pad of celite and the filtrate concentrated under vacuum. The crude products was purified by silica gel chromatography (Gradient: 0% to 10% MeOH in DCM) to give L-valyl-N-{(1S)-1-(chloromethyl)-3-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-2,3-dihydro-1H-benzo[e]indol-5-yl}-L-alaninamide 265 as a yellow solid (25 mg, 18%). LC-MS (Protocol B): m/z 839 [M+H]$^+$, retention time=1.54 minutes.

Step 5

In a round bottom flask equipped with a stir bar and pentafluorophenyl 6-(2,5-dioxo-2,5-dihydro-1H-pyrrol-1-yl)hexanoate (18 mg, 0.046 mmol) was added 5 mL of anhydrous DCM and purged the system with $N_2$. To this solution added of 265 (40 mg, 0.046 mmol)) and TEA (0.05 mL). The system was let to stir for 1 hour. The reaction was concentrated under vacuum and purified by provided 267 (20% 9 mg Method N), retention time=15.462 minutes. LC-MS (Protocol B): m/z 1032 [M+H]$^+$, retention time=1.55 minutes. $^1$H NMR (400 MHz, DMSO-d$_6$) δ 11.34 (s, 1H), 9.89 (s, 1H), 8.43 (s, 1H), 8.20 (d, J=6.8 Hz, 2H), 7.91 (dd, J=14.4, 8.4 Hz, 3H), 7.85-7.74 (m, 2H), 7.49 (t, J=7.7 Hz, 1H), 7.35 (t, J=7.8 Hz, 1H), 6.96 (d, J=25.4 Hz, 4H), 4.52 (t, J=7.1 Hz, 1H), 4.37 (dq, J=22.0, 10.7 Hz, 4H), 4.18 (dt, J=19.7, 8.5 Hz, 2H), 4.07-3.85 (m, 4H), 3.58 (t, J=9.8 Hz, 1H), 3.43-3.12 (m, 34H), 2.71 (d, J=8.2 Hz, 1H), 2.62-2.37 (m, 49H), 2.28 (s, 3H), 2.09 (qt, J=14.0, 7.1 Hz, 3H), 1.98-1.86 (m, 1H), 1.39 (dt, J=22.2, 7.2 Hz, 11H), 1.22-1.05 (m, 6H), 0.78 (dd, J=9.7, 6.7 Hz, 10H).

Preparation of N-[6-(2,5-dioxo-2,5-dihydro-1H-pyrrol-1-yl)hexanoyl]-L-valyl-N-{(1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl}-L-alaninamide 270

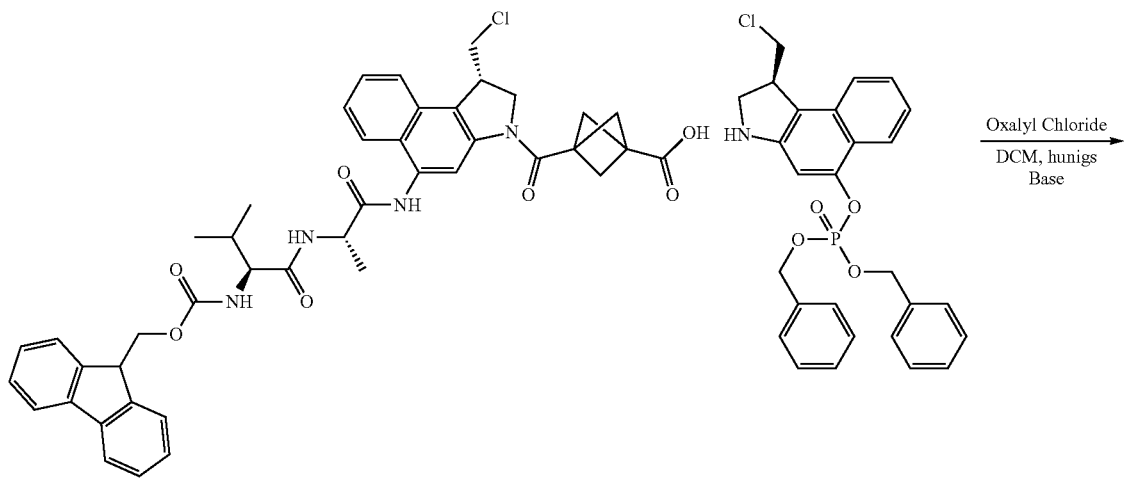

262

226

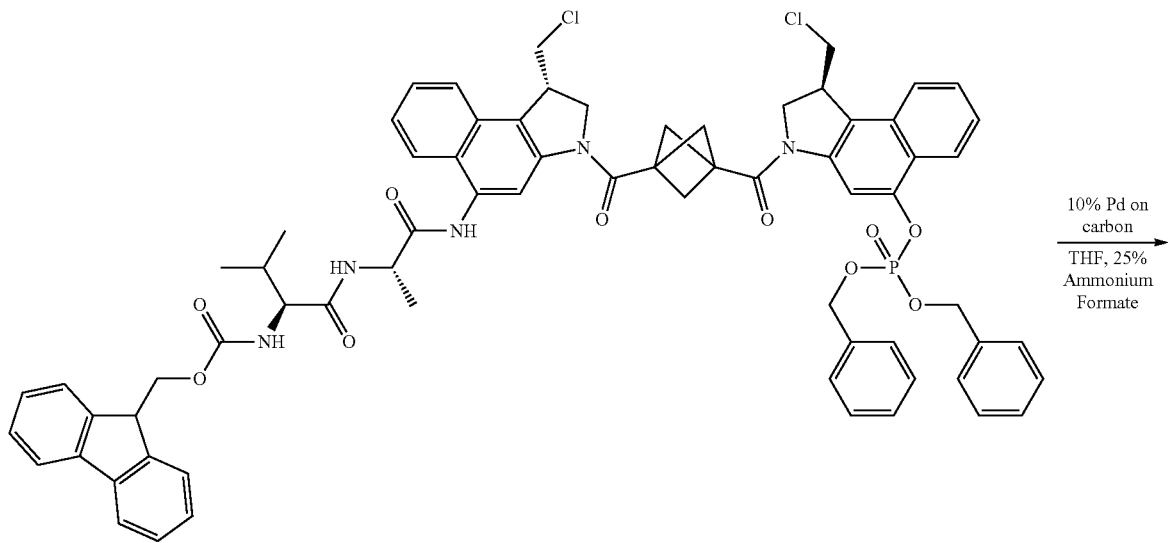

268

-continued

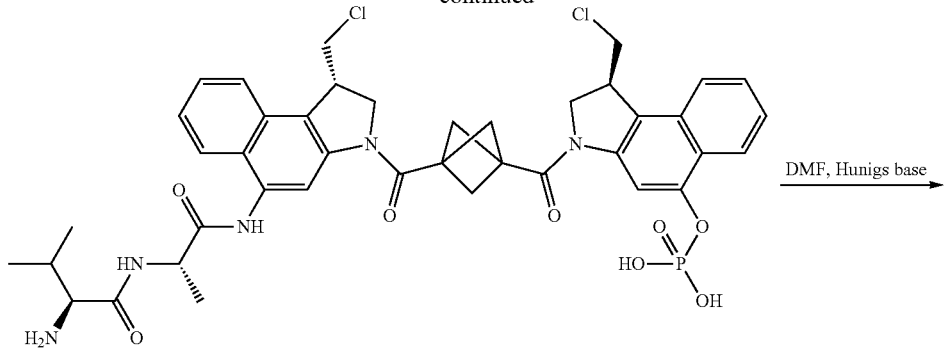

269

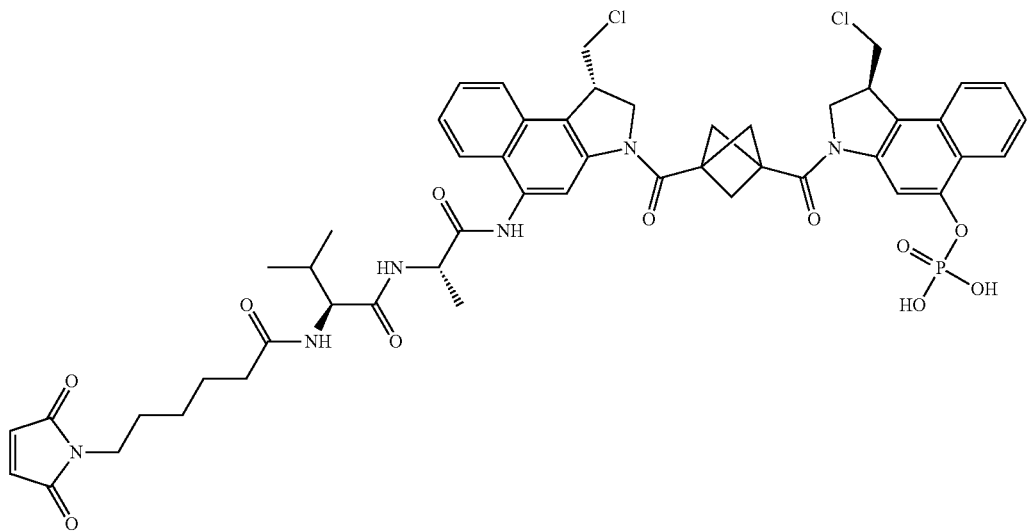

270

Step 1

226 (214 mg, 0.36 mmol) was taken up in CH$_2$Cl$_2$ (2 mL) and TFA (0.5 mL) was added and after deprotection was complete solvent was removed. In a round bottom flask purged with N$_2$, containing 262 (200 mg, 0.26 mmol)) in 5 mL of anhydrous DCM was added oxalyl chloride (0.024 mL, 0.26 mmol). To this solution was added 1 drop of DMF and the system was stirred for 3 hours.

The reaction was concentrated by vacuum. The residue was taken up in DCM and added to a round bottom flask containing deprotected 226 in 15 mL of DCM and TEA (0.144 mL). The reaction was stirred at room temperature for 2 hours. The crude reaction mixture was concentrated by vacuum and taken up in 25 mL of DCM and transferred to a separatory funnel. Washed organic layer with 1M HCl (3×), Water (3×), and Brine (2×). Dried organic layer over Na$_2$SO$_4$ filtered and concentrated the filtrate to a crude solid. The crude products was purified by silica gel chromatography (Gradient: 0% to 10% MeOH in DCM) to give N-[(9H-fluoren-9-ylmethoxy)carbonyl]-L-valyl-N-[(1S)-3-[(3-{[(1S)-5-{[bis(benzyloxy)phosphoryl]oxy}-1-(chloromethyl)-1,2-dihydro-3H-benzo[e]indol-3-yl]carbonyl}bicyclo[1.1.1]pent-1-yl)carbonyl]-1-(chloromethyl)-2,3-dihydro-1H-benzo[e]indol-5-yl]-L-alaninamide 268 as a yellow solid (75 mg, 23%). LC-MS (Protocol B): m/z 1238 [M+H]$^+$, retention time=2.53 minutes.

Step 2

A stirring solution of 268 (75 mg, 0.061 mmol) in 5 mL of THF under nitrogen was cooled to 0 C using an ice bath. Palladium 10 wt. % on activated carbon (5 mg) was then added followed by the slow drop wise addition of 0.5 mL of 25% ammonium formate in water. The reaction was allowed to stir at 0 C. for 3 hours. Upon completion the reaction mixture was filtered through a pad of celite and the filtrate concentrated under vacuum. The crude product was taken up in Ethyl Acetate and the solids filtered to give L-valyl-N-{(1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl}-L-alanin 269 as a light yellow solid (20 mg, 30%). %). LC-MS (Protocol B): m/z 838 [M+H]$^+$, retention time=1.27 minutes.

Step 3

In a round bottom flask equipped with a stir bar and pentafluorophenyl 6-(2,5-dioxo-2,5-dihydro-1H-pyrrol-1-yl)hexanoate (9.0 mg, 0.024 mmol) was added 5 mL of anhydrous DCM and purged the system with N$_2$. To this solution added 269 (20 mg, 0.024 mmol)) and TEA (0.05 mL). The system was let to stir for 1 hour. The reaction was concentrated under vacuum and purified by HPLC Method N provided 270 (5 mg, 20%) retention time=10.734 minutes. LC-MS (Protocol B): m/z 1031 [M+H]$^+$, retention time=1.54 minutes.

Preparation of (2S,3S,4S,5S,6S)-6-(((S)-1-(chloromethyl)-3-(5-((S)-1-(chloromethyl)-5-(((2-((((4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosan-27-amido)benzyl)oxy)carbonyl)(methyl)amino)ethyl)(methyl)carbamoyl)oxy)-2,3-dihydro-1H-benzo[e]indole-3-carbonyl)thiophene-2-carbonyl)-2,3-dihydro-1H-benzo[e]indol-5-yl)oxy)-3,4,5-trihydroxytetrahydro-2H-pyran-2-carboxylic acid 278
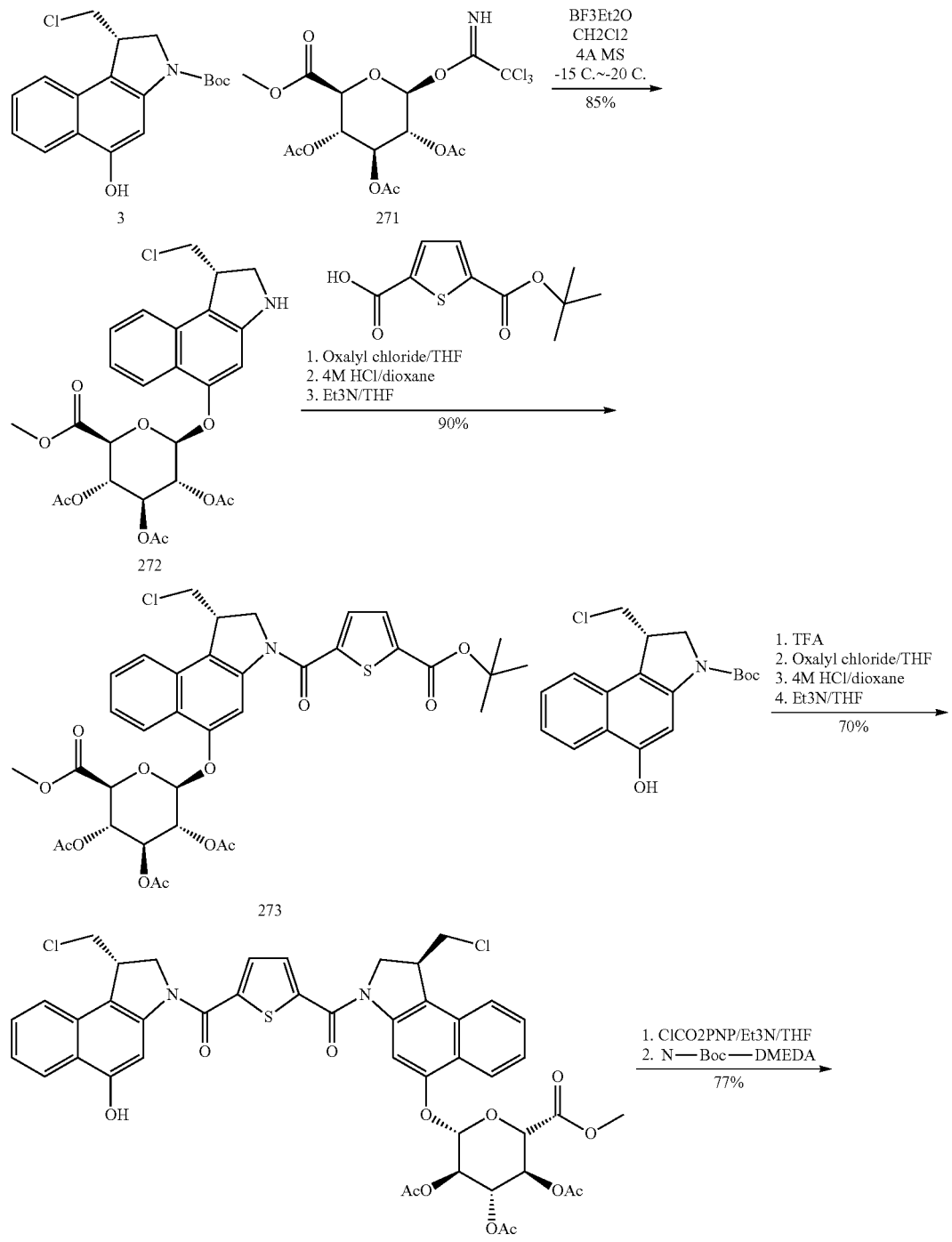

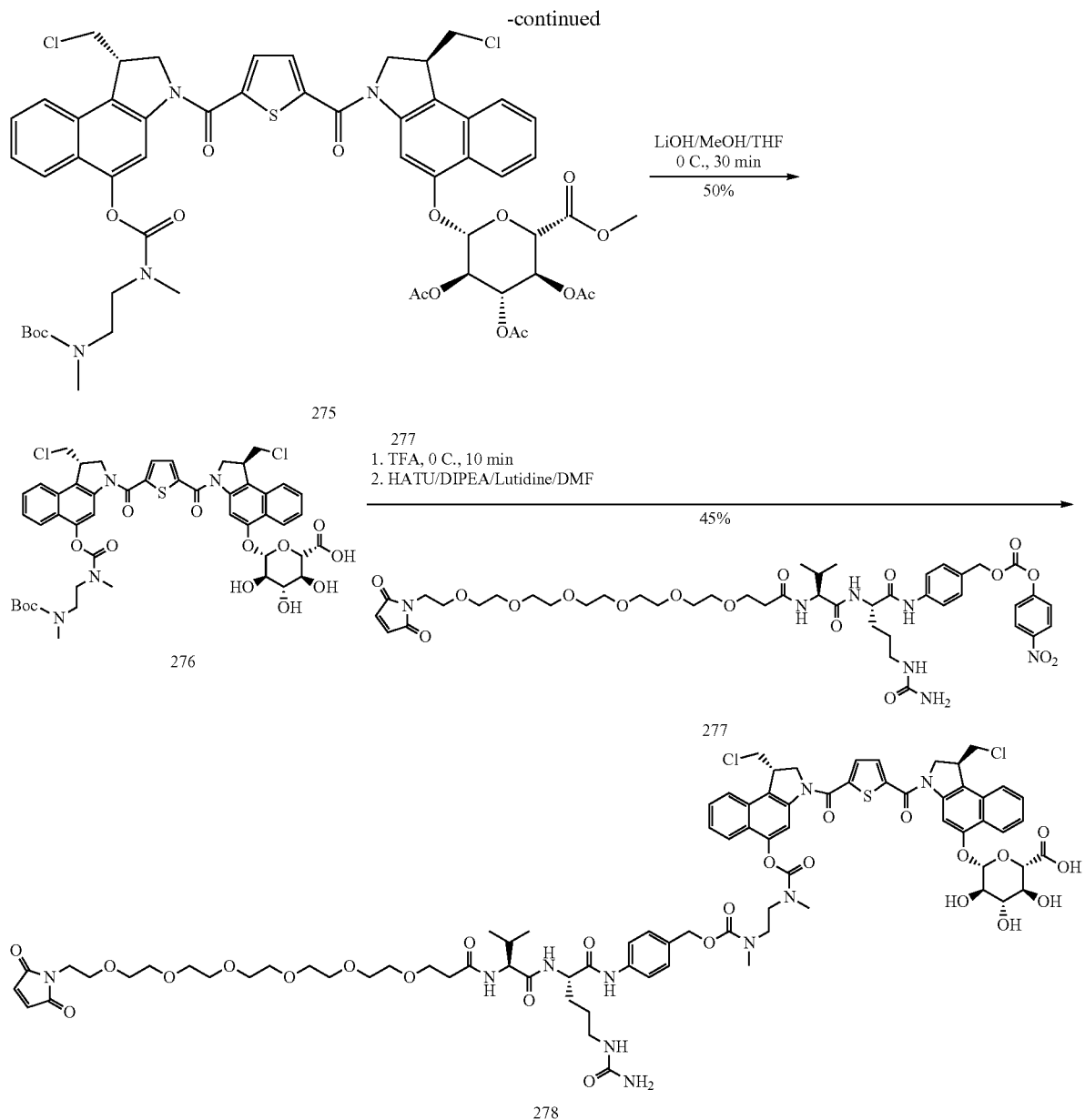

Step 1 tert-Butyl(1S)-1-(chloromethyl)-5-hydroxy-1,2-dihydro-3H-benzo[e]indole-3-carboxylate 3 (683 mg, 2.05 mmol) was dissolved in DCM (70 mL), added 4 Å MS (3.8 g, powder, <5 micro, activated), and the mixture was stirred at room temperature for 30 min. To the reaction mixture, alpha-D-glucuronide methyl ester 2,3,4-triacetate 1-2,2,2-trichloroethanimidate 271 (1178 mg, 2.45 mmol) was added, and cooled to −15° C. A solution of BF$_3$.Et$_2$O (0.13 mL, 1.02 mmol) in DCM (10 mL) was added slowly, and the reaction mixture was stirred at below −20° C. for 1 h. To the mixture, a solution of BF$_3$.Et$_2$O (0.76 mL, 6 mmol) in DCM (10 mL) was added to remove the Boc group, and the reaction mixture was allow to warm to rt for 2 h. The mixture was filtered through a pad of Celite, and the filtrate was concentrated to give a green foam (sticky). It was added 4M HCl (2 mL), and concentrated again to give a green foam as crude product 272, 1130 mg (94%), which was used in next step without further purification.

Step 2

Mono-tBu ester of thiophene diacid 187 (189 mg, 0.83 mmol) was dissolved in THF (10 mL), cooled to 0 C, and added oxalyl chloride (2M in DCM, 0.8 mL, 1.6 mmol), followed by DMF (2 drops). The mixture was stirred at 0 C for 5 min, and then at room temperature for 1 h. Concentrated in vacuo to give the corresponding acid chloride as off-white solid. The above solids were mixed with 272 (246 mg, 0.42 mmol) and treated with THF (10 mL) at 0 C, followed by Et3N (0.29 mL, 2 mmol). The mixture was stirred at 0 C for 5 min, and room temperature for 30 min. The mixture was concentrated, and the residue was purified by column chromatography in silica gel using EA/Hep (50/50) to give the product as yellow solid 273 (302 mg, 90%) LC-MS: 760.1.

Step 3

273 (790 mg, 1.04 mmol) was treated with TFA (2 mL) and DCM (4 mL) at rt for 1 h. concentrated to give a yellow solid. The solid was dissolved in THF (10 mL), cooled to 0 C, added oxalyl chloride (2M in DCM, 1 mL, 2 mmol), followed by DMF (1 drop). The mixture was stirred at 0 C for 5 min, and then rt for 1 h. Concentrated to give the acid chloride as a yellow solid. 3 (118 mg, 1.56 mmol) was treated with 4M HCl (4 mL) for 1 h. concentrated in vacuo to give the deBoc compound as green solid. It was dissolved in THF (10 mL), added a solution of the above acid chloride in THF (10 mL) at 0 C, followed by addition of Et3N (0.58 mL, 4.16 mmol), and the mixture was stirred at rt for 30 min. The mixture was diluted with EA, washed with water and brine, dried over MgSO4. It was concentrated in vacuo, and the residue was treated with MeOH, the resulting solid was collected by filtration to give the product as yellow solid 274 (668 mg, 70%). LC-MS: 919.1

Step 4

274 (576 mg, 0.63 mmol) was dissolved in THF (20 mL), cooled to 0 C, added a solution of paranitrophenyl chloroformate (263 mg, 1.26 mmol) in DCM (2 mL), followed by Et3N (0.52 mL, 3.76 mmol). The mixture was stirred at 0 C for 5 min, and then at rt for 2 h. LC-MS indicated completion of the formation of the carbonate. 213 (354 mg, 1.88 mmol) in THF (2 mL) was added to the above mixture, and stirred at rt for 30 min. The mixture was diluted with EtOAc, washed with water and brine, and dried over MgSO4. Concentrated in vacuo to give a solid residue, which was treated with MeOH to form precipitates. The resulting solid was collected by filtration to give the product as yellow solid 275 (550 mg, 77%).

Step 5

275 (550 mg, 0.48 mmol) was dissolved in THF/MeOH (1/1, 10 mL), cooled to 0 C, added a solution of LiOHH2O (206 mg, 4.8 mmol) in water (3 mL), and the mixture was stirred at 0 C for 1 h. HOAc (300 mg) was added to neutralize the above solution, concentrated in vacuo. The residue was purified by Gilson HPLC (0.02% TFA) to give the product as yellow solid 276 (243 mg, 50%).

Step 6

276 (50 mg, 0.05 mmol) was treated with pre-cooled TFA (2 mL) at 0 C for 5 min, and concentrated in vacuo to give deBoc compound as yellow solid. The above solid was dissolved in DMF (2 mL), added 277 (48 mg, 0.05 mmol), followed by lutidine (0.035 mL, 0.3 mmol), DIPEA (0.052 m, 0.3 mmol), and HOAt (7 mg, 0.05 mmol). The mixture was stirred at 30 C for 7 h. The crude was subjected to Gislon HPLC (0.02% TFA) to give the product 278 as yellow solid 39 mg (45%). LC-MS: 1715.8/1737.8 (1.71 min at Larry); 1713.7 (−).

Preparation of (2S,3S,4S,5R,6S)-6-(((S)-3-(5-((S)-5-(((2-(((((4-((S)-2-((S)-2-((S)-2-acetamido-6-amino-hexanamido)-3-methylbutanamido)-5-ureidopentanamido)benzyl)oxy)carbonyl)(methyl)amino)ethyl)(methyl)carbamoyl)oxy)-1-(chloromethyl)-2,3-dihydro-1H-benzo[e]indole-3-carbonyl)thiophene-2-carbonyl)-1-(chloromethyl)-2,3-dihydro-1H-benzo[e]indol-5-yl)oxy)-3,4,5-trihydroxytetrahydro-2H-pyran-2-carboxylic acid 280

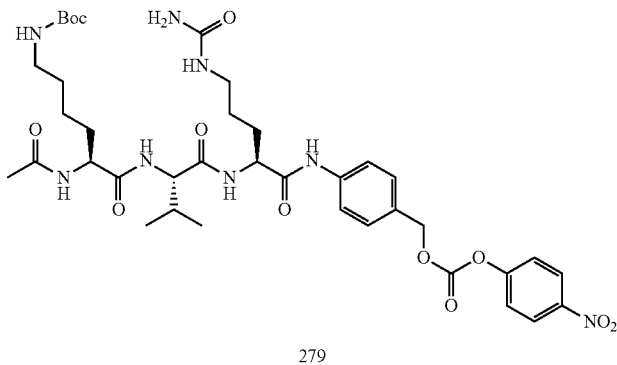

279

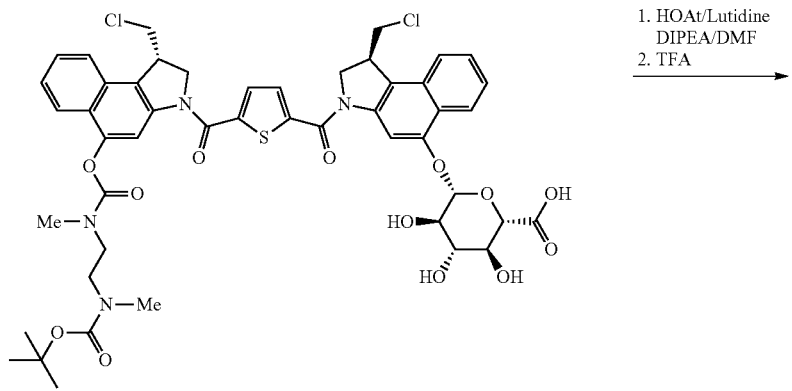

276

1. HOAt/Lutidine DIPEA/DMF
2. TFA

235

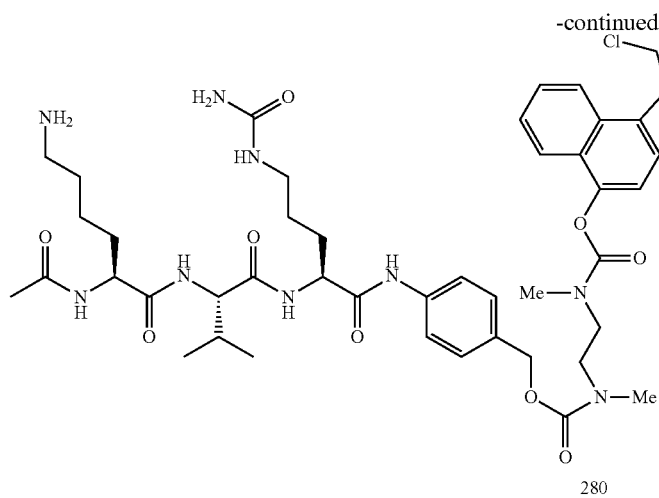

236

-continued

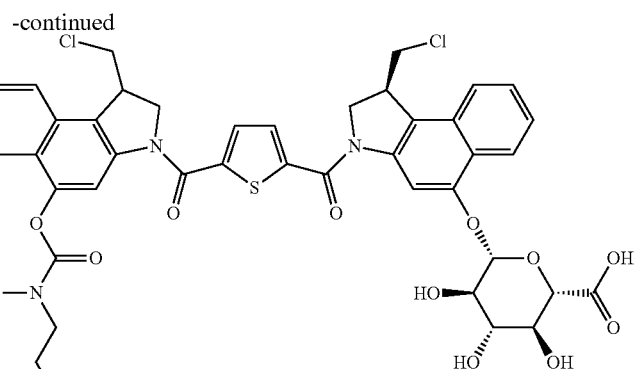

280

276 was treated with TFA (2 mL) at 0 C for 1 h. It was concentrated in vacuo to give the It was dissolved in DMF (2 mL), added 279 (59 mg, 0.07 mmol), followed by lutidine (0.033 mL, 0.29 mmol), DIPEA (0.051 mL, 0.29 mmol) and HOAt (7 mg, 0.05 mmol). The mixture was stirred at 30 C for 4 h. Concentrated, and the residue was purified by Gilson HPLC (0.02% TFA) to give the product as yellow solid 48 mg (62%). It was treated with pre-cooled TFA (1.5 mL) for 5 min, then concentrated in vacuo to give the crude as yellow solid. The crude was purified by Gilson HPLC (0.02% TFA) to give the product 280 as yellow powder after freeze dry (21 mg, 43%). LC-MS: 1470.6

Preparation of (S)-1-(chloromethyl)-3-(5-((S)-1-(chloromethyl)-5-((((2S,3S,4S,5S,6S)-3,4,5-trihydroxy-6-(hydroxymethyl)tetrahydro-2H-pyran-2-yl)oxy)-2,3-dihydro-1H-benzo[e]indole-3-carbonyl)thiophene-2-carbonyl)-2,3-dihydro-1H-benzo[e]indol-5-yl(4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosan-27-amido)benzyl)ethane-1,2-diylbis(methylcarbamate)

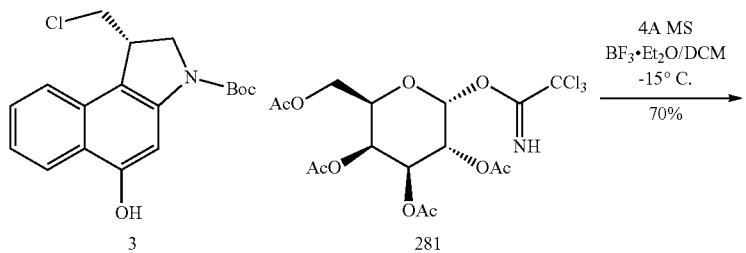

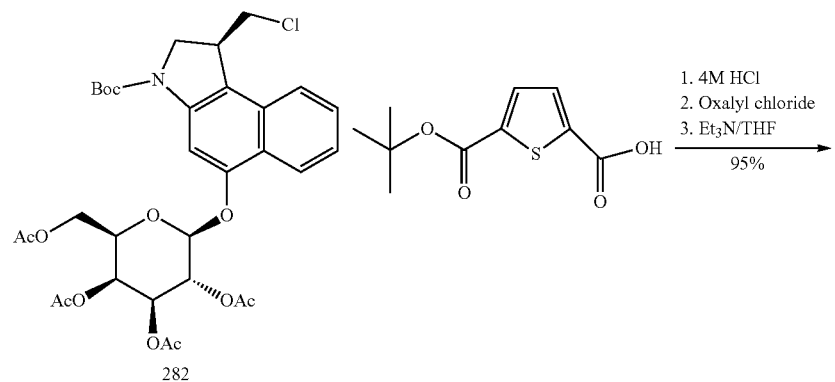

282

-continued
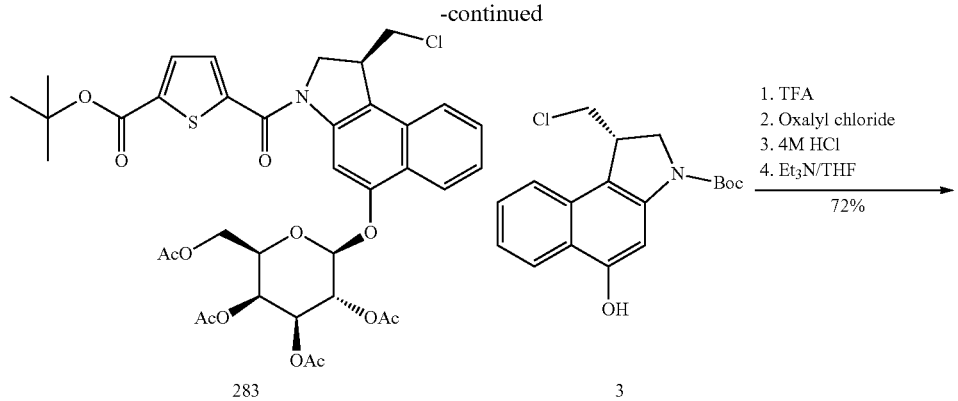
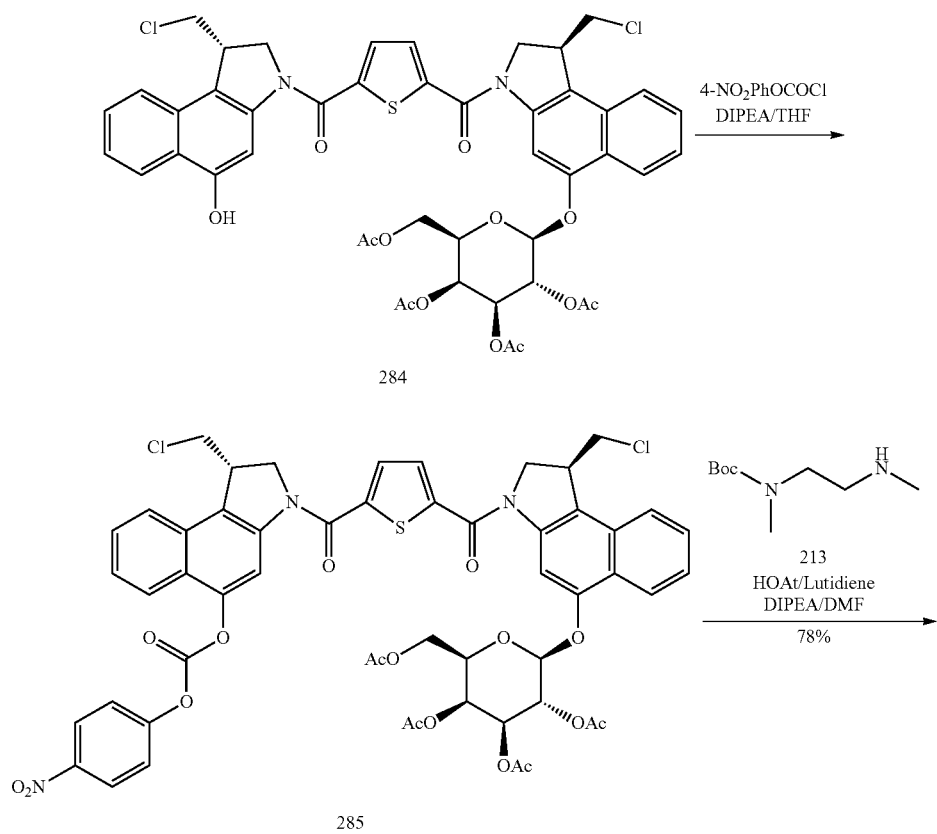
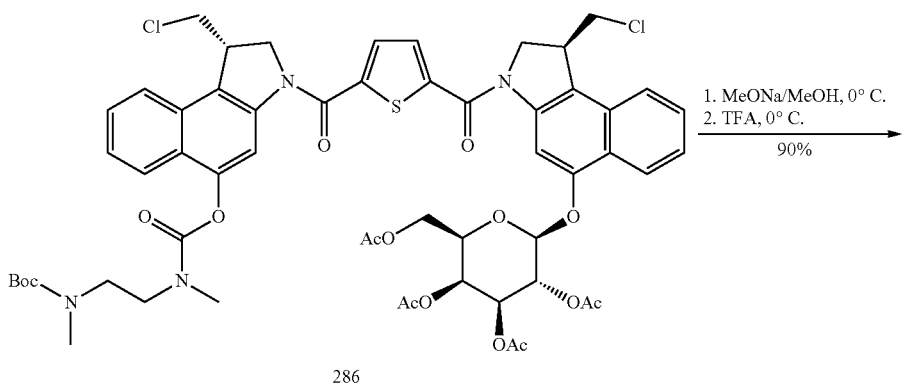

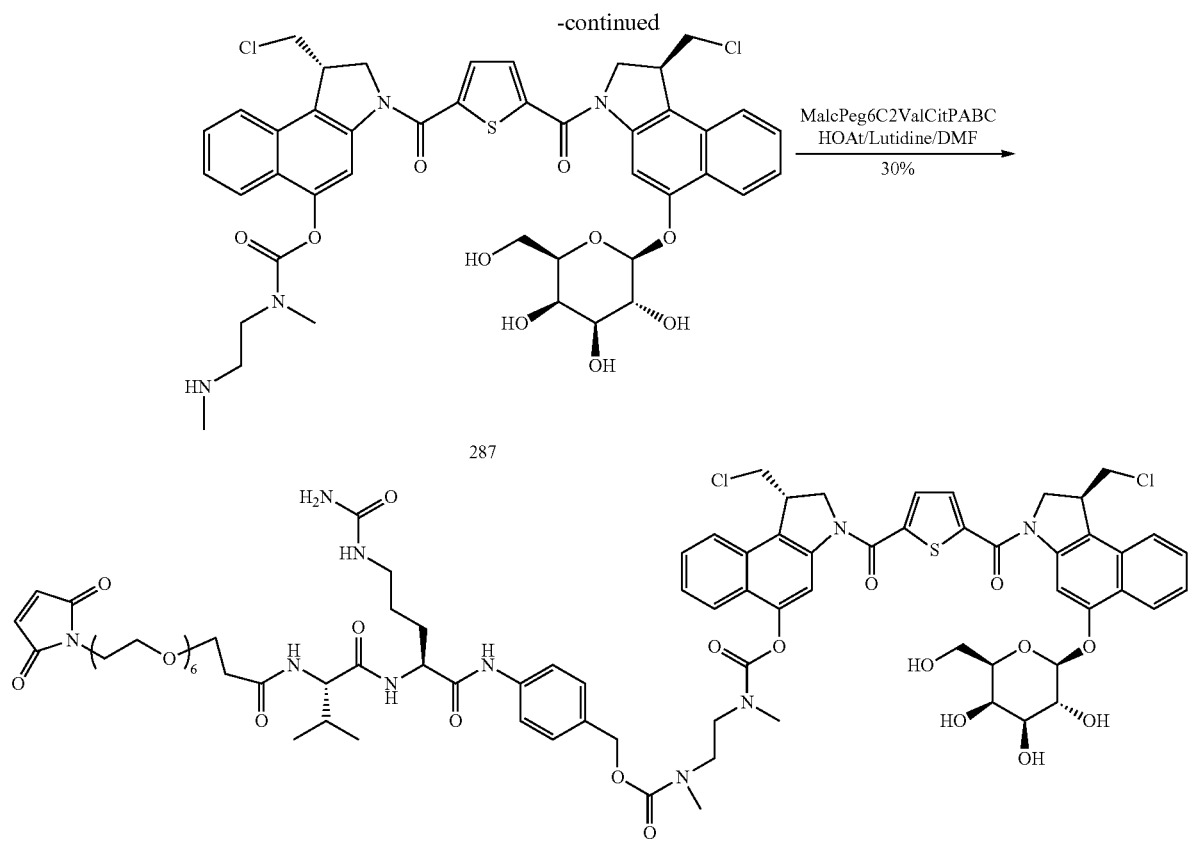

287

288

Step 1

3 (775 mg, 2.3 mmol) was dissolved in DCM (80 mL), added 4 Å MS (6.2 g, poder, <5 micro, activated), and the mixture was stirred at room temperature for 30 min. To the reaction mixture, alpha-D-galactopanose, 2,3,4,6-tetraacetate 1-2,2,2-trichloroethanimidate 281 (1260 mg, 2.3 mmol) was added, and cooled to −15° C. a solution of $BF_3.Et_2O$ (0.144 mL, 1.2 mmol) in DCM (10 mL) was added slowly, and the reaction mixture was stirred at −15° C.--20° C. for 1 h. The reaction mixture was filtered through a pad of Celite, and the filtrate was concentrated. The crude was purified by ISCO using MeOH/DCM (0-20%) to give the product as green solid 282 (1400 mg, 91%).

Step 2

Mono-tBu ester of thiophene diacid 187 (300 mg, 1.3 mmol) was dissolved in THF (10 mL), cooled to 0 C, and added oxalyl chloride (2M in DCM, 1 mL, 2 mmol), followed by DMF (2 drops). The mixture was stirred at 0 C for 5 min, and then at room temperature for 1 h. Concentrated in vacuo to give the corresponding acid chloride as white solid. 282 (664 mg, 1 mmol) was treated with 4M HCl (4 mL) for 1 h at room temperature. It was concentrated in vacuo to give the deBoc amine green solid. The above solids were mixed with THF (10 mL) at 0 C, added $Et_3N$ (0.83 mL, 6 mmol). The mixture was stirred at 0 C for 5 min, and room temperature for 30 min. The mixture was diluted with EtOAc, washed with water and brine, dried over $MgSO_4$. Concentrated in vacuo, and the residue was treated with MeOH, and concentrated again to give a solid residue, which was recrystallized from MeOH. The resulting yellow solid was collected by filtration to give the product as yellow solid 283 (500 mg, 65%).

Step 3

283 (200 mg, 0.26 mmol) was dissolved in THF (6 mL), added oxalyl chloride (0.64 mL, 2M in DCM) at 0° C., followed by DMF (2 drops). The mixture was stirred at 0° C. for 5 min, then room temperature for 0.5 h. Concentrated in vacuo to give the corresponding acid chloride as yellow solid. 3 (138 mg, 0.41 mmol) was treated with 4M HCl (1 mL in dioxane) for 2 h. concentrated in vacuo to give the deBoc amine as green form. This was dissolved in THF (5 mL), added the above acid chloride in THF (5 mL) at 0° C., followed by Et3N (0.23 mL, 1.55 mmol). The mixture was stirred at 0° C. for 5 min, then room temperature for 1 h. The mixture was diluted with EtOAc, washed with water and brine, dried over MgSO4. Concentrated in vacuo to give a solid residue, which was treated with MeOH, and the resulting solid was collected by filtration and washed with ether to give the product as yellow solid. The filtrate was concentrated, and purified by Gilson HPLC separation using ACN/water (0.02% TFA) to give the product as yellow solid 284 (200 mg, 83%).

Step 4

284 (68 mg, 0.073 mmol) was dissolved in THF (3 mL), cooled to 0° C., a solution of 4-nitrophenyl chloroformate (46 mg, 0.22 mmol) in DCM (0.6 mL) was added, followed by Et₃N (0.061 mL, 0.44 mmol). The mixture was stirred at 0° C. for 5 min, and room temperature for 1 h to provide 285. To the above reaction mixture was added N-Boc DMFDA (55 mg, 0.29 mmol), and stirred at room temperature for additional 1 h. Concentrated in vacuo, and the residue was purified by Gilson HPLC to give the product as yellow solid 286 (65 mg, 78%).

Step 5

286 (10 mg, 0.009 mmol) was dissolved in MeOH (1 mL) at 0 C, added MeONa (0.054 mL, 0.5M in MeOH, 0.027 mmol), and the mixture was stirred at 0 C for 5 min. The mixture was neutralized with HOAc (0.4 mL, 0.1M in MeOH), and concentrated in vacuo to give the product as yellow solid. It was treated pro-cooled TFA (0.8 mL) for 2 min, and concentrated in vacuo to give the deBoc compound as yellow solid 287 (8.3 mg, 90%).

Step 6

287 (8.3 mg, 0.008 mmol) was dissolved in DMF (1 mL), added Malc-Peg6C2ValCitPABC (9.6 mg, 0.01 mmol), followed by Lutidine (0.004 mL), DIPEA (0.006 mL) and HOAt (1.1 mg, 0.008 mmol). The mixture was stirred at room temperature for 4 h. The crude was purified by Gilson HPLC (0.02% TFA) to give the product 288 as yellow solid (4 mg, 30%). ¹H NMR (400 MHz, METHANOL-d₄) □=8.42 (d, J=8.2 Hz, 1H), 8.15 (d, J=7.4 Hz, 1H), 7.95 (d, J=8.2 Hz, 1H), 7.91 (d, J=8.2 Hz, 1H), 7.84 (d, J=8.6 Hz, 1H), 7.80-7.66 (m, 2H), 7.63-7.48 (m, 4H), 7.43 (br. s., 3H), 7.23 (d, J=7.8 Hz, 1H), 6.81 (s, 2H), 5.26-5.12 (m, 2H), 5.09 (d, J=8.6 Hz, 1H), 4.71-4.54 (m, 4H), 4.49 (br. s., 1H), 4.33-4.15 (m, 3H), 4.10-3.95 (m, 4H), 3.93-3.77 (m, 6H), 3.77-3.64 (m, 8H), 3.64-3.54 (m, 24H), 3.51 (br. s., 1H), 3.23-3.03 (m, 5H), 3.03-2.95 (m, 2H), 2.60-2.51 (m, 2H), 2.13 (d, J=7.0 Hz, 1H), 1.90 (br. s., 1H), 1.72 (br. s., 1H), 1.57 (br. s., 2H), 0.99 (t, J=6.4 Hz, 6H). LC-MS: 1702.3/ 829.9/748.7

Preparation of 4-((23S,26S)-1-amino-23-isopropyl-21,24-dioxo-26-(3-ureidopropyl)-3,6,9,12,15,18-hexaoxa-22,25-diazaheptacosan-27-amido)benzyl ((S)-1-(chloromethyl)-3-(5-((S)-1-(chloromethyl)-5-(((2S,3R,4S,5R,6R)-3,4,5-trihydroxy-6-(hydroxymethyl)tetrahydro-2H-pyran-2-yl)oxy)-2,3-dihydro-1H-benzo[e]indole-3-carbonyl)thiophene-2-carbonyl)-2,3-dihydro-1H-benzo[e]indol-5-yl) ethane-1,2-diylbis(methylcarbamate) 289

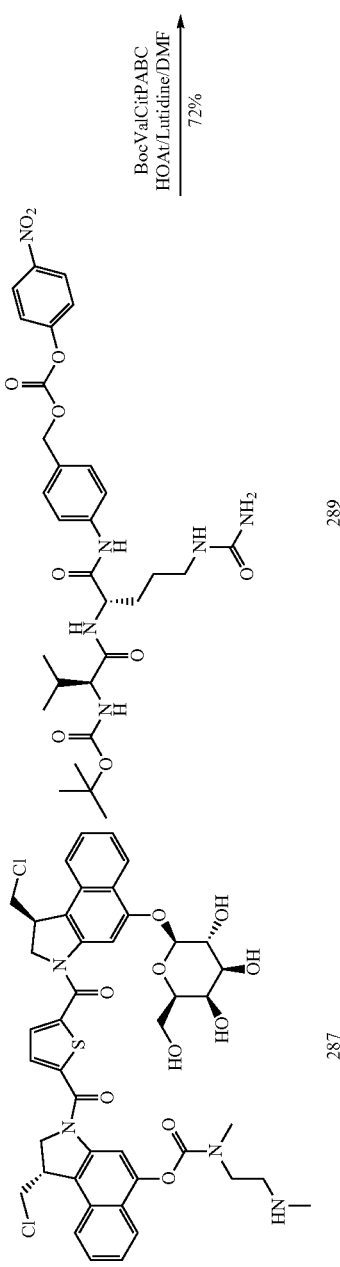
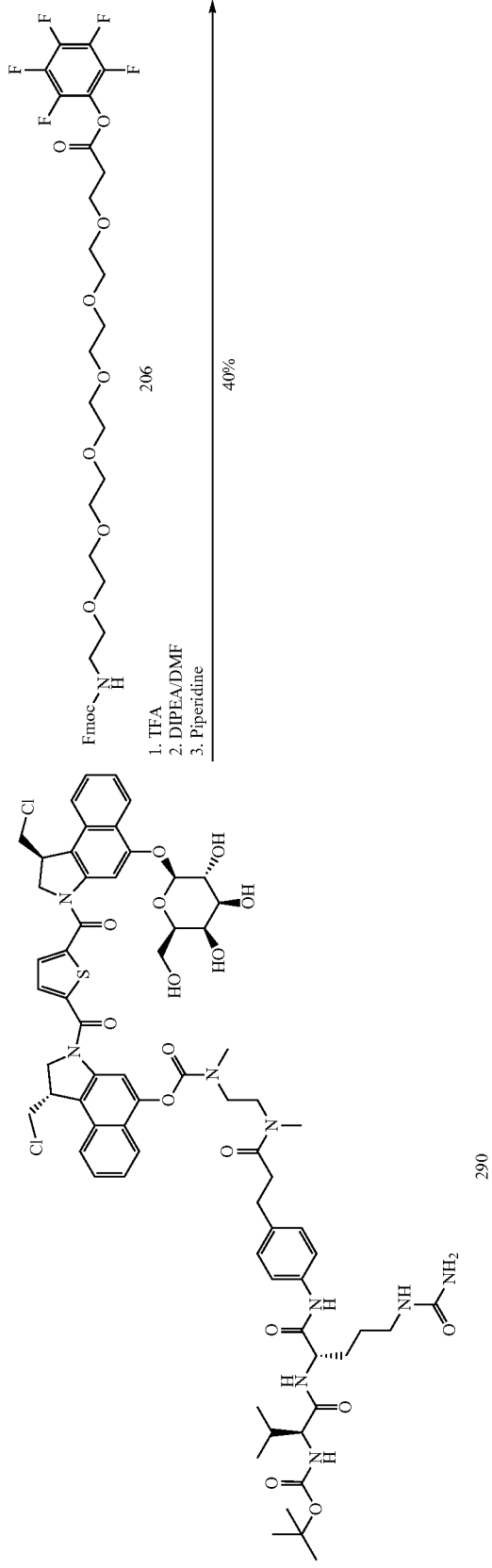

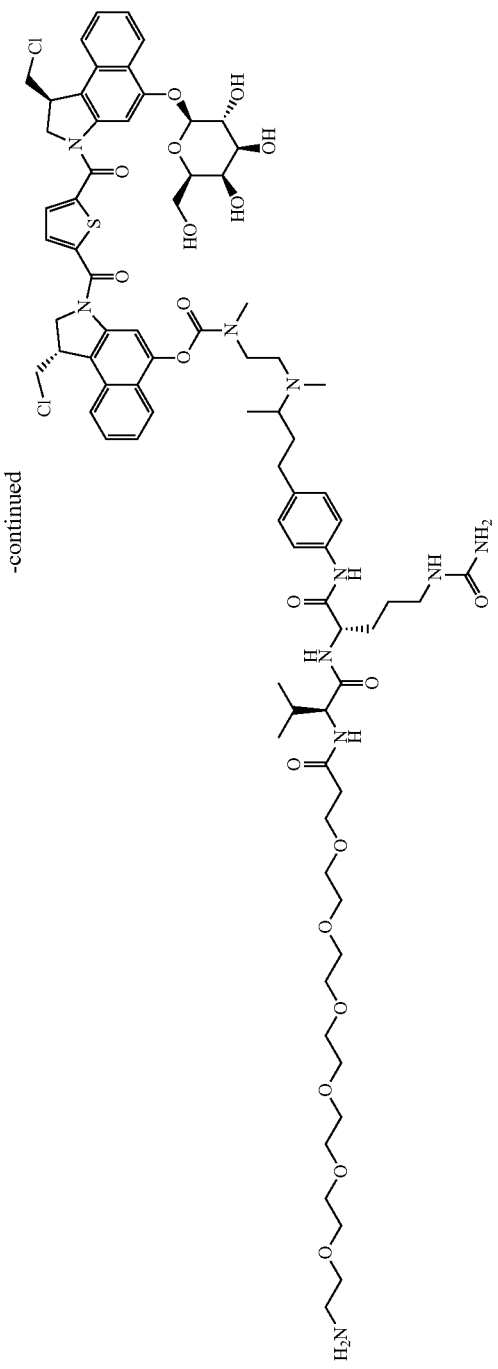

Step 1

BocValCitPABC 287 (30.9 mg, 0.048 mmol) was added to a solution of 286 (32 mg, 0.032 mmol) in DMF (2 mL), followed by lutidine (0.015 mL), DIPEA (0.022 mL) and HOAt (4.4 mg). The mixture was stirred at rt for 5 h. The crude was subjected to Gilson HPLC separation (0.02% TFA) to give the product as yellow solid 288 (32 mg, 72%).

Step 2

288 (16 mg, 0.012 mmol) was treated with pre-cooled TFA (1 mL) for 5 min, and concentrated in vacuo to give deBoc compound as yellow solid. The above solid was dissolved in DMF (0.5 mL), added DIPEA (0.013 mL), followed by a solution of 206 (12 mg, 0.016 mmol) in DCM (0.1 mL). The mixture was stirred at room temperature for 1 h. To the above solution was added piperidine (0.2 mL), and stirred for 30 min. Concentrated in vacuo, the residue was purified by Gilson HPLC using ACN/water (0.02% TEA) to give the product 289 as yellow solid (8 mg, 40%). NMR (400 MHz, DMSO-$d_6$) δ=9.89 (br. s., 1H), 8.35-8.21 (m, 1H), 8.15-8.00 (m, 2H), 7.96 (d, J=7.8 Hz, 1H), 7.91-7.84 (m, 1H), 7.84-7.72 (m, 4H), 7.63 (br. s., 2H), 7.58-7.50 (m, 3H), 7.50-7.44 (m, 2H), 7.40 (d, J=6.2 Hz, 2H), 7.18 (br. s., 2H), 5.90 (br. s., 1H), 5.06-4.90 (m, 2H), 4.87 (d, J=7.4 Hz, 1H), 4.83-4.68 (m, 2H), 4.42 (t, J=12.3 Hz, 2H), 4.32 (br. s., 2H), 4.23 (br. s., 1H), 4.19-4.11 (m, 1H), 4.10-3.95 (m, 3H), 3.95-3.80 (m, 2H), 3.77-3.62 (m, 3H), 3.60-3.46 (m, 15H), 3.15 (br. s., 2H), 3.06 (br. s., 1H), 2.89 (d, J=5.1 Hz, 3H), 2.92 (d, J=5.1 Hz, 3H), 2.86-2.74 (m, 3H), 2.35-2.21 (m, 1H), 1.96-1.82 (m, 1H), 1.61 (br. s., 1H), 1.52 (br. s., 1H), 1.43-1.21 (m, 2H), 0.76 (d, J=6.6 Hz, 3H), 0.79 (d, J=6.2 Hz, 3H); 1622.2 [M+H]$^+$;

TABLE 3

Additional Linker Payloads

| ID | Structure | Prepared Using Method Similar to Compound ID | MS: m/z |
|---|---|---|---|
| 292 | 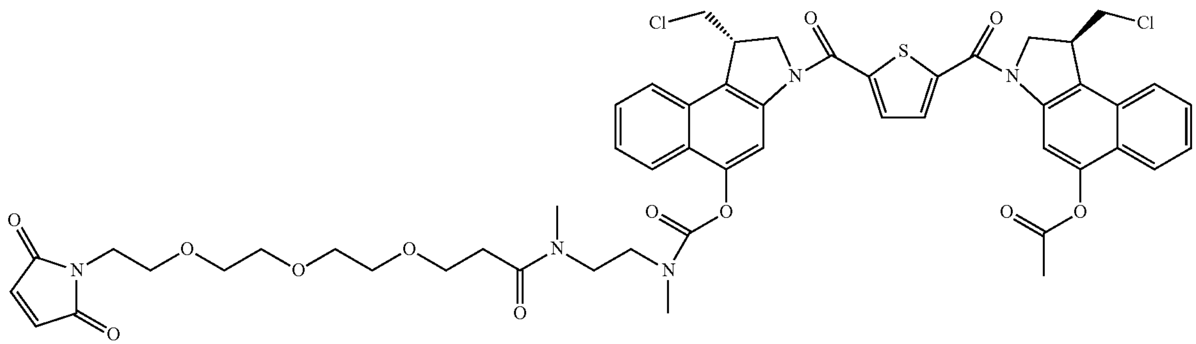 [SMILES: CC(=O)Oc1cc2c(c3ccccc13)[C@H](CCl)CN2C(=O)c1ccc(C(=O)N2C[C@@H](CCl)c3c2cc(OC(=O)N(C)CCN(C)C(=O)CCOCCOCCOCCN2C(=O)C=CC2=O)c2ccccc32)s1] | 198 | 1042.2 [M + H]+ |
| 293 | 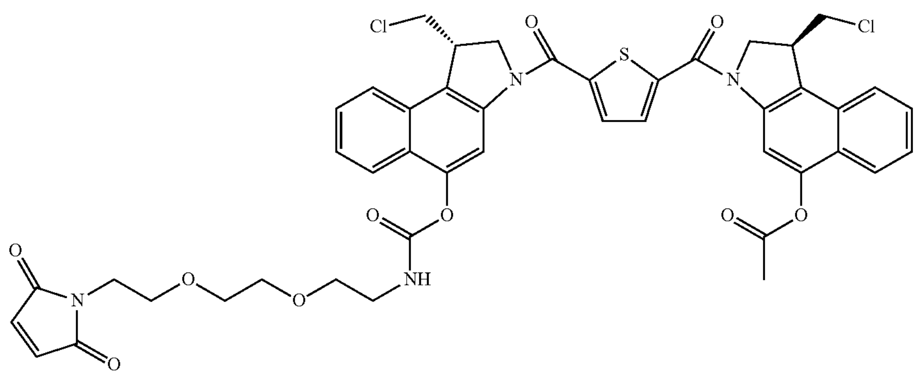 [SMILES: CC(=O)Oc1cc2c(c3ccccc13)[C@H](CCl)CN2C(=O)c1ccc(C(=O)N2C[C@@H](CCl)c3c2cc(OC(=O)NCCOCCOCCN2C(=O)C=CC2=O)c2ccccc32)s1] | 198 | 921.1 [M + Na] |

TABLE 3-continued

Additional Linker Payloads

| ID | Structure | Prepared Using Method Similar to Compound ID | MS: m/z |
|---|---|---|---|
| 294 | 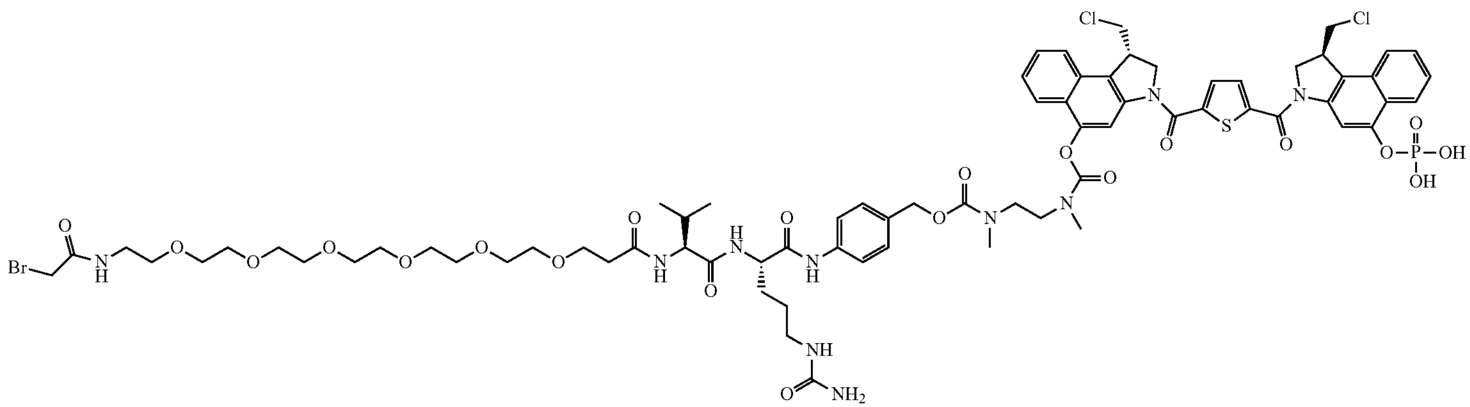 [SMILES: CC(C)[C@H](NC(=O)CCOCCOCCOCCOCCOCCOCCNC(=O)CBr)C(=O)N[C@@H](CCCNC(N)=O)C(=O)Nc1ccc(COC(=O)N(C)CCN(C)C(=O)Oc2cc3c(c4ccccc24)[C@H](CCl)CN3C(=O)c2ccc(C(=O)N3C[C@@H](CCl)c4c3cc(OP(=O)(O)O)c3ccccc43)s2)cc1] | 198 | 1659.70 [M + 3H]+ |
| 295 | 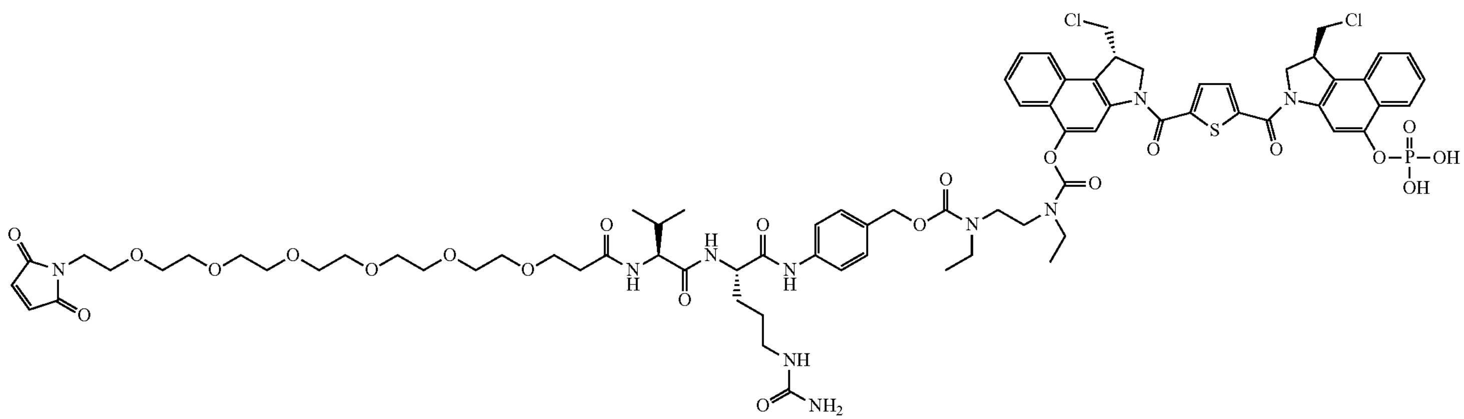 [SMILES: CCN(CCN(CC)C(=O)Oc1cc2c(c3ccccc13)[C@H](CCl)CN2C(=O)c1ccc(C(=O)N2C[C@@H](CCl)c3c2cc(OP(=O)(O)O)c2ccccc32)s1)C(=O)OCc1ccc(NC(=O)[C@H](CCCNC(N)=O)NC(=O)[C@@H](NC(=O)CCOCCOCCOCCOCCOCCOCCN2C(=O)C=CC2=O)C(C)C)cc1] | 198 | 1647.1 [M + 3H]+ |

TABLE 3-continued
Additional Linker Payloads
| ID | Structure | ID | Prepared Using Method Similar to Compound ID | MS: m/z |
|---|---|---|---|---|
| 296 | 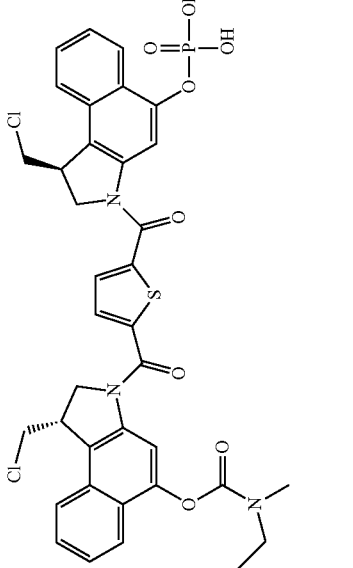 | | 198 | 1614.6 [M − H] |

TABLE 3-continued
Additional Linker Payloads
| ID | Structure | Prepared Using Method Similar to Compound ID | MS: m/z |
|---|---|---|---|
| 297 | 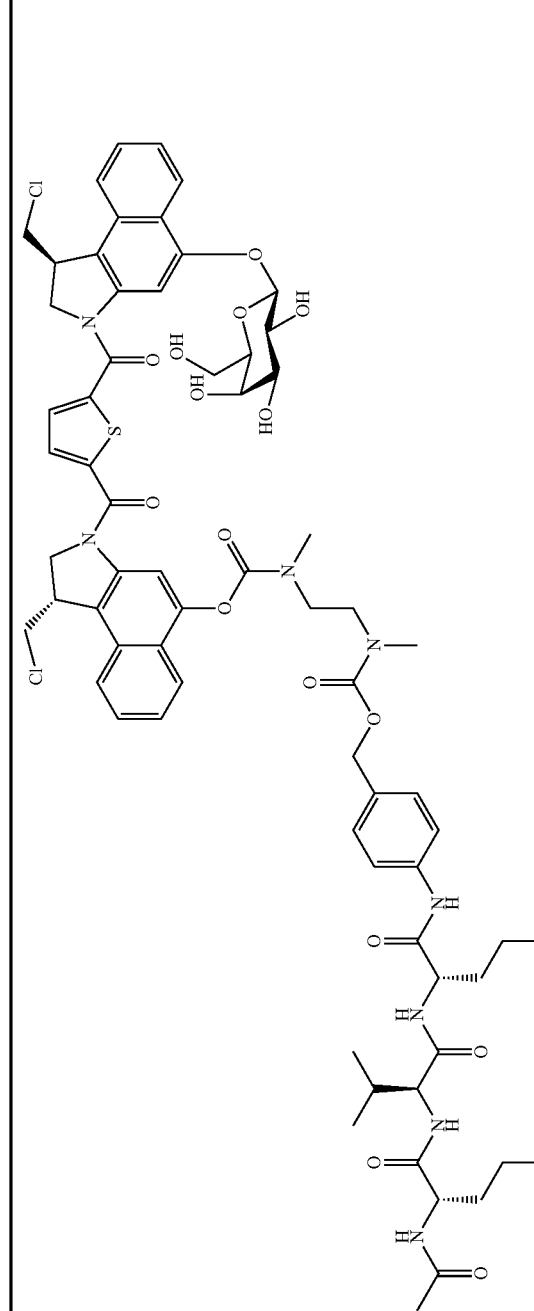 | 104[1] | 1454.5 [M + H]+ |

TABLE 3-continued
Additional Linker Payloads
| ID | Structure | Prepared Using Method Similar to Compound ID | MS: m/z |
|---|---|---|---|
| 298 | 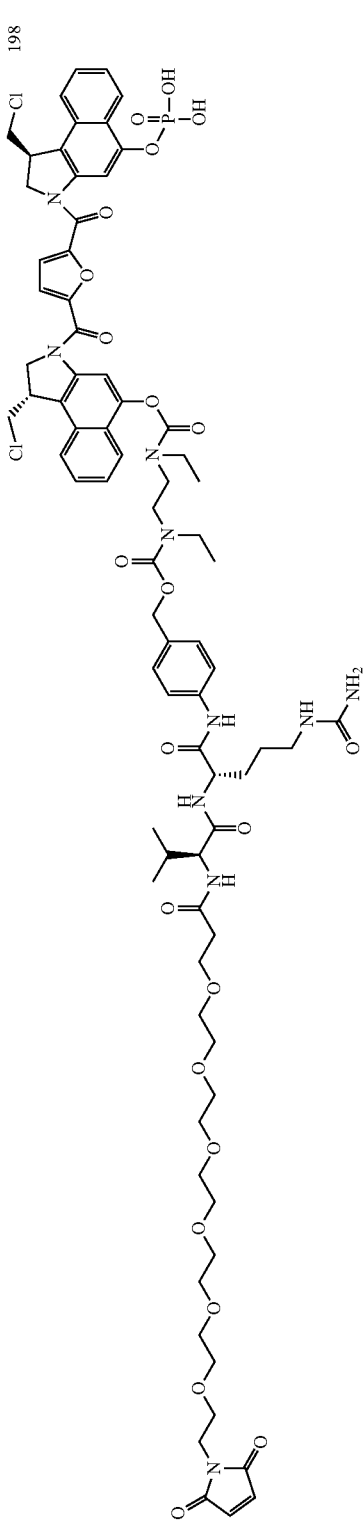 | 198 | 1629.6 [M + H]+ |
| 299 | 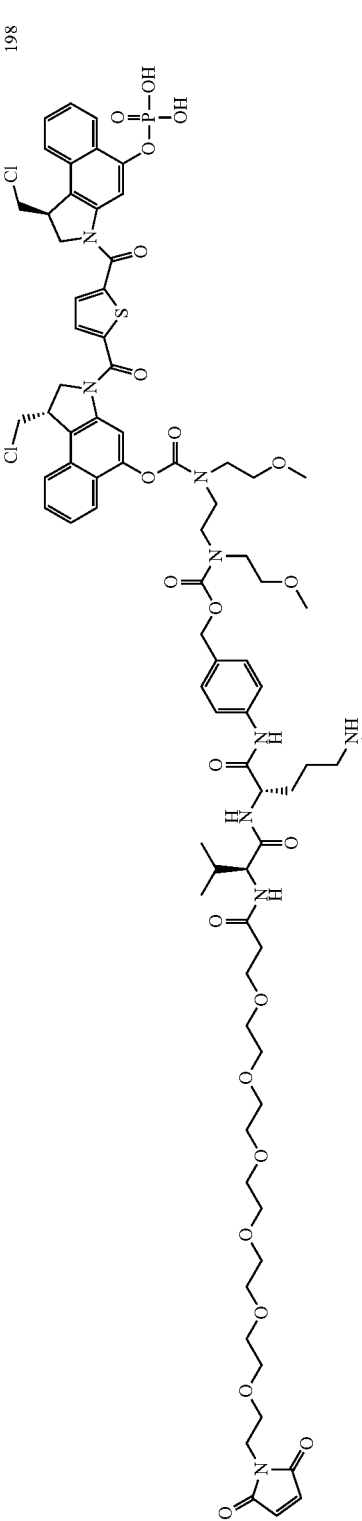 | 198 | 1705.6 [M + H]+ |

TABLE 3-continued
Additional Linker Payloads
| ID | Structure | Prepared Using Method Similar to Compound ID | MS: m/z |
|---|---|---|---|
| 300 | 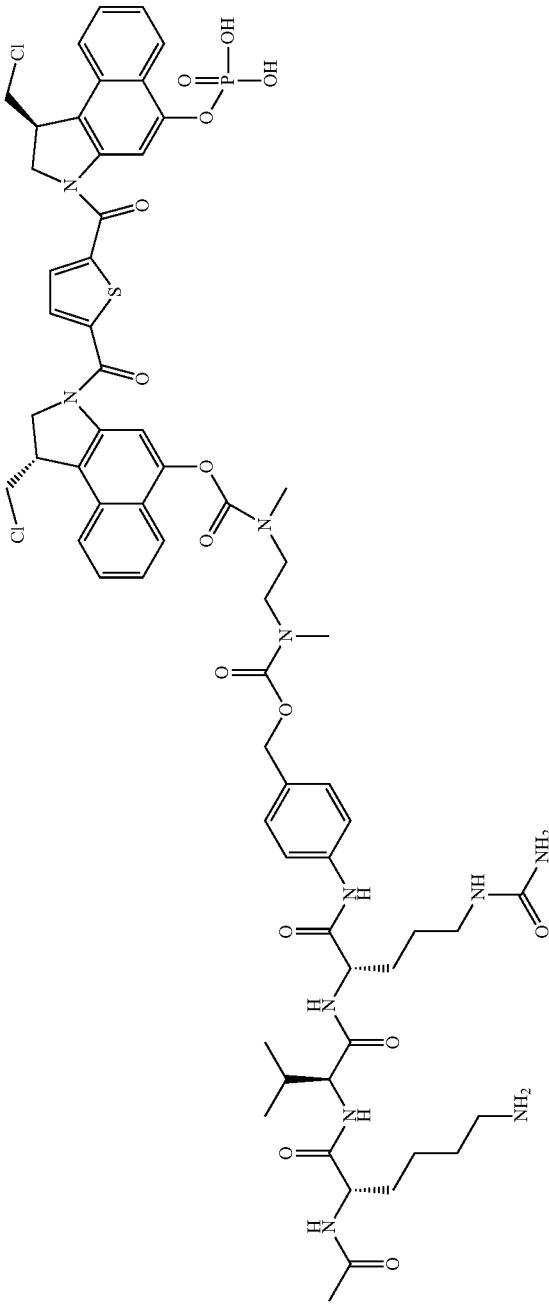 | 198 | 1372.4 [M + H]+ |

TABLE 3-continued

Additional Linker Payloads

| ID | Structure | Prepared Using Method Similar to Compound ID | MS: m/z |
|---|---|---|---|
| 301 | 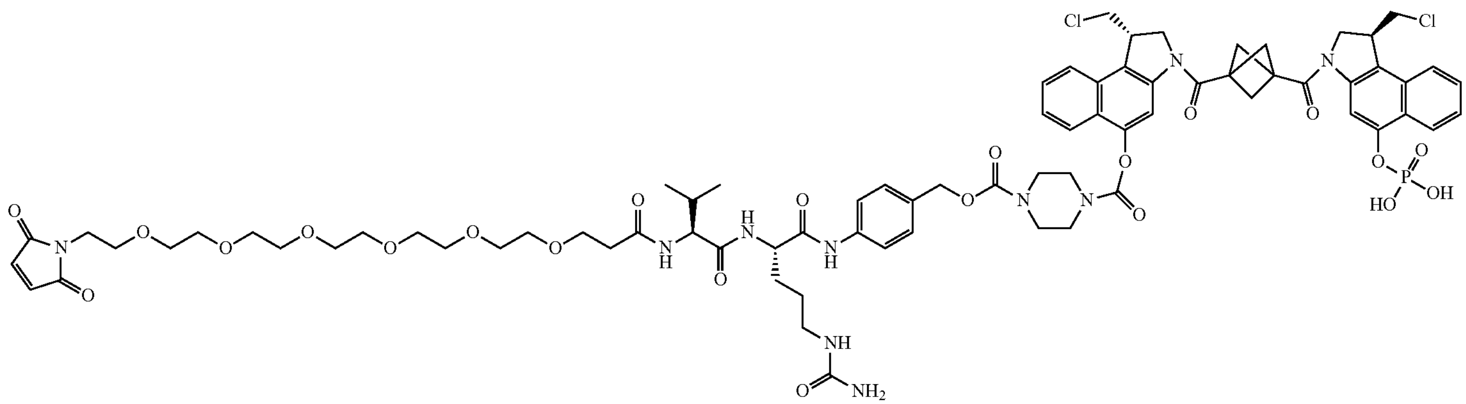 [SMILES: CC(C)[C@H](NC(=O)CCOCCOCCOCCOCCOCCOCCN1C(=O)C=CC1=O)C(=O)N[C@@H](CCCNC(N)=O)C(=O)Nc1ccc(COC(=O)N2CCN(C(=O)Oc3cc4c(c5ccccc35)[C@H](CCl)CN4C(=O)C34CC(C(=O)N5C[C@@H](CCl)c6c5cc(OP(=O)(O)O)c5ccccc65)(C3)C4)CC2)cc1] | 198 | 1599.6 [M + H]+ |
| 302 | 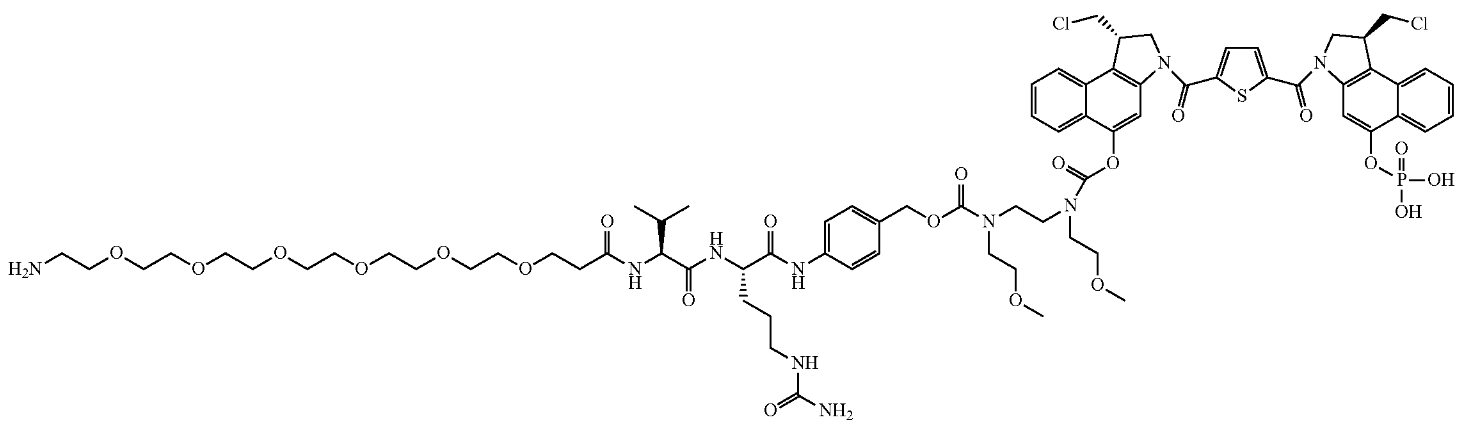 [SMILES: COCCN(CCN(CCOC)C(=O)Oc1cc2c(c3ccccc13)[C@H](CCl)CN2C(=O)c1ccc(C(=O)N2C[C@@H](CCl)c3c2cc(OP(=O)(O)O)c2ccccc32)s1)C(=O)OCc1ccc(NC(=O)[C@H](CCCNC(N)=O)NC(=O)[C@@H](NC(=O)CCOCCOCCOCCOCCOCCOCCN)C(C)C)cc1] | 198 | 1625.6 [M + H]+ |

TABLE 3-continued
Additional Linker Payloads
| ID | Structure | Prepared Using Method Similar to Compound ID | MS: m/z |
|---|---|---|---|
| 303 | 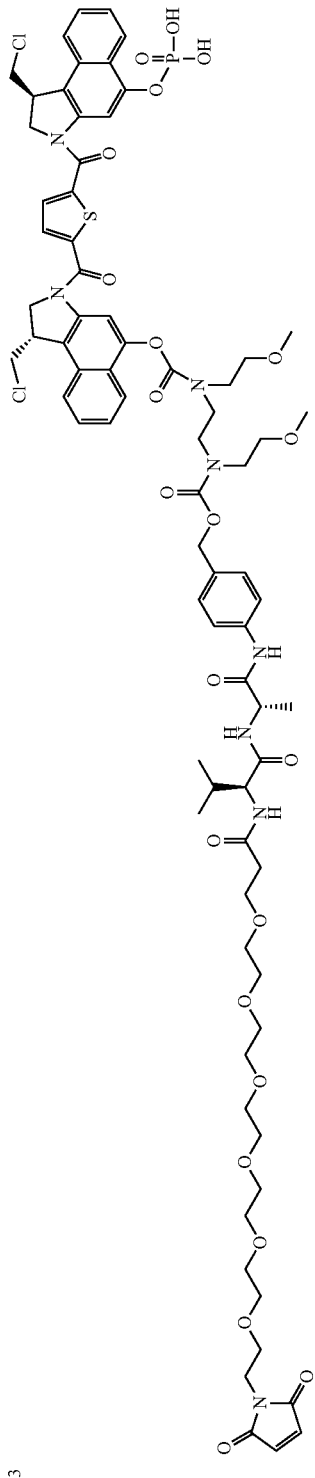 | 198 | 1619.5 [M + H]$^+$ |
| 304 | 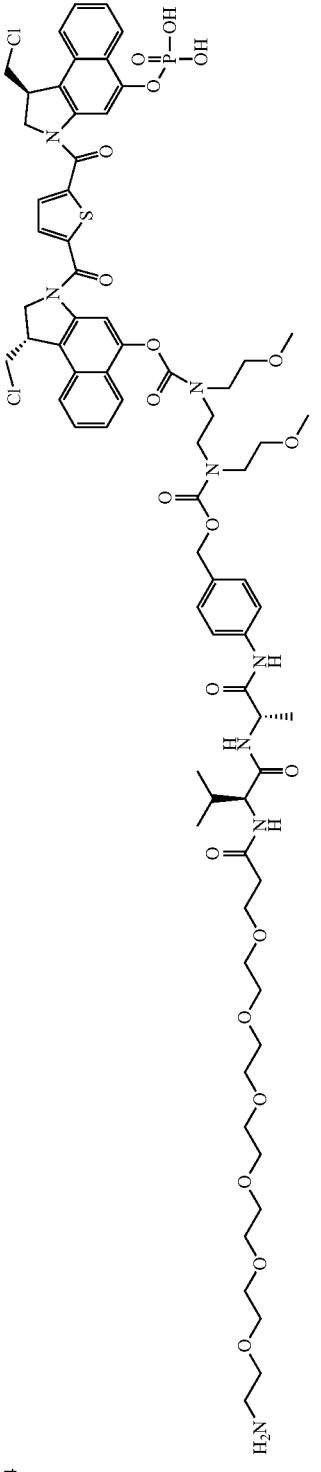 | 198 | 1539.5 [M + H]$^+$ |

TABLE 3-continued
Additional Linker Payloads
| ID | Structure | Prepared Using Method Similar to Compound ID | MS: m/z |
|---|---|---|---|
| 305 | 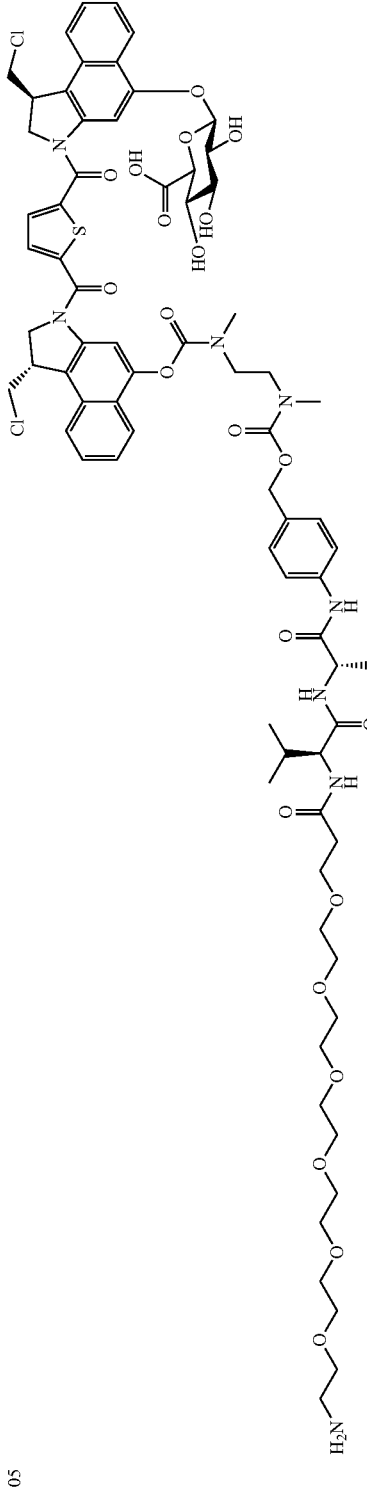 | 291 | 1633.6 [M + H]+ |
| 306 | 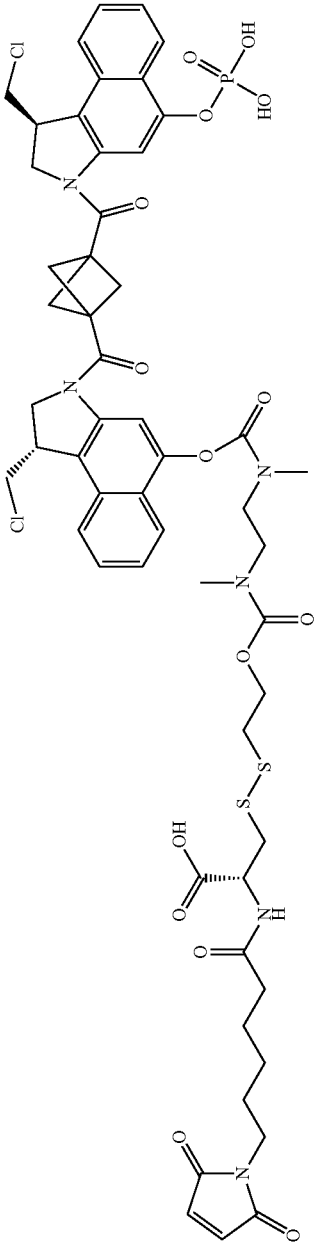 | 250 | 1199.3 [M + H]+ |

TABLE 3-continued
Additional Linker Payloads
| ID | Structure | Prepared Using Method Similar to Compound ID | MS: m/z |
|---|---|---|---|
| 307 | 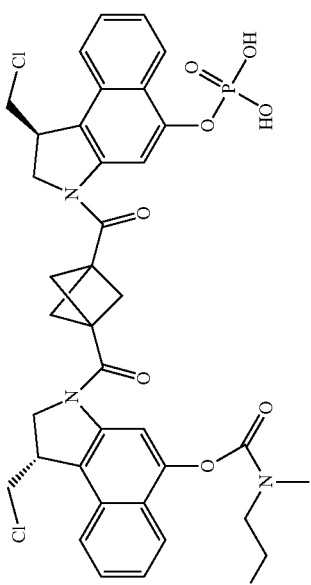 | 250 | 1227.1 [M + H]+ |
| 308 | 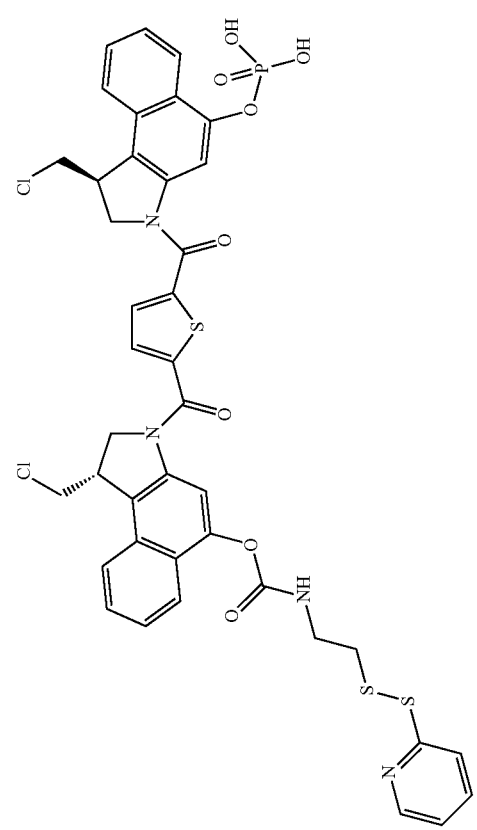 | 267 | 895.7 [M + H]+ |

TABLE 3-continued

Additional Linker Payloads

| ID | Structure | Prepared Using Method Similar to Compound ID | MS: m/z |
|---|---|---|---|
| 309 | 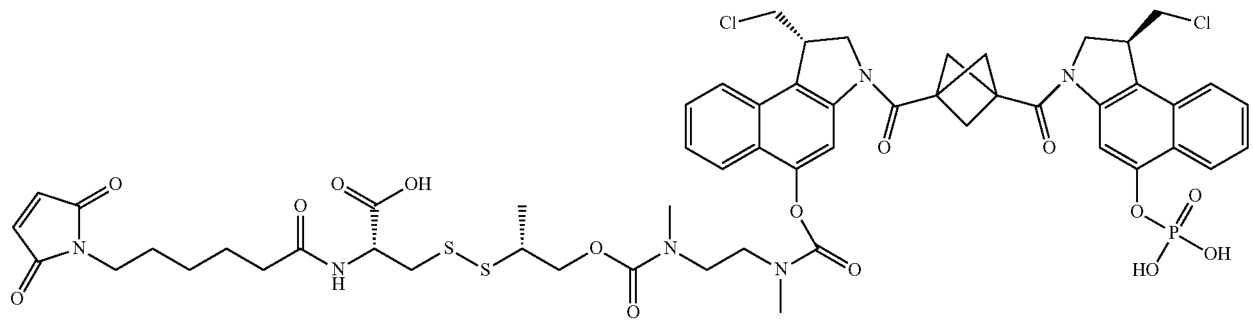 [SMILES: C[C@H](COC(=O)N(C)CCN(C)C(=O)Oc1cc2c(c3ccccc13)[C@H](CCl)CN2C(=O)C12CC(C(=O)N3C[C@@H](CCl)c4c3cc(OP(=O)(O)O)c3ccccc43)(C1)C2)SSC[C@H](NC(=O)CCCCCN1C(=O)C=CC1=O)C(=O)O] | 250 | 1213.1 [M + H]+ |
| 310 | 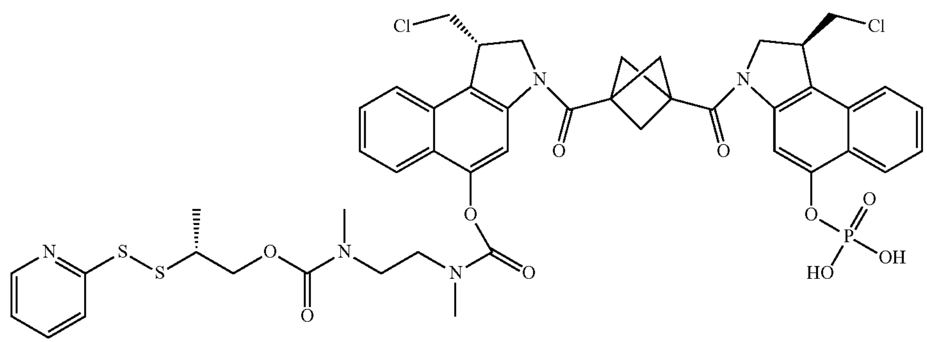 [SMILES: C[C@H](COC(=O)N(C)CCN(C)C(=O)Oc1cc2c(c3ccccc13)[C@H](CCl)CN2C(=O)C12CC(C(=O)N3C[C@@H](CCl)c4c3cc(OP(=O)(O)O)c3ccccc43)(C1)C2)SSc1ccccn1] | 250 | 1009.9 [M + H]+ |

TABLE 3-continued
Additional Linker Payloads
| ID | Structure | Prepared Using Method Similar to Compound ID | MS: m/z |
|---|---|---|---|
| 311 | 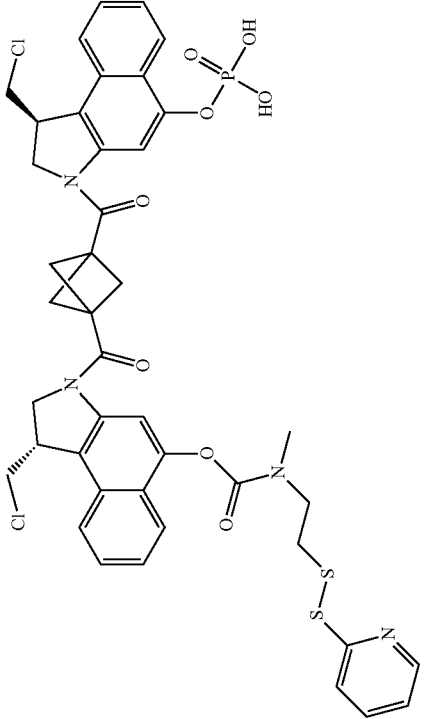 | 267 | 892.9 [M + H]+ |
| 312 | 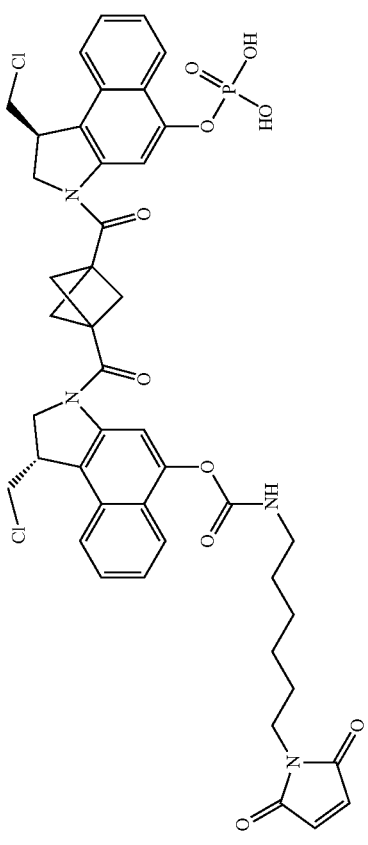 | 267 | 889.2 [M + H]+ |

TABLE 3-continued
Additional Linker Payloads
| ID | Structure | Prepared Using Method Similar to Compound ID | MS: m/z |
|---|---|---|---|
| 313 | 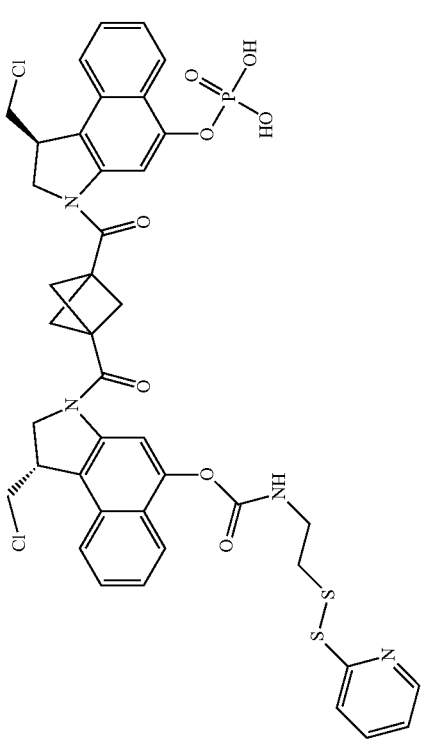 | 267 | 880.9 [M + H]+ |
| 314 | 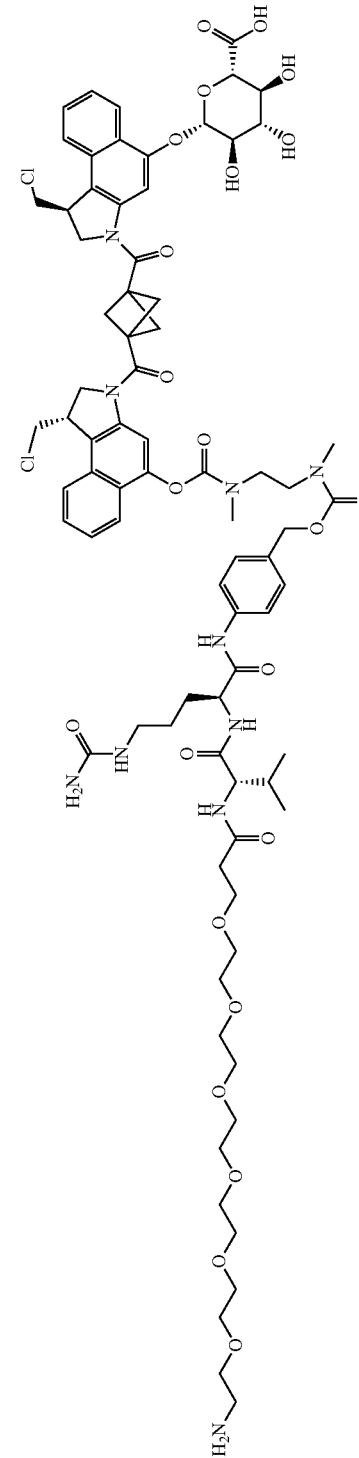 | 291 | 1618.6 [M + H]+ |

TABLE 3-continued
Additional Linker Payloads
| ID | Structure | Prepared Using Method Similar to Compound ID | MS: m/z |
|---|---|---|---|
| 315 | 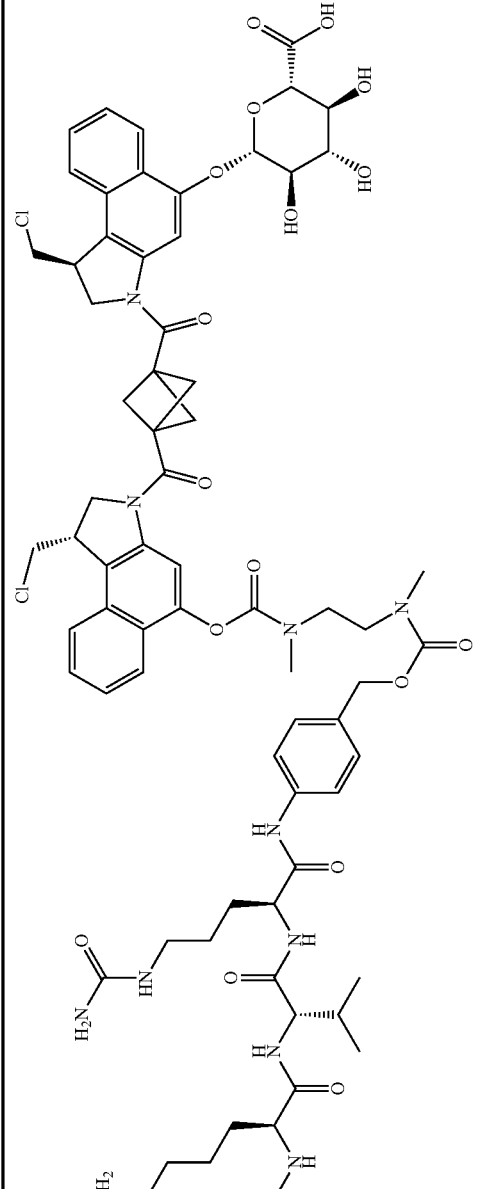 | 280 | 1453.9 [M + H]+ |
| 316 | 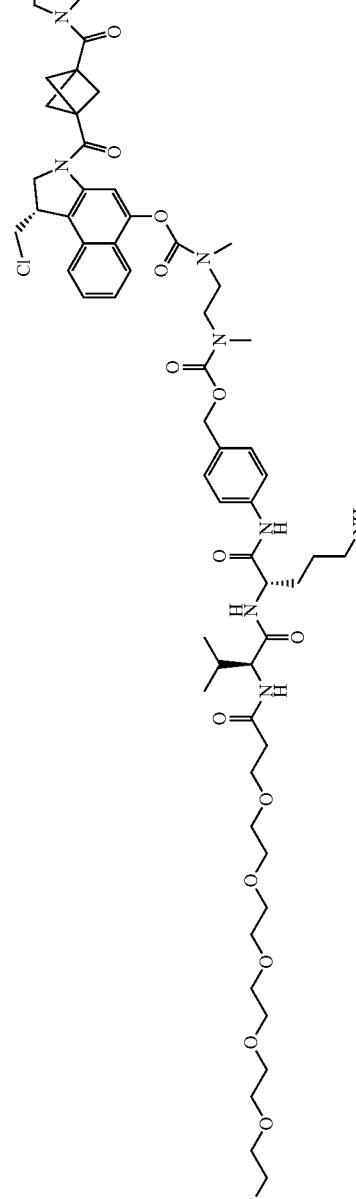 | 204 | 1604.2 [M + H]+ |

TABLE 4

Additional Linker-Payloads, IUPAC names

ID Chemical Name 292 (1S)-1-(chloromethyl)-3-[(5-{[(1S)-1-(chloromethyl)-5-({[1-(2,5-dioxo-2,5-dihydro-1H-pyrrol-1-yl)-13-methyl-12-oxo-3,6,9-trioxa-13-azapentadecan-15-yl](methyl)carbamoyl}oxy)-1,2-dihydro-3H-benzo[e]indol-3-yl}carbonyl}thiophen-2-yl)carbonyl]-2,3-dihydro-1H-benzo[e]indol-5-yl acetate 293 (1S)-1-(chloromethyl)-3-[(5-{[(1S)-1-(chloromethyl)-5-{[(2-{2-[2-(2,5-dioxo-2,5-dihydro-1H-pyrrol-1-yl)ethoxy]ethoxy}ethyl)carbamoyl]oxy}-1,2-dihydro-3H-benzo[e]indol-3-yl]carbonyl}thiophen-2-yl)carbonyl]-2,3-dihydro-1H-benzo[e]indol-5-yl acetate 294 N-(24-bromo-23-oxo-4,7,10,13,16,19-hexaoxa-22-azatetracosan-1-oyl)-L-valyl-N~5~-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide 295 N-[1-(2,5-dioxo-2,5-dihydro-1H-pyrrol-1-yl)-21-oxo-3,6,9,12,15,18-hexaoxahenicosan-21-yl]-L-valyl-N~5~-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl](ethyl)amino}ethyl)(ethyl)carbamoyl]oxy}methyl)phenyl]-L-ornithinamide 296 3-[(2,2-dimethylpropoxy)sulfonyl]-N-[6-(2,5-dioxo-2,5-dihydro-1H-pyrrol-1-yl)hexanoyl]-L-alanyl-L-valyl-N~5~-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide 297 4-((S)-2-((S)-2-((S)-2-acetamido-6-aminohexanamido)-3-methylbutanamido)-5-ureidopentanamido)benzyl ((S)-1-(chloromethyl)-3-(5-((S)-1-(chloromethyl)-5-(((2S,3R,4S,5R,6R)-3,4,5-trihydroxy-6-(hydroxymethyl)tetrahydro-2H-pyran-2-yl)oxy)-2,3-dihydro-1H-benzo[e]indole-3-carbonyl)thiophene-2-carbonyl)-2,3-dihydro-1H-benzo[e]indol-5-yl) ethane-1,2-diylbis(methylcarbamate)

298 N-[1-(2,5-dioxo-2,5-dihydro-1H-pyrrol-1-yl)-21-oxo-3,6,9,12,15,18-hexaoxahenicosan-21-yl]-L-valyl-N~5~-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}furan-2-yl)carbonyl]-2,3-dihydro-1H-benzo[e]indol-5-yl}oxy)carbonyl](ethyl)amino}ethyl)(ethyl)carbamoyl]oxy}methyl)phenyl]-L-ornithinamide 299 N-[1-(2,5-dioxo-2,5-dihydro-1H-pyrrol-1-yl)-21-oxo-3,6,9,12,15,18-hexaoxahenicosan-21-yl]-L-valyl-N~5~-carbamoyl-N-(4-{7-[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl]-4-(2-methoxyethyl)-3-oxo-2,10-dioxa-4,7-diazaundec-1-yl}phenyl)-L-ornithinamide 300 N~2~-acetyl-L-lysyl-L-valyl-N~5~-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide 301 N-[1-(2,5-dioxo-2,5-dihydro-1H-pyrrol-1-yl)-21-oxo-3,6,9,12,15,18-hexaoxahenicosan-21-yl]-L-valyl-N~5~-carbamoyl-N-(4-{[({4-[({(1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl}oxy)carbonyl]piperazin-1-yl}carbonyl)oxy]methyl}phenyl)-L-ornithinamide 302 N-(21-amino-4,7,10,13,16,19-hexaoxahenicosan-1-oyl)-L-valyl-N~5~-carbamoyl-N-(4-{7-[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl]-4-(2-methoxyethyl)-3-oxo-2,10-dioxa-4,7-diazaundec-1-yl}phenyl)-L-ornithinamide 303 N-[1-(2,5-dioxo-2,5-dihydro-1H-pyrrol-1-yl)-21-oxo-3,6,9,12,15,18-hexaoxahenicosan-21-yl]-L-valyl-N-(4-{7-[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl]-4-(2-methoxyethyl)-3-oxo-2,10-dioxa-4,7-diazaundec-1-yl}phenyl)-L-alaninamide 304 N-(21-amino-4,7,10,13,16,19-hexaoxahenicosan-1-oyl)-L-valyl-N-(4-{7-[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl]-4-(2-methoxyethyl)-3-oxo-2,10-dioxa-4,7-diazaundec-1-yl}phenyl)-L-alaninamide 305 (2S,3S,4S,5R,6S)-6-(((S)-3-(5-((S)-5-(((2-((((4-((23S,26S)-1-amino-23-isopropyl-21,24-dioxo-26-(3-ureidopropyl)-3,6,9,12,15,18-hexaoxa-22,25-diazaheptacosan-27-amido)benzyl)oxy)carbonyl)(methyl)amino)ethyl)(methyl)carbamoyl)oxy)-1-(chloromethyl)-2,3-dihydro-1H-benzo[e]indole-3-carbonyl)thiophene-2-carbonyl)-1-(chloromethyl)-2,3-dihydro-1H-benzo[e]indol-5-yl)oxy)-3,4,5-trihydroxytetrahydro-2H-pyran-2-carboxylic acid 306 3-[(2-{[(2-{[({(1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl}oxy)carbonyl](methyl)amino}ethyl)(methyl)carbamoyl]oxy}ethyl)disulfanyl]-N-[6-(2,5-dioxo-2,5-dihydro-1H-pyrrol-1-yl)hexanoyl]-L-alanine 307 3-[(2-{[(2-{[({(1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl}oxy)carbonyl](methyl)amino}ethyl)(methyl)carbamoyl]oxy}ethyl)disulfanyl]-N-[6-(2,5-dioxo-2,5-dihydro-1H-pyrrol-1-yl)hexanoyl]-L-valine 308 (1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl [2-(pyridin-2-yldisulfanyl)ethyl]carbamate TABLE 4-continued Additional Linker-Payloads, IUPAC names

| ID | Chemical Name |
|---|---|
| 309 | 3-{[(2R)-1-{[(2-{[({(1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl} oxy)carbonyl](methyl)amino}ethyl)(methyl)carbamoyl]oxy}propan-2-yl]disulfanyl}-N-[6-(2,5-dioxo-2,5-dihydro-1H-pyrrol-1-yl)hexanoyl]-L-alanine |
| 310 | (1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl (2R)-2-(pyridin-2-yl disulfanyl)propyl ethane-1,2-diylbis(methylcarbamate) |
| 311 | (1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl methyl[2-(pyridin-2-yldisulfanyl)ethyl]carbamate |
| 312 | (1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl [6-(2,5-dioxo-2,5-dihydro-1H-pyrrol-1-yl)hexyl]carbamate |
| 313 | (1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl [2-(pyridin-2-yldisulfanyl)ethyl]carbamate |
| 314 | N-(21-amino-4,7,10,13,16,19-hexaoxahenicosan-1-oyl)-L-valyl-N~5~-carbamoyl-N-[4-({[(2-{[({(1S)-1-(chloromethyl)-3-[(3-{[(1S)-1-(chloromethyl)-5-(beta-D-glucopyranuronosyloxy)-1,2-dihydro-3H-benzo[e]indol-3-yl]carbonyl}bicyclo[1.1.1]pent-1-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide |
| 315 | N~2~-acetyl-L-lysyl-L-valyl-N~5~-carbamoyl-N-[4-({[(2-{[({(1S)-1-(chloromethyl)-3-[(3-{[(1S)-1-(chloromethyl)-5-(beta-D-glucopyranuronosyloxy)-1,2-dihydro-3H-benzo[e]indol-3-yl]carbonyl}bicyclo[1.1.1] pent-1-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide |
| 316 | N-[1-(2,5-dioxo-2,5-dihydro-1H-pyrrol-1-yl)-21-oxo-3,6,9,12,15,18-hexaoxahenicosan-21-yl]-L-valyl-N~5~-carbamoyl-N-[4-({[[(2-{[({(1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide |

The invention further provides the compounds described in Tables 5A and 5B.

TABLE 5A

Representative Thiocarbamate Linker Payoads

| ID | Structure | Suggested method of synthesis | M/S (predicted) |
|---|---|---|---|
| 317 | 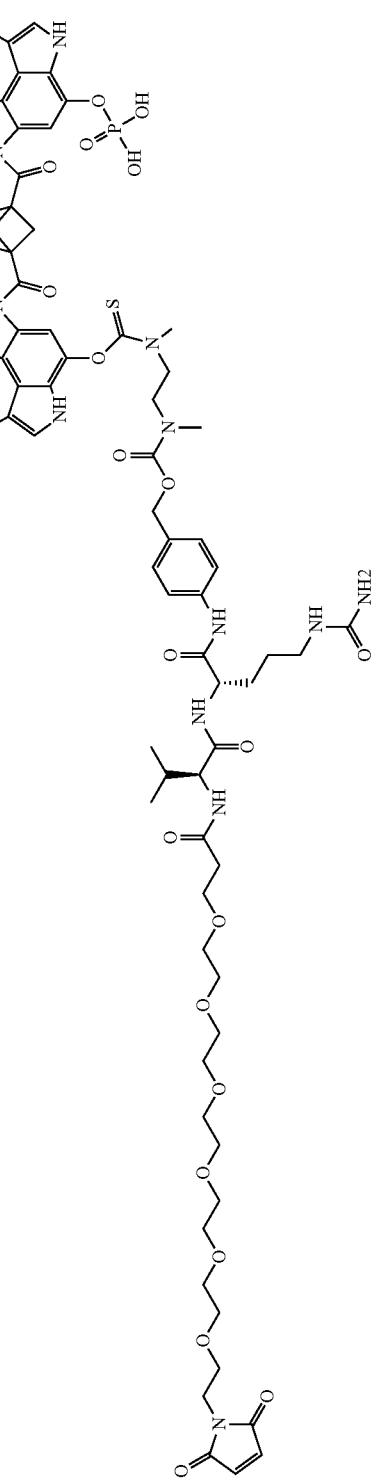 4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosan-27-amido)benzyl (2-((((S)-8-(chloromethyl)-6-(3-((S)-1-(chloromethyl)-8-methyl-5-(phosphonooxy)-1,2,3,6-tetrahydropyrrolo[3,2-e]indole-3-carbonyl)bicyclo[1.1.1]pentane-1-carbonyl)-1-methyl-3,6,7,8-tetrahydropyrrolo[3,2-e]indol-4-yl)oxy)carbonothioyl)(methyl)amino)ethyl)(methyl)carbamate | 231 | 1622.57 |

TABLE 5A-continued

Representative Thiocarbamate Linker Payoads

| ID | Structure | Suggested method of synthesis | M/S (predicted) |
|---|---|---|---|
| 318 | (S)-8-(chloromethyl)-6-(3-((S)-1-(chloromethyl)-8-methyl-5-(phosphonooxy)-1,2,3,6-tetrahydropyrrolo[3,2-e]indole-3-carbonyl)bicyclo[1.1.1]pentane-1-carbonyl)-1-methyl-3,6,7,8-tetrahydropyrrolo[3,2-e]indol-4-yl (2-((((4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosan-27-amido)benzyl)oxy)carbonothioyl)(methyl)amino)ethyl)(methyl)carbamate | 231 | 1622.57 |

TABLE 5A-continued

Representative Thiocarbamate Linker Payoads

| ID | Structure | Suggested method of synthesis | M/S (predicted) |
|---|---|---|---|
| 319 | O'-((S)-8-(chloromethyl)-6-(3-((S)-1-(chloromethyl)-8-methyl-5-(phosphonooxy)-1,2,3,6-tetrahydropyrrolo[3,2-e]indole-3-carbonyl)bicyclo[1.1.1]pentane-1-carbonyl)-1-methyl-3,6,7,8-tetrahydropyrrolo[3,2-e]indol-4-yl) O-(4-((23S,26S)-1-(2,5-dioxo-2,5-dihydro-1H-pyrrol-1-yl)-23-isopropyl-21,24-dioxo-26-(3-ureidopropyl)-3,6,9,12,15,18-hexaoxa-22,25-diazaheptacosan-27-amido)benzyl) ethane-1,2-diylbis(methylcarbamothioate) | 231 | 1641.65 |

TABLE 5A-continued

Representative Thiocarbamate Linker Payoads

| ID | Structure | Suggested method of synthesis | M/S (predicted) |
|---|---|---|---|
| 320 | 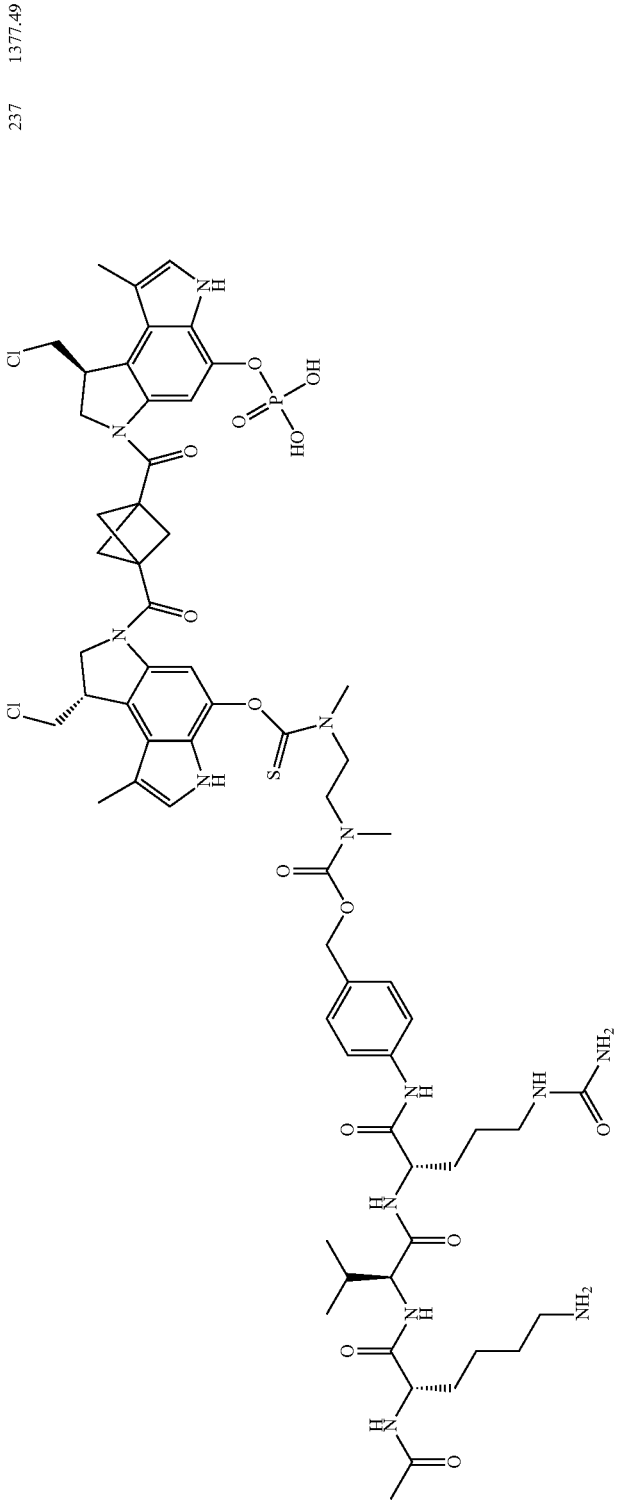 4-(((S)-2-((S)-2-((S)-2-acetamido-6-aminohexanamido)-3-methylbutanamido)-5-ureidopentanamido)benzyl (2-((((S)-8-(chloromethyl)-6-(3-(((S)-1-(chloromethyl)-8-methyl-5-(phosphonooxy)-1,2,3,6-tetrahydropyrrolo[3,2-e]indole-3-carbonyl)bicyclo[1.1.1]pentane-1-carbonyl)-1-methyl-3,6,7,8-tetrahydropyrrolo[3,2-e]indol-4-yl)oxy)carbonothioyl)(methyl)amino)ethyl)(methyl)carbamate | 237 | 1377.49 |

TABLE 5A-continued

Representative Thiocarbamate Linker Payoads

| ID | Structure | Suggested method of synthesis | M/S (predicted) |
|---|---|---|---|
| 321 | (S)-8-(chloromethyl)-6-(3-((S)-1-(chloromethyl)-8-methyl-5-(phosphonooxy)-1,2,3,6-tetrahydropyrrolo[3,2-e]indole-3-carbonyl)bicyclo[1.1.1]pentane-1-carbonyl)-1-methyl-3,6,7,8-tetrahydropyrrolo[3,2-e]indol-4-yl (2-(((4-((S)-2-((S)-2-((S)-2-acetamido-6-aminohexanamido)-3-methylbutanamido)-5-ureidopentanamido)benzyl)oxy)carbonothioyl)(methyl)amino)ethyl)(methyl)carbamate | 237 | 1377.49 |

TABLE 5A-continued

Representative Thiocarbamate Linker Payoads

| ID | Structure | Suggested method of synthesis | M/S (predicted) |
|---|---|---|---|
| 322 | O-(4-((S)-2-((S)-2-((S)-2-acetamido-6-aminohexanamido)-3-methylbutanamido)-5-ureidopentanamido)benzyl) O'-((S)-8-(chloromethyl)-6-(3-((S)-1-(chloromethyl)-8-methyl-5-(phosphonooxy)-1,2,3,6-tetrahydropyrrolo[3,2-e]indole-3-carbonyl)bicyclo[1.1.1]pentane-1-carbonyl)-1-methyl-3,6,7,8-tetrahydropyrrolo[3,2-e]indol-4-yl) ethane-1,2-diylbis(methylcarbamothioate) | 237 | 1393.47 |

TABLE 5B
Representative Cubane Linker Payoads
| ID | Structure | Method of synthesis | M/S (predicted) |
|---|---|---|---|
| 323 | 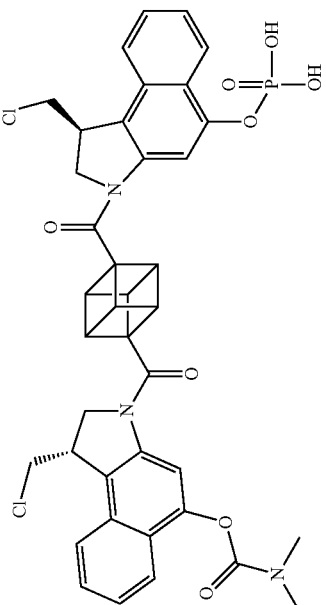 | 237 | 1392.5 [M + H]+ |

TABLE 5B-continued
Representative Cubane Linker Payoads
| ID | Structure | Method of synthesis | M/S (predicted) |
|---|---|---|---|
| 324 | 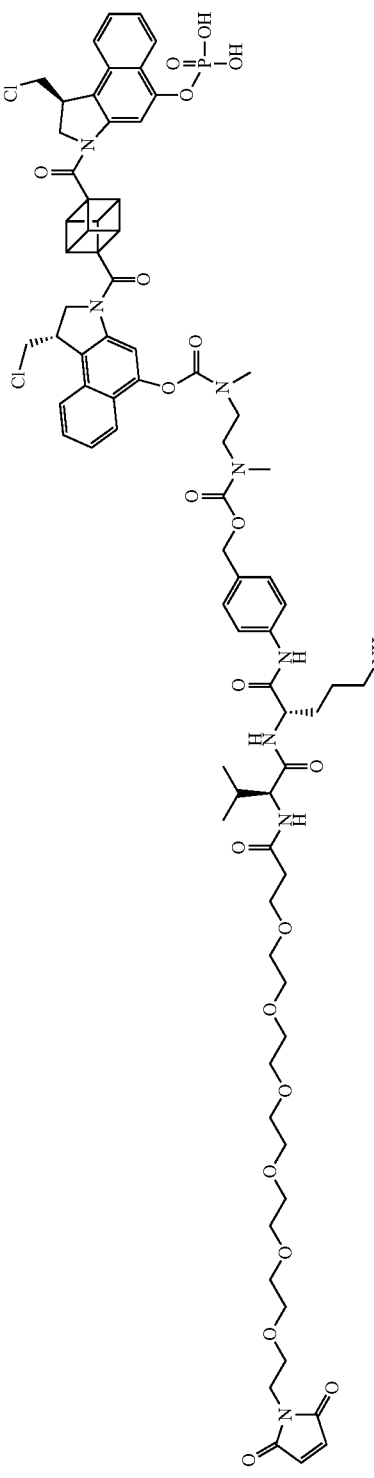 | 237 | 1636.1 [M + H]+ |

HPLC and LC-MS Conditions Used for Analysis

Protocol A:

Column: Waters Acquity UPLC HSS T3, 2.1 mm×50 mm, C18, 1.7 μm; Mobile phase A: 0.1% formic acid in water (v/v); Mobile phase B: 0.1% formic acid in acetonitrile (v/v); Gradient: 5% B over 0.1 minute, 5% to 95% B over 0.9 minutes, 95% B over 0.1 minute; Flow rate: 1.25 mL/minute. Temperature: 60° C.; Detection: 200-450 nm; MS (+) range 100-2000 daltons; Injection volume: 5 μL; Instrument: Waters Acquity.

Protocol B:

Column: Waters Acquity UPLC HSS T3, 2.1 mm×50 mm, C18, 1.7 μm; Mobile phase A: 0.1% formic acid in water (v/v); Mobile phase B: 0.1% formic acid in acetonitrile (v/v); Gradient: 5% B over 0.1 minute, 5% to 95% B over 2.5 minutes, 95% B over 0.35 minute; Flow rate: 1.25 mL/minute. Temperature: 60° C.; Detection: 200-450 nm; MS (+) range 100-2000 daltons; Injection volume: 5 μL; Instrument: Waters Acquity.

Protocol C:

Column: Phenomenex Luna C18 (2), 150×3.0 mm, 5 μm; Mobile phase A: 0.1% formic acid in water (v/v); Mobile phase B: 0.1% formic acid in acetonitrile (v/v); Gradient: 50% B over 1.5 minutes, 50% to 100% B over 6.5 minutes, then 100% B over 3 minutes; Flow rate: 0.75 mL/minute. Temperature: 45° C.; Detection: DAD 215 nm, 254 nm; MS (+) range 150-2000 daltons; Injection volume: 10 μL; Instrument: Agilent 1200 LCMS.

Protocol D:

Column: Phenomenex Luna C18 PFP(2), 150×3.0 mm, 5 μm; Mobile phase A: 0.1% formic acid in water (v/v); Mobile phase B: 0.1% formic acid in acetonitrile (v/v); Gradient: 0% to 5% B over 1.5 minutes, 5% to 100% B over 8.5 minutes, then 100% B over 2 minutes; Flow rate: 0.75 mL/minute. Temperature: not controlled; Detection: DAD 215 nm, 254 nm; MS (+) range 150-2000 daltons; Injection volume: 10 μL; Instrument: Agilent 1200 LCMS.

Protocol E:

Column: Phenomenex Luna C18 PFP(2), 150×3.0 mm, 5 μm; Mobile phase A: 0.1% formic acid in water (v/v); Mobile phase B: 0.1% formic acid in acetonitrile (v/v); Gradient: 5% B over 1.5 minutes, 5% to 100% B over 8.5 minutes, then 100% B over 2 minutes; Flow rate: 0.75 mL/minute. Temperature: not controlled; Detection: DAD 215 nm, 254 nm; MS (+) range 150-2000 daltons; Injection volume: 10 μL; Instrument: Agilent 1200 LCMS.

Protocol F:

Column: Xtimate C18, 30×2.1 mm, 3 μm; Mobile phase A: 0.037% TFA in water (v/v); Mobile phase B: 0.037% TFA in acetonitrile (v/v); Gradient: 10% B over 0.1 minutes, 10% to 80% B over 3 minutes, then 80% B over 0.1 minutes; Flow rate: 1.5 mL/minute. Temperature: 40° C.; Detection: DAD 220 nm; MS (+) range 100-1000 daltons; Injection volume: 3 μL; Instrument: Shimadzu.

Protocol G:

Column: Xtimate C18, 30×2.1 mm, 3 μm; Mobile phase A: 0.037% TFA in water (v/v); Mobile phase B: 0.037% TFA in acetonitrile (v/v); Gradient: 10% B over 0.1 minutes, 10% to 80% B over 3 minutes, then 80% B over 0.1 minutes; Flow rate: 1.5 mL/minute. Temperature: 40° C.; Detection: DAD 220 nm; MS (+) range 100-1000 daltons; Injection volume: 3 μL; Instrument: Shimadzu.

Protocol H:

Column: Xtimate C18, 30×2.1 mm, 3 μm; Mobile phase A: 0.037% TFA in water (v/v); Mobile phase B: 0.037% TFA in acetonitrile (v/v); Gradient: 0% B over 0.1 minutes, 0% to 60% B over 2 minutes, then 60% B over 0.1 minutes; Flow rate: 1.5 mL/minute. Temperature: 40° C.; Detection: DAD 220 nm; MS (+) range 100-1000 daltons; Injection volume: 2 μL; Instrument: Shimadzu.

HPLC Conditions Used for Purification

Method A:

Column: Phenomenex Luna C18(2), 150×21.2 mm, 5 μm; Mobile phase A: 0.02% formic acid in water; Mobile phase B: 0.02% formic acid in acetonitrile; Gradient: 40% B over 1.5 minutes, 40% to 100% B over 8.5 minutes, 100% B over 0.5 minutes; Flow rate: 27 mL/minute; Detection: DAD 215 nm, 254 nm; MS (+) range 150-2000 daltons; Instrument: Waters FractionLynx.

Method B:

Column: Phenomenex Luna PFP (2), 150×21.2 mm, 5 μm; Mobile phase A: 0.02% formic acid in water; Mobile phase B: 0.02% formic acid in acetonitrile; Gradient: 30% B over 1.5 minutes, 30% to 60% B over 8.5 minutes, 60% B to 100% B over 0.5 minutes, 100% B over 2 minutes; Flow rate: 27 mL/minute; Detection: DAD 215 nm, 254 nm; MS (+) range 150-2000 daltons; Instrument: Waters Fraction Lynx.

Method C:

Column: Phenomenex Synergi Polar RP, 150×21.2 mm, 4 μm; Mobile phase A: 0.02% formic acid in water; Mobile phase B: 0.02% formic acid in acetonitrile; Gradient: 20% B over 1.5 minutes, 20% to 50% B over 8.5 minutes, 50% B to 100% B over 0.5 minutes, 100% B over 2 minutes; Flow rate: 27 mL/minute; Detection: DAD 210-360 nm; MS (+) range 150-2000 daltons; Instrument: Waters Fraction Lynx.

Method D:

Column: Xtimate C18, 30×2.1 mm, 3 μm; Mobile phase A: 0.2% TFA in water (v/v); Mobile phase B: 0.2% TFA in acetonitrile (v/v); Gradient: 25% B over 1.5 minutes, 25% to 50% B over 25 minutes, then 100% B over 5.0 minutes; Flow rate: 90 mL/minute. Temperature: not controlled; Detection: DAD 220 nm; MS (+) range 100-1000 daltons; Instrument: Shimadzu.

Method E:

Column: LUNA C18, 250×50 mm, 10 μm; Mobile phase A: 0.2% TFA in water (v/v); Mobile phase B: 0.2% TFA in acetonitrile (v/v); Gradient: 25% B over 1.5 minutes, 25% to 55% B over 25 minutes, then 100% B over 5.0 minutes; Flow rate: 90 mL/minute. Temperature: not controlled; Detection: DAD 220 nm; MS (+) range 100-1000 daltons; Instrument: Shimadzu.

Method F:

Column: Phenomenex Luna C18(2), 250×50 mm, 10 μm; Mobile phase A: 0.2% TFA in water (v/v); Mobile phase B: 0.2% TFA in acetonitrile (v/v); Gradient: 35% to 65% B over 30 minutes, then 100% B over 5.0 minutes; Flow rate: 90 mL/minute. Temperature: not controlled; Detection: DAD 220 nm; MS (+) range 100-1000 daltons; Instrument: Shimadzu.

Method G:

Column: Phenomenex Luna C18(2), 250×50 mm, 10 μm; Mobile phase A: 0.2% TFA in water (v/v); Mobile phase B: 0.2% TFA in acetonitrile (v/v); Gradient: 10% B over 1.5 minutes, 10% B to 55% B over 8.5 minutes, 55% B to 100% B over 0.5 minutes, then held at 100% B for 1.5 minutes; Flow rate: 27 mL/minute. Temperature: not controlled; Detection: DAD 210-360 nm; MS (+) range 150-2000 daltons; Instrument: 305 RP Waters Fractional Lynx LCMS Method H:

Column: Phenomenex Luna C18(2), 150×21.2 mm, 5 μm; Mobile phase A: 0.2% TFA in water (v/v); Mobile phase B: 0.2% TFA in acetonitrile (v/v); Gradient: 10% B over 1.5 minutes, 10% B to 75% B over 8.5 minutes, then 75% B to 100% B over 2.0 minutes; Flow rate: 27 mL/minute. Temperature: not controlled; Detection: DAD 210-360 nm; MS (+) range 150-2000 daltons; Instrument: 305 RP Waters Fractional Lynx LCMS.

Method H1:

Column: Phenomenex Luna C18(2), 150×21.2 mm, 5 µm; Mobile phase A: 0.2% TFA in water (v/v); Mobile phase B: 0.2% TFA in acetonitrile (v/v); Gradient: 1% B over 1.5 minutes, 1% B to 100% B over 8.5 minutes, then 100% B over 2.0 minutes; Flow rate: 27 mL/minute. Temperature: not controlled; Detection: DAD 210-360 nm; MS (+) range 150-2000 daltons; Instrument: 305 RP Waters Fractional Lynx LCMS.

Method I1:

Column: Phenomenex Luna PFP (2), 150×21.2 mm, 5 µm; Mobile phase A: 0.02% TFA in water; Mobile phase B: 0.02% TFA in acetonitrile; Gradient: 40% B over 1.5 minutes, 40% to 100% B over 8.5 minutes, 100% B over 2.0 minutes; Flow rate: 27 mL/minute; Detection: DAD 215 nm, 254 nm; MS (+) range 150-2000 daltons; Instrument: 305 Waters FractionLynx LCMS.

Method I2:

Column: Phenomenex Luna PFP (2), 150×21.2 mm, 5 µm; Mobile phase A: 0.02% TFA in water; Mobile phase B: 0.02% TFA in acetonitrile; Gradient: 1% B over 1.5 minutes, 1% to 100% B over 8.5 minutes, 100% B over 2.0 minutes; Flow rate: 27 mL/minute; Detection: DAD 215 nm, 254 nm; MS (+) range 150-2000 daltons; Instrument: 305 Waters FractionLynx LCMS.

Method J1:

Column: Phenomenex Synergi Polar RP, 150×21.2 mm, 4 µm; Mobile phase A: 0.02% TFA in water; Mobile phase B: 0.02% TFA in acetonitrile; Gradient: 10% B over 1.5 minutes, 10% to 75% B over 8.5 minutes, 75% B to 100% B over 0.5 minutes, 100% B over 2 minutes; Flow rate: 27 mL/minute; Detection: DAD 210-360 nm; MS (+) range 150-2000 daltons; Instrument: Waters FractionLynx.

Method K1:

Column: Phenomenex Luna C18(2), 250×50 mm, 10 µm; Mobile phase A: 0.2% TFA in water (v/v); Mobile phase B: 0.2% TFA in acetonitrile (v/v); Gradient: 1% B over 1.5 minutes, 1% B to 75% B over 8.5 minutes, 75% B to 100% B over 0.5 minutes, then held at 100% B for 1.5 minutes; Flow rate: 27 mL/minute. Temperature: not controlled; Detection: DAD 210-360 nm; MS (+) range 150-2000 daltons; Instrument: 305 RP Waters Fractional Lynx LCMS.

Method L1:

Column: ChiralTech AD-H, 500×21.5 mm, 5 µm; Mobile phase A: $CO_2$ (v/v); Mobile phase B: methanol (v/v); Gradient: Iscocractic conditions 60% $CO_2$, 40% methanol; Flow rate: 36 mL/minute $CO_2$, 24 mL/minute methanol. Backpressure 100 bar; Detection: DAD 210; Instrument: Thar 80 (Waters).

Method M:

Column: Phenomenex Synergi, 250×50 mm, 10 µm; Mobile phase A: 0.1% TFA in water; Mobile phase B: 0.1% TFA in acetonitrile; Gradient: 40% to 70% B over 30 minutes, then 95% B over 5.0 minutes; Flow rate: 80 mL/minute; Detection: DAD 220, 254 nm; MS (+) range 100-1000 daltons; Instrument: Shimadzu LC-20AP.

Method N

Column: Phenomenex Luna Phenylhexyl 150×21.2 mm, 5 µm; Mobile phase A: 0.2% TFA in water (v/v); Mobile phase B: 0.2% TFA in acetonitrile (v/v); Gradient: 35% B over 1.5 minutes, 35% B to 100% B over 18.5 minutes, then 100% B over 2.0 minutes; Flow rate: 27 mL/minute. Temperature: not controlled; Detection: DAD 210-360 nm; MS (+) range 150-2000 daltons; Instrument: 305 RP Waters Fractional Lynx LCMS.

Exemplification of Antibody Drug Conjugates

Protocol A: General Procedure for Conjugation of Antibody with Linker-Payload Via Internal Disulfides IL13Rα2-AB08-v1.0/1.0-human IgG1 antibody [Pfizer, 12-13 mg/mL solution in Dulbecco's Phosphate Buffered Saline (DPBS, Lonza, pH 7.4)] or VEGFR-1121 B-human IgG1 antibody [Pfizer, 19.3 mg/mL solution in Dulbecco's Phosphate Buffered Saline (DPBS, Lonza, pH 7.4)] was reduced with addition of 2.9-3 equivalents of tris(2-carboxyethyl)phosphine hydrochloride (TCEP, 5 mM solution in DPBS). The reaction was incubated at 37° C. for 1-1.25 h and then allowed to cool to ambient temperature. Conjugation was performed by addition of 7 equivalents of linker-payload [10 mM solution in N,N-dimethylacetamide (DMA)]. Additional DMA was added to reaction mixture to achieve 10-15% (v/v) total organic solvent component in final reaction mixture. The reaction was incubated for 1 h at ambient temperature. For ADCs 1-5, after 1 h at ambient temperature, excess linker-payload was quenched via addition of 10 equivalents of cysteine (20 mM solution in DPBS). The quenched reaction mixture was aged at ambient temperature for 15 minutes, and then stored at 4° C. until purified. For ADCs 6-14, after 1 h at ambient temperature, the reaction mixture was desalted via GE Sephadex gel desalting columns and DPBS (pH7.4) eluent, and then stored at 4° C. until purified. Crude material was purified by size exclusion chromatography (SEC) using GE AKTA Explorer system with GE Superdex 200 (10/300 GL) column and DPBS (pH7.4) eluent.

Protocol B:

Column: Agilent Poroshell 300SB-C8, 75×2.1 mm, 2.6 µm; Mobile phase A: 0.1% formic acid in water (v/v); Mobile phase B: 0.1% formic acid in acetonitrile (v/v); Gradient: Initial Conditions: 20% B to 45% B over 4 minutes; Flow rate: 1.0 mL/minute. Temperature: 60° C.; Detection: 220 nm; MS (+) range 400-2000 Da; Injection volume: 10 µL; Instrument: Agilent 1100 LC, Waters MicromassZQ MS. Deconvolution was performed using MaxEnt1.

Protocol C:

Column: GE Superdex 200 (5/150 GL); Mobile phase: Phosphate buffered saline (PBS, 1×, pH 7.4) with 2% acetonitrile; Isocratic; Flow rate: 0.25 mL/minute. Temperature: room temperature; Injection Volume: 10 µL; Instrument: Agilent 1100 HPLC.

Protocol D:

Preparation of transglutaminase ADC's, exemplified for the linker payload AcLys-vc-MMAD ("Location matters: site of conjugation modulates stability and pharmacokinetics of antibody drug conjugates", Chem Biol. 2013, 20, 161-7). For the conjugation of C16-HC and C16-LC to AcLys-vcMMAD, antibody was adjusted to 5 mg/mL in buffer containing 25 mM Tris-HCl at pH 8.0, and 150 mM NaCl, AcLys-vc-MMAD was added in either a 5-fold (C16-HC) or 10-fold (C16-LC) molar excess over antibody and the enzymatic reaction initiated by addition of 1% (w/v) (C16-HC) or 2% (w/v) (C16-LC) bacterial transglutaminase (Ajinomoto Activa TI, Japan). Following incubation with gentle shaking at 22° C. (C16-HC) or 37° C. (C16-LC) for 16 hours, the ADC was purified using MabSelect SuRe (GE Healthcare, Inc) using standard procedures.

The invention further provides the compounds described in Tables 6A and 6B.

TABLE 6A
Antibody Drug Conjugates
| ID | Structure |
|---|---|
| ADC1 | 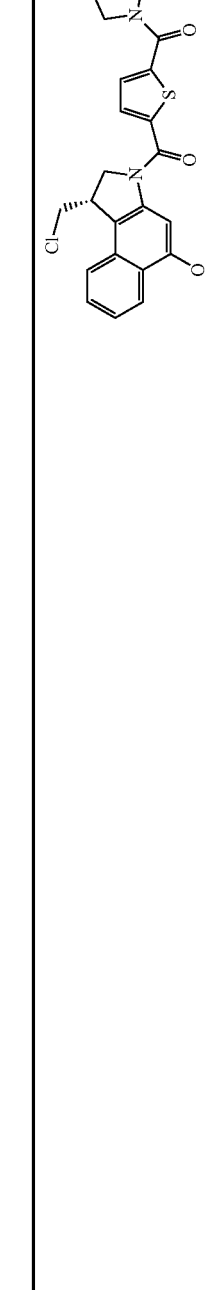 |

TABLE 6A-continued

Antibody Drug Conjugates

| ID | Structure |
|---|---|
| ADC2 | 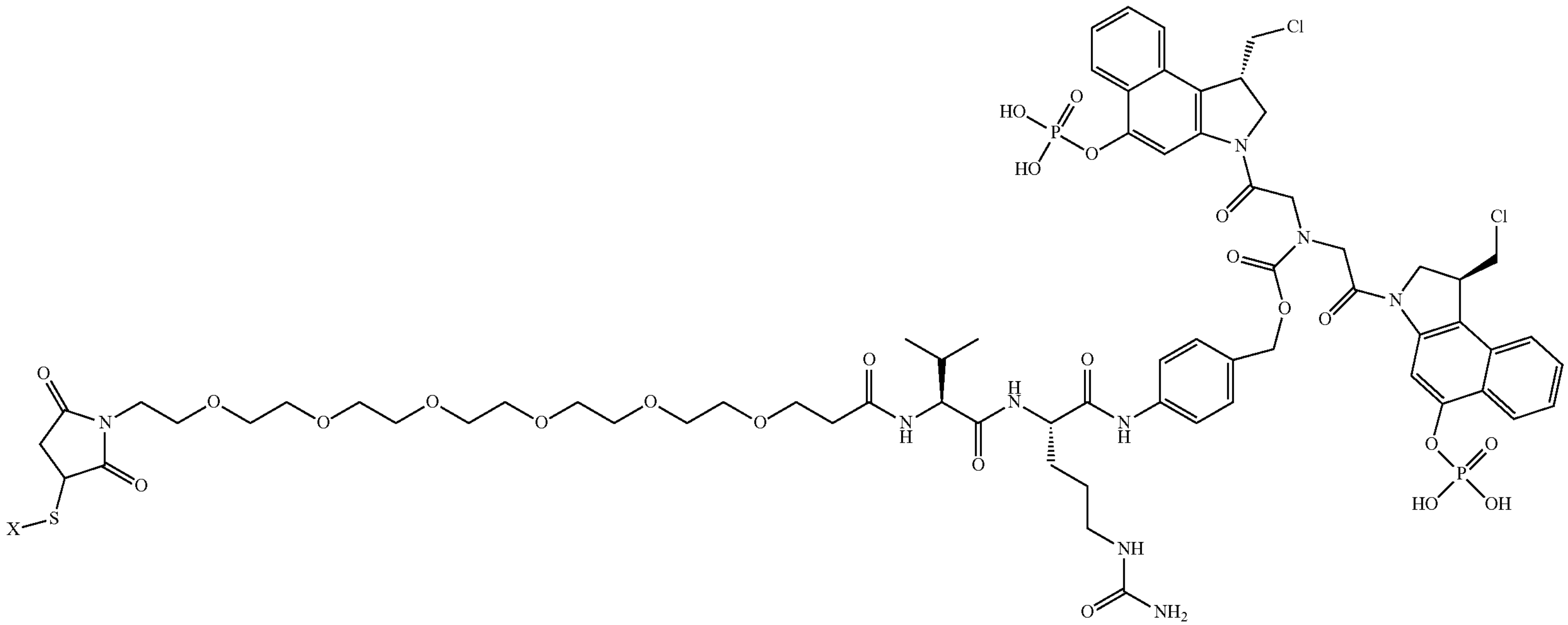 |
| ADC3 | 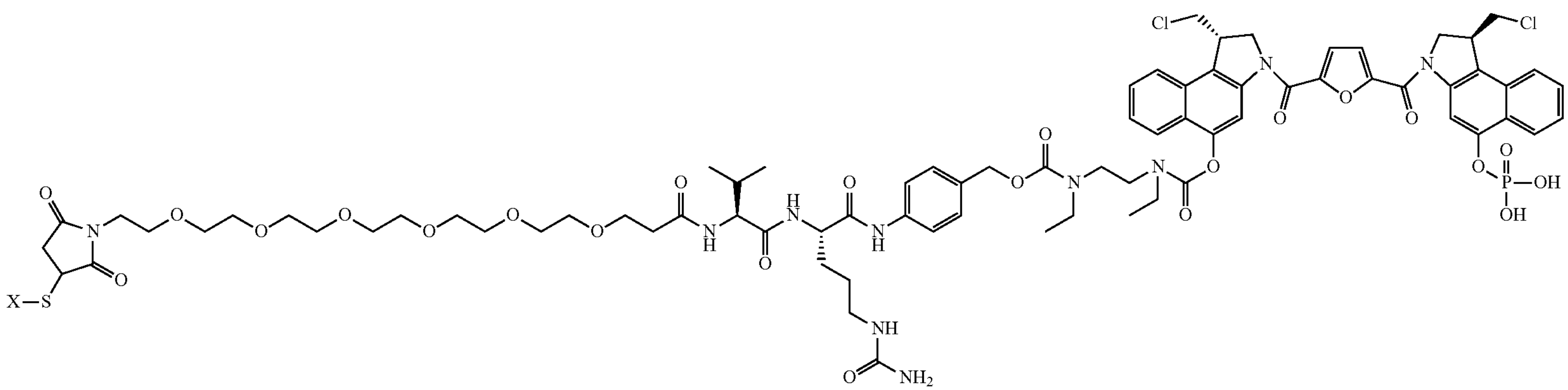 |

TABLE 6A-continued

Antibody Drug Conjugates

| ID | Structure |
|---|---|
| ADC4 | 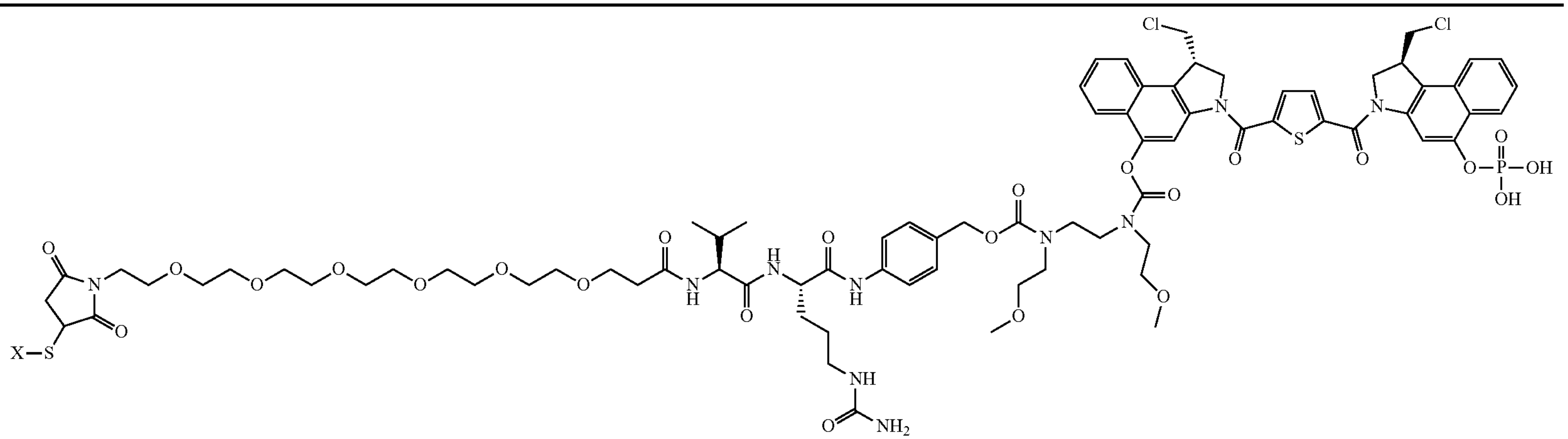 |
| ADC5 | 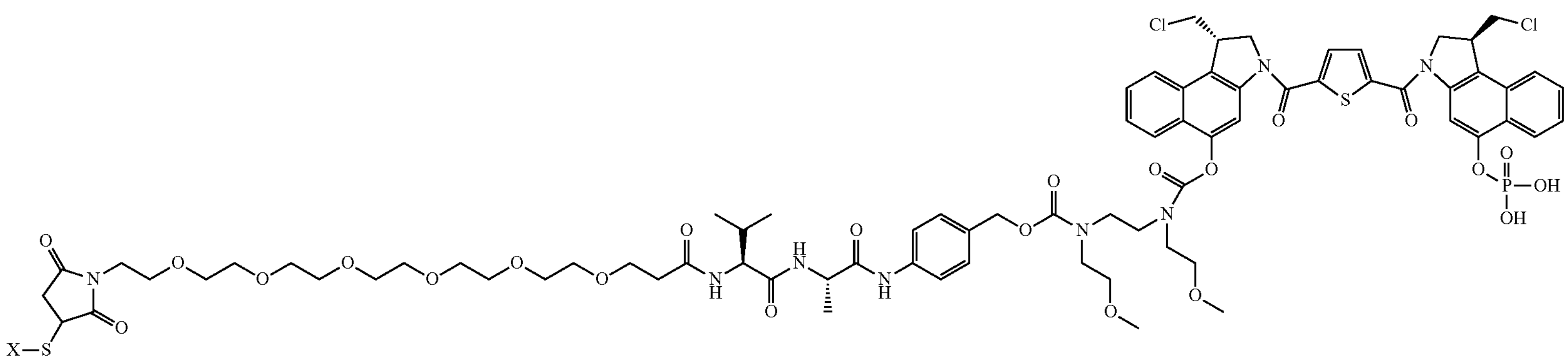 |

TABLE 6A-continued
Antibody Drug Conjugates
| ID | Structure |
|---|---|
| ADC6 | 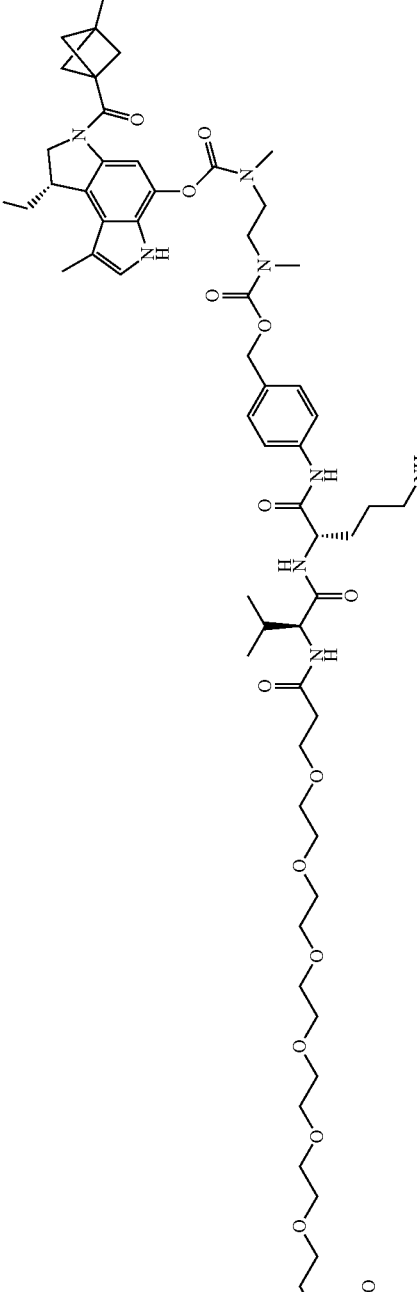 |
| ADC7 | 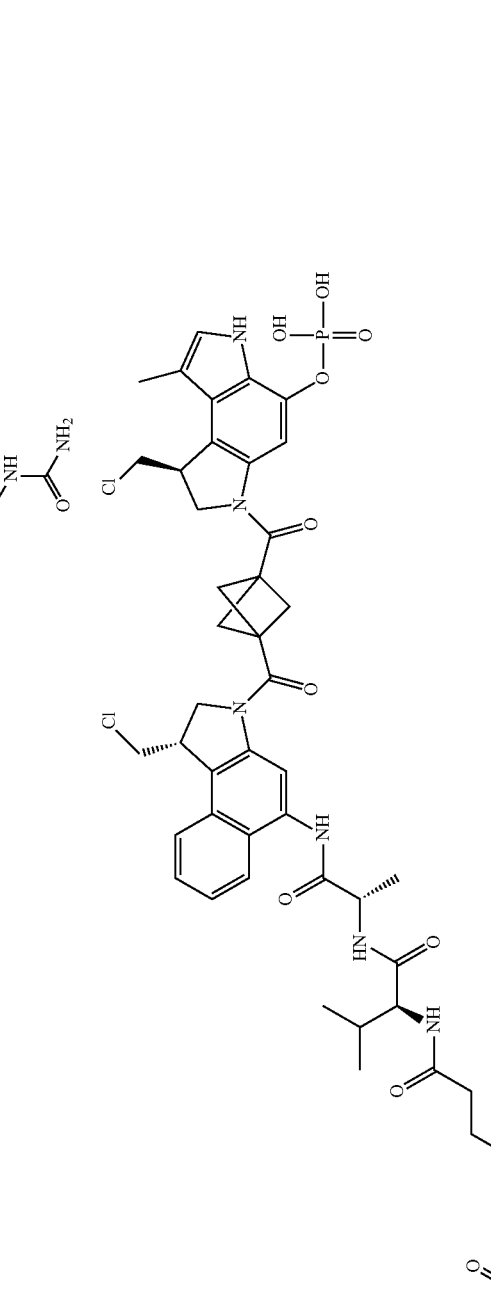 |

TABLE 6A-continued
Antibody Drug Conjugates
| ID | Structure |
|---|---|
| ADC8 | 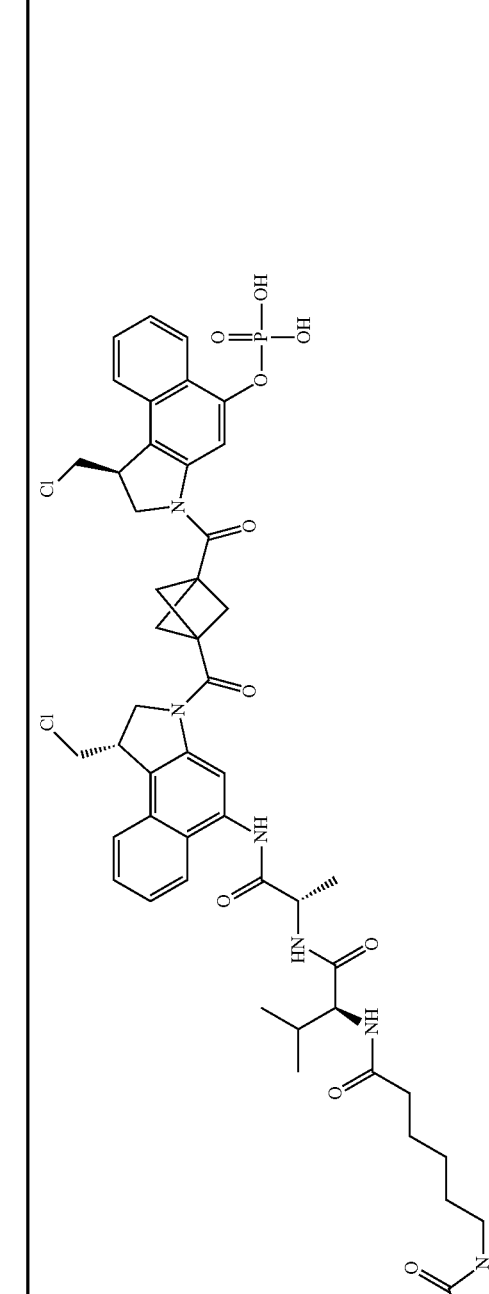 |

TABLE 6A-continued
Antibody Drug Conjugates
| ID | Structure |
|---|---|
| ADC9 | 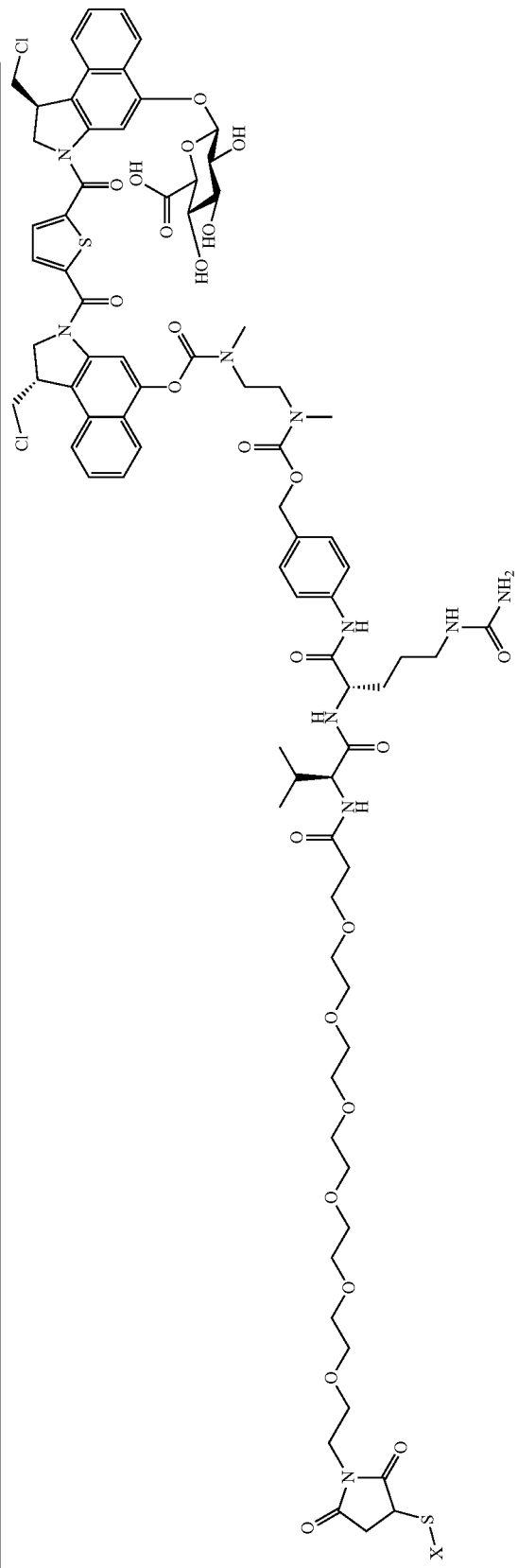 |

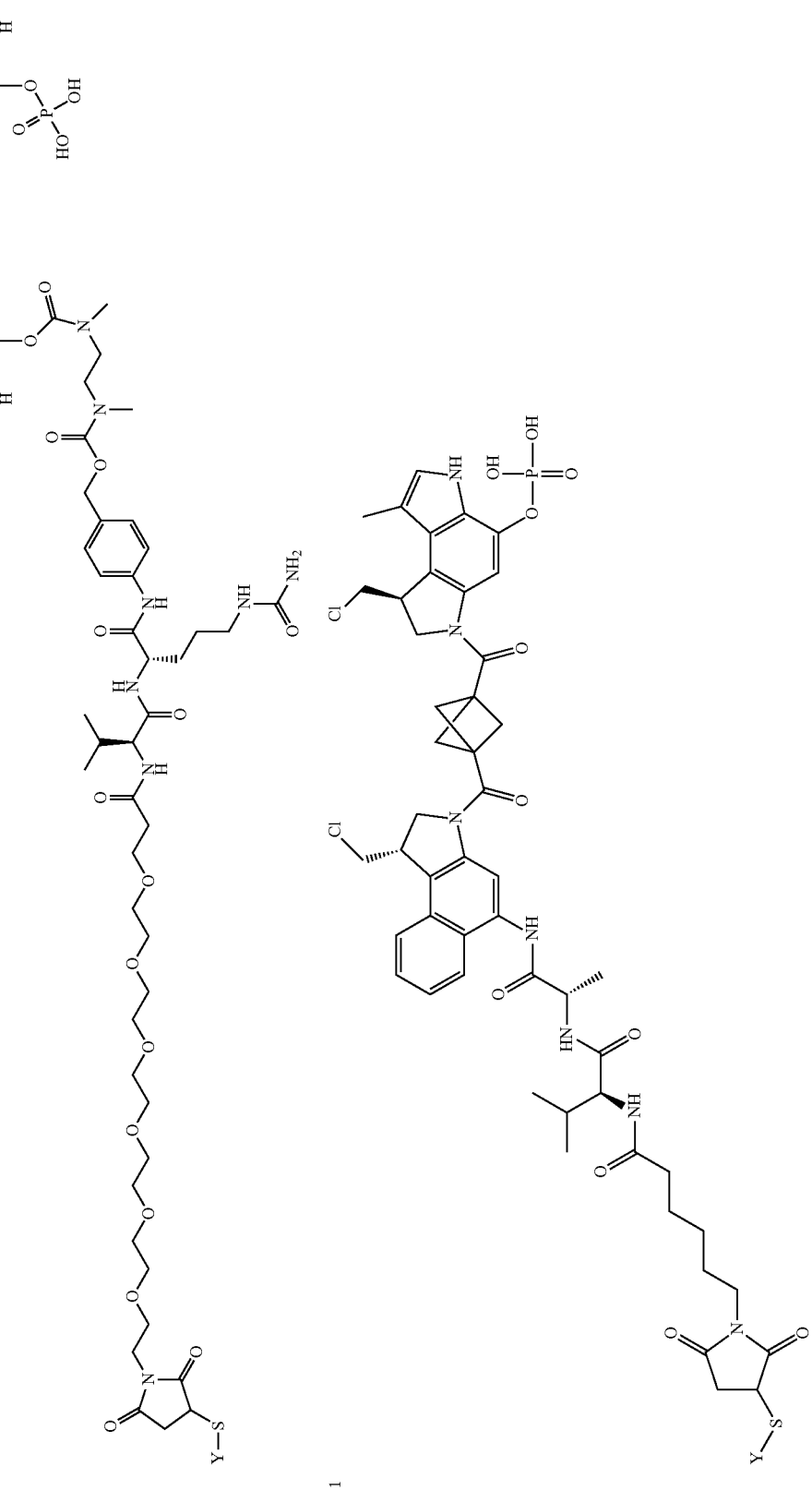

TABLE 6A-continued
Antibody Drug Conjugates
| ID | Structure |
|---|---|
| ADC12 | 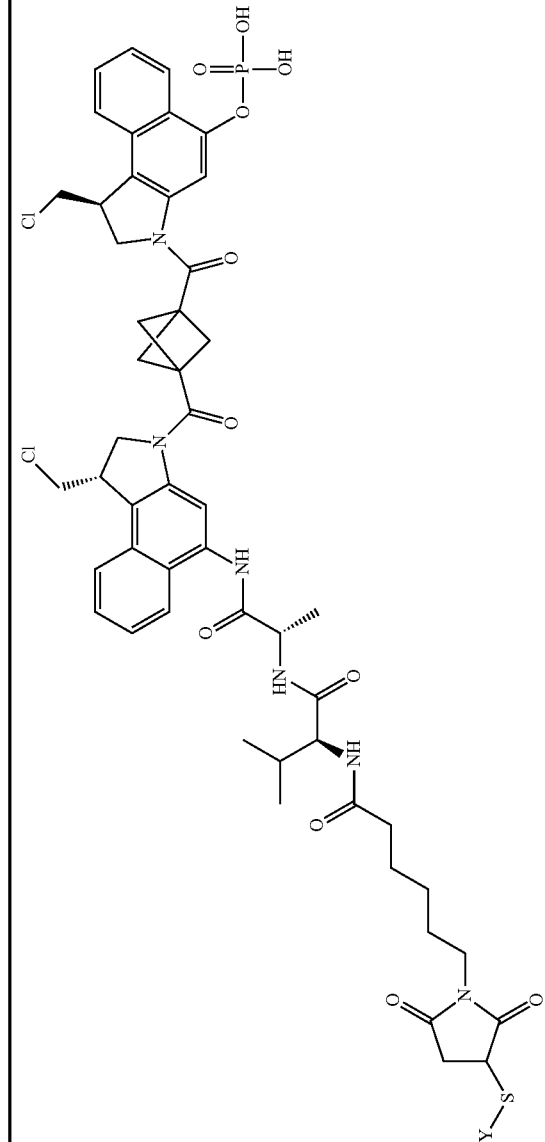 |

TABLE 6A-continued
Antibody Drug Conjugates
| ID | Structure |
|---|---|
| ADC13 | 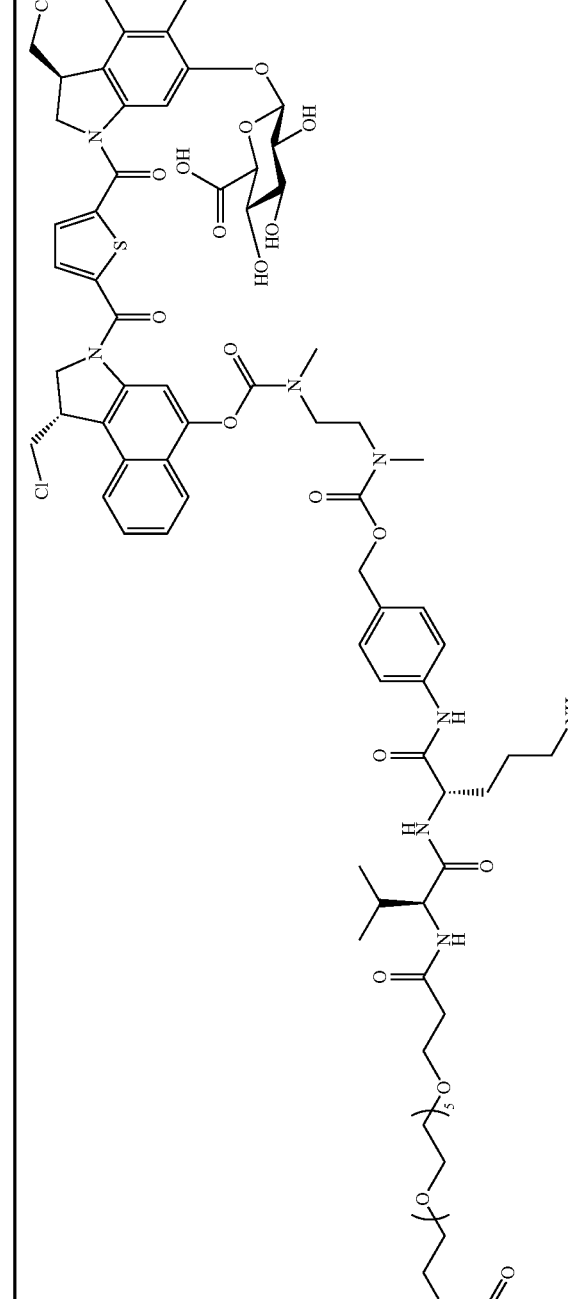 |

TABLE 6A-continued
Antibody Drug Conjugates
| ID | Structure |
|---|---|
| ADC14 | 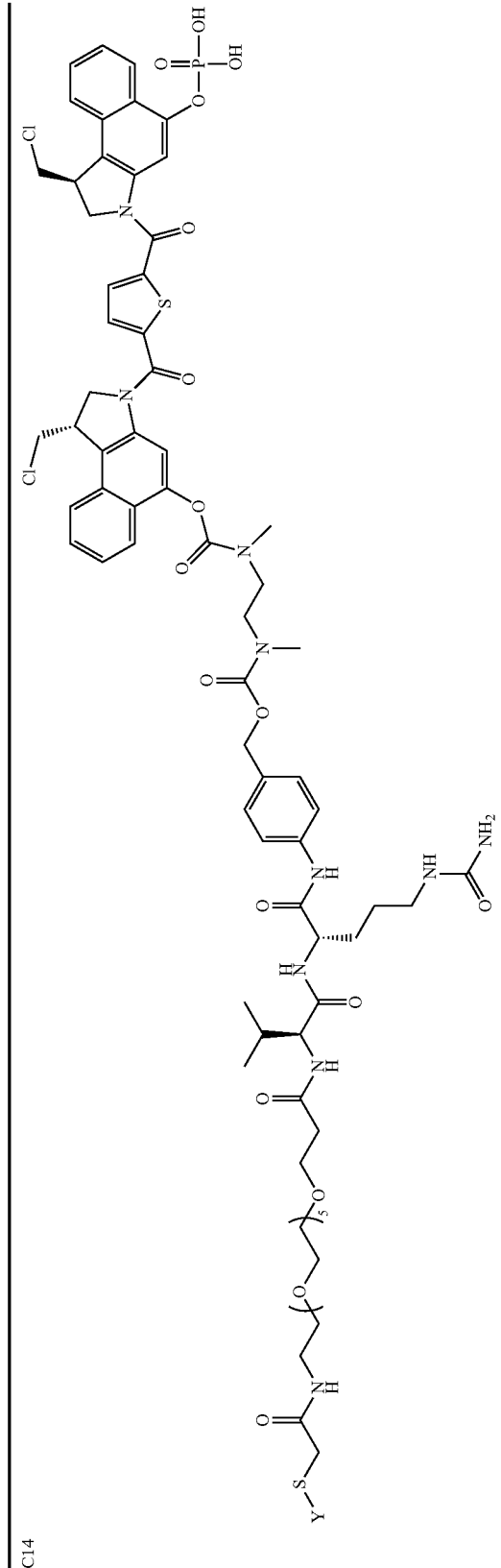 |

In the above table, "X and Y" indicates an antibody. The exemplified ADCs were conjugated to an IL13 antibody (IL13Rα2-AB08-v1.0/1.0-human IgG1 antibody) as denoted by X and VEGF antibody VEGFR-1121B-hG1 as denoted by Y.

TABLE 6B
Additional Antibody Drug Conjugates
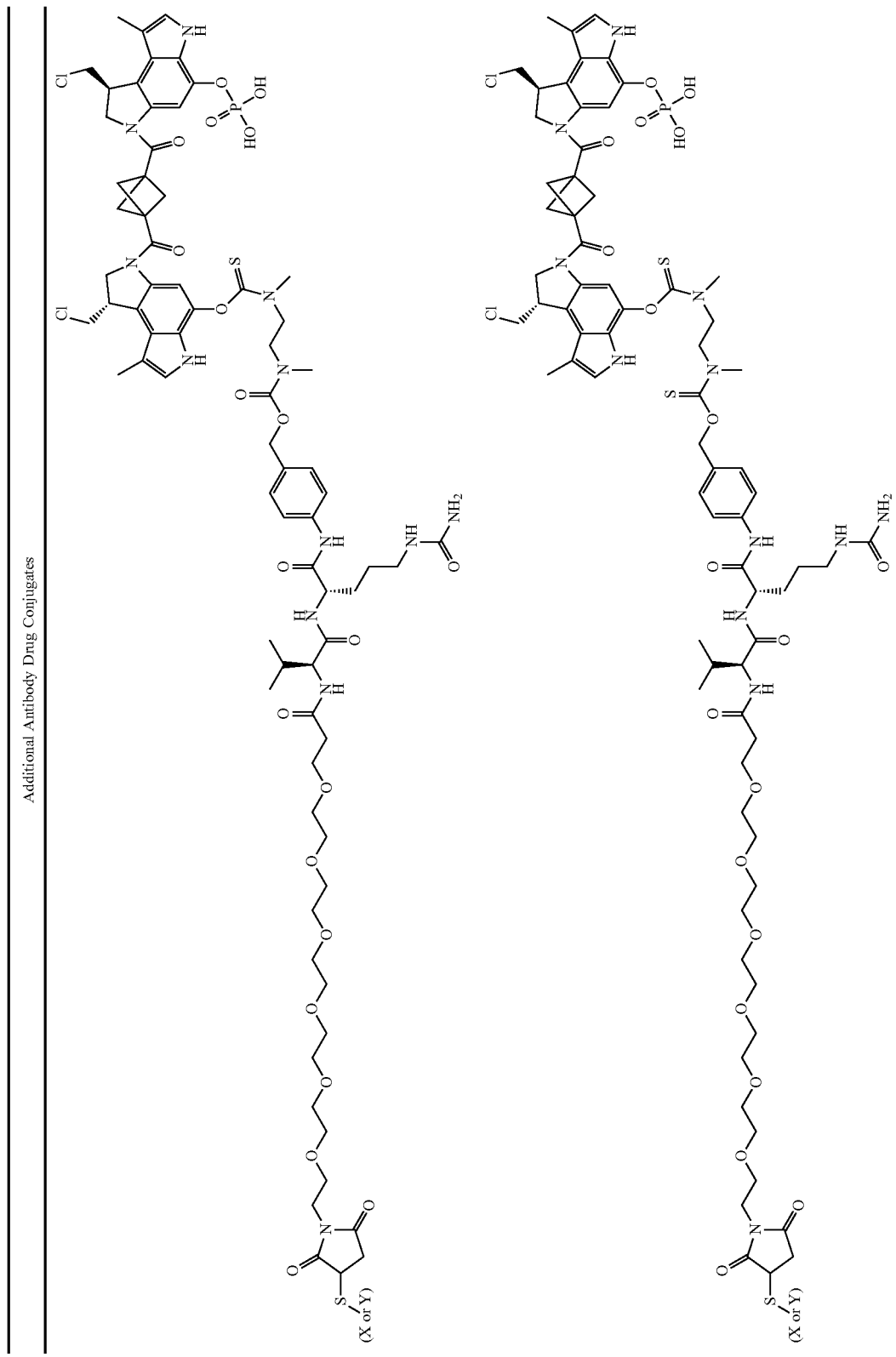

TABLE 6B-continued
Additional Antibody Drug Conjugates
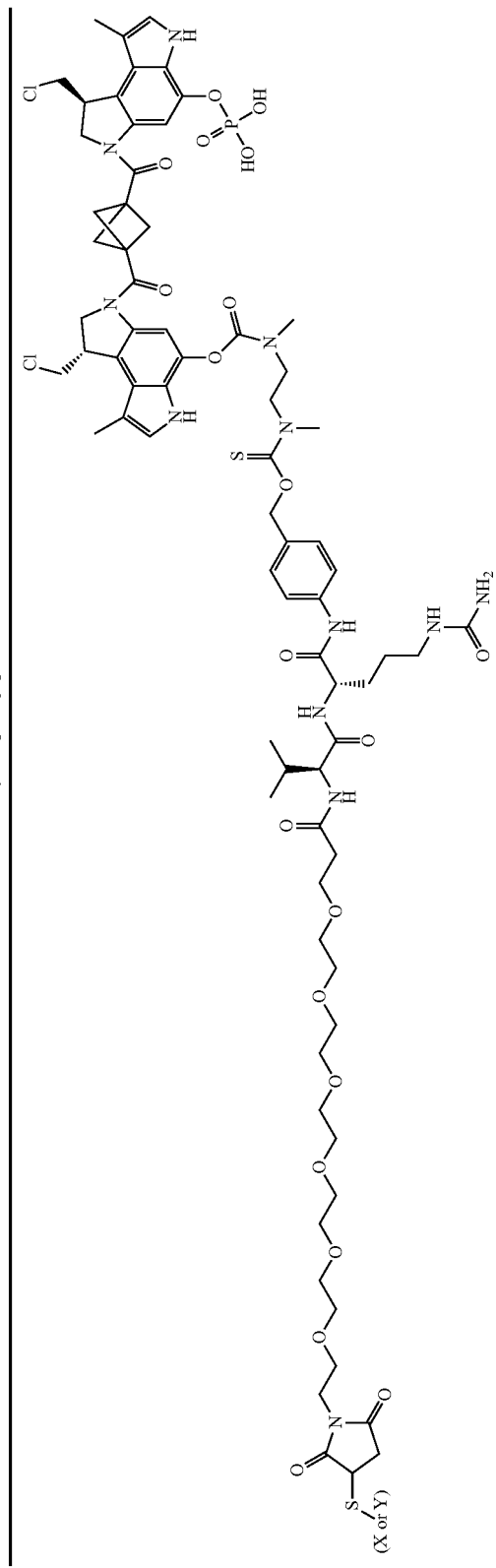

TABLE 6B-continued
Additional Antibody Drug Conjugates
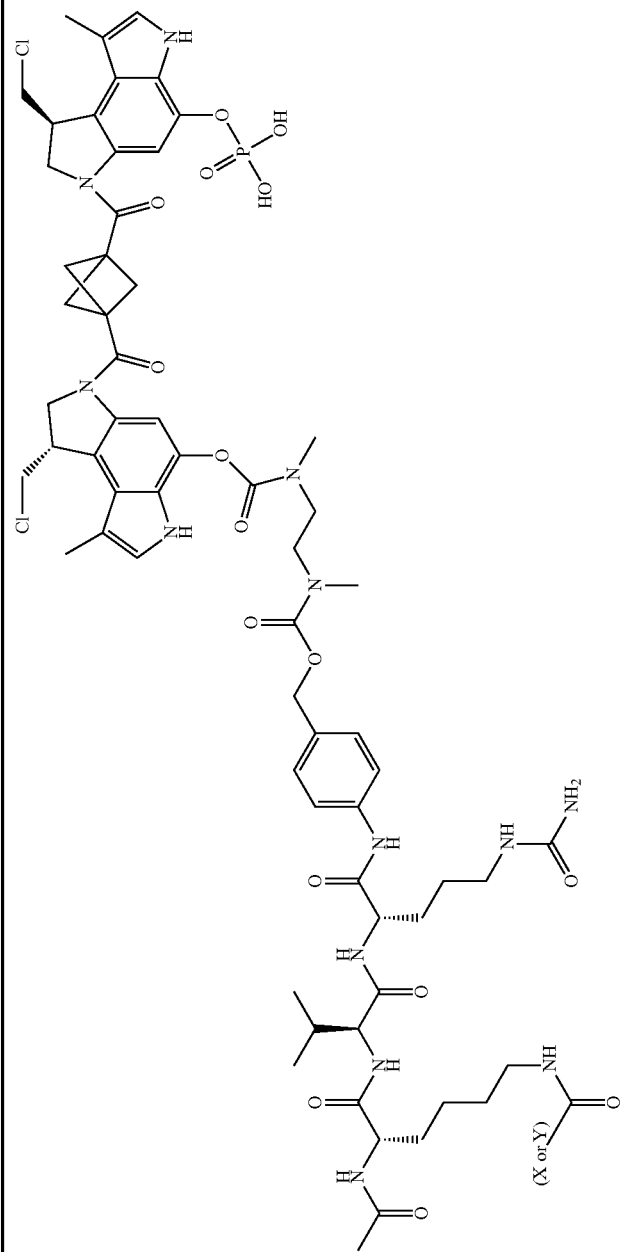

TABLE 6B-continued
Additional Antibody Drug Conjugates
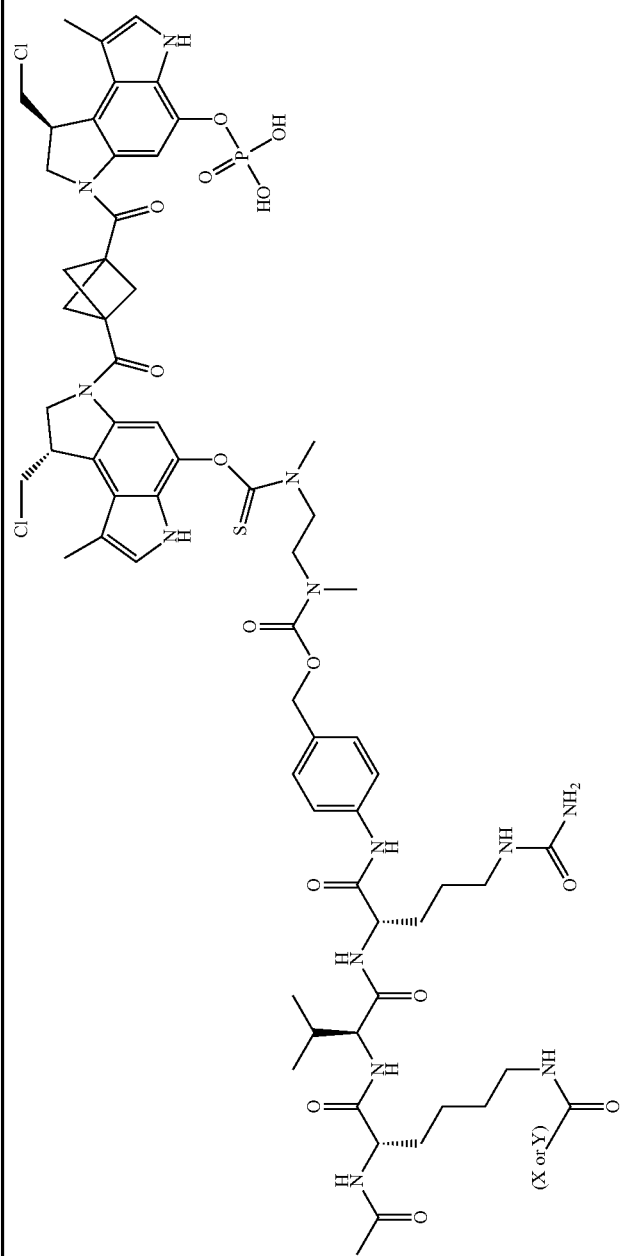

TABLE 6B-continued
Additional Antibody Drug Conjugates
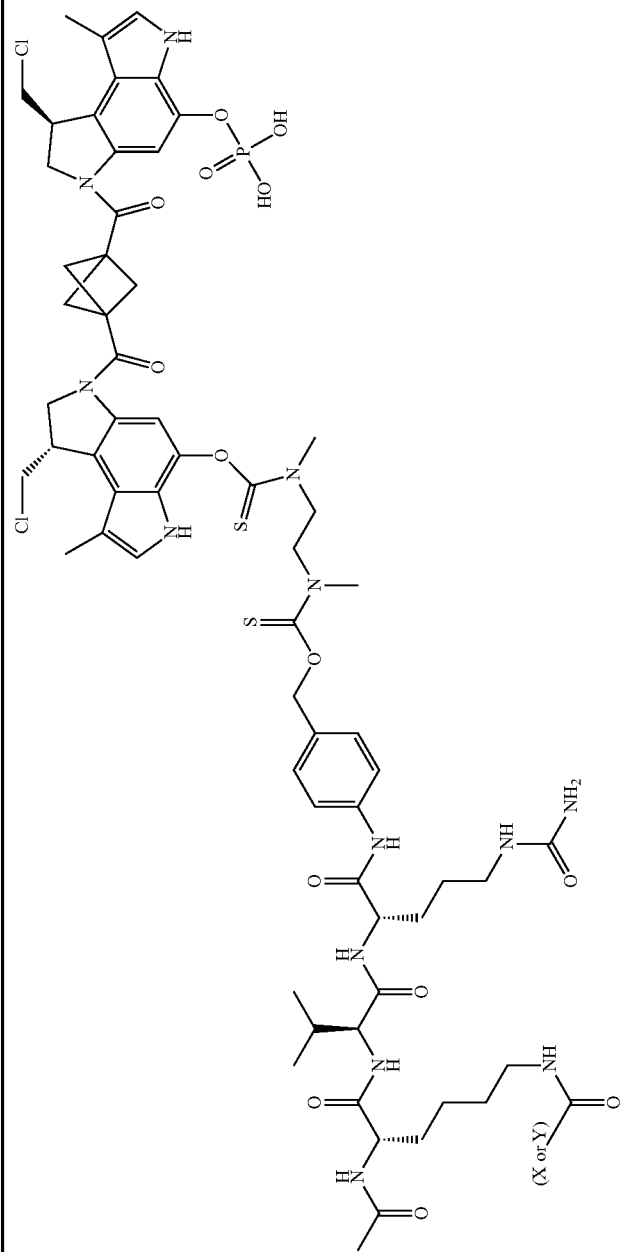

TABLE 6B-continued
Additional Antibody Drug Conjugates
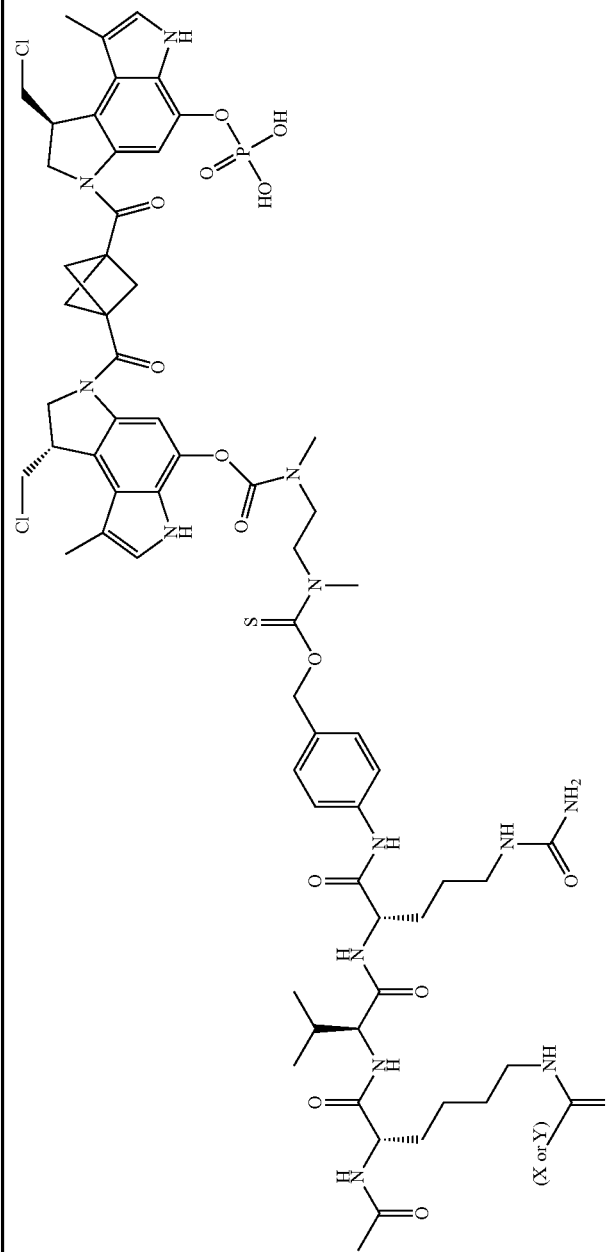

In the above table, "X and Y" indicates an antibody. The exemplified ADCs are conjugated to an IL13 antibody (IL13Rα2-AB08-v1.0/1.0-human IgG1 antibody) as denoted by X and VEGF antibody VEGFR-1121B-hG1 as denoted by Y.

Exemplified ADCs—Analytical Data

TABLE 7

ADC Analytical Data

| ADC ID | Linker/ Payload ID | Theoretical Δ mass or linker-payload molecular weight | Mass Spectra: SEC-HPLC retention time and HPLC Δ mass for the Light Chain (LC) portion | Loading or Drug per Antibody Ratio (DAR) |
|---|---|---|---|---|
| ADC1 | 223 | 1618 | SEC (Protocol C): 6.352 minutes; HPLC (Protocol B): LC Δ mass = 1619 | 4.0 |
| ADC2 | 189 | 1545 | SEC (Protocol C): 6.388 minutes; HPLC (Protocol B): LC Δ mass = 1545 | 2.7 |
| ADC3 | 298 | 1630 | SEC (Protocol C): 6.276 minutes; HPLC (Protocol B): LC Δ mass = 1631 | 5.2 |
| ADC4 | 299 | 1706 | SEC (Protocol C): 6.331 minutes; HPLC (Protocol B): LC Δ mass = 1707 | 3.5 |
| ADC5 | 303 | 1620 | SEC (Protocol C): 6.323 minutes; HPLC (Protocol B): LC Δ mass = 1621 | 3.3 |
| ADC6 | 231 | 1607 | SEC (Protocol C): 6.606 minutes; HPLC (Protocol B): LC Δ mass = 1609 | 3.2 |
| ADC7 | 266 | 1032 | SEC (Protocol C): 6.637 minutes; HPLC (Protocol B): LC Δ mass = 1032 | 3.9 |
| ADC8 | 279 | 1029 | SEC (Protocol C): 6.639 minutes; HPLC (Protocol B): LC Δ mass = 1030 | 4.1 |
| ADC9 | 278 | 1713 | SEC (Protocol C): 5.779 minutes; HPLC (Protocol B): LC Δ mass = 1716 | 5.1 |
| ADC10 | 231 | 1607 | SEC (Protocol C): 6.567 minutes; HPLC (Protocol B): LC Δ mass = 1609 | 3.3 |
| ADC11 | 266 | 1032 | SEC (Protocol C): 6.590 minutes; HPLC (Protocol B): LC Δ mass = 1032 | 4.6 |
| ADC12 | 279 | 1029 | SEC (Protocol C): 6.582 minutes; HPLC (Protocol B): LC Δ mass = 1030 | 4.5 |
| ADC13 | 278 | 1713 | SEC (Protocol C): 5.577 minutes; HPLC (Protocol B): LC Δ mass = 1718 | 4 |
| ADC14 | 294 | 1578 | SEC (Protocol C): 6.491 minutes; HPLC (Protocol B): LC Δ mass = 1578 | 3.1 |

Experimental Procedures for Biological Assessment of Payloads and Antibody Drug Conjugates Cell Lines Cancer cell lines were obtained from ATCC (Manassas, Va.). N87 (human gastric carcinoma derived from metastatic liver site). HL60 (leukemia), A375 (melanoma) and HUVEC (human umbilical vein endothelial cells). were grown in RPMI 1640 media. All media were supplemented with 10% fetal bovine serum, 1% sodium pyruvate, and 1% L-glutamine (Invitrogen, Grand Island, N.Y.). Human umbilical vein endothelial cells (HUVEC) were obtained from Lonza (Allendale, N.J.) and maintained in EGM2 media supplemented with EGM-2 SingleQuots (Lonza # CC-4176). All cells were maintained in a humidified incubator (37° C., 5% CO2).

Cytotoxicity Assay Procedure for Payloads

Cells in 100 μl medium were cultured in a 96-well plate. Cancer cell lines treated with the indicated compounds by adding 50 μl of 3× stocks in duplicate at 10 concentrations. Cells were incubated with compounds for four days, then 30 μl of CellTiter® 96 AQueous One MTS Solution (Promega Cat # G3582) was added to the cells, incubated 1.5 hr at 37° C., then absorbance measured at 490 nm on a Victor plate reader (Perkin Elmer, Waltham, Mass.). Relative cell viability was determined as a percentage of untreated control wells. IC50 values were calculated using four parameter logistic model #203 with XLfit v4.2 (IDBS, Guildford, Surry, UK).

Cytotoxicity Assay Procedure for ADCs

Day 0: seed cells in 100 ul of complete media in 96 flat clear bottom black plate and culture O/N. Day 1: add 50 ul of 3× titrated test compounds to make final volume 150 ul, and culture for 72 hours at 370 C, 5% CO2. Day 4: add 50 ul Cell TiterGlo into all wells, vortex for 20-30 min, read with Victor 3 under luminescent program. Data analysis: The % survival is calculated as 100× (readings of each data point-ave of BKG) ave of cell only control-ave of BKG.

The table below provides IC50 data for selected payloads of the present invention.

TABLE 8

Payload IC50 Data

| compound Number | N87 IC50 (nM) | HL-60 IC50 (nM) |
|---|---|---|
| 13 | 0.138 | 0.014 |
| 16 | 1.761 | 0.163 |
| 18 | 173.740 | 2.188 |
| 20 | 296.612 | 1.624 |
| 23 | 0.252 | 0.072 |
| 26 | 10.000 | — |
| 29 | 0.009 | <0.001 |
| 32 | 0.052 | 0.005 |
| 35 | 1.210 | — |
| 38 | 10.000 | — |
| 40 | 1.882 | 0.177 |
| 44 | 10.000 | 5.292 |
| 48 | 12.163 | 1.754 |
| 53 | — | 0.012 |
| 56 | 100.000 | 6.934 |
| 60 | 10.000 | — |
| 65 | 0.554 | 0.004 |
| 68 | 0.033 | — |
| 71 | 0.085 | — |
| 74 | 76.494 | 7.488 |
| 79 | 7.962 | 0.496 |
| 82 | 3.242 | 0.359 |
| 85 | 0.053 | 0.005 |
| 88 | 0.502 | 0.022 |
| 91 | 0.057 | 0.004 |
| 97 | 0.222 | 0.009 |
| 108 | 3.981 | 0.431 |
| 109 | 2.296 | 0.095 |
| 115 | 1.439 | 0.015 |
| 117 | 0.004 | — |
| 119 | 0.004 | — |

TABLE 8-continued

Payload IC50 Data

| compound Number | N87 IC50 (nM) | HL-60 IC50 (nM) |
|---|---|---|
| 123 | 0.003 | — |
| 126 | 0.004 | — |
| 130 | 1.804 | 0.227 |
| 134 | — | 0.099 |
| 135 | 0.019 | 0.005 |
| 136 | 0.003 | 0.005 |
| 141 | 12.689 | 0.361 |
| 142 | 100.000 | 10.000 |
| 143 | 100.000 | 10.000 |
| 144 | >10.000 | 3.004 |
| 145 | 0.130 | 0.051 |
| 146 | 3.102 | — |
| 147 | 0.017 | 0.003 |
| 149 | 0.132 | 0.007 |
| 152 | 0.278 | 0.008 |
| 153 | 4.474 | |
| 154 | 0.026 | 0.003 |
| 156 | 10.000 | 61.079 |
| 157 | 10.000 | 77.406 |
| 158 | 14.334 | 4.911 |
| 159 | 2.389 | 0.045 |
| 160 | 12.692 | — |
| 161 | 10.000 | 27.250 |
| 162 | 0.749 | 0.020 |
| 163 | 6.895 | 0.179 |
| 164 | — | 0.057 |
| 165 | 8.259 | 0.107 |
| 166 | 5.689 | 0.659 |
| 167 | 10.000 | 1.451 |
| 168 | — | 0.097 |
| 169 | 9.821 | 0.388 |
| 170 | 0.005 | — |
| 171 | 1.554 | 0.131 |
| 172 | 13.800 | 0.474 |
| 173 | 13.097 | 0.169 |
| 174 | 87.918 | 1.971 |
| 175 | — | 11.843 |
| 176 | 26.413 | 0.199 |
| 177 | 2.125 | 0.196 |
| 178 | 0.484 | 0.036 |
| 179 | 172.553 | 14.322 |
| 180 | 0.425 | 0.048 |
| 181 | 0.005 | — |

The table below provides IC50 data for selected ADCs of the present invention.

TABLE 9

ADC IC50 Data

| ID | A375 IC50 ng/ml | HUVEC IC50 ng/ml |
|---|---|---|
| ADC1 | 0.15 | — |
| ADC2 | 6.36 | — |
| ADC3 | 2.64 | — |
| ADC4 | 0.14 | — |
| ADC5 | 0.14 | — |
| ADC6 | 0.8 | — |
| ADC7 | 2.0 | — |
| ADC8 | 1.8 | — |
| ADC9 | 0.2 | — |
| ADC10 | — | 9.4 |
| ADC11 | — | 137 |
| ADC12 | — | 7655 |
| ADC13 | — | 5.92 |
| ADC14 | — | 0.88 |

The drawing below illustrates how the payload is liberated upon administration to the patient and after linker cleavage from the ADC, exemplified with one linker type. Various species are formed after linker release that interconvert in the biological medium. All formed species are claimed as part of this invention and relate to the general formula $F^1-L^1-T-L^2-F^2$.

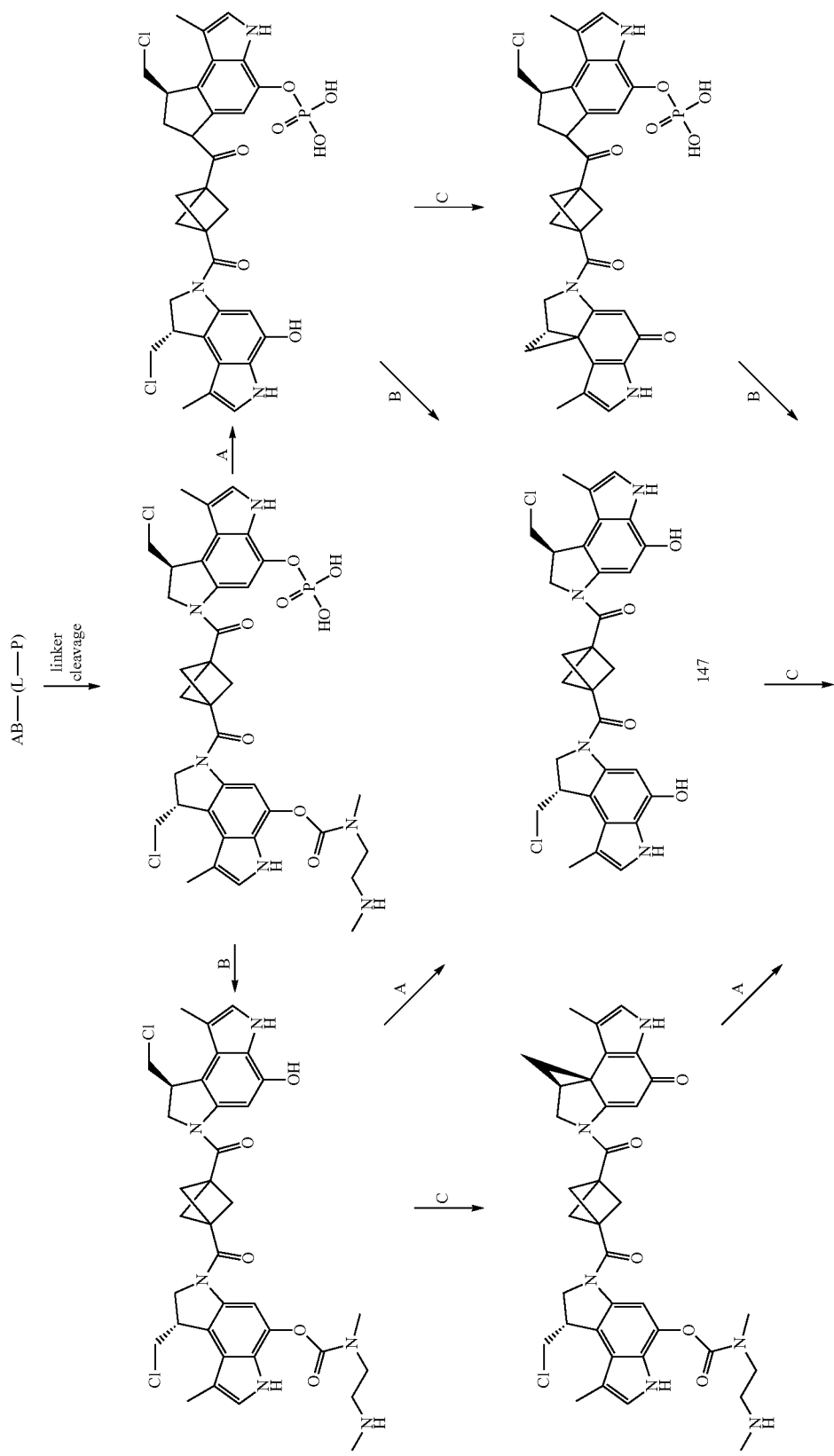

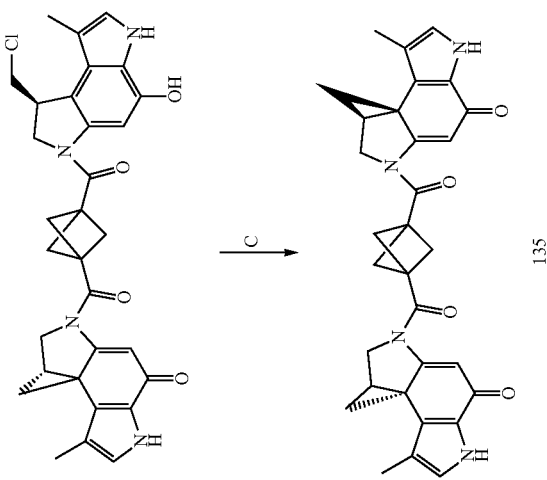
A = self immolation of the diamino ethane
B = hydrolysis of phosphate
C = cyclopropane formation

We claim:
1. A compound of Formula (I):

$F^1$-$L^1$-T-$L^2$-$F^2$ (I)

or a pharmaceutically acceptable salt or solvate thereof, wherein:

$F^1$ and $F^2$ are each independently selected from ring systems A, and B:

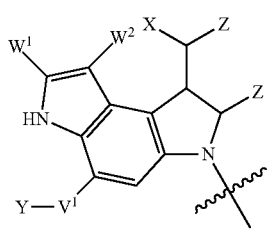

(Ring System A)

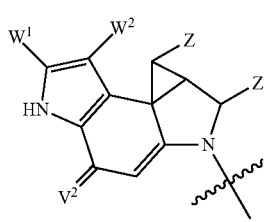

(Ring System B)

wherein:
each $V^1$ is independently a bond, O, N(R) or S, for each ring system A in which $V^1$ appears;
each $V^2$ is independently O, N(R) or S, for each ring system B in which $V^2$ appears;
$W^1$ and $W^2$ are each independently H, —$C_1$-$C_5$ alkyl or -phenyl, for each ring system A and ring system B in which $W^1$ and $W^2$ appear;
each X is independently —OH, —O-acyl, azido, halo, cyanate, thiocyanate, isocyanate, thioisocyanate, or

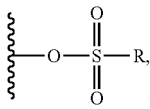

for each ring system A in which X appears;
each Y is independently selected from the group consisting of H, —$C_1$-$C_6$ alkyl-$R^A$, —C(O)$R^A$, —C(S)$R^A$, —C(O)O$R^A$, —S(O)$_2$O$R^A$, —C(O)N($R^A$)$_2$, —C(S)N($R^A$)$_2$, and —PO(O$R^A$)$_2$, for each ring system A in which Y appears, wherein each $R^A$ is independently selected from the group consisting of H, —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl and —$C_1$-$C_{20}$ alkylN(R)$_2$, wherein said —$C_1$-$C_{20}$ alkyl, —$C_1$-$C_8$ heteroalkyl, —$C_6$-$C_{14}$ aryl, aralkyl, —$C_1$-$C_{10}$ heterocyclyl, —$C_3$-$C_8$ carbocyclyl and —$C_1$-$C_{20}$ alkylN(R)$_2$ are optionally substituted with 1 to 3 substituents independently selected from R;
each Z is independently selected from the group consisting of H, —$C_1$-$C_8$ alkyl, —$C_1$-$C_8$ heteroalkyl, —$C_6$-$C_{14}$ aryl, -aralkyl, —$C_1$-$C_{10}$ heterocyclyl and —$C_3$-$C_8$ carbocyclyl, and wherein said $C_1$-$C_8$ alkyl, —$C_1$-$C_8$ heteroalkyl, —$C_6$-$C_{14}$ aryl, -aralkyl, —$C_1$-$C_{10}$ heterocyclyl and —$C_3$-$C_8$ carbocyclyl,
are each optionally substituted with 1 to 3 substituents independently selected from R, for each ring system A and ring system B in which Z appears;
$L^1$ and $L^2$ are each independently a direct bond;
T is selected from:
—C($A^1$)$X^1$-$T^2$-$X^1$C($B^1$)—, where $T^2$ is:

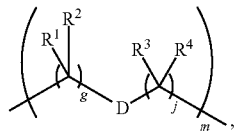

wherein each $X^1$ is independently a bond, —$NR^E$—, —O— or —S—, wherein $A^1$ and $B^1$ are each independently =O or =S,
wherein $R^1$, $R^2$, $R^3$, and $R^4$ are each independently $R^E$, or $R^1$ and $R^2$ form a ring system, or $R^3$ and $R^4$ form a ring system, or both $R^1$ and $R^2$, and $R^3$ and $R^4$, each independently form ring systems, or $R^1$ and $R^3$ form a ring system, or $R^2$ and $R^4$ form a ring system, or both $R^1$ and $R^3$, and $R^2$ and $R^4$, each independently form ring systems, where said ring systems are independently selected from —$C_3$-$C_8$ carbocyclycl, or $R^1$, $R^2$, $R^3$ and $R^4$ are each bonds to different carbons on D, wherein g and j are each independently an integer from 0 to 50 and m is an integer from 1 to 50, and wherein D is —$C_3$-$C_8$ carbocyclo, —$C_3$-$C_8$ carbocyclo is optionally substituted with —$R^E$, —C(O)$R^E$, —C(O)O$R^E$, —N($R^E$)$_2$, —N(R)C(O)$R^E$ or —N(R)C(O)O$R^E$, and D is additionally optionally substituted by 1 to 2 R, and
-$G^1$-$T^2$-$G^2$-, where $G^1$ and $G^2$ are each independently —S(O)$X^1$— or —S(O)$_2X^1$,
wherein each $R^E$ is independently selected from the group consisting of H, —$C_1$-$C_8$ alkyl, —$C_1$-$C_8$ heteroalkyl, —$C_6$-$C_{14}$ aryl, -aralkyl, —$C_1$-$C_{10}$ heterocyclyl, —$C_3$-$C_8$ carbocyclyl, —C(O)O$C_1$-$C_8$ alkyl, —C(O)N($C_1$-$C_8$ alkyl)$_2$, and —C(O)-halo, and wherein each $R^E$ is optionally substituted with 1 to 3 substituents independently selected from R, and wherein each R is independently selected from the group consisting of H, —$C_1$-$C_{20}$ alkyl, —$C_2$-$C_6$ alkenyl, —$C_2$-$C_6$ alkynyl, halo, hydroxyl, alkoxy, —$NH_2$, —NH($C_1$-$C_8$ alkyl), —N($C_1$-$C_8$ alkyl)$_2$, —$NO_2$, —$C_6$-$C_{14}$ aryl and —$C_6$-$C_{14}$ heteroaryl, wherein two or more R optionally join to form a ring or rings, and wherein said —$C_6$-$C_{14}$ aryl and —$C_6$-$C_{14}$ heteroaryl are optionally substituted with 1 to 5 substituents independently selected from —$C_1$-$C_{10}$ alkyl, —$C_1$-$C_{10}$ alkoxy, -halo, —$C_1$-$C_{10}$ alkylthio, -trifluoromethyl, —$NH_2$, —NH($C_1$-$C_8$ alkyl), —N($C_1$-$C_8$ alkyl)$_2$, —$C_1$-$C_{10}$ alkyl-N($C_1$-$C_8$ alkyl)$_2$, —$C_1$-$C_3$ alkylthio, —$NO_2$ or —$C_1$-$C_{10}$ heterocyclyl, for each ring system in which R appears.

2. The compound or a pharmaceutically acceptable salt or solvate of claim 1, wherein:
each $V^1$ is independently O or N(R) for each ring system A in which $V^1$ appears;
each $V^2$ is independently O or N(R) for each ring system B in which $V^2$ appears;
$W^1$ and $W^2$ are each independently H or —$C_1$-$C_5$ alkyl, for each ring system A and ring system B in which $W^1$ and $W^2$ appear;

each X is independently halo, for each ring system A in which X appears;

each Y is independently selected from the group consisting of H, —C(O)R$^4$, —C(O)N(R$^4$)$_2$, and —PO(OR$^4$)$_2$, for each ring system A in which Y appears, wherein each R$^4$ is independently selected from the group consisting of H, —C$_1$-C$_{20}$ alkyl, —C$_1$-C$_8$ heteroalkyl, —C$_3$-C$_8$ carbocyclyl and —C$_1$-C$_{20}$ alkylN(R)$_2$, wherein said —C$_1$-C$_{20}$ alkyl, —C$_1$-C$_8$ heteroalkyl, —C$_3$-C$_8$ carbocyclyl and —C$_1$-C$_{20}$ alkylN(R)$_2$ are optionally substituted with 1 to 3 substituents independently selected from R; and T is selected from:

—C(A$^1$)X$^1$-T$^2$-X$^1$C(B$^1$)—, where T$^2$ is:

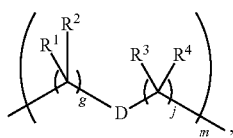

wherein each X$^1$ is a bond, wherein A$^1$ and B$^1$ are each independently =O, wherein R$^1$, R$^2$, R$^3$, and R$^4$ are each independently H or R$^1$ and R$^2$ form a ring system, or R$^3$ and R$^4$ form a ring system, or both R$^1$ and R$^2$, and R$^3$ and R$^4$, each independently form ring systems, or R$^1$ and R$^3$ form a ring system, or R$^2$ and R$^4$ form a ring system, or both R$^1$ and R$^3$, and R$^2$ and R$^4$, each independently form ring systems, where said ring systems are independently selected from —C$_3$-C$_8$ carbocyclycl, and wherein D is —C$_3$-C$_8$ carbocyclo, —C$_3$-C$_8$ carbocyclo is optionally substituted with —NH$_2$, —N(R)C(O)H or —N(R)C(O)OH;

and wherein each R is independently selected from the group consisting of H, —C$_1$-C$_{20}$ alkyl and —NH$_2$.

3. The compound or a pharmaceutically acceptable salt or solvate of claim 1, wherein two R optionally join to form a ring.

4. The compound or a pharmaceutically acceptable salt or solvate of claim 1, wherein each V$^1$ is O, for each ring system A in which V$^1$ appears; and each Y is independently selected from the group consisting of H, —C(O)N(R$^4$)$_2$, —C(S)N(R$^4$)$_2$, and —PO(OR$^4$)$_2$ for each ring system A in which Y appears, wherein each R$^4$ is independently selected from the group consisting of H, —C$_1$-C$_{20}$ alkyl, and —C$_1$-C$_{20}$ alkylN(R)$_2$, and wherein said —C$_1$-C$_{20}$ alkyl, and —C$_1$-C$_{20}$ alkylN(R)$_2$ are optionally substituted with 1 to 3 substituents independently selected from R.

5. The compound or a pharmaceutically acceptable salt or solvate according to claim 1, wherein one to four W is C$_1$-C$_3$ alkyl.

6. The compound or a pharmaceutically acceptable salt or solvate according to claim 1, wherein one or two X is chloro.

7. The compound or a pharmaceutically acceptable salt or solvate according to claim 1, wherein one Y is H or —C(O)C$_1$-C$_{10}$alkyl.

8. The compound or a pharmaceutically acceptable salt or solvate according to claim 1, wherein one to four Z is H.

9. A compound, or a pharmaceutically acceptable salt or solvate thereof, selected from:

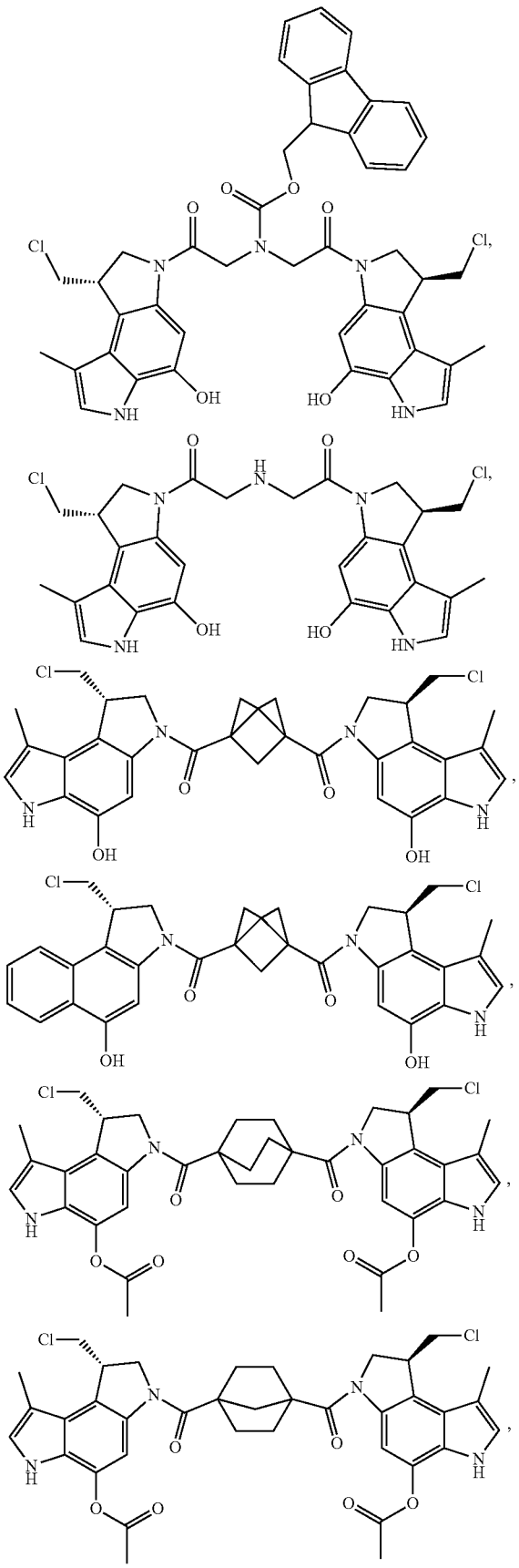

347
-continued
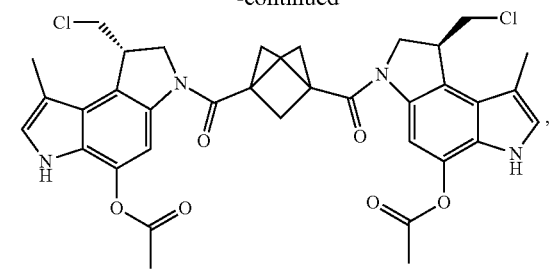
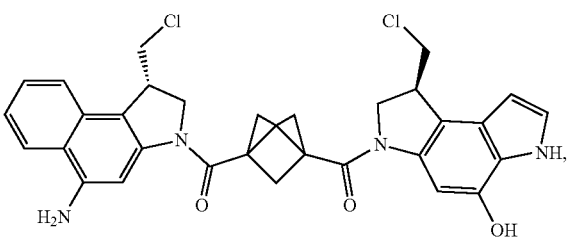
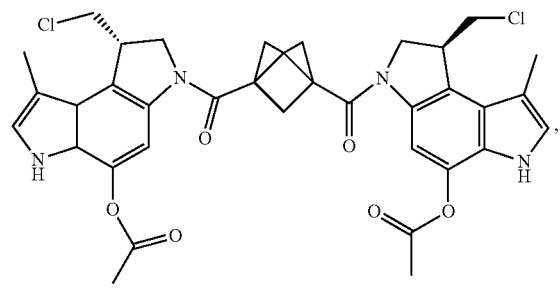
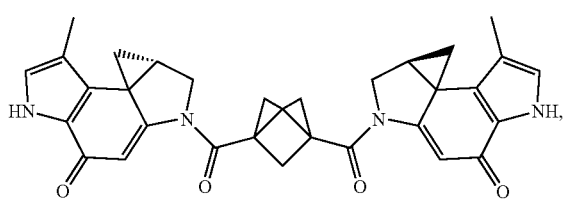
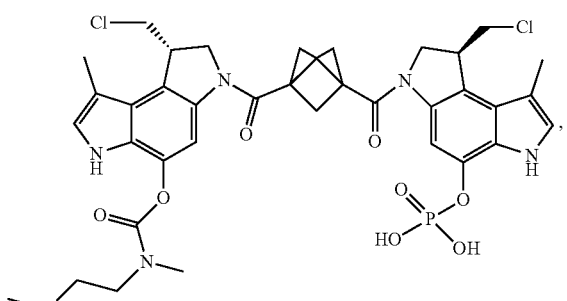
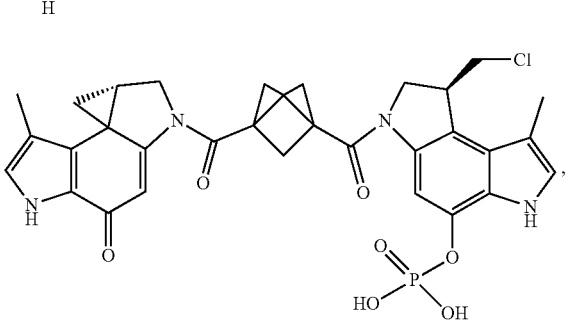
348
-continued
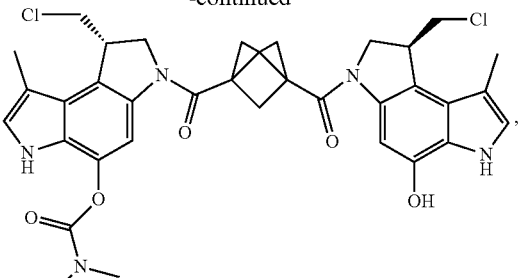
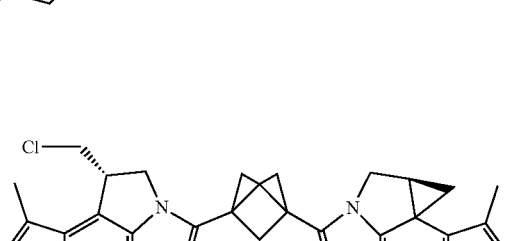
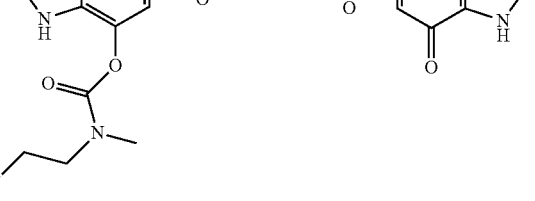
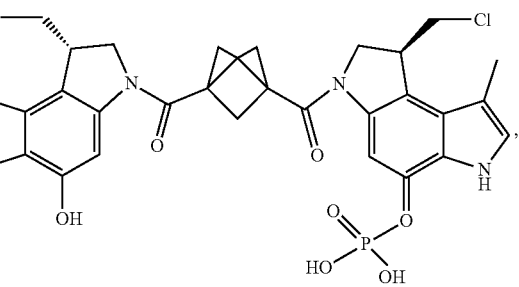
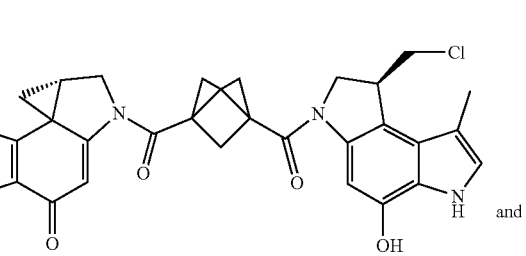
and
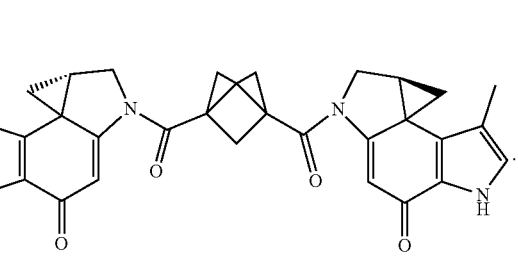
10. A compound, or a pharmaceutically acceptable salt or solvate thereof, selected from:

349
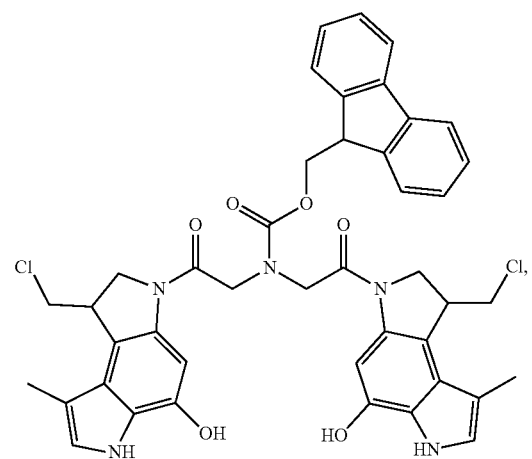
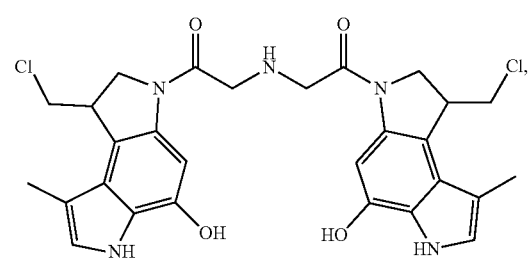
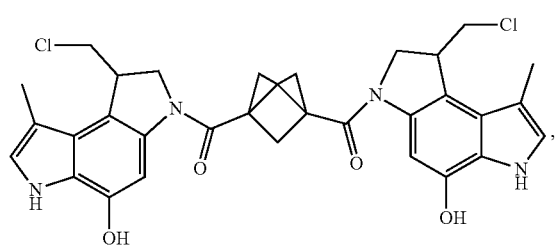
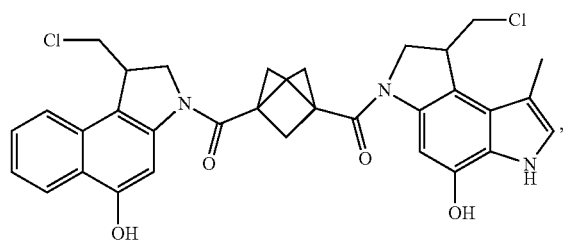
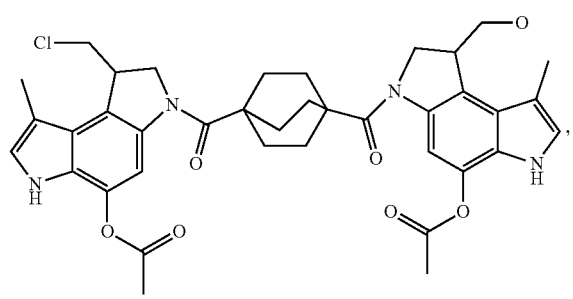
350
-continued
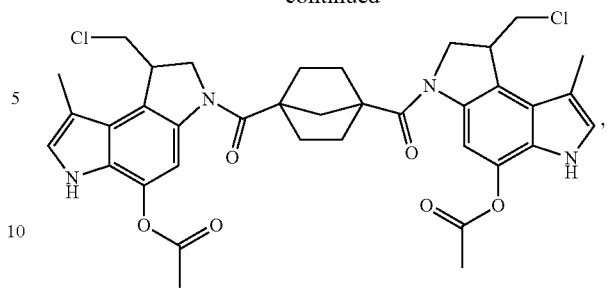
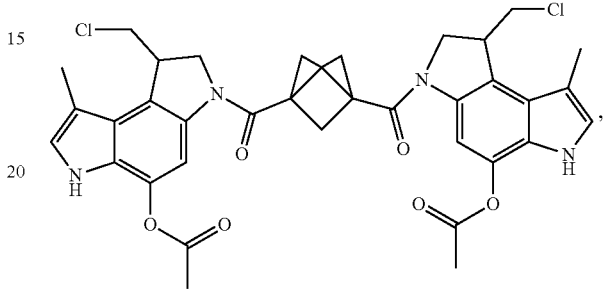
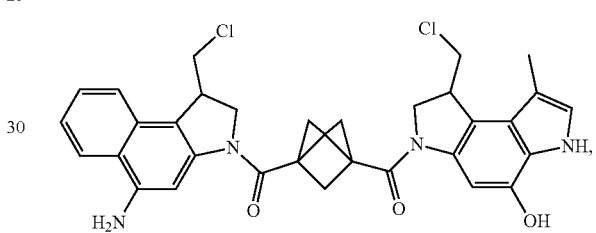
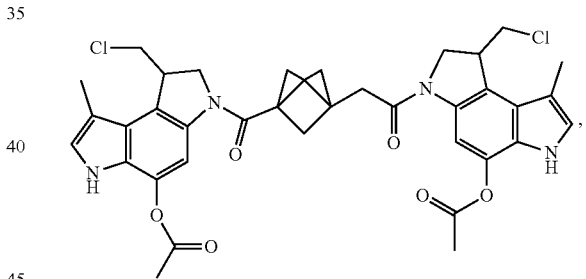
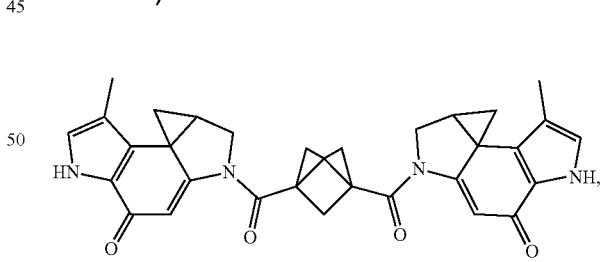
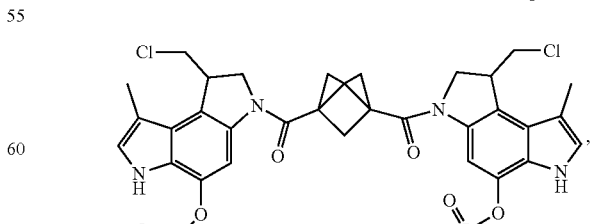

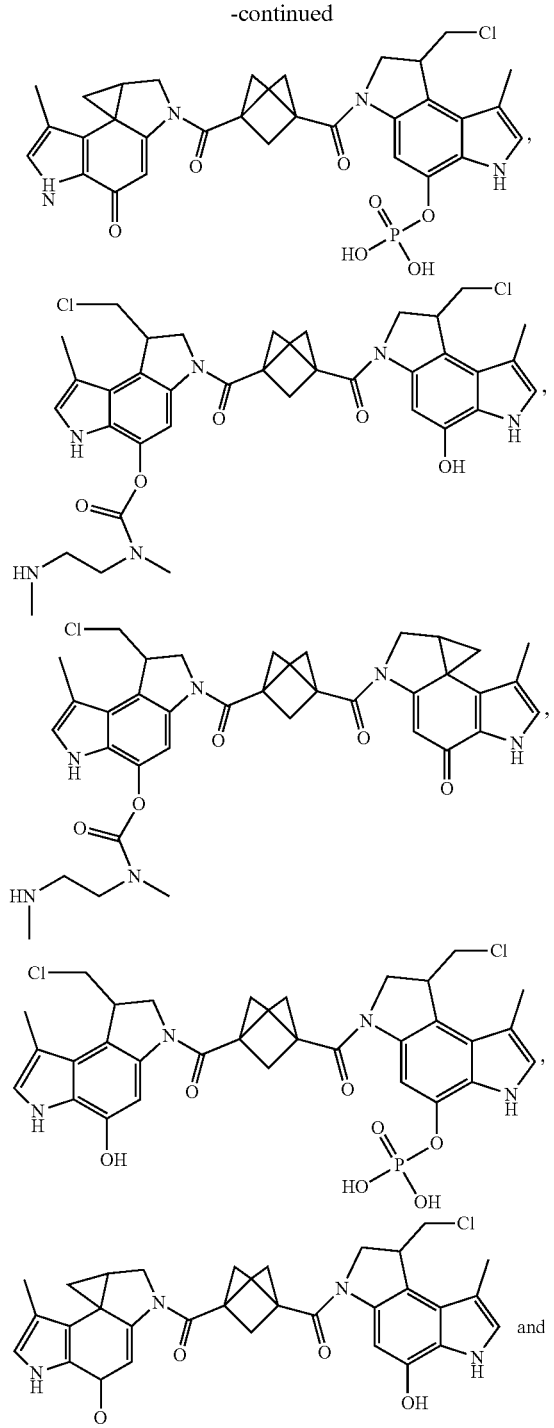

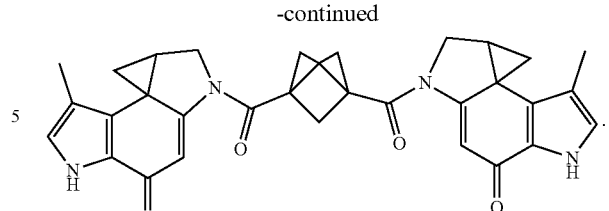

11. A pharmaceutical composition comprising a compound of claim 1 or a pharmaceutically acceptable salt or solvate thereof, and pharmaceutically acceptable excipient.

12. The compound of claim 1, or a pharmaceutically acceptable salt or solvate thereof, wherein D is selected from the group consisting of:

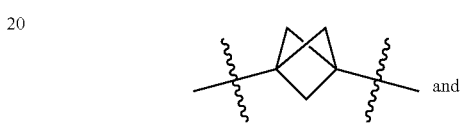

and

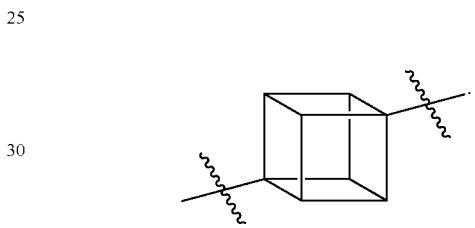

13. The compound of claim 2, or a pharmaceutically acceptable salt or solvate thereof, wherein D is selected from the group consisting of:

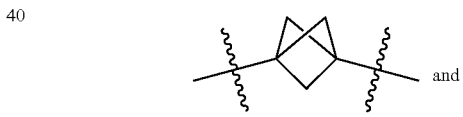

and

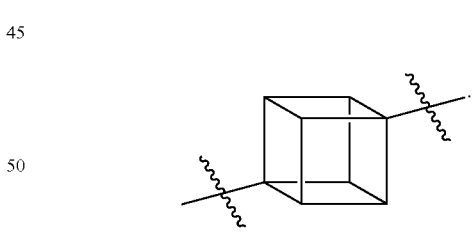

* * * * *